(12) United States Patent
Narayanan et al.

(10) Patent No.: US 9,623,021 B2
(45) Date of Patent: *Apr. 18, 2017

(54) NUCLEAR RECEPTOR BINDING AGENTS

(75) Inventors: Ramesh Narayanan, Cordova, TN (US); Muralimohan Yepuru, Bartlett, TN (US); James T. Dalton, Lakeland, TN (US)

(73) Assignee: GTX, Inc., Memphis, TN (US)

( * ) Notice: Subject to any disclaimer, the term of this patent is extended or adjusted under 35 U.S.C. 154(b) by 110 days.

This patent is subject to a terminal disclaimer.

(21) Appl. No.: 12/773,515

(22) Filed: May 4, 2010

(65) Prior Publication Data

US 2010/0267767 A1  Oct. 21, 2010

Related U.S. Application Data

(63) Continuation-in-part of application No. 12/010,225, filed on Jan. 22, 2008, now Pat. No. 9,078,888.

(60) Provisional application No. 60/881,476, filed on Jan. 22, 2007, provisional application No. 60/907,754, filed on Apr. 16, 2007, provisional application No. 61/177,214, filed on May 11, 2009.

(51) Int. Cl.
    *A61K 31/33*      (2006.01)
    *A61K 31/4709*    (2006.01)
    *A61K 31/472*     (2006.01)
    *C07D 217/22*     (2006.01)
    *C07D 217/24*     (2006.01)

(52) U.S. Cl.
    CPC ........ *A61K 31/4709* (2013.01); *A61K 31/472* (2013.01); *C07D 217/22* (2013.01); *C07D 217/24* (2013.01)

(58) Field of Classification Search
    None
    See application file for complete search history.

(56) References Cited

U.S. PATENT DOCUMENTS

| | | | |
|---|---|---|---|
| 2,848,356 A | 8/1958 | Pritchard et al. | |
| 4,910,208 A | 3/1990 | Misra et al. | |
| 4,942,163 A | 7/1990 | Behrens et al. | |
| 5,004,747 A | 4/1991 | Ashton et al. | |
| 5,112,869 A | 5/1992 | Watanabe et al. | |
| 5,177,075 A | 1/1993 | Suto et al. | |
| 5,416,094 A | 5/1995 | Lal et al. | |
| 5,612,359 A | 3/1997 | Murugesan et al. | |
| 5,719,144 A | 2/1998 | Hartman et al. | |
| 5,968,949 A | 10/1999 | Dondio et al. | |
| 6,034,097 A | 3/2000 | Dimaio et al. | |
| 6,043,265 A | 3/2000 | Murugesan et al. | |
| 6,486,155 B1 | 11/2002 | Pamukcu et al. | |
| 6,630,508 B1 | 10/2003 | Dodge et al. | |
| 6,664,269 B2 | 12/2003 | Martin et al. | |
| 6,686,351 B2 | 2/2004 | Bhagwat et al. | |
| 6,723,747 B2 | 4/2004 | Keith, Jr. et al. | |
| 6,756,375 B2 | 6/2004 | Veeneman et al. | |
| 6,774,248 B2 | 8/2004 | Miller et al. | |
| 6,794,403 B2 | 9/2004 | Malamas et al. | |
| 6,835,745 B2 | 12/2004 | Coghlan et al. | |
| 6,852,727 B2 | 2/2005 | Goulet et al. | |
| 6,870,055 B2 | 3/2005 | Claremon et al. | |
| 6,903,238 B2 | 6/2005 | McDevitt et al. | |
| 6,914,074 B2 | 7/2005 | Mewshaw et al. | |
| 6,943,162 B2 | 9/2005 | Hale et al. | |
| 6,960,607 B2 | 11/2005 | Malamas et al. | |
| 7,015,219 B2 | 3/2006 | Dickson et al. | |
| 7,034,039 B2 | 4/2006 | Oi et al. | |
| 7,084,276 B2 | 8/2006 | Vu et al. | |
| 7,087,599 B2 | 8/2006 | Parker et al. | |
| 7,138,426 B2 | 11/2006 | DiNinno et al. | |
| 7,151,196 B2 | 12/2006 | Wilkening et al. | |
| 7,157,491 B2 | 1/2007 | Mewshaw et al. | |
| 7,157,492 B2 | 1/2007 | Mewshaw et al. | |
| 7,256,201 B2 | 8/2007 | Barlaam et al. | |
| 7,265,131 B2 | 9/2007 | Johnson et al. | |
| 7,279,499 B2 | 10/2007 | Durst et al. | |
| 7,294,635 B2 | 11/2007 | Scarborough et al. | |
| 7,354,951 B2 | 4/2008 | Norman et al. | |
| 8,188,117 B2 | 5/2012 | Plettenburg et al. | |
| 2001/0041718 A1 | 11/2001 | Thompson et al. | |

(Continued)

FOREIGN PATENT DOCUMENTS

| AU | 2003264386 A1 | 4/2004 |
|---|---|---|
| CN | 101072564 A | 11/2007 |

(Continued)

OTHER PUBLICATIONS

STN Search Report and Summary (Accession No. 2004:41298).*
Pinto de Souza (Indian J Chem, 29B:961-965, 1990).*
Anderson (Chem and Biol 10:787-797, 2003).*
Thiel (Nature Biotechnol 2:513-519, 2004).*
U.S. Appl. No. 09/519,079, filed Mar. 6, 2000, Robl et al.
Kalin MF, et al, "Sex hormones and coronary disease: a review of the clinical studies", Steroids; 55:330-352, 1990.
Wenger NK, et al, "Cardiovascular health and disease in women", N. England J. Med., 329:247-256, 1993.
Mendelsohn ME et al. "Mechanism of disease: the protective effects of estrogen on the cardiovascular system", N. England J. Med., 340:1801-1811, 1999.

(Continued)

*Primary Examiner* — Craig Ricci
(74) *Attorney, Agent, or Firm* — Mark S. Cohen; Pearl Cohen Zedek Latzer Baratz LLP

(57) ABSTRACT

The present invention relates to methods for prevention and/or treatment of metabolic disorders, post-menopausal obesity and conditions associated with high fat diet consumption including, obesity, body weight gain, fat mass formation, bone mineral content reduction, white adipose tissue weight gain, increased cholesterol levels, increased leptin levels, insulin resistance, type II diabetes, increased blood glucose levels, inflammatory diseases, cardiovascular diseases, fatty liver condition (accumulation of fat in the liver), decreased uncoupling protein-1 (UCP-1) levels and increased lipogenesis.

6 Claims, 27 Drawing Sheets

(56) References Cited

U.S. PATENT DOCUMENTS

| | | |
|---|---|---|
| 2002/0077486 A1 | 6/2002 | Scarborough et al. |
| 2003/0008896 A1 | 1/2003 | Martin et al. |
| 2003/0013699 A1 | 1/2003 | Davis et al. |
| 2003/0069303 A1 | 4/2003 | Veeneman et al. |
| 2003/0119800 A1 | 6/2003 | Manolagas et al. |
| 2003/0220227 A1 | 11/2003 | Gungor et al. |
| 2003/0220377 A1 | 11/2003 | Chesworth et al. |
| 2004/0038959 A1 | 2/2004 | Bunker et al. |
| 2004/0044030 A1 | 3/2004 | Claremon et al. |
| 2004/0082575 A1 | 4/2004 | Bhagwat et al. |
| 2004/0082607 A1 | 4/2004 | Oi et al. |
| 2004/0092506 A1 | 5/2004 | Thompson et al. |
| 2004/0138244 A1 | 7/2004 | Dalton et al. |
| 2004/0171006 A1 | 9/2004 | Xiao |
| 2004/0176361 A1 | 9/2004 | Fujio et al. |
| 2004/0204447 A1 | 10/2004 | Johnson et al. |
| 2004/0214790 A1 | 10/2004 | Borgens et al. |
| 2005/0009784 A1 | 1/2005 | Vu et al. |
| 2005/0059723 A1 | 3/2005 | Mewshaw et al. |
| 2005/0101584 A1 | 5/2005 | Barlaam et al. |
| 2005/0113399 A1 | 5/2005 | Scarborough et al. |
| 2005/0148560 A1 | 7/2005 | Fritzemeier et al. |
| 2005/0148624 A1 | 7/2005 | Itoh et al. |
| 2005/0182045 A1* | 8/2005 | Nagase et al. ........... 514/217.06 |
| 2005/0256210 A1 | 11/2005 | Olsson et al. |
| 2006/0004087 A1 | 1/2006 | Miller et al. |
| 2006/0052410 A1 | 3/2006 | Vu |
| 2006/0111318 A1 | 5/2006 | Okamoto et al. |
| 2006/0173039 A1 | 8/2006 | Shiga et al. |
| 2006/0183744 A1 | 8/2006 | Rohrer et al. |
| 2006/0199858 A1 | 9/2006 | Durst et al. |
| 2006/0211602 A1 | 9/2006 | Ansorge et al. |
| 2006/0211672 A1 | 9/2006 | Jacobson et al. |
| 2006/0222721 A1 | 10/2006 | Cohen et al. |
| 2006/0241094 A1 | 10/2006 | Chen et al. |
| 2006/0270591 A1 | 11/2006 | Chang |
| 2006/0270704 A1 | 11/2006 | Isaacs et al. |
| 2006/0281743 A1 | 12/2006 | Dinsmore et al. |
| 2007/0010526 A1 | 1/2007 | Haeberlein et al. |
| 2007/0021495 A1 | 1/2007 | Katzenellenbogen et al. |
| 2007/0027177 A1 | 2/2007 | Trotter et al. |
| 2007/0043077 A1 | 2/2007 | Mewshaw et al. |
| 2007/0049605 A1 | 3/2007 | Mewshaw et al. |
| 2007/0072810 A1 | 3/2007 | Asakawa |
| 2007/0099880 A1 | 5/2007 | Blizzard et al. |
| 2007/0099912 A1 | 5/2007 | Zhou et al. |
| 2007/0105827 A1 | 5/2007 | Blizzard et al. |
| 2007/0197488 A1 | 8/2007 | Peters et al. |
| 2007/0203102 A1 | 8/2007 | Blizzard et al. |
| 2007/0225330 A1 | 9/2007 | Merrill et al. |
| 2009/0030036 A1 | 1/2009 | Dalton et al. |
| 2009/0076019 A1 | 3/2009 | Tyers et al. |
| 2010/0009960 A1 | 1/2010 | Robl et al. |
| 2010/0029734 A1 | 2/2010 | White et al. |
| 2010/0256698 A1 | 10/2010 | Trotter et al. |
| 2010/0267767 A1 | 10/2010 | Narayanan et al. |
| 2010/0286204 A1 | 11/2010 | Vicker et al. |
| 2011/0071146 A1 | 3/2011 | Niimi et al. |
| 2012/0009204 A1 | 1/2012 | Reinhardt et al. |

FOREIGN PATENT DOCUMENTS

| | | |
|---|---|---|
| CN | 101641013 A | 2/2010 |
| EP | 00326386 A2 | 8/1989 |
| EP | 00482939 A1 | 4/1992 |
| EP | 00502575 A1 | 9/1992 |
| EP | 01414443 B1 | 5/2004 |
| EP | 1454898 A1 | 9/2004 |
| EP | 01484320 A1 | 12/2004 |
| EP | 1537880 A1 | 6/2005 |
| EP | 1604983 A1 | 12/2005 |
| JP | H10-259176 | 9/1998 |
| JP | 2005513027 | 5/2005 |
| JP | 2000-072675 A | 3/2010 |
| WO | WO 89/00165 | 1/1989 |
| WO | WO9509842 A1 | 4/1995 |
| WO | WO9730047 | 8/1997 |
| WO | WO9731940 | 9/1997 |
| WO | WO9838168 A1 | 2/1998 |
| WO | WO9829407 | 7/1998 |
| WO | WO9851307 A1 | 11/1998 |
| WO | WO 98/11624 A1 | 3/1999 |
| WO | WO 00/01389 | 1/2000 |
| WO | WO 00/19994 | 4/2000 |
| WO | WO0109096 A2 | 2/2001 |
| WO | WO0122960 A1 | 4/2001 |
| WO | WO0168603 | 9/2001 |
| WO | WO02024655 A1 | 3/2002 |
| WO | WO 02/26325 | 4/2002 |
| WO | WO 02032373 | 4/2002 |
| WO | WO 02/41835 | 5/2002 |
| WO | WO0246164 | 6/2002 |
| WO | WO0246168 | 6/2002 |
| WO | WO0251821 | 7/2002 |
| WO | WO 0258639 | 8/2002 |
| WO | WO02062764A1 | 8/2002 |
| WO | WO 02/091993 | 11/2002 |
| WO | WO02090334 A1 | 11/2002 |
| WO | WO 03015761 | 2/2003 |
| WO | WO03037887 | 5/2003 |
| WO | WO03045930 | 6/2003 |
| WO | WO03053994 | 7/2003 |
| WO | WO 03074044 | 9/2003 |
| WO | WO 2004/004750 * | 1/2004 ............. A61K 38/00 |
| WO | WO 2004/026823 A1 | 1/2004 |
| WO | WO 2004006906 A2 | 1/2004 |
| WO | WO2004014378 A1 | 2/2004 |
| WO | WO 2004/009912 | 4/2004 |
| WO | WO2004048339 A1 | 6/2004 |
| WO | WO2004058717 A1 | 7/2004 |
| WO | WO 2004/073612 | 9/2004 |
| WO | WO 2004094400 | 11/2004 |
| WO | WO2005035520 A1 | 4/2005 |
| WO | WO 2005/082880 | 9/2005 |
| WO | WO 2005/099700 | 10/2005 |
| WO | WO 2005123757 | 12/2005 |
| WO | WO 2006/007503 | 1/2006 |
| WO | WO 2006009912 | 1/2006 |
| WO | WO 2006/026395 | 3/2006 |
| WO | WO 2006044176 A1 | 4/2006 |
| WO | WO 2006/061437 A1 | 6/2006 |
| WO | WO 2006062876 | 6/2006 |
| WO | WO 2006/081152 | 8/2006 |
| WO | WO2006088716 | 8/2006 |
| WO | WO 2006/116401 | 11/2006 |
| WO | WO2006108107 | 12/2006 |
| WO | WO 2007093364 A1 | 2/2007 |
| WO | WO 2007093366 | 2/2007 |
| WO | WO2007053353 A2 | 5/2007 |
| WO | WO2007149031 | 6/2007 |
| WO | WO 07-089291 | 8/2007 |
| WO | WO2007137000 A2 | 11/2007 |
| WO | WO 2008/016768 | 2/2008 |
| WO | WO 2010/096801 A1 | 8/2010 |
| WO | WO 2012/006634 | 1/2012 |

OTHER PUBLICATIONS

Karas RH, et al., "Human Vascular smooth muscle cells contain functional estrogen receptor", Circulation, 89:1943-1950, 1994.

Lindner V, et al, "Increased expression of ER b mRNA in male blood vessels following vascular injury", Circ. Res., 83:224-229, 1998.

Wada-Hirake O, et al, "Role of estrogen receptor beta in uterine stroma and epithelium: insights from estrogen receptor beta −/− mice", PNAS, 103(48):18350-5, 2006.

Dubey RK, et al., "Phytoestrogens inhibit growth and MAP kinase activity in human aortic smooth muscle cells", Hypertension; 33:177-182, 1999.

Siow RCM, et al, Cardiovascular targets for estrogens and phytoestrogens; Transcriptional regulation of nitric oxide synthase and antioxidant defense genes. Free Radical biology and Medicine; 42:909-925, 2007.

(56) References Cited

OTHER PUBLICATIONS

Langer, "New methods of Drug Delivery", Science 249:1627-1633, 1990.
Treat et al, "Liposomes in the Therapy of Infectious Disease and Cancer" Liss, New York pp. 353-365, 1989.
Buchwald et al., "Long-term, continuous intravenous heparin administration by an implantable infusion pump in ambulatory patients with recurrent venous thrombosis.", Surgery 88:507, 1980.
Saudek et al., "A preliminary trial of the programmable implantable medication system for insulin delivery.", N. Engl. J. Med. 321:574, 1989.
Goodson, "Dental Applications", Medical Applications of Controlled Release, supra, vol. 2, pp. 116-138, 1984.
Gungor T. et al., "Synthesis and characterization of 3-arylquinazolinone and 3-arylquinazolinethione derivatives as selective estrogen receptor beta modulators" J. Med. Chem., 49, 2440-2455, 2006.
Crabtree JS et al., "Activity of three selective estrogen receptor modulators on hormone-dependant responses in the mouse uterus and mammary gland", Molecular and Cellular Endocrinology, Feb. 12, 2008.
Leventhal et al., "An estrogen receptor-β agonist is active in models of inflammatory and chemical-induced pain" European Journal of Pharmacology, 553: 146-148, 2006.
Harris HA., "The unexpected science of estrogen receptor-β selective agonists: a new class of anti-inflammatory agents?" Nuclear Receptor Signaling, 2006, pp. 1-4.
Kajta, M. et al., "Genistein inhibits glutamate-induced apoptosis in primary neuronal cell cultures of mouse brain cortex and cerebellum". Behav Pharmacol: 549 (EBPS Workshop, Abstract P27), 2006.
Katzenellenbogen J. A. et al, "Workshop 1.4: Nature of the ligand-binding pocket of estrogen receptor alpha and beta: The search for subtype-selective ligands and implications for the prediction of estrogenic activity", Pure Appl. Chem, 75(11-12), 2397-2403, 2003.
Krishnan, G. et al., "Pharmacological actions of a selective estrogen receptor beta (ER beta} agonist in ovarlectomized rats", J. Bone Miner. Res. 20(Suppl. 1): Abst SA427. 27th Annual Meeting American Society Bone Miner. Res. (ASBHR) (Sep. 23-27r Nashville, United States), 2005.
Sun, W. et al., "6H-Benzo[c]chromen-6-one derivatives as selective ERbeta agonists" 230th ACS Natl Meet (Aug. 28-Sep. 1, Washington DC), Abst MEDI 25, 2005.
Ullrich, J.W. et al., "4-Hydroxy-N-phenyl substituted phthalimides as selective estrogen receptor beta (ER.b) ligands", 230th ACS Nat! Meet (Aug. 28-Sep. 1, Washington DC), Abst MEDI 27 (Wyeth), 2005.
Akiyama, T. et al., "Genistein, a specific inhibitor of tyrosine-specific protein kinases", JBiol Chem 262(12), 5592-5, 1987.
Arias-Loza, P. A. et al., "Both estrogen receptor subtypes, alpha and beta, attenuate cardiovascular remodeling in aldosterone salt-treated rats", Hypertension 5(1(2), 432-8, 2007.
Arias-Loza, P. A., et al, "Both estrogen receptor subtypes, alpha and beta, attenuate cardiovascular remodeling in aldosterone salt-treated rats", Hypertension 5(1(2), 432-8, 2007.
Ascenzi P., et al., "Structure-function relationship of estrogen receptor alpha and beta: Impact on human health", Mol. Aspects Med. 27 (4) 299-402, 2006.
Barkhem, T., et al., "Differential response of estrogen receptor alpha and estrogen receptor beta to partial estrogen agonists/antagonists", Mol. Pharmacol. 54(1), 10512, 1998.
Blizzard, T. A., et al., "Bridged androstenediol analogs as ER-beta selective SERMs", Bioorg Med Chem Lett 17(10), 2944-8, 2007a.
Blizzard, T. A., "Androstene-3,5-dienes as ER-beta selective SERMs", Bioorg. Med. Chem. Lett. 17(22), 6295-8, 2007b.
Bodo, C. and Rissman, E. F. (2006), "New roles for estrogen receptor beta in behavior and neuroendocrinology", Front Neuroendocrinology 27(2), 217-32.
Booth, E. A., et al. (2007). "The pathway-selective estrogen receptor ligand WAY-169916 reduces infarct size after myocardial ischemia and reperfusion by an estrogen receptor dependent mechanism", J. Cardiovascular Pharmacology, 49(6), 401-7.
Chadwick, C, et al (2005), "Identification of pathway-selective estrogen receptor ligands that inhibit NF-kappaB transcriptionsal activity", Proc. Natl. Acad. Sci. USA 102(7), 2543-8.
Remmers et al. (1997) "Testosterone receptor blockade after trauma-hemorrhage improves cardiac and hepatic functions in males" Am. J. Physiol.—Heart Circ. Physiol., 287: 2919-2925, esp abstract, p. H2924, col. 1.
Mckinnon et al. (2003) "Glaucoma: ocular Alzheimer's disease? Frontiers in Bioscience" 8:s 1140-1156, esp, abstract; p. 1141, col. 2, para 2; p. 1150, col. 1, para 2.
Chan, K. K., et al (2008), "Estrogen receptor subtypes in ovarian, cancer: a clinical correlation", Obstet. Gynecol. 111(1) 144-51.
Chan, Y. C. et al.; "Raloxifene Relaxes Rat Pulmonary Arteries and Veins: Roles of Gender, Endothelium, and Antagonism of Ca2+ Influx."; The Journal of Pharmacology and Experimental Therapeutics; 312(3), pp. 1266-1271, 2005.
Chang, E. C, et al (2006), "Impact of estrogen receptor beta on gene networks regulated by estrogen receptor alpha in breast cancer cells", Endocrinology 147(10), 4831-42.
Chen, W., et al. (2007), Aza analogues of equol: novel ligands for estrogen receptor beta, Bioorg Med Chem 15(17), 5828-36.
Chesworth R, et al. (2005), "Estrogen receptor beta selective ligands: discovery and SAR of novel heterocyclic ligands", Bioorg. Med. Chem. Lett. 15(24), 5562-6.
Chesworth, R., et al. (2004), "Tetrahydroisoquinolines as subtype selective estrogen agonists/antagonists", Bioorg. Med. Chem. Lett. 14(11), 2729-33.
Christian, R. C, et al (2006). "Initial estrogen receptor (ER)beta, but not ERalpha expression. Is correlated with coronary calcification and atherosclerosis in pre- and postmenopausal women", J.Clin. Endocrinol. Metab. 91(7)j 2713-20.
Collini M.D. et al. (2004). "7-Substituted 2-phenyl-benzofurans as ER beta selective ligands", Bioorg. Med. Chem. Lett. 14(19), 4925-9.
Compton, D. R., et al (2004). "Pyrazolo[1,5-a] pyrimidines as estrogen receptor ligands: defining the orientation of a novel heterocyclic core". Bioorg. Med. Chem. Lett. 14(22), 5681-4.
Compton, D. R. et al. (2004). "Pyrazolo[1,5-a]pyrimidines: estrogen receptor ligands possessing estrogen receptor beta antagonist activity", J. Med. Chem. 47(24), 5872-93.
Cvoro, A., et al. (2008), "Selective estrogen receptor-beta agonists repress transcription of proinflammatory genes", J. Immunol. 180(1), 630-6.
De Angelis, et al (2005a), "Indazole estrogens: highly selective ligands for the estrogen receptor beta". J. Med. Chem. 4S(4)s 1132-44.
De Angelis, et al (2005b). "Isocoumarins as estrogen receptor beta selective ligands: Isomers of Isoflavone phytoestrogens and their metabolites", Bioorg. Med. Chem. 13(23), 6529-42.
Dick, G. M. et al. "(Xeno)Estrogen Sensitivity of Smooth Muscle BK Channels Conferred by the Regulatory β1 Subunit, a Study of β1Knockout Mice"; The Journal of Biological Chemistry; 276(48); pp. 44835-44840; (2001).
Pinthus et al. (2007) "Androgen Induces Adaptation to Oxidative Stress in Prostate Cancer: Implications for Treatment with Radiation Theraphy", Neoplasia, vol. 9:68-80, esp. Abstract; p. 70, col. 2, para 6; p. 71, col. 1, para 2.
Edsall, R. J., et al. (2003). "ERbeta ligands. Part 1: the discovery of ERbeta selective ligands which embrace the 4-hydroxy-biphenyl template", Bioorg. Med. Chem. 11(16), 3457-74.
Fotsis, T. et al, (1993). "Genistein, a dietary-derived Inhibitor of in vitro angiogenesis", Proc. Natl. Acad. Sci. USA 90(7), 2690-4.
Fritzemeier, K. H., et al (2004). Biological effects of ERalpha- and ERbeta-selective estrogens, Ernst Schering Res. Found Workshop (46), 127-50.
Fu X. H., et al (2008). "Synthesis of genistein derivatives and determination of their protective effects against vascular endothelial cell damages caused by hydrogen peroxide", Bioorg. Med. Chem. Lett. 18(2), 513-7.

(56) References Cited

OTHER PUBLICATIONS

Green, Kl A., and Carroll, J. S (2007). "Oestrogen-receptor-mediated transcription and the influence of co-factors and chromatin state", Nat. Rev. Cancer 7(9), 713-22.
Greene, G. L., Shiau A. K., and Nettles, K. W. (2004). A structural explanation for ERalpha/ERbeta SERM discrimination. Ernst Schering Res Found Workshop (46), 33-45.
Güngör, T. et al. (2006) "Synthesis and Characterization of 3-Arylquinazolinone and 3- Arylquinazolinethione Derivatives as Selective Estrogen Receptor Beta Modulators", J. Med. Chem. 2006, 49, 2440-2455.
Gupta, A. K., et al (2007). "QSAR analysis of indazole estrogens as selective beta- estrogen receptor ligands: rationalization of physicochemical properties", Med Chem 3(4), 347-53.
Fotsis, T. et al, (1993). "Genistein, a dietary-derived Inhibitor of in vitro angiogenesis", Proc. Nat.l Acad. Sci. USA 90(7), 2690-4.
Fritzemeier, K. H., et al (2004)."Biological effects of ERalpha- and ERbeta-selective estrogens". Ernst Schering Res. Found Workshop(46), 127-50.
Fu X. H., et al (2008). "Synthesis of genistein derivatives and determination of their protective effects against vascular endothelial cell damages caused by hydrogen peroxide" Bioorg. Med. Chem. Lett. 18(2), 513-7.
Green, KL A., and Carroll, J. S (2007). "Oestrogen-receptor-mediated transcription and the influence of co-factors and chromatin state". Nat. Rev. Cancer 7(9), 713-22.
Greene, G. L., Shiau A. K., and Nettles, K. W. (2004). "A structural explanation for ERalpha/ERbeta SERM discrimination". Ernst Schering Res Found Workshop (46), 33-45.
Güngör, T. et al. (2006) "Synthesis and Characterization of 3-Arylquinazolinone and 3-Arylquinazolinethione Derivatives as Selective Estrogen Receptor Beta Modulators". J. Med. Chem. 2006, 49, 2440-2455.
Gupta, A. K., et al (2007). "QSAR analysis of indazole estrogens as selective beta- estrogen receptor ligands: rationalization of physicochemical properties", Med. Chem. 3(4), 347-53.
Gustafsson, J. A. (2006). "ERbeta scientific visions translate to clinical uses", Climacteric 9(3) 156-60.
Haas, E. et al.; "Differential Effects of 17β-Estradiol on Function and Expression of Estrogen Receptor α, Estrogen Receptor β, and GPR30 in Arteries and Veins of Patients with Atherosclerosis"; Hypertension 49(6); pp. 1358-1363; (2007).
Harrington, W, et al. (2003), "Activities of estrogen receptor alpha- and beta-selective ligands at diverse estrogen responsive gene sites mediating transactivation or transrepression". Mol. Cell Endocrinol. 206(1-2), 13-22.
Harris, H. A. (2006). "The unexpected science of estrogen receptor-beta selective agonists; a new class of anti-inflammatory agents?" Nucl. Recept. Signal 4, eO12.
Harris, H. A. (2007). "Estrogen receptor-beta: recent lessons from, in vivo studies", Mol. Endocrinol. 21(1), 1-13.
Harris, H. A., et al (2003), "Evaluation of an estrogen receptor-beta agonist in animal models of human disease". Endocrinology 144(10), 4241-9.
Hayashi, A., et al (1997). "Genistein, a protein tyrosine kinase inhibitor, ameliorates retinal degeneration after ischemia-reperfusion injury in rat". Invest. Opthalmol. Vis. Sci. 38(6), 1193-202.
Henke, B. R., et al (2002). „A new series of estrogen receptor modulators that display selectivity for estrogen receptor beta J. Med. Chem. 45(25), 5492-505.
Heynekamp, J. J., et al (2006). "Substituted trans-stilbenes, including analogues of the natural product resveratrol, inhibit the human tumor necrosis factor alpha-induced activation of transcription factor nuclear factor kappaB". J. Med. Chem. 49(24), 7182-9.
Hillisch, A., et al. (2004b). "Dissecting physiological roles of estrogen receptor alpha and beta with potent selective ligands from structure-based design", Mol. Endocrinol. 18(7), 1599-609.
Ho, S. M. (2004). "Estrogens and anti-estrogens: key mediators of prostate carcinogenesis and new therapeutic candidates". J. Cell Biochem. 91(3), 491-503.

Hoekstra, W.J., et al. (2005) :Discovery of novel quinoline-based estrogen receptor ligands using peptide interaction profiling, J. Med. Chem. 48(6), 2243-7.
Imamov, O., et al. (2004). "Estrogen receptor beta in prostate cancer". N. Engl. J. Med. 351(26), 2773-4.
Imamov, O., et al (2005). "Estrogen receptor beta in health and disease". Biol. Reprod. 73(5) 866-71.
Jazbutyte, V. et al. (2008). "Ligand-dependent activation of ER{beta} lowers blood pressure and attenuates cardiac hypertrophy in ovariectomized spontaneously hypertensive rats". Cardiovasc. Res. 77(4), 774-81.
Kai M., et al (2004). "Soybean isoflavones eliminate nifedipine-induced flushing of tail skin in ovariectomized mice". J. Pharmacol. Set. 95(4), 476-8.
Kajta, M., et al. (2007). "Genistein inhibits glutamate-induced apoptotic processes in primary neuronal cell cultures: an involvement of aryl hydrocarbon receptor and estrogen receptor/glycogen synthase kinase-3beta intracellular signaling pathway", Neuroscience 145(2), 592-604.
Karas, R. H., et al. (1998), "Growth factor activation of the estrogen receptor in vascular cells occurs via a mitogen-activated protein kinase-independent pathway". J. Clin. Invest. 101(12), 2851-61.
Kim, S et al (2004), "Estrogen receptor ligands. Part 4: The SAR of the syn-dihydrobenzoxathiin SERAMs". Bioorg. Med. Chem. Lett. 14(11), 2741-5.
Koehler K., et al., (2005). "Reflections on the discovery and significance of estroger receptor beta", Endocr. Rev. 26(3), 465-78.
Kuiper, G.G. et al. (1997). "Comparison of the ligand binding specificity and transcript tissue distribution of estrogen receptors alpha and beta". Endocrinology 138(3), 863-70.
Lai S., et al (2004). "Metastases of prostate cancer express estrogen receptor-beta". Urology 64(4), S14-20.
Leung, Y.K., et al (2006). „Estrogen receptor (ER)-beta isoforms: a key to understanding ER-Beta signaling. Proc. Natl. Acad. Sci. USA 103(35), 13162-7.
Luan F., et al., (2008) "Classification of estrogen receptor-beta ligands on the basis of their binding affinities using support vector machine and linear discriminant analysis". Eur. J. Med. Chem. 43(1), 43-52.
Lund, T. D., et al (2004a), "Androgen receptor expression in the rat prostate is down-regulated by dietary phytoestrogens". Reprod. Biol. Endocrinol. 2, 5.
Lund, T.D et al (2004b). "Equal is a novel anti-androgen that inhibits prostate growth and hormone feedback". Biol. Reprod. 70(4), 1188-95.
Lutty, G. et al (1999). "Changes in choriocapiliaris and retinal pigment epithelium in age-related macular degeneration". Mol. Vis. 5, 35.
Malamas, M.S., et al. (2004). "Design and synthesis of aryl diphenolic azoles as potent and selective estrogen receptor-beta ligands". J. Med. Chem. 47(21), 5021-40.
Manas, E.S.,et al (2004), "Structure-based design of estrogen receptor-beta selective ligands". J.Arn. Chem. Soc. 126(46), 1510649.
McDevitt, R. E., et al. (2005). "Estrogen receptor ligands: design and synthesis of new 2-arylindene-1-ones". Bioorg. Med. Chem. Lett. 15(12), 3137-42.
McPherson, S. J., et al. (2006). "The role of ERalpha and ERheta in the prostate: insights from genetic models and isoform-selective ligands". Ernst Schering Found Symp. Proc. 1, 131-47.
Mewshaw, R, E. et al. (2007). "ERbeta ligands. Part 5: synthesis and structure-activity relationships of a series of 4'-hydroxyphenyl-aryl-carbaldehyde oxime derivatives". Bioorg. Med. Chem. Lett. 17(4), 902-6.
Mewshaw, R. E., et al (2005). "ERbeta ligands. 3. Exploiting two binding orientations of the 2-phenylnaphthalene scaffold to achieve ERbeta selectivity". J. Med. Chem. 48(12), 3953-79.
Miller, C. P., et al. (2003). "Constrained phytoestrogens and analogues as ERbeta selective ligands", Bioorg. Med. Chem. Lett. 13(14), 2399-403.
Minutolo, F., et al. (2008). "Monoaryl-substituted salicylaldoximines as ligands for estrogen receptor Beta". J. Med. Chem. 51(5), 1344-51.

(56) References Cited

OTHER PUBLICATIONS

Morani, A. et al (2006). "Lung dysfunction causes systemic hypoxia in estrogen receptor beta knockout (ERbeta−/−) mice". *Proc. Natl. Acad. Set. USA* 103(18), 7165-9.
Morissette, M et al., (2008), "Contribution of estrogen receptors alpha and beta to the effects of estradiol in the brain". *J. Steroid Biochem. Mol. Biol.* 108(3-5), 327-38.
Muthyala, R, et al (2003). "Exploration of the bicyclo[3.3.1]nonane system as a template for the development of new ligands for the estrogen receptor". *Bioorg. Med. Chem. Lett.* 13(24). 4485-8.
Muthyala, R. et al. (2003), "Bridged bicyclic-cores containing a 1,1-diarylethylene motif are high-affinity subtype-selective ligands for the estrogen receptor", *J. Med. Chem.* 46(9), 1589-602.
Nakajima, M, et al. (2001). "Normalization of retinal, vascular permeability in experimental diabetes with genistein". *Invest. Ophthalmol. Vis. Sci.* 42(9),2U0-4.
Norman, B. H., et al. (2006). "Benzopyrans are selective estrogen receptor beta agonists with novel activity in models of benign prostatic hyperplasia", *J. Med. Chem.* 49(21) 6155-7.
Norman, B. H., et al. (2007). "Benzopyrans as selective estrogen receptor beta agonists (SERBAs). Part 4: functionalization of the benzopyran A-ring". Bioorg. Med. Chem. Left 17(18), 5082-5.
Ohshiro, K. et al. (2006). "Biological role of estrogen receptor beta in salivary gland adenocarcinoma cells". Clin. Cancer Res. 12(20 Pt I\ 5994-9.
Parker, D.L., et al. (2006), "Triazoio-tetrahydrofluorenones as selective estrogen receptor beta agonists". Bioorg. Med. Chem. Lett. 16(17), 4652-6.
Pike, A, et al. (1999). "Structure of the ligand-binding domain of oestrogen receptor beta in, the presence of a partial agonist and a MI antagonist" Embo. J. 18(17) 4608-18.
Pravettoni, A., et al. (2007). "Estrogen receptor beta (ERbeta) and inhibition of prostate cancer cell proliferation: studies on the possible mechanism of action in DU145 cells". Mol. Cell Endocrinol. 263(1-2), 46-54.
Prossnitz, E R., et al. (2008). "GPR30; a novel therapeutic target in estrogen-related disease", Trends Pharmacol. Sci. 29(3% 116-23.
Qin C, et al., (2008) "Understanding the Cardioprotective Effects of Flavonols: Discovery of Relaxant Flavonols without Antioxidant Activity". J. Med. Chem. 51(6) 1874-84.
Rhodes, M. E. et al. (2006), "ERbeta-selective SERMs produce mnemonic-enhancing effects in the inhibitory avoidance and water maze tasks". Neurobiol. Learn Mem. 85(2), 183-91.
Richardson. T. L., et al. (2007a), "Benzopyrans as selective estrogen receptor beta agonists (SERBAs). Part 3: synthesis of cyclopentanone and cyclohexanone intermediates for C-ring; modification". *Bioorg. Med. Chem. Lett.* 17(17), 4824-8.
Richardson, T.L., et al. (2007b). "Benzopyrans as selective estrogen receptor beta agonists (SERBAs). Part 5: Combined A- and C-ring structure-activity relationship studies". *Bioorg. Med. Chem. Lett.* 17(20), 5563-6.
Richardson, TL., et al. (2007c). "Benzopyrans as selective estrogen receptor beta agonists (SERBAs). Part 2: structure-activity relationship studies on the benzopyran scaffold". *Bioorg. Med. Chem. Lett.* 17(13), 3570-2.
Roelens, F., et al. (2006). "Subtle side-chain modifications of the hop phytoestrogen 8-prenylnaringenin result in distinct agonist/antagonist activity profiles for estrogen receptors alpha and beta". *J. Med. Chem.* 49(25)$_{48}$ 7357-65.
Safe, S., et al. (2006). "The role of xenoestrogenic compounds in the development of breast cancer". *Trends Pharmacol. Sci.* 27(8), 447-54.
Seo J. et al. (2006). "Fluorine-substituted cyclofenil derivatives as estrogen receptor ligands: synthesis and structure-affinity relationship study of potential positron emission tomography agents for imaging estrogen receptors in breast cancer". *J. Med. Chem.* 49(8)7 2496-511.
Setchell K. D. (2006), "Assessing risks and benefits of genistein and soy". *Environ. Health Perspect.* 114(6), A332-3.

Setchell, K. D., et al. (2005). "S-equol, a potent ligand for estrogen receptor beta, is the exclusive enantiomeric form of the soy isoflavone metabolite produced by human intestinal bacterial flora", *Am. J. Gin. Nutr.* 81(5), 1072-9.
Shen, S. S, et al. (2006). "Expression of estrogen receptors-alpha and -beta in bladder cancer cell lines and human bladder tumor tissue". Cancer 106(12), 2610-6.
Shiau, A. K, et al. (2002). "Structural characterization of a subtype-selective ligand reveals a novel mode of estrogen receptor antagonism". *Nat. Struct. Biol.* 9(5), 359-64.
Skliris G.P. et al., (2008) "Estrogen receptor alpha negative breast cancer patients: Estrogen receptor beta as a therapeutic target" *J. Steroid Biochem. Mol. Biol.* 109(1-2), 140.
Somjen, D., et al (2002), "6-Carboxymethyl genistein: a novel selective oestrogen receptor modulator (SERM) with unique, differential, effects on the vasculature, bone -and uterus". *J. Endocrinol.* 173(3), 415-27.
Strom, A., et al. (2004). "Estrogen receptor beta inhibits 17beta-estradiol-stimulated proliferation of the breast cancer cell line T47D". *Proc. Natl. Acad. Sci. USA* 101(6) 1566-71.
Sun, J., et al (2003). "Molecular basis for the subtype discrimination of the estrogen receptor-beta-selective ligand, diarylpropionitrile". *Mol. Endocrinol.* 17(2), 247-58.
Sun, Wet al. (2006). "6H-Benzo[c]chromen-6-one derivatives as selective ERbeta agonists". *Bioorg. Med. Chem. Lett.* 16(6), 1468-72.
Szkudelska, K., and Nogowski, L. (2007). "Genistein-a dietary compound inducing hormonal and metabolic changes". *J. Steroid. Biochem. Mol. Biol.* 105(1-5), 37-45.
Takahashi, W., et al. (1997). "Effect of estrogen on nitric oxide-induced relaxation of the rabbit urethra". *Eur. J. Pharmacol.* 339(2-3), 165-71.
Tan, Q et al. (2004a). "Estrogen receptor ligands. Part 5: Tue SAR of dihydrobenzoxathiins containing modified basic side chains". *Bioorg. Med. Chem. Lett.* 14(14), 3747-51.
Tan, Q. et al. (2004b). "Estrogen receptor ligands. Part 6: Synthesis and binding affinity of dihydrobenzodithiins". *Bioorg. Med. Chem. Lett.* 14(14), 3753-5.
Tiwari-Woodruff, S., e tal (2007). "Differential neuroprotective and antiinflammatory effects of estrogen receptor (ERalpha and ERbeta ligand treatment". *Proc. Natl. Acad. Sci. USA* 104(37), 14813-8.
Traupe, T. et al. (2007). "Distinct roles of estrogen receptors alpha and beta mediating acute vasodilation of epicardial coronary arteries". *Hypertension* 49(6)1364-70.
Treeck, O., et al. (2007). "Novel estrogen receptor beta transcript variants identified in human breast cancer cells affect cell growth and apoptosis of COS-1 cells". *Mol. Cell Endocrinol.* 264(1-2) 50-60.
Tremblay, A., et al. (1999). "Ligand-independent recruitment of SRC-1 to estrogen receptor beta through phosphorylation of activation function AF-1". *Mol. Cell* 3(4), 513-9.
Trotter, B. W., et al. (2006). "Design and synthesis of novel isoquinoline-3-nitriles as orally bioavailable Kv1.5 antagonists for the treatment of atrial fibrillation". *J. Med. Chem.* 49(24), 6954-7.
Ullrich, J. W. et al. (2007). "Estrogen receptor beta ligands: design and synthesis of new 2-phenyl-isoindole-1,3-diones", *Bioorg. Med. Chem. Lett.* 17(1), 118-22.
Vivacqua, A. et al. (2006); "The G protein-coupled receptor GPR30 mediates the proliferative effects induced by 17beta-estradiol and hydroxytamoxifen in endometrial cancer cells", *Mol. Endocrinol.* 20(3), 631-46.
Vu, A. T, et al. (2007). "ERbeta ligands. Part 6; 6H-Chromeno[4,3-b]quinolines as a new series of estrogen receptor beta-selective ligands". *Bioorg. Med. Chem. Lett.* 17(14), 4053-6.
Vu, A. T., et al. (2005). "ERbeta ligands. Part 4: Synthesis and structure-activity relationships of a series of 2-phenyiquinoline derivatives". *Bioorg. Med. Chem. Lett.* 15(20), 4520-5.
Walker, H. A, et al. (2001). "The phytoestrogen genistein produces acute nitric oxide-dependent dilation of human forearm vasculature with similar potency to 17beta-estradiol." *Circulation* 103(2), 258-62.

(56) References Cited

OTHER PUBLICATIONS

Wang. S. F.. et al, (2005). "Genistein derivatives as selective estrogen receptor modulators: sonochemical synthesis and in vivo anti-osteoporotic action". *Bioorg. Med. Chem.* 13(16) 4§80-90.
Wang, Y., et al. (2006), "A second binding site for hydroxytamoxifen within the coactivator-binding groove of estrogen receptor beta". *Proc. Natl. Acctd. Sci. USA* 103(26), 9908-fl.
Waring, R. H., et al. (2008). "Phytoestrogens and xenoestrogens: the cotribution of diet and environment to endocrine disruption". *J. Steroid. Biochem. Mol. BM* 108(3-5), 213-20.
Weihua, Z., et al. (2002). "An endocrine pathway in the prostate, ERbeta, AR, 5alpha-androstane-3beta,17beta-diol, and CYP7B1, regulates prostate growth". *Proc. Natl. Acad. Sci. USA* 99(21), 13589-94.
Wildonger, K. L., et al (2006). "Tetrahydrofluorenones with conformationally restricted side chains as selective estrogen receptor beta ligands". *Bioorg. Med. Chem. Lett.* 16(17), 4462-6.
Wilkening, R. R., et al. (2006a). "Estrogen receptor beta-subtype selective tetrahydrofluorenones: use of a fused pyrazole as a phenol bioisostere", *Bioorg. Med. Chem. Lett.* 16(15), 3896-901.
Wilkening, R. R. (2006) "The discovery of tetrahydrofluorenones as a new class of estrogen receptor beta-subtype selective ligands". *Bioorg. Med. Chem. Lett.* 16(13) 3489-94.
Yang, C. et al. (2004a). "ERbeta ligands. Part 2: Synthesis and structure-activity relationships of a series of 4-hydroxy-biphenyl-carbaldehyde oxime derivatives", *Bioorg. Med. Chem.* 12(10), 2553-70.
Yang, W., et al. (2004b). "Synthesis and structure-activity relationship of 3-arylbenzoxazines as selective estrogen receptor beta agonists", *Bioorg. Med. Chem. Lett.* 14(9), 2327-30.
Yoo, J. et al. (2005). "Synthesis of an estrogen receptor beta-selective radioligand: 5-[18F]fl-uoro-(2R,3S)-2,3-bis(4-hydroxyphenyl)pentanenitrile and comparison of in vivo distribution with 16alpha-[18F]fluoro-17beta-estradiol". *J. Med. Chem.* 48(20), 6366-78.
Yu, H. P., et al. (2006). "Salutary effects of estrogen receptor-beta agonist on lung injury after trauma-hemorrhage", *Am. J. Physiol. Lung. Cell Mol. Physiol.* 290(5), L1004-9.
Zhou, H. B, et al. (2005). "Synthesis and evaluation of estrogen receptor ligands with bridged oxabicyclic cores containing a diarylethylene motif: estrogen antagonists of unusual structure". *J. Med. Chem.* 48(23), 7261-74.
Munaut "Presence of Estreogen receptor type beta in human retina" Br. J. Opthalmol. 2001; 85: 877-882.
Kaja, "Estrogen protects the inner retina from apoptosis and ischemia-induced loss of Vsl-1L/Homer 1C immunoreactive synoptic connections" Inv. Opthalmol and Vis. Sci, Jul. 2005, vol. 44, No. 7, pp. 3155-3162.
Nakajima "Normalization of retinal vascular permeability in experimental diabetes with genistein" Inv. Opthalmol and Vis. Sci, Aug. 2001, vol. 42, No. 9, pp. 2110-2114.
Ogueta "Estrogen receptor in the human eye: influence of gender and age on gene expression" Inv. Opthalmol and Vis. Sci, Aug. 1999, vol. 40, No. 9, pp. 1906-1911.
Yager, "Mitochondrial estrogen receptors—new insights into specific functions", Trends in Endocr. and Metabol., vol. 18, No. 3, pp. 89-91, 2007.
Elloso et al, "Suppression of experimental autoimmune encephalomyelitis using estrogen receptor-selective ligands" Journal of Endocrinology, 2005, vol. 185, 243-252.
Follettie et al "Organ messenger Ribonucleic Acid and plasma proteome Changes in the Adjuvant-Induced Arthritis model: Responses to Diseas Induction and Theraphy with the Estogen Receptor-βSelective Agonist ERB-041" Endocrinology 1472):714-723 (2006).
Harris et al "Characterization of the Biological Roles of the Estrogen Receptors, ERα-Selective Ligand" Endocrinology 143 (11):4172-4177 (2002).

Blizzard, T. A. et al (2004). "Estrogen receptor ligands. Part 7: Dihydrobenzoxathiin SERAMs with bicyclic amine side chains". Bioorg. Med. Chem. Lett. 14(15), 3861-4.
Diamanti-Kandarakis et al. (1998) "The Effect of a Pure Anti-androgen Receptor Blocker, Flutamide, on the Lipid Profile in the Polycystic Ovary Syndrome". Journal of Clinical Endocrinology and Metabolism, 1998, 83:2699-2705; esp. abstract; p. col. 1, para 3.
Price et al. (2006) "Toremifene for the Prevention of Prostate Cancer in Men with High grade prostatic Intraephlthelial neoplasia; Results of a Double-Blind, Placebo Controlled, Phase iiB Clinical Trial" The Journal of Urology, 176:965-971, abstract only.
Palanki M. et al. (2007) "Development of Prodrug 4-Chloro-3-(5-methyl-3{[4-(2-pyrrolidin-1-ylethoxy) phenyl]amino}-1,2,4-benzotriazin-7-yl)phenyl Benzoate (TG100801): A Topically Administered Therapeutic Candidate in Clinical Trials for the Treatment of Age-Related Macular Degeneration" J..Med..Chem.
Meyers et al. (2001) "Estrogen Receptor βPotency-Selective Ligands: Structure-Activity Relationship Studies fo Diarylpropionitriles and Their Acetylene and Polar Analogues" J..Med. Chem. 44, 4230-4251.
Schopfer U. et al (2002) "Toward Selective Erβ Agonists for Central Nervous System Disorders: Synthesis and Characterization of Aryl Benzthiophenes" J..Med..Chem. 45, 1399-1401.
Chaum E (2002) "Retinal Neuroprotection by Growth Factors: A Mechanistic Perspecitve" JCB-02s-204.
Lavie et al, "Obesity and Cardiovascular Disease: Risk Factor, Paradox, and Impact of Weight Loss" 2009 J. Am. Coll. Cardiol. 53:1925-32.
Fabricatore et al, "Obesity", 2006 *Annu Rev Clin Psychol* 2:357-77.
Cooke et al, "The obesity pipeline: current strategies in the development of anti-obesity drugs", 2006 *Nat. Rev. Drug. Discov.* 5:919-31.
Yu et al, "Inflamattory components of adipose tissue as target for treatment of metabolic syndrome", 2009 *Forum. Nutr.* 61:95-103.
Reisin et al , "Obesity and Hyper tension: Mechanisms, Cardio-Renal Consequences, and Therapeutic Approaches", 2009 *Med. Clin. North Am.* 93:733-51.
Allende-Vigo MZ. "Women and metabolic syndrome: an overview of its peculiarities", 2008 *P.R. Health Sci. J.* 27:190-5.
Geer et al "Gender Differences in Insulin Resistance, Body Composition, and Energy Balance" 2009 *Gend. Med. 6 Suppl.* 1:60-75.
Thomas et al, "Targeting bile-acid signaling for metabolic diseases", 2008 *Nat. Rev. Drug Discov.* 7:678-93.
Cariou B et al, "FXR: a promising target for the metabolic syndrome?" 2007 *Trends Pharmacol. Sci.* 28:236-43.
Ariazi EA et al "Estrogen-Related Receptors as Emerging Targets in Cancer and Metabolic Disorders" 2006 *Curr. Top Med. Chem.* 6:203-15.
Kintscher U et al, "INT-131, a PPAR-gamma agonist for the treatment of type 2 diabetes", 2009 *Curr. Opin. Investig. Drugs* 10:381-7.
Beekum O et al , "Posttranslational Modifications of PPAR-gamma: Fine-tuning the Metabolic Master Regulator" 2009 *Obesity (Silver Spring)* 17:213-9.
Billin AN , "PPAR-beta/gamma agonists for Type 2 diabetes and dyslipidemia: an adopted orphan still looking for a home", 2008 *Expert Opin. Investig. Drugs* 17:1465-71.
Barros RP et al , "Estrogen receptors: new players in diabetes mellitus" 2006 *Trends Mol. Med.* 12:425-31.
Cypess AM et al. , "Identification and Importance of Brown Adipose Tissue in Adult Humans" 2009 *N. Engl. J. Med.* 360:1509-17.
Harris HA "Estrogen Receptor-_: Recent Lessons from in Vivo Studies" 2007 *Mol. Endocrinol.* 21:1-13.
Foryst-Ludwig A et al "Metabolic Actions of Estrogen Receptor Beta (ER-beta) are Mediated by a Negative Cross-Talk with PPAR-gamma" 2008 *PLoS Genet.* 4:e1000108.
Pallottini V et al "Estrogen Regulation of Adipose Tissue Functions: Involvement of Estrogen Receptor Isoforms" 2008 *Infect. Disord. Drug Targets* 8:52-60.
Liang YQ et al "Estrogen receptor beta is involved in the anorectic action of estrogen", 2002 *Int. J. Obes. Relat. Metab. Disord.* 26:1103-9.

(56) References Cited

OTHER PUBLICATIONS

Lopez-Berestein, "Treatment of systemic fungal infections with liposomal-amphotericin B" Liposomes in the Therapy of Infectious Disease and Cancer, Lopez- Berestein and Fidler (eds.), pp. 317-327, 1989.
Sefton, "Implantable pumps", CRC Crit. Ref. Biomed. Eng. 14:201 (1987).
Abuchowski et al., "Immunosuppressive properties and circulating life of achromobacter glutaminase-asparaginase covalently attached to polyethylene glycol in man", Cancer Treat. Rep. 65: 1077-1081, 1981.
Katre et al., "Chemical modification of recombinant interleukin 2 by polyethylene glycol increases its potency in the murine Meth A sarcoma model" Proc. Natl. Acad. Sci., vol. 84, pp. 1487-1491, 1987.
Morani A et al "Biological functions and clinical implications of oestrogen receptors alfa and beta in epithelial tissues", 2008 *J. Intern. Med.* 264:128-42 (From Example 22A).
Turgeon JL et al "Complex Actions of Sex Steroids in Adipose Tissue, the Cardiovascular System, and Brain: Insights from Basic Science and Clinical Studies" 2006 *Endocr. Rev.* 27:575-605 (From Example 23.13).
Tontonoz P et al "Fat and Beyond: The Diverse Biology of PPAR-gamma" 2008 *Annu. Rev. Biochem.* 77:289-312 (From Example 23.14).
Kersten S "Peroxisome proliferator activated receptors and lipoprotein metabolism", 2008 *PPAR Res* 2008:132960 (From Example 23.14).
Nishigori H et al "Mutations in the Small Heterodimer Partner Gene are Associated with Mild Obesity in Japanese subjects" 2001 *Proc. Natl. Acad. Sci. U S A* 98:575-80 (From Example 23.14).
Lai K et al "Estrogen Receptor _Regulates Expression of the Orphan Receptor Small Heterodimer Partner" 2003 *J. Biol. Chem.* 278:36418-29 (From Example 23.14).
Anderson, "The Process of Structure-Based Drug Design" Chem. and Biol. 10, 787-197, 2003.
Thiel, "Structure-aided drug design's next generation" Nature Biotechnol. 2, 513-519, 2004.
Han, "Advances in characterization of pharmaceutical hydrates", Trends in Bio/Pharmaceutical Industry, pp. 25-29, 2006.
Vippagunta et al., "Crystalline solids" Adv. Drug Rev. 48: 3-26, 2001.
Pinto de Souza et al., "Synthesis of 3-methyl-1-(2H)-isoquinolinone derivates and their biological activities", Ind. J. Chem. B. Org. 29B(10): 961-965, 1990.
Hellwinkel et al, "Synthesis of heterocycles with MF/A1203 base-systems: 2-arylbenzofurans and 2,3-diarylisoquinolin-1(2H)-ones", Synthesis 9: 1135-1141, 1995, STN Search Report Accession No. 1995:866647.
Veeneman, "Non-steroidal subtype selective endrogens", Current Medicinal Chemistry, vol. 12, No. 9, 2005, pp. 1077-1136.
CAS Registry No. 252061-78-2; 6-hydroxy-1(2H)-isoquinolinone.
CAS Registry No. 491-30-5; 1(2H)-Isoquinolinone.
Mahajan et. al.; "T-1032, a cyclic GMP phosphodiesterase-5 inhibitor, acutely blocks physiologic insulin-mediated muscle haemodynamic effects and glucose uptake in vivo", British J Pharmaco, vol. 140(7), 1283-1291, (2003).
Inoue et. al., "Acute and chronic effects of T-1032, a novel selective phosphodiesterase type 5 inhibitor, on monocrotaline-induced pulmonary hypertenstion in rats", Biol. Pharm. Bull., , 1422-1426, (2002).
Yepuru et al.; "Estrogen Receptor-β-selective Ligands Alleviate High-fat Diet- and Ovariectomy-induced Obesity in Mice", Journal of Biological Chemistry, vol. 285, No. 41, Jul. 23, 201, pp. 31292-31303.
Day et al.; "Design and validation of specific Inhibotors of 17b-hydroxysteroid dehydrogenases for therapeutic application in breast and prostate cancer, and in endometriosis", Endocrine-Related Cancer (2008), vol. 15, pp. 665,692.
Rose et al.; "The effects of a low-fat dietary intervention and tamoxifen adjuvant therapy on the serum estrogen and sex hormone-binding globulin concentrations of postmenopausal breast cancer patients", Breast Cancer Research and Treatment, 1993, vol. 27:253-262, p. 253.
Wu et al.; "Meta-Analysis: Dietary Fat Intake, Serum Estrogen Levels, and the irsk of Breast Cancer", Journal of the National Cancer Institute, Mar. 17, 1999, vol. 91, No. 6.
Byrns et al.; "An Indomethacin Analogues, N-(4-Chlorobenzoyl)-melatonin, s a Selective Inhibitor or Aldo-keto Reductase 1C3 (Type 2 3Alpha-HSD, Type 5 17Beta-HSD, and Prostaglandin F Synthase), a Potential Target for the Treatment of Hormone Dependent and Hormone Independent Malignancies", Biochem Pharmacol. Jan. 15, 2008, vol. 75 No. 2, pp. 484-493.
European Search Report for European Application No. 13174659.6 dated Aug. 2, 2013.
Supplementary European Search Report for European Application No. 11778267.2 dated Oct. 7, 2013.
International Search Report for PCT Application No. PCT/US13/58506 dated Jan. 22, 2014.
Roman et al.; "Association of Carotid Atherosclerosis and Left Ventricular Hypertrophy", JACC, vol. 25 No. 1, pp. 83-90, Jan. 1995.
Stanbrough et al.; "Increased expression of genes converting adrenal androgens to testosterone in androgen-independent prostate cancer", Cancer Res, 66: 2815-2825, 2006.
Qiu et al.; "Crystal structures of the multispecific 17beta-hydroxysteroid dehydrogenase type 5: critical androgen regulation in human peripheral tissues", Mol Endocrinol, 18: 1798-1807, 2004.
Soderberg et al.; "Direct observation of individual endogenous protein complexes in situ by proximity ligation", Nat Methods, 3: 995-1000, 2006.
Penning et al.; "Structure-function of human 3 alpha-hydroxysteroid dehydrogenases: genes and proteins", Mol Cell Endocrinol, 215: 63-72, 2004.
Narayanan et al.; "Cyclin-dependent kinase activity is required for progesterone receptor function: novel role for cyclin A/Cdk2 as a progesterone receptor coactivator", Mol Cell Biol 25(1):264-277, 2005.
Narayanan et al.; "Human progesterone receptor displays cell cycle-dependent changes in transcriptional activity", Mol Cell Biol 25(8):2885-2898, 2005.
Office Action issued on Nov. 11, 2014 for Japanese Application No. 2013-271202.
Office Action issued on Apr. 13, 2015 for Russian Patent Application No. 2012151846.

* cited by examiner

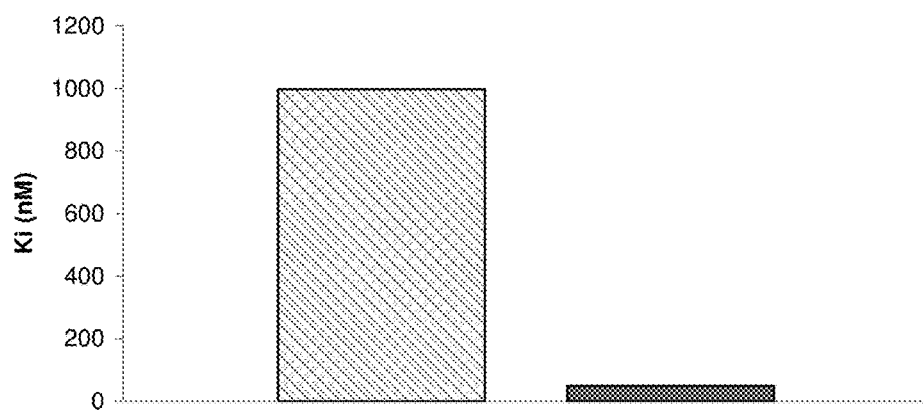
FIGURE 1 A (12b)
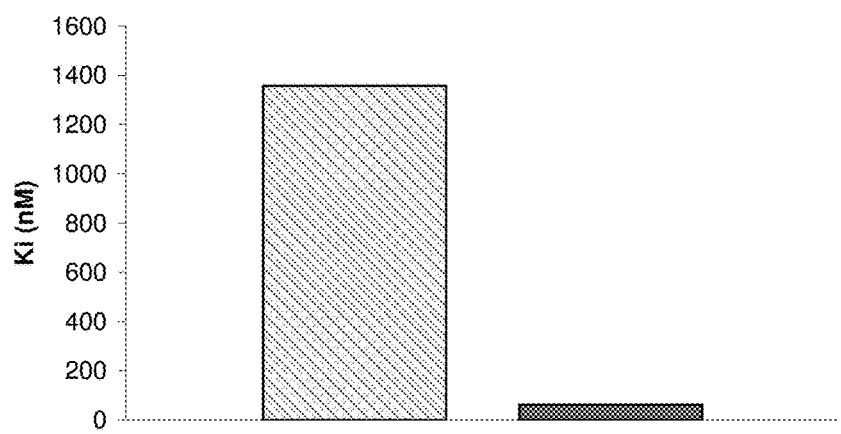
FIGURE 1 B (12f)
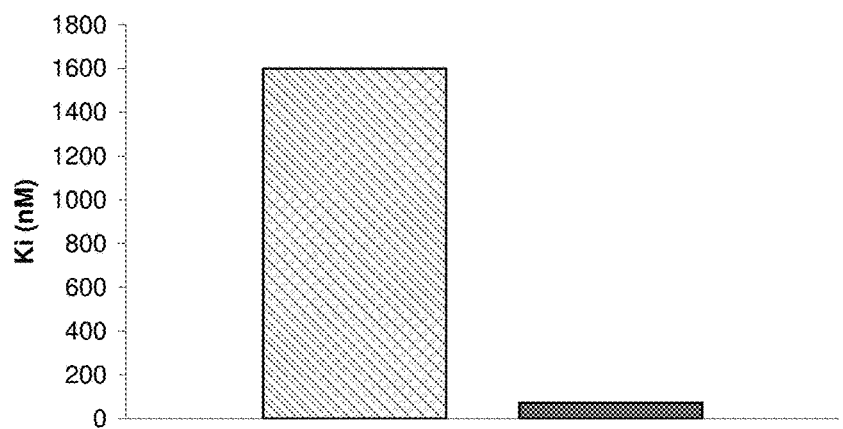
FIGURE 1 C (12h)

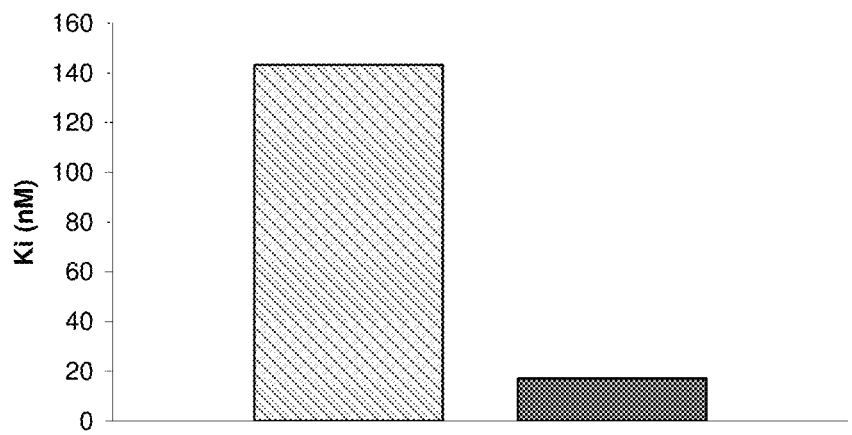
FIGURE 1 D (12p)
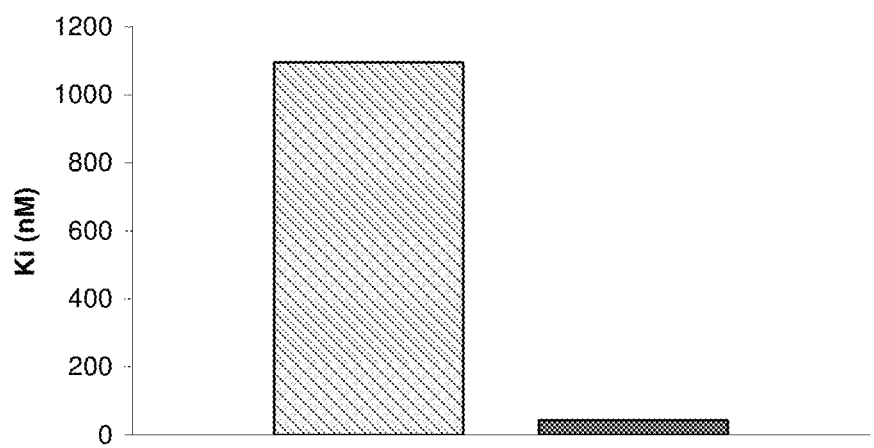
FIGURE 1E (12S)
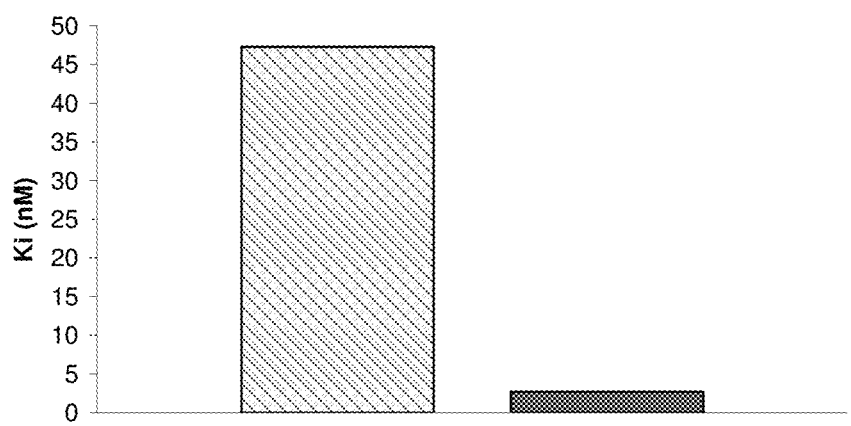
FIGURE 1 F (12u)

Estradiol

A

B

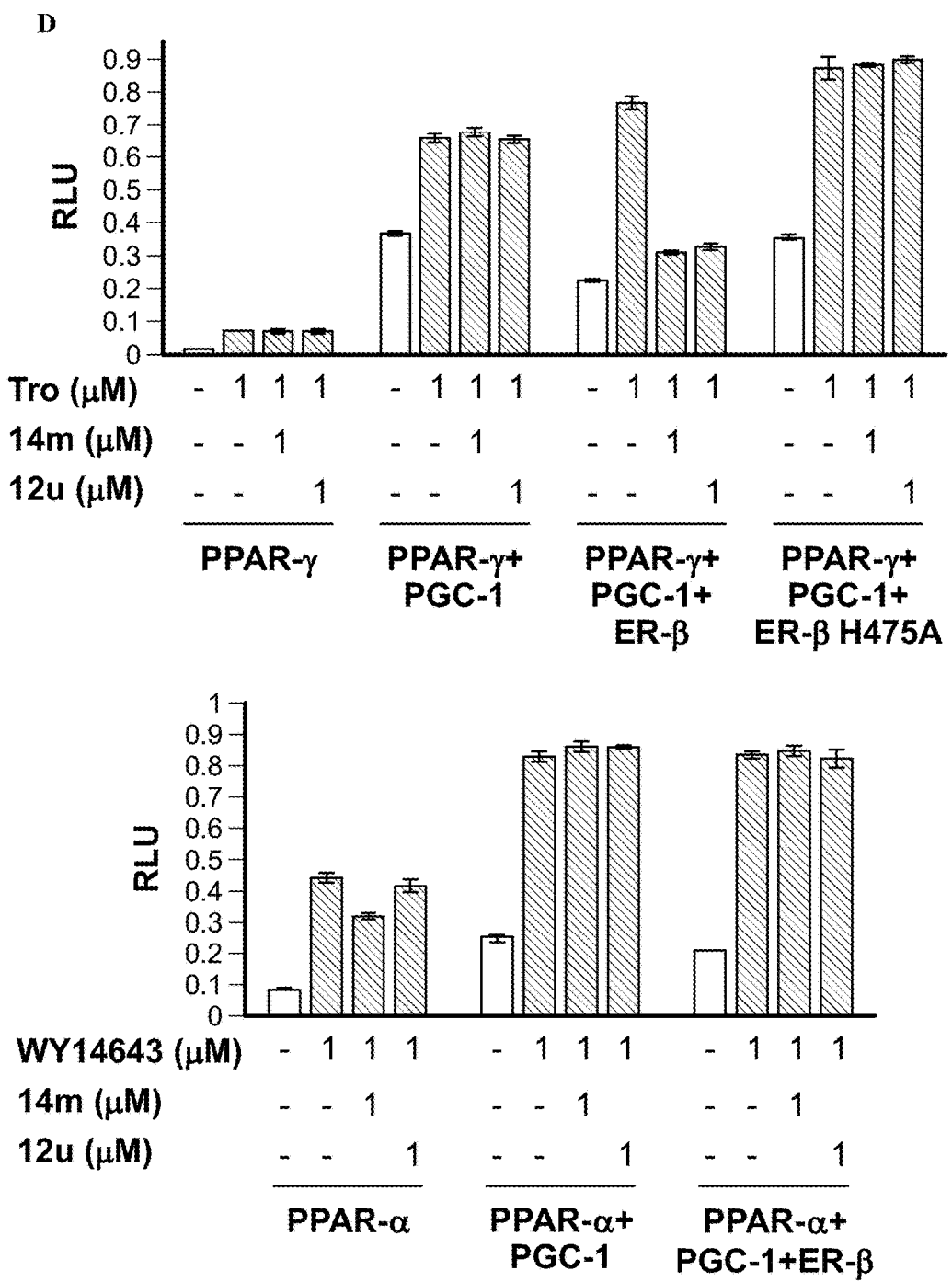
FIGURE 12-Cont

E
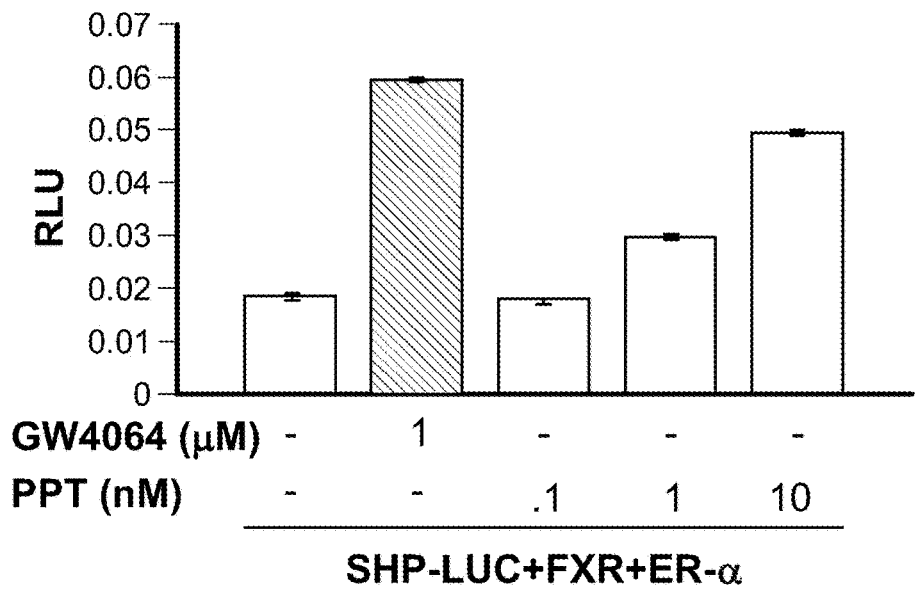
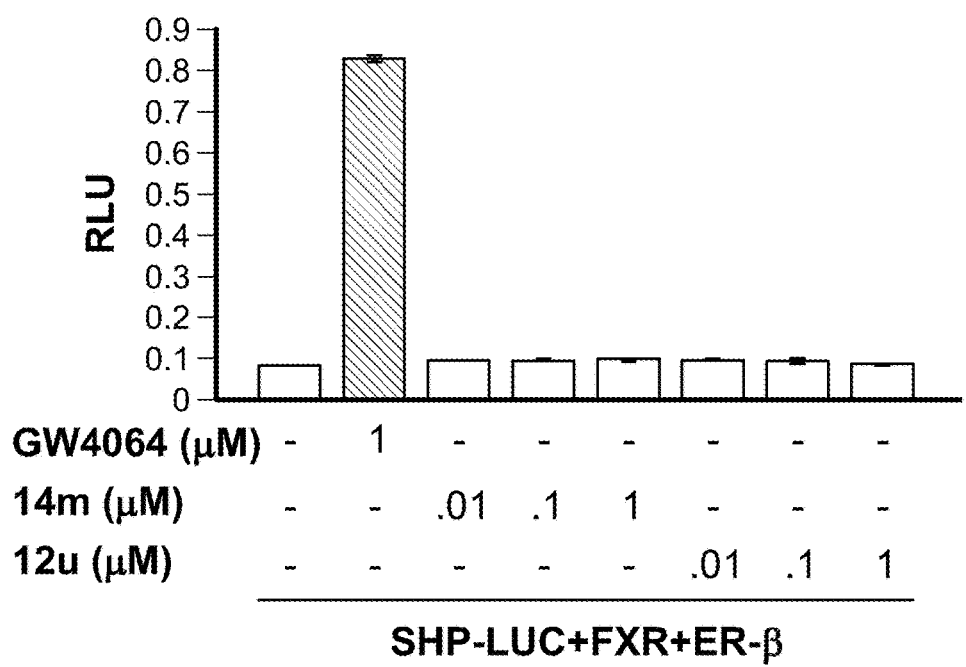
FIGURE 12-Cont (A)

(B)

NUCLEAR RECEPTOR BINDING AGENTS

CROSS REFERENCE TO RELATED APPLICATIONS

This Application is Continuation-In-Part Application of U.S. patent application Ser. No. 12/010,225, filed Jan. 22, 2008 now U.S. Pat. No. 9,078,888 which claims the benefit of U.S. Provisional Patent Application Ser. No. 60/881,476, filed Jan. 22, 2007 and U.S. Provisional Patent Application Ser. No. 60/907,754, filed Apr. 16, 2007 and This Application claims the benefit of U.S. Provisional Patent Application Ser. No. 61/177,214, filed May 11, 2009, all of which are hereby incorporated by reference in their entirety.

FIELD OF THE INVENTION

The present invention relates to methods for prevention and/or treatment of metabolic disorders, post-menopausal obesity and conditions associated with high fat diet consumption including, obesity, body weight gain, fat mass formation, bone mineral content reduction, white adipose tissue weight gain, increased cholesterol levels, increased leptin levels, insulin resistance, type II diabetes, increased blood glucose levels, inflammatory diseases, cardiovascular diseases, fatty liver condition (accumulation of fat in the liver), decreased uncoupling protein-1 (UCP-1) levels and increased lipogenesis.

BACKGROUND OF THE INVENTION

The nuclear hormone receptor superfamily of ligand activated transcription factors is present in various tissues, and responsible for a multitude of effects in these tissues.

The nuclear receptor (NR) superfamily presently comprises approximately 48 different proteins, of which 27 are ligand regulated, most of which are believed to function as ligand activated transcription factors, exerting widely different biological responses by regulating gene expression. Members of this family include receptors for endogenous small, lipophilic molecules, such as steroid hormones, retinoids, vitamin D and thyroid hormone.

The nuclear receptor (NR) superfamily includes the steroid nuclear receptor subfamily, including the mineralocorticoid receptor (MR) (or aldosterone receptor), the estrogen receptors (ER), ER alpha (ER-α) and ER beta (ER-β), the androgen receptor (AR), the progesterone receptors (PR), glucocorticoid receptors (GR) and others. Also closely related in structure are the estrogen related receptors (ERRs) ERR-α, ERR-β and ERR-γ. The steroid nuclear receptors perform important functions in the body, some of which are related to the transcriptional homeostasis of electrolyte and water balance, growth, development and wound healing, fertility, stress responses, immunological function, and cognitive functioning. The effects may be mediated by cytosolic, mitochondrial or nuclear events. Accordingly, compounds that modulate (i.e. antagonize, agonize, partially antagonize, partially agonize) the activity of steroid nuclear receptors are important pharmaceutical agents that have specific utility in a number of methods, as well as for the treatment and prevention of a wide range of diseases and disorders modulated by the activity of steroid nuclear receptors.

The biological actions of estrogens and antiestrogens are manifest through two distinct intracellular receptors, estrogen receptor alpha (ER-α) and estrogen receptor beta (ER-β). For instance, ER-β is present in, among other tissues, brain, bone, immune system, gastrointestinal tract, lung, ovary, endometrium, prostate, vasculature, urogenital tract, salivary gland, etc. The role of ER-β in these tissues has been confirmed by observed phenotypes in ER-β knockout mice. Pathologies in these tissues may be treated by administration of ER-β selective ligands.

The prevalence of metabolic diseases, such as obesity, insulin resistance and type II diabetes has increased dramatically in the past decade. For example, it is estimated that 400 million people were obese or overweight globally in 2008, and approximately two-thirds of Americans are overweight or obese, making obesity a serious health risk and economic burden to society. Obesity is not a stand-alone disease, as its emergence leads to various complications including type-2-diabetes mellitus (T2DM), hypertension, atherosclerosis and other cardiovascular diseases, osteoporosis and clinical depression [Lavie et al, 2009 *J Am Coll Cardiol* 53:1925-32; Fabricatore et al 2006 *Annu Rev Clin Psychol* 2:357-77]. Currently there are no effective pharmaceutical treatments for this pandemic problem. Although surgical procedures can reduce weight by 50-90%, it is restricted due to the risk of surgery and associated side effects. The best drugs currently in the market typically reduce weight by about 5-10% per year at most. Only two FDA approved drugs are available for treating over-weight indication: 1. Amphetamines and sibutramine that act on the hypothalamus to control appetite stimulation in the CNS. 2. Orlistat that is a lipase inhibitor that blocks gastrointestinal absorption of fat and decreases energy uptake [Cooke et al 2006 *Nat Rev Drug Discov* 5:919-31]. Common side effects associated with these drugs including tachycardia, hypertension, fecal incontinence and/or cardiac valvopathy, making anti-obesity drug development of paramount importance. Therefore, there is a need in the art for more effective and safe drugs to treat conditions such as obesity, and other related conditions and metabolic disorders.

Obesity is a heterogeneous disease which occurs when energy uptake exceeds energy expenditure. Though the etiology of obesity remains uncertain, several mechanisms such as alterations in feeding behavior signals in the hypothalamus, levels of leptin, adipokines secreted by white adipose tissue (WAT), neuropeptides and neurotransmitters that control behavior, hormonal changes associated with age, inflammatory signals in adipose, stress and others trigger the onset of obesity [Yu et al 2009 *Forum Nutr* 61:95-103; Rother et al 2009 *Dtsch Med Wochenschr* 134:1057-9; Reisin et al 2009 *Med Clin North Am* 93:733-51].

Increase in the incidence of post-menopausal obesity, visceral obesity at andropause and gender differences in the incidence of metabolic diseases indicate the importance of the nuclear hormone receptor (NR) superfamily in regulating body weight [Allende-Vigo MZ 2008 *P R Health Sci J* 27:190-5; Geer et al 2009 *Gend Med* 6 Suppl 1:60-75]. Many of the NRs play pivotal roles in regulating the emergence of metabolic diseases. Activation of bile acid NRs such as Farnesoid X Receptor (FXR), Constitutive Androstane Receptor (CAR) and Pregnane X Receptor (PXR) promotes weight loss and also increases insulin sensitivity [Thomas et al 2008 *Nat Rev Drug Discov* 7:678-93; Cariou B et al 2007 *Trends Pharmacol Sci* 28:236-43]. Similarly, Estrogen Related Receptors (ERRα, ERRβ and ERRγ) play significant roles in increasing energy expenditure, reducing adipogenesis and body weight gain [Ariazi E A et al 2006 *Curr Top Med Chem* 6:203-15]. Other members of the NR belonging to the Peroxisome Proliferator Activated Receptor (PPARs) and Estrogen Receptors (ERs) also play a role in maintenance of blood glucose and body fat, making the NRs an attractive target to prevent/treat obesity and metabolic diseases [Kintscher U et al 2009 *Curr Opin Investig Drugs* 10:381-7; Beekum O et al 2009 *Obesity* (Silver Spring) 17:213-9; Billin A N 2008 *Expert Opin Investig Drugs* 17:1465-71; Barros R P et al 2006 *Trends Mol Med* 12:425-31].

ER-β in some cases functions as an antagonist of ER-α through heterodimerization with ER-α. For instance, agonists of ER-β may block the proliferative influence of ER-α in tissues such as prostate and breast where ER-α is known to promote neoplasia. In addition to its anti-ER-α mediated growth inhibition, ER-β autonomously inhibits proliferation and promotes differentiation of prostate and other cancers. ER-β is also believed to antagonize the proliferative effects AR in prostatic tissues. Prostatic hypertrophy and hyperplasia/dysplasia may result from a combination of androgenic stimulation of proliferation and/or failed activation of ER-β by locally synthesized estrogens. This hypertrophy or hyperplasia/dysplasia often leads to a variety of prostatic maladies such as BPH, prostatic inflammatory atropy (a precursor to neoplasia), PIN, and CaP. Administration of exogenous ER-β agonists can be expected to provide prostatic anti-proliferation thereby being beneficial in the prevention or treatment of these prostatic diseases. Additionally, decreased side effects can be expected for ER-β selective agents compared to isoform nonselective ligands for treating many of these diseases.

Compounds that act as estrogen receptor ligands are, therefore, useful in treating a variety of conditions and disorders. Selective estrogen receptor modulators (estrogen receptor ligands, such as ERβ agonists) are disclosed, for example, in U.S. Patent Publication No. 2009/0030036.

Hormones are important regulators of adipose function and epidemiological studies suggest that estrogens regulate metabolism and fat distribution. The presence of ER-α and ER-β, the two receptors that mediate the actions of estradiol, in adipose tissue implicates a direct role of the ligands in adipose function. Moreover, the observed gender and age differences in the discovery of brown adipose tissue (BAT) in humans point towards the possibility that circulating estradiol levels may be an important contributor toward the development of BAT [Cypess A M et al. 2009 *N Engl J Med* 360:1509-17]. Studies with individual ER Knockout (KO) mice indicated the importance of these isoforms in maintaining lipid and glucose homeostasis [Harris H A 2007 *Mol Endocrinol* 21:1-13]. ER-αKO mice exhibit insulin resistance, whereas, high fat diet fed ER-βKO mice demonstrate a higher magnitude of obesity than wildtype mice [Foryst-Ludwig A et al 2008 *PLoS Genet* 4:e1000108]. Though some of these studies speculated that estrogenic control of body weight is mediated by ER-β, it is still not clear which isoform mediates the beneficial effects of estradiol on body fat, glucose and cholesterol [Pallottini V et al 2008 *Infect Disord Drug Targets* 8:52-60; Liang Y Q et al 2002 *Int J Obes Relat Metab Disord* 26:1103-9].

SUMMARY OF THE PRESENT INVENTION

In one embodiment, this invention provides a) a method of treating, delaying the onset of, reducing the incidence of, or reducing the severity of a condition associated with high fat diet consumption; b) a method of preventing a condition associated with high fat diet consumption; c) a method of treating, delaying the onset of, reducing the incidence of, or reducing the severity of a condition associated with post-menopausal obesity; d) a method of preventing a condition associated with post-menopausal obesity; e) a method of increasing energy expenditure in a subject; f) a method of increasing lean body mass; g) a method of treating, preventing delaying the onset of, reducing the incidence of, or reducing the severity of a metabolic disorder; h) a method of increasing muscle weight, comprising administering to a subject in need thereof a therapeutically effective amount of an estrogen receptor-beta ligand compound.

In one embodiment, this invention provides a) a method of treating, delaying the onset of, reducing the incidence of, or reducing the severity of a condition associated with high fat diet consumption; b) a method of preventing a condition associated with high fat diet consumption; c) a method of treating, delaying the onset of, reducing the incidence of, or reducing the severity of a condition associated with post-menopausal obesity; d) a method of preventing a condition associated with post-menopausal obesity; e) a method of increasing energy expenditure in a subject; f) a method of increasing lean body mass; g) a method of treating, preventing delaying the onset of, reducing the incidence of, or reducing the severity of a metabolic disorder; h) a method of increasing muscle weight, comprising administering to a subject in need thereof a therapeutically effective amount of a compound of this invention.

In one embodiment, this invention provides a method of treating, delaying the onset of, reducing the incidence of, or reducing the severity of a condition associated with high fat diet consumption, comprising administering to a subject in need thereof a therapeutically effective amount of an estrogen receptor ligand compound represented by the structure of Formula XI:

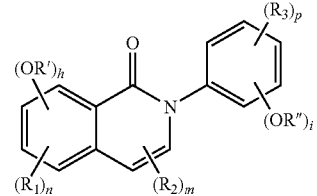

wherein $R_1$, $R_2$, $R_3$ are each, independently, hydrogen, aldehyde, COOH, —C(=NH)—OH, CHNOH, CH=CHCO$_2$H, CH=CHCO$_2$R, —CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, cycloalkyl, haloalkyl, aryl, phenyl, benzyl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered saturated or unsaturated, substituted or unsubstituted heterocyclic ring;

R is alkyl, cycloalkyl, hydrogen, haloalkyl, dihaloalkyl, trihaloalkyl, CH$_2$F, CHF$_2$, CF$_3$, CF$_2$CF$_3$, aryl, phenyl, benzyl, -Ph-CF$_3$, -Ph-CH$_2$F, -Ph-CHF$_2$, -Ph-CF$_2$CF$_3$, halogen, alkenyl, CN, NO$_2$ or OH;

R' is hydrogen, Alk or COR;

R" is hydrogen, Alk or COR;

$R_4$ and $R_5$ are independently hydrogen, phenyl, benzyl, an alkyl group of 1 to 6 carbon atoms, a 3 to 7 member cycloalkyl, heterocycloalkyl, aryl or heteroaryl group;

Z is O, NH, CH$_2$ or

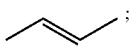

Q is SO$_3$H, CO$_2$H, CO$_2$R, NO$_2$, tetrazole, SO$_2$NH$_2$ or SO$_2$NHR;

h is 0, 1, 2 or 3;
i is 0, 1, 2, 3 or 4;
n is 1, 2, 3 or 4;
m is 1 or 2;
p is 0, 1, 2, 3, 4 or 5; and
Alk is a linear alkyl of 1-7 carbons, branched alkyl of 1-7 carbons, or cycloalkyl of 3-8 carbons;

or its isomer, pharmaceutically acceptable salt, pharmaceutical product, polymorph, crystal, N-oxide, ester, hydrate or any combination thereof.

In one embodiment this invention provides a method of preventing a condition associated with high fat diet consumption, comprising administering to a subject in need thereof a therapeutically effective amount of an estrogen receptor ligand compound represented by the structure of Formula XI as described herein above or its isomer, pharmaceutically acceptable salt, pharmaceutical product, polymorph, crystal, N-oxide, ester, hydrate or any combination thereof.

In one embodiment this invention provides a method of treating, delaying the onset of, reducing the incidence of, or reducing the severity of a condition associated with post-menopausal obesity, comprising administering to a subject in need thereof a therapeutically effective amount of an estrogen receptor ligand compound represented by the structure of Formula XI as described herein above or its isomer, pharmaceutically acceptable salt, pharmaceutical product, polymorph, crystal, N-oxide, ester, hydrate or any combination thereof.

In one embodiment this invention provides a method of preventing a condition associated with post-menopausal obesity, comprising administering to a subject in need thereof a therapeutically effective amount of an estrogen receptor ligand compound represented by the structure of Formula XI as described herein above or its isomer, pharmaceutically acceptable salt, pharmaceutical product, polymorph, crystal, N-oxide, ester, hydrate or any combination thereof.

In one embodiment this invention provides a method of increasing energy expenditure in a subject, comprising administering to a subject in need thereof a therapeutically effective amount of a compound of Formula XI as described herein above or its isomer, pharmaceutically acceptable salt, pharmaceutical product, polymorph, crystal, N-oxide, ester, hydrate or any combination thereof.

In one embodiment this invention provides a method of increasing lean body mass, comprising administering to a subject in need thereof a therapeutically effective amount of a compound of Formula XI as described herein above or its isomer, pharmaceutically acceptable salt, pharmaceutical product, polymorph, crystal, N-oxide, ester, hydrate or any combination thereof.

In one embodiment this invention provides a method of treating, preventing delaying the onset of, reducing the incidence of, or reducing the severity of a metabolic disorder comprising administering to a subject in need thereof a therapeutically effective amount of an estrogen receptor ligand compound represented by the structure of Formula XI as described herein above or its isomer, pharmaceutically acceptable salt, pharmaceutical product, polymorph, crystal, N-oxide, ester, hydrate or any combination thereof.

In one embodiment, this invention provides a method of increasing muscle weight comprising administering to a subject in need thereof a therapeutically effective amount of a compound of Formula XI as described herein above or its isomer, pharmaceutically acceptable salt, pharmaceutical product, polymorph, crystal, N-oxide, ester, hydrate or any combination thereof In one embodiment this invention provides a selective estrogen receptor ligand compound, wherein said compound is 4-cyano-6,8-dihydroxy-2-(4-hydroxyphenyl)isoquinolin-1(2H)-one or its isomer, pharmaceutically acceptable salt, pharmaceutical product, polymorph, crystal, N-oxide, ester, hydrate or any combination thereof.

DETAILED DESCRIPTION OF THE PRESENT INVENTION

Figure 1:
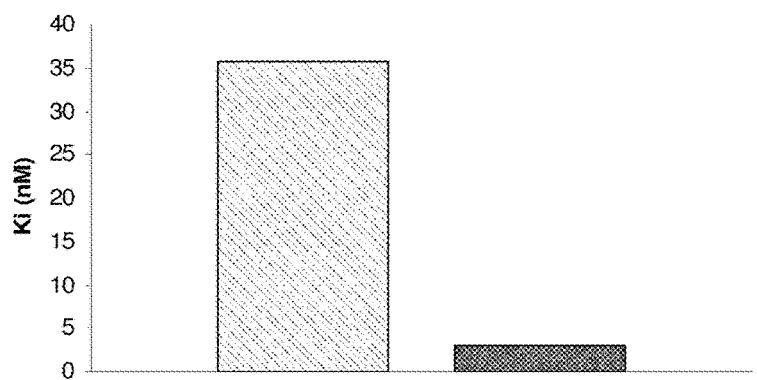
FIG. 1 depicts binding constants of 12b (A), 12f (B), 12h (C), 12p (D), 12s (E), 12u (F), 12y (G), 12z (H), and estradiol (last pane) (I) to ER-α (dashed) and ER-β (filled).
Figure 1:
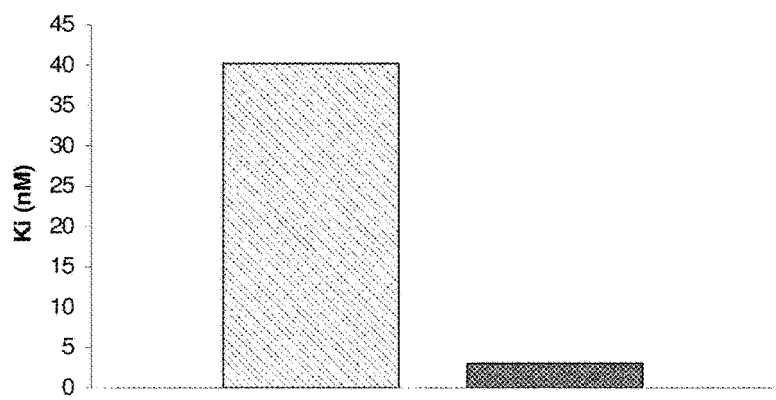
Figure 1:
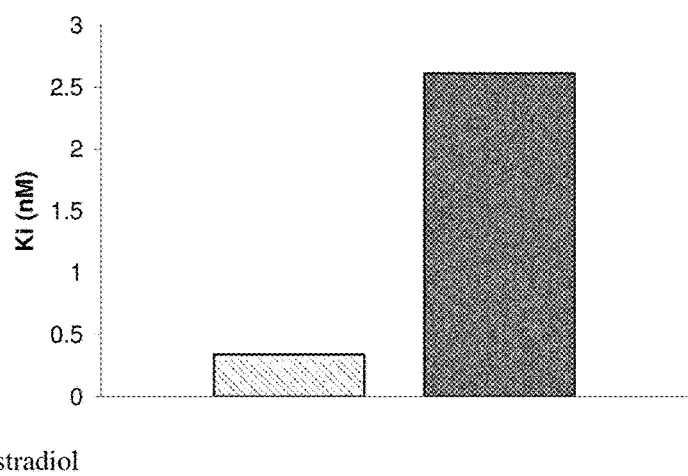

In one embodiment, a NRBA refers to a compound that affects estrogen receptor activity. In one embodiment, a NRBA exhibits activity as an agonist, or, in another embodiment, as an antagonist, or in another embodiment, as a partial agonist, or in another embodiment, as a partial antagonist of the estrogen receptor.

In some embodiments the NRBAs are estrogen receptor ligand compounds. In one embodiment, the estrogen receptor ligand compound is a selective estrogen receptor modulator (SERM). In one embodiment, the estrogen receptor ligand compound is a selective estrogen receptor β modulator (β-SERM or ER-β SERM or ER-β selective SERM). In one embodiment, the estrogen receptor ligand compound is an estrogen receptor agonist. In one embodiment, the estrogen receptor ligand compound is an estrogen receptor β (ER-β) agonist. In one embodiment, the estrogen receptor ligand compound is an estrogen receptor β (ER-β) antagonist.

In one embodiment the estrogen receptor ligand compound is selective to ER-β. In one embodiment the estrogen receptor ligand compound does not cross react with ER-α. In one embodiment the estrogen receptor ligand compound does not cross react with ER-α up to concentration of 10 μM. In one embodiment the estrogen receptor ligand compound does not cross react with ER-α up to concentration of 1 μM. In one embodiment the estrogen receptor ligand compound is bound to ER-β with at least 5 fold selectivity compared to ER-α. In one embodiment the estrogen receptor ligand compound is bound to ER-β with at least 10 fold selectivity compared to ER-α. In one embodiment the estrogen receptor ligand compound is bound to ER-β with at least 50 fold selectivity compared to ER-α. In one embodiment the estrogen receptor ligand compound is bound to ER-β with almost 100 fold selectivity compared to ER-α. In one embodiment the estrogen receptor ligand compound is β-SERM agonist.

In one embodiment the estrogen receptor ligand compound functions as agonist to ER-β. In one embodiment the estrogen receptor ligand compound functions as antagonist to ER-β. In one embodiment the estrogen receptor ligand compound functions as agonist to ER-α. In one embodiment the estrogen receptor ligand compound functions as antagonist to ER-α. In one embodiment the estrogen receptor ligand compound functions as agonist to both ER-β and ER-α. In one embodiment the estrogen receptor ligand compound functions as agonist to both ER-β and ER-α with a selectivity of at least 5 fold towards ER-β. In one embodiment the estrogen receptor ligand compound functions as agonist to both ER-β and ER-α with a selectivity of at least 10 fold towards ER-3. In one embodiment the estrogen receptor ligand compound functions as agonist to both ER-β and ER-α with a selectivity of 20-30 fold towards ER-β and with $EC_{50}$ of less than 10 nM.

In one embodiment, the NRBA exerts its effects on the estrogen receptor (e.g., ER-α, ER-β or ERRs) in a tissue-dependent manner. In some embodiments, the NRBA of this invention can act as estrogen receptor agonists in some tissues (e.g., bone, brain, and/or heart) and as antagonists in other tissue types, for example in the breast and/or uterine lining.

In one embodiment, a NRBA of this invention will have an $IC_{50}$ or $EC_{50}$ with respect to ERα and/or ERβ of up to about 10 μM as determined using the ERα and/or ERβ transactivation assays, as known in the art, or, in other embodiments, as described herein. In some embodiments, the NRBA exhibit $EC_{50}$ or $IC_{50}$ values (as agonists or antagonists, respectively) of about 5 μM, or less than about 5 μM. Representative compounds of the present invention have been discovered to exhibit agonist or antagonist activity with respect to the estrogen receptor. Compounds of the present invention exhibit, in some embodiments, an antagonist or agonist $IC_{50}$ or $EC_{50}$ with respect to ERα and/or ERβ of about 5 μM or less than about 5 μM, or in some embodiments, up to about 500 nM, or in other embodiments, up to about 50 nM, or in other embodiments, up to about 10 nM, or in other embodiments, up to about 1 nM, as measured in ERα and/or ERβ transactivation assays.

The term "$IC_{50}$" refers, in some embodiments, to a concentration of the NRBA which reduces the activity of a target (e.g., ERα or ERβ) to half-maximal level.

The term "$EC_{50}$" refers, in some embodiments, to a concentration of the NRBA that produces a half-maximal effect.

In some embodiments of this invention, the compounds of this invention are bisphenolic agents. In some embodiments of this invention, the compounds of this invention are mono- or nonphenolic agents. In some embodiments of this invention, the compounds of this invention are substituted isoquinolines. In some embodiments of this invention, the compounds of this invention are substituted isoquinolinones. In some embodiments of this invention, the compounds of this invention are substituted dihydroisoquinolinones. In some embodiments of this invention, the NRBAs have selectivity for ER-β. In some embodiment of this invention, the NRBAs are agonists of ER-β. In some embodiment of this invention, the NRBAs are partial agonists of ER-β. In some embodiment of this invention, the NRBAs are antagonists of ER-β.

In some embodiments of this invention, the NRBAs have anti-oxidant activity. In some embodiments, the antioxidant activity is independent of the nuclear receptor binding activity. In some embodiments, the NRBAs of this invention exhibit non-genomic signaling in cells. In some embodiments, the NRBAs of this invention exhibit mitochondrial signaling.

In one embodiment, the present invention provides a NRBA or its prodrug, analog, isomer, metabolite, derivative, pharmaceutically acceptable salt, pharmaceutical product, polymorph, crystal, impurity, N-oxide, ester, hydrate or any combination thereof, represented by the structure of Formula I:

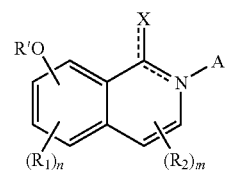

wherein

A is a 5-14 membered saturated or unsaturated, substituted or unsubstituted carbocyclic or heterocyclic ring which is optionally a fused ring system, or a combination thereof; wherein the saturated or unsaturated carbocyclic or heterocyclic rings are optionally substituted by 1 to 5 substituents independently selected from $R_3$ or OR"; and X is O or S; or A is nothing, N forms a double bond with the cyclic carbon and X is OH or $OCH_2CH_2$-heterocycle in which the heterocycle is a 3-7 membered saturated or unsaturated substituted or unsubstituted heterocyclic ring;

$R_1$, $R_2$ and $R_3$ are independently hydrogen, aldehyde, COOH, —C(=NH)—OH, CHNOH, CH=CHCO$_2$H, CH=CHCO$_2$R, —CH=CH$_2$, hydroxyalkyl, halogen, hydroxyl, alkoxy, cyano, nitro, CF$_3$, NH$_2$, 4-Ph-OMe, 4-Ph-OH SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$. Z-Alk-heterocycle or OCH$_2$CH$_2$-heterocycle, in which the heterocycle is a 3-7 membered saturated or unsaturated, substituted or unsubstituted heterocyclic ring;

R is alkyl, hydrogen, haloalkyl, dihaloalkyl, trihaloalkyl, $CH_2F$, $CHF_2$, $CF_3$, $CF_2CF_3$, aryl, heteroaryl, phenyl, benzyl, -Ph-$CF_3$, -Ph-$CH_2F$, -Ph-$CHF_2$, -Ph-$CF_2CF_3$, halogen, alkenyl, CN, $NO_2$, or OH;

R' is hydrogen, Alk, or COR;

R" is hydrogen, Alk, or COR;

$R_4$ and $R_5$ are independently hydrogen, phenyl, benzyl, an alkyl group of 1 to 6 carbon atoms, a 3 to 7 member cycloalkyl, heterocycloalkyl, aryl or heteroaryl group;

Z is O, NH, $CH_2$ or

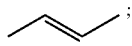

Q is $SO_3H$, $CO_2H$, $CO_2R$, $NO_2$, tetrazole, $SO_2NH_2$ or $SO_2NHR$;

n is an integer of between 1-3;

m is an integer between 1-2; and

Alk is a linear alkyl of 1-7 carbons, branched alkyl of 1-7 carbons, or cyclic alkyl of 3-8 carbons.

In some embodiments the NRBA of Formula I is an estrogen receptor ligand compound. In one embodiment, the estrogen receptor ligand compound is a selective estrogen receptor modulator (SERM). In one embodiment, the estrogen receptor ligand compound is a selective estrogen receptor modulator (β-SERM). In one embodiment, the estrogen receptor ligand compound is an estrogen receptor agonist. In one embodiment, the estrogen receptor ligand compound is an estrogen receptor β (ERβ) agonist. In one embodiment, the estrogen receptor ligand compound is an estrogen receptor β (ERβ) antagonist.

In one embodiment, the NRBA is represented by the structure of Formula I:

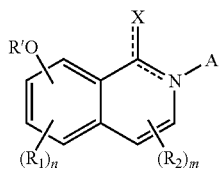

I wherein A, X, $R_1$, $R_2$, R', n and m are as described above, wherein if X is oxo and A is phenyl, then A is not substituted with:

NHCOR and halogen without further substitution, or

NHCOR and an alkyl without further substitution.

In one embodiment, A is

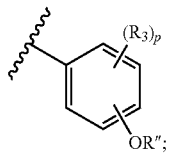

p is an integer between 1-4; R" is hydrogen, Alk, or COR; $R_3$ is hydrogen, aldehyde, COOH, C(=N)—OH, CHNOH, CH=$CHCO_2H$, —CH=$CH_2$, hydroxyalkyl, halogen, hydroxyl, alkoxy, cyano, nitro, $CF_3$, $NH_2$, 4-Ph-OMe, 4-Ph-OH, SH, COR, COOR, OCOR, alkenyl, allyl, 2-methylallyl, alkynyl, propargyl, $OSO_2CF_3$, $OSO_2CH_3$, NHR, NHCOR, $N(R)_2$, sulfonamide, $SO_2R$, alkyl, haloalkyl, aryl, phenyl, benzyl, protected hydroxyl, $OCH_2CH_2NR_4R_5$, Z-Alk-Q, Z-Alk-$NR_4R_5$, Z-Alk-heterocycle or $OCH_2CH_2$-heterocycle, in which the heterocycle is a 3-7 membered saturated or unsaturated, substituted or unsubstituted heterocyclic ring.

In one embodiment of the compound of Formula I, A is nothing, N forms a double bond with the cyclic carbon and X is $OCH_2CH_2$-heterocycle in which the heterocycle is a 3-7 membered heterocycloalkyl. In one embodiment, when X is $OCH_2CH_2$-heterocycle, the heterocycle is substituted or unsubstituted piperidine, pyrrolidine, morpholine or piperazine. In another embodiment, when $R_1$, $R_2$, $R_3$ are independently Z-Alk-heterocycle or, in another embodiment, $OCH_2CH_2$-heterocycle, either heterocycle may be substituted or unsubstituted piperidine, pyrrolidine, morpholine or piperazine. In another embodiment, when $R_4$ and $R_5$ are independently a 3 to 7 membered heterocycloalkyl, either heterocycle may be substituted or unsubstituted piperidine, pyrrolidine, morpholine or piperazine. In another embodiment, any heterocycle is optionally substituted by one or more substituents comprising halogen, cyano, nitro, COOH, COOR, NHCOR, hydroxyl, amine, alkyl, cycloalkyl, heterocycloalkyl, alkenyl, alkynyl, alkanoyl, alkylthio, alkylamino, N,N dialkylamino, aminoalkyl, haloalkyl, aryl, heteroaryl, alkoxy or haloalkoxy, wherein R is as defined for Formula I.

In another embodiment of the compound of Formula I, $R_2$ is a halogen. In another embodiment $R_2$ is a bromide. In another embodiment $R_2$ is a chloride. In another embodiment $R_2$ is a fluoride. In another embodiment $R_2$ is an iodide. In another embodiment $R_2$ is hydrogen. In another embodiment $R_2$ is a cyano. In another embodiment, $R_2$ is a phenyl. In another embodiment, $R_2$ is —CH=CH. In another embodiment, $R_2$ is —CH=CH—$CH_3$. In another embodiment, $R_2$ is —CH=CH—COOEt. In another embodiment $R_1$ is a hydroxyl group. In another embodiment $R_1$ is O—(CO)-Ph-$CF_3$. In another embodiment $R_1$ is COOH. In another embodiment $R_1$ is COOMe. In another embodiment $R_1$ is hydrogen. In another embodiment $R_1$ is a hydroxyl group and n is 1. In another embodiment $R_1$ is in position 8 of the isoquinolinone group. In another embodiment $R_3$ is halogen. In another embodiment $R_3$ is fluoride. In another embodiment $R_3$ is chloride. In another embodiment $R_3$ is bromide. In another embodiment $R_3$ is iodide. In another embodiment $R_3$ is hydrogen. In another embodiment R' is H. In another embodiment R' is a methyl group. In another embodiment R' is a COMe group. In another embodiment R" is H. In another embodiment R" is a methyl group. In another embodiment R" is a COMe group.

In another embodiment this invention provides a NRBA or its prodrug, analog, isomer, metabolite, derivative, pharmaceutically acceptable salt, pharmaceutical product, polymorph, crystal, impurity, N-oxide, ester, hydrate or any combination thereof, represented by the structure of Formula II:

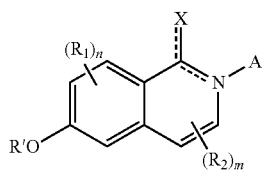

II wherein

A is a 5-14 membered saturated or unsaturated, substituted or unsubstituted carbocyclic or heterocyclic ring which is optionally a fused ring system, or a combination thereof; wherein the saturated or unsaturated carbocyclic or heterocyclic ring are optionally substituted by 1 to 5 substituents independently selected from $R_3$ or OR"; and X is O or S; or A is nothing, N forms a double bond with the cyclic carbon and X is OH or $OCH_2CH_2$-heterocycle in which the heterocycle is a 3-7 membered saturated or unsaturated, substituted or unsubstituted heterocyclic ring;

$R_1$, $R_2$, $R_3$ are independently hydrogen, aldehyde, COOH, —C(=NH)—OH, CHNOH, CH=CHCO$_2$H, CH=CHCO$_2$R, —CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered saturated or unsaturated, substituted or unsubstituted heterocyclic ring;

R is alkyl, hydrogen, haloalkyl, dihaloalkyl, trihaloalkyl, CH$_2$F, CHF$_2$, CF$_3$, CF$_2$CF$_3$, aryl, phenyl, benzyl, -Ph-CF$_3$, -Ph-CH$_2$F, -Ph-CHF$_2$, -Ph-CF$_2$CF$_3$, halogen, alkenyl, CN, NO$_2$ or OH;

R' is hydrogen, Alk or COR;

R" is hydrogen, Alk or COR;

$R_4$ and $R_5$ are independently hydrogen, phenyl, benzyl, an alkyl group of 1 to 6 carbon atoms, a 3 to 7 member cycloalkyl, heterocycloalkyl, aryl or heteroaryl group;

Z is O, NH, CH$_2$ or

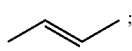

Q is SO$_3$H, CO$_2$H, CO$_2$R, NO$_2$, tetrazole, SO$_2$NH$_2$ or SO$_2$NHR;

n is an integer between 1-3;

m is an integer between 1-2;

p is an integer between 1-4; and

Alk is a linear alkyl of 1-7 carbons, branched alkyl of 1-7 carbons, or cyclic alkyl of 3-8 carbons.

In some embodiments the NRBA of Formula II is an estrogen receptor ligand compound. In one embodiment, the estrogen receptor ligand compound is a selective estrogen receptor modulator (SERM). In one embodiment, the estrogen receptor ligand compound is a selective estrogen receptor β modulator (β-SERM). In one embodiment, the estrogen receptor ligand compound is an estrogen receptor agonist. In one embodiment, the estrogen receptor ligand compound is an estrogen receptor β (ERβ) agonist. In one embodiment, the estrogen receptor ligand compound is an estrogen receptor β (ERβ) antagonist.

In another embodiment this invention provides a NRBA or its prodrug, analog, isomer, metabolite, derivative, pharmaceutically acceptable salt, pharmaceutical product, polymorph, crystal, impurity, N-oxide, ester, hydrate or any combination thereof, represented by the structure of Formula II:

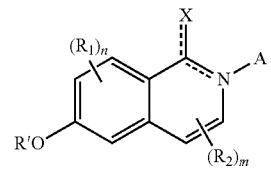

II

A, X, $R_1$, $R_2$, R', n and m are as described above, wherein if X is oxo and A is phenyl, then A is not substituted with:
NHCOR and halogen without further substitution, or
NHCOR and an alkyl without further substitution.

In one embodiment, A is

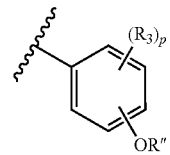

wherein p is an integer between 1-4; R" is hydrogen, Alk, or COR; $R_3$ is hydrogen, aldehyde, COOH, C(=N)—OH, CHNOH, CH=CHCO$_2$H, —CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$. Z-Alk-heterocycle or OCH$_2$CH$_2$-heterocycle, in which the heterocycle is a 3-7 membered saturated or unsaturated, substituted or unsubstituted heterocyclic ring;

In one embodiment of the compound of Formula II, A is nothing, N forms a double bond with the cyclic carbon and X is OCH$_2$CH$_2$-heterocycle, in which the heterocycle is a 3-7 membered heterocycloalkyl. In one embodiment, when X is OCH$_2$CH$_2$-heterocycle, the heterocycle is substituted or unsubstituted piperidine, pyrrolidine, morpholine or piperazine. In another embodiment, when $R_1$, $R_2$, $R_3$ are independently Z-Alk-heterocycle or, in another embodiment, OCH$_2$CH$_2$-heterocycle, either heterocycle may be substituted or unsubstituted piperidine, pyrrolidine, morpholine or piperazine. In another embodiment, when $R_4$ and $R_5$ are independently a 3 to 7 membered heterocycloalkyl, either heterocycle may be substituted or unsubstituted piperidine, pyrrolidine, morpholine or piperazine. In another embodiment, any heterocycle is optionally substituted by one or more substituents comprising halogen, cyano, nitro, COOH, COOR, NHCOR, hydroxyl, amine, alkyl, cycloalkyl, heterocycloalkyl, alkenyl, alkynyl, alkanoyl, alkylthio, alkylamino, N,N dialkylamino, aminoalkyl, haloalkyl, aryl, heteroaryl, alkoxy or haloalkoxy, wherein R is as defined for Formula II.

In another embodiment of the compound of Formula II, $R_2$ is a halogen. In another embodiment $R_2$ is a bromide. In another embodiment $R_2$ is a chloride. In another embodiment $R_2$ is a fluoride. In another embodiment $R_2$ is an iodide. In another embodiment $R_2$ is hydrogen. In another embodiment $R_2$ is a cyano. In another embodiment $R_2$ is a phenyl. In another embodiment, $R_2$ is —CH=CH—CH$_3$. In another embodiment, $R_2$ is —CH=CH$_2$. In another embodiment, $R_2$ is —CH=CH—COOEt. In another embodiment $R_1$ is O—(CO)-Ph-CF$_3$. In another embodiment $R_1$ is COOH. In another embodiment $R_1$ is COOMe. In another embodiment $R_1$ is a hydroxyl group. In another embodiment $R_1$ is hydrogen. In another embodiment $R_1$ is a hydroxyl group and n is 1. In another embodiment $R_1$ is in position 8 of the isoquinolinone group. In another embodiment $R_3$ is halogen. In another embodiment $R_3$ is fluoride. In another embodiment $R_3$ is chloride. In another embodiment $R_3$ is bromide. In another embodiment $R_3$ is iodide. In another embodiment $R_3$ is hydrogen. In another embodiment R' is H. In another embodiment R' is a methyl group. In another embodiment R' is a COMe group. In another embodiment R" is H. In another embodiment R" is a methyl group. In another embodiment R" is a COMe group.

In another embodiment this invention provides a NRBA or its prodrug, analog, isomer, metabolite, derivative, pharmaceutically acceptable salt, pharmaceutical product, polymorph, crystal, impurity, N-oxide, ester, hydrate or any combination thereof, represented by the structure of Formula III:

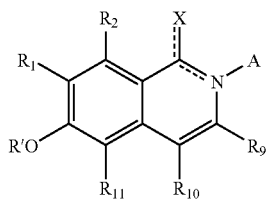

III wherein

A is a 5-14 membered saturated or unsaturated, substituted or unsubstituted carbocyclic or heterocyclic ring which is optionally a fused ring system, or a combination thereof; wherein the saturated or unsaturated carbocyclic or heterocyclic ring are optionally substituted by 1 to 5 substituents independently selected from $R_3$ or OR"; and X is O or S; or A is nothing and N forms a double bond with the cyclic carbon and X is OH or OCH$_2$CH$_2$-heterocycle in which the heterocycle is a 3-7 membered saturated or unsaturated, substituted or unsubstituted heterocyclic ring;

$R_1$, $R_2$, $R_3$, $R_9$, $R_{10}$, $R_{11}$ are independently selected from hydrogen, aldehyde, COOH, —C(=NH)—OH, CHNOH, CH=CHCO$_2$H, CH=CHCO$_2$R, —CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-NR$_4$R$_5$, Z-Alk-heterocycle or OCH$_2$CH$_2$-heterocycle in which the heterocycle is a 3-7 membered saturated or unsaturated, substituted or unsubstituted heterocyclic ring;

R is alkyl, hydrogen, haloalkyl, dihaloalkyl, trihaloalkyl, CH$_2$F, CHF$_2$, CF$_3$, CF$_2$CF$_3$, aryl, phenyl, benzyl, -Ph-CF$_3$, -Ph-CH$_2$F, -Ph-CHF$_2$, -Ph-CF$_2$CF$_3$, halogen, alkenyl, CN, NO$_2$, or OH;

R' is hydrogen, Alk, or COR;

R" is hydrogen, Alk, or COR $R_4$ and $R_5$ are independently hydrogen, phenyl, benzyl, an alkyl group of 1 to 6 carbon atoms, a 3 to 7 member cycloalkyl, heterocycloalkyl, aryl or heteroaryl group;

Z is O, NH, CH$_2$, or

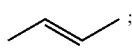

Q is SO$_3$H, CO$_2$H, CO$_2$R, NO$_2$, tetrazole, SO$_2$NH$_2$, or SO$_2$NHR; and Alk is a linear alkyl of 1-7 carbons, branched alkyl of 1-7 carbons, or cyclic alkyl of 3-8 carbons;

wherein if A is a phenyl, X is an oxo group and $R_{10}$ is a benzene ring, then:

$R_9$ is not COOR, if R is a hydrogen or an ester; or $R_9$ is not CONR$_4$R$_5$, if $R_4$ and $R_5$ are as described above.

In some embodiments the NRBA of Formula III is an estrogen receptor ligand compound. In one embodiment, the estrogen receptor ligand compound is a selective estrogen receptor modulator (SERM). In one embodiment, the estrogen receptor ligand compound is a selective estrogen receptor β modulator (β-SERM). In one embodiment, the estrogen receptor ligand compound is an estrogen receptor agonist. In one embodiment, the estrogen receptor ligand compound is an estrogen receptor β (ERβ) agonist. In one embodiment, the estrogen receptor ligand compound is an estrogen receptor β (ERβ) antagonist.

In another embodiment this invention provides a NRBA or its prodrug, analog, isomer, metabolite, derivative, pharmaceutically acceptable salt, pharmaceutical product, polymorph, crystal, impurity, N-oxide, ester, hydrate or any combination thereof, represented by the structure of Formula III:

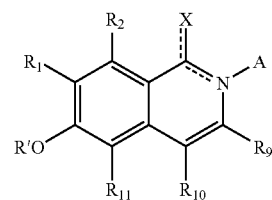

III

A, X, $R_1$, $R_2$, $R_9$, $R_{10}$, $R_{11}$ and R' are as described above, wherein if X is oxo and A is phenyl, then A is not substituted with:

NHCOR and halogen without further substitution; or

NHCOR and an alkyl without further substitution.

In one embodiment, A is

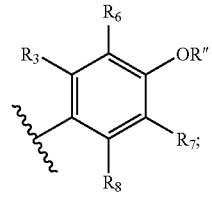

$R_3$, $R_6$, $R_7$, $R_8$, are independently selected from hydrogen, aldehyde, COOH, —C(=NH)—OH CHNOH, CH=CHCO$_2$H, CH=CHCO$_2$R—CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered saturated or unsaturated, substituted or unsubstituted heterocyclic ring; R" is hydrogen, Alk, or COR;

In another embodiment, if A is

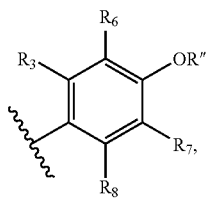

X is an oxo group and $R_{10}$ is a benzene ring, then $R_9$ is not COOR, if R is an ester residue or $CONR_4R_5$. In one embodiment of the compound of Formula III, A is nothing, N forms a double bond with the cyclic carbon and X is $OCH_2CH_2$-heterocycle in which the heterocycle is a 3-7 membered heterocycloalkyl. In one embodiment, when X is $OCH_2CH_2$-heterocycle, the heterocycle is substituted or unsubstituted piperidine, pyrrolidine, morpholine or piperazine. In another embodiment, when $R_1$, $R_2$, $R_3$ are independently Z-Alk-heterocycle or, in another embodiment, $OCH_2CH_2$-heterocycle, either heterocycle may be substituted or unsubstituted piperidine, pyrrolidine, morpholine or piperazine. In another embodiment, when $R_4$ and $R_5$ are independently a 3 to 7 membered heterocycloalkyl, either heterocycle may be substituted or unsubstituted piperidine, pyrrolidine, morpholine or piperazine. In another embodiment, any heterocycle is optionally substituted by one or more substituents comprising halogen, cyano, nitro, COOH, COOR, NHCOR, hydroxyl, amine, alkyl, cycloalkyl, heterocycloalkyl, alkenyl, alkynyl, alkanoyl, alkylthio, alkylamino, N,N dialkylamino, aminoalkyl, haloalkyl, aryl, heteroaryl, alkoxy or haloalkoxy, wherein R is as defined for Formula III.

In another embodiment of the compound of Formula III, $R_{10}$ is a halogen. In another embodiment $R_{10}$ is a bromide. In another embodiment $R_{10}$ is a chloride. In another embodiment $R_{10}$ is a fluoride. In another embodiment $R_{10}$ is an iodide. In another embodiment $R_{10}$ is hydrogen. In another embodiment $R_{10}$ is a cyano. In another embodiment, $R_{10}$ is a phenyl. In another embodiment, $R_{10}$ is —CH=CH—$CH_3$. In another embodiment, $R_{10}$ is —CH=$CH_2$. In another embodiment, $R_{10}$ is —CH=CH—COOEt. In another embodiment $R_2$ is a hydroxyl group. In another embodiment $R_2$ is hydrogen. In another embodiment $R_2$ is O—(CO)-Ph-$CF_3$. In another embodiment $R_2$ is COOH. In another embodiment $R_2$ is COOMe. In another embodiment $R_7$ is a halogen. In another embodiment $R_7$ is fluoride. In another embodiment $R_7$ is chloride. In another embodiment $R_7$ is bromide. In another embodiment $R_7$ is iodide. In another embodiment $R_3$, $R_6$, $R_7$ and $R_8$ are hydrogens. In another embodiment R' is H. In another embodiment R' is a methyl group. In another embodiment R is a COMe. In another embodiment R" is H. In another embodiment R" is a methyl group. In another embodiment R" is COMe. In another embodiment $R_1$, $R_3$, $R_6$, $R_7$, $R_8$, $R_9$ and $R_{11}$ are hydrogens.

In one embodiment, the compound of Formula I may be represented by the structure of Formula IV:

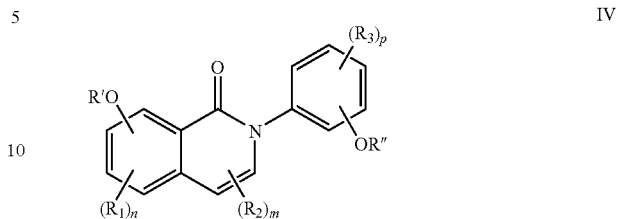

IV wherein
$R_1$, $R_2$, $R_3$ are independently hydrogen, aldehyde, COOH, —C(=NH)—OH, CHNOH, CH=$CHCO_2H$, CH=$CHCO_2R$, —CH=$CH_2$, hydroxyalkyl, halogen, hydroxyl, alkoxy, cyano, nitro, $CF_3$, $NH_2$, 4-Ph-OMe, 4-Ph-OH, SH, COR, COOR, OCOR, alkenyl, allyl, 2-methylallyl, alkynyl, propargyl, $OSO_2CF_3$, $OSO_2CH_3$, NHR, NHCOR, $N(R)_2$, sulfonamide, $SO_2R$, alkyl, haloalkyl, aryl, phenyl, benzyl, protected hydroxyl, $OCH_2CH_2NR_4R_5$, Z-Alk-Q, Z-Alk-$NR_4R_5$, Z-Alk-heterocycle or $OCH_2CH_2$-heterocycle in which the heterocycle is a 3-7 membered saturated or unsaturated, substituted or unsubstituted heterocyclic ring;
R is alkyl, hydrogen, haloalkyl, dihaloalkyl, trihaloalkyl, $CH_2F$, $CHF_2$, $CF_3$, $CF_2CF_3$, aryl, phenyl, benzyl, -Ph-$CF_3$, -Ph-$CH_2F$, -Ph-$CHF_2$, -Ph-$CF_2CF_3$, halogen, alkenyl, CN, $NO_2$ or OH;
R' is hydrogen, Alk or COR;
R" is hydrogen, Alk or COR;
$R_4$ and $R_5$ are independently hydrogen, phenyl, benzyl, an alkyl group of 1 to 6 carbon atoms, a 3 to 7 member cycloalkyl heterocycloalkyl, aryl or heteroaryl group;
Z is O, NH, $CH_2$ or

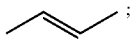;

Q is $SO_3H$, $CO_2H$, $CO_2R$, $NO_2$, tetrazole, $SO_2NH_2$ or $SO_2NHR$;
n is an integer between 1-3;
m is an integer between 1-2;
p is an integer between 1-4; and
Alk is a linear alkyl of 1-7 carbons, branched alkyl of 1-7 carbons, or cyclic alkyl of 3-8 carbons.

In some embodiments the NRBA of Formula IV is an estrogen receptor ligand compound. In one embodiment, the estrogen receptor ligand compound is a selective estrogen receptor modulator (SERM). In one embodiment, the estrogen receptor ligand compound is a selective estrogen receptor β modulator (β-SERM). In one embodiment, the estrogen receptor ligand compound is an estrogen receptor agonist. In one embodiment, the estrogen receptor ligand compound is an estrogen receptor β (ERβ) agonist. In one embodiment, the estrogen receptor ligand compound is an estrogen receptor β (ERβ) antagonist.

In another embodiment of the compound of Formula IV, $R_2$ is a halogen. In another embodiment $R_2$ is a bromide. In another embodiment $R_2$ is a chloride. In another embodiment $R_2$ is a fluoride. In another embodiment $R_2$ is an iodide. In another embodiment $R_2$ is hydrogen. In another embodiment $R_2$ is a cyano. In another embodiment, $R_2$ is a phenyl. In another embodiment, $R_2$ is —CH=CH—$CH_3$. In another embodiment, $R_2$ is —CH=$CH_2$. In another embodiment, $R_2$ is —CH═CH—COOEt. In another embodiment $R_1$ is O—(CO)-Ph-$CF_3$. In another embodiment $R_1$ is COOH. In another embodiment $R_1$ is COOMe. In another embodiment $R_1$ is a hydroxyl group. In another embodiment $R_1$ is hydrogen. In another embodiment $R_3$ is halogen. In another embodiment $R_3$ is fluoride. In another embodiment $R_3$ is chloride. In another embodiment $R_3$ is bromide. In another embodiment $R_3$ is iodide. In another embodiment $R_3$ is hydrogen. In another embodiment R' is H. In another embodiment R' is a methyl group. In another embodiment R' is COMe. In another embodiment R" is H. In another embodiment R" is a methyl group. In another embodiment R" is COMe. In another embodiment, when $R_1$, $R_2$, $R_3$ are independently Z-Alk-heterocycle or, in another embodiment, $OCH_2CH_2$-heterocycle, either heterocycle may be substituted or unsubstituted piperidine, pyrrolidine, morpholine or piperazine. In another embodiment, when $R_4$ and $R_5$ are independently a 3 to 7 membered heterocycloalkyl, either heterocycle may be substituted or unsubstituted piperidine, pyrrolidine, morpholine or piperazine. In another embodiment, the heterocycles are optionally substituted by one or more substituents comprising halogen, cyano, nitro, COOH, COOR, NHCOR, hydroxyl, amine, alkyl, cycloalkyl, heterocycloalkyl, alkenyl, alkynyl, alkanoyl, alkylthio, alkylamino, N,N dialkylamino, aminoalkyl, haloalkyl, aryl, heteroaryl, alkoxy or haloalkoxy, wherein R is as defined for Formula IV.

In another embodiment, the compound of formula II may be represented by the structure of Formula V:

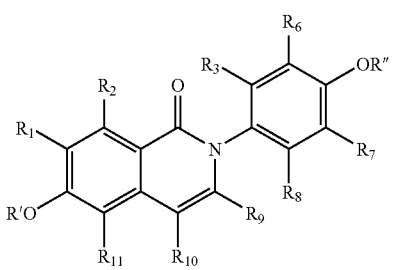

wherein $R_1$, $R_2$, $R_3$ are independently hydrogen, aldehyde, COOH, —C(═NH)—OH, CHNOH, CH═CHCO_2H, CH═CHCO_2R, —CH═CH_2, hydroxyalkyl, halogen, hydroxyl, alkoxy, cyano, nitro, $CF_3$, $NH_2$, 4-Ph-OMe, 4-Ph-OH, SH, COR, COOR, OCOR, alkenyl, allyl, 2-methylallyl, alkynyl, propargyl, $OSO_2CF_3$, $OSO_2CH_3$, NHR, NHCOR, $N(R)_2$, sulfonamide, $SO_2R$, alkyl, haloalkyl, aryl, phenyl, benzyl, protected hydroxyl, $OCH_2CH_2NR_4R_5$, Z-Alk-Q, Z-Alk-$NR_4R_5$, Z-Alk-heterocycle or $OCH_2CH_2$-heterocycle in which the heterocycle is a 3-7 membered saturated or unsaturated, substituted or unsubstituted heterocyclic ring; R is alkyl, hydrogen, haloalkyl, dihaloalkyl, trihaloalkyl, $CH_2F$, $CHF_2$, $CF_3$, $CF_2CF_3$, aryl, phenyl, benzyl, -Ph-$CF_3$, -Ph-$CH_2F$, -Ph-$CHF_2$, -Ph-$CF_2CF_3$, halogen, alkenyl, CN, $NO_2$ or OH;

R' is hydrogen, Alk or COR;
R" is hydrogen, Alk or COR;
$R_4$ and $R_5$ are independently hydrogen, phenyl, benzyl, an alkyl group of 1 to 6 carbon atoms, a 3 to 7 member cycloalkyl, heterocycloalkyl, aryl or heteroaryl group;
Z is O, NH, $CH_2$ or

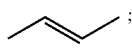;

Q is $SO_3H$, $CO_2H$, $CO_2R$, $NO_2$, tetrazole, $SO_2NH_2$ or $SO_2NHR$;
n is an integer between 1-3;
m is an integer between 1-2;
p is an integer between 1-4; and
Alk is a linear alkyl of 1-7 carbons, branched alkyl of 1-7 carbons or cyclic alkyl of 3-8 carbons.

In some embodiments the NRBA of Formula V is an estrogen receptor ligand compound. In one embodiment, the estrogen receptor ligand compound is a selective estrogen receptor modulator (SERM). In one embodiment, the estrogen receptor ligand compound is a selective estrogen receptor modulator (β-SERM). In one embodiment, the estrogen receptor ligand compound is an estrogen receptor agonist. In one embodiment, the estrogen receptor ligand compound is an estrogen receptor β (ERβ) agonist. In one embodiment, the estrogen receptor ligand compound is an estrogen receptor (ERβ) antagonist.

In another embodiment of the compound of Formula V, $R_2$ is a halogen. In another embodiment $R_2$ is a bromide. In another embodiment $R_2$ is a chloride. In another embodiment $R_2$ is a fluoride. In another embodiment $R_2$ is an iodide. In another embodiment $R_2$ is hydrogen. In another embodiment $R_2$ is a cyano. In another embodiment, $R_2$ is a phenyl. In another embodiment, $R_2$ is —CH═CH—$CH_3$. In another embodiment, $R_2$ is —CH═$CH_2$. In another embodiment, $R_2$ is —CH═CH—COOEt. In another embodiment $R_1$ is O—(CO)-Ph-$CF_3$. In another embodiment $R_1$ is COOH. In another embodiment $R_1$ is COOMe. In another embodiment $R_1$ is a hydroxyl group. In another embodiment $R_1$ is hydrogen. In another embodiment $R_3$ is halogen. In another embodiment $R_3$ is fluoride. In another embodiment $R_3$ is chloride. In another embodiment $R_3$ is bromide. In another embodiment $R_3$ is iodide. In another embodiment $R_3$ is hydrogen. In another embodiment R' is H. In another embodiment R' is a methyl group. In another embodiment R' is a COMe group In another embodiment R" is H. In another embodiment R" is a methyl group. In another embodiment R" is a COMe. In another embodiment, when $R_1$, $R_2$, $R_3$ are independently Z-Alk-heterocycle or, in another embodiment, $OCH_2CH_2$-heterocycle, either heterocycle may be substituted or unsubstituted piperidine, pyrrolidine, morpholine or piperazine. In another embodiment, when $R_4$ and $R_5$ are independently a 3 to 7 membered heterocycloalkyl, either heterocycle may be substituted or unsubstituted piperidine, pyrrolidine, morpholine or piperazine. In another embodiment, any heterocycle is optionally substituted by one or more substituents comprising halogen, cyano, nitro, COOH, COOR, NHCOR, hydroxyl, amine, alkyl, cycloalkyl, heterocycloalkyl, alkenyl, alkynyl, alkanoyl, alkylthio, alkylamino, N,N dialkylamino, aminoalkyl, haloalkyl, aryl, heteroaryl, alkoxy or haloalkoxy; and R is as defined for Formula V.

In another embodiment, the compound of formula III may be represented by the structure of Formula VI:

wherein $R_1$, $R_2$, $R_3$, $R_6$, $R_7$, $R_8$, $R_9$, $R_{10}$, $R_{11}$ are independently selected from hydrogen, aldehyde, COOH, —C(=NH)—OH, CHNOH, CH=CHCO$_2$H, CH=CHCO$_2$R, —CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered saturated or unsaturated, substituted or unsubstituted heterocyclic ring;

R' is hydrogen, Alk or COR;

R" is hydrogen, Alk or COR;

$R_4$ and $R_5$ are independently hydrogen, phenyl, benzyl, an alkyl group of 1 to 6 carbon atoms, a 3 to 7 member cycloalkyl, heterocycloalkyl, aryl or heteroaryl group;

Z is O, NH, CH$_2$ or

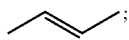

Q is SO$_3$H, CO$_2$H, CO$_2$R, NO$_2$, tetrazole, SO$_2$NH$_2$ or SO$_2$NHR;

R is alkyl, hydrogen, haloalkyl, dihaloalkyl, trihaloalkyl, CH$_2$F, CHF$_2$, CF$_3$, CF$_2$CF$_3$, aryl, phenyl, benzyl, -Ph-CF$_3$, -Ph-CH$_2$F, -Ph-CHF$_2$, -Ph-CF$_2$CF$_3$, halogen, alkenyl, CN, NO$_2$ or OH and;

and Alk is a linear alkyl of 1-7 carbons, branched alkyl of 1-7 carbons or cyclic alkyl of 3-8 carbons;

wherein, if $R_{10}$ is a benzene ring, then:

$R_9$ is not COOR, if R is hydrogen or an ester residue; or $R_9$ is not CONR$_4$R$_5$, if $R_4$ and $R_5$ are as described above.

In some embodiments the NRBA of Formula VI is an estrogen receptor ligand compound. In one embodiment, the estrogen receptor ligand compound is a selective estrogen receptor modulator (SERM). In one embodiment, the estrogen receptor ligand compound is a selective estrogen receptor β modulator (β-SERM). In one embodiment, the estrogen receptor ligand compound is an estrogen receptor agonist. In one embodiment, the estrogen receptor ligand compound is an estrogen receptor β (ERβ) agonist. In one embodiment, the estrogen receptor ligand compound is an estrogen receptor β (ERβ) antagonist.

In another embodiment of the compound of Formula VI, $R_{10}$ is a halogen. In another embodiment $R_{10}$ is a bromide. In another embodiment $R_{10}$ is a chloride. In another embodiment $R_2$ is a fluoride. In another embodiment $R_{10}$ is an iodide. In another embodiment $R_{10}$ is hydrogen. In another embodiment $R_{10}$ is a cyano. In another embodiment, $R_{10}$ is a phenyl. In another embodiment, $R_{10}$ is —CH=CH—CH$_3$. In another embodiment, $R_{10}$ is —CH=CH$_2$. In another embodiment, $R_{10}$ is —CH=CH—COOEt. In another embodiment $R_2$ is a hydroxyl group. In another embodiment $R_2$ is hydrogen. In another embodiment $R_2$ is O—(CO)-Ph-CF$_3$. In another embodiment $R_2$ is COOH. In another embodiment $R_2$ is COOMe. In another embodiment $R_7$ is a halogen. In another embodiment $R_7$ is fluoride. In another embodiment $R_7$ is chloride. In another embodiment $R_7$ is bromide. In another embodiment $R_7$ is iodide. In another embodiment $R_3$, $R_6$, $R_7$ and $R_8$ are hydrogens. In another embodiment R' is H. In another embodiment R' is a methyl group. In another embodiment R' is a COMe. In another embodiment R" is H. In another embodiment R" is a methyl group. In another embodiment R" is COMe. In another embodiment $R_1$, $R_3$, $R_6$, $R_7$, $R_8$, $R_9$ and $R_{11}$ are hydrogens. In another embodiment, when $R_1$, $R_2$, $R_3$, $R_6$, $R_7$, $R_8$, $R_9$, $R_{10}$, $R_{11}$ are independently Z-Alk-heterocycle or, in another embodiment, OCH$_2$CH$_2$-heterocycle, either heterocycle may be substituted or unsubstituted piperidine, pyrrolidine, morpholine or piperazine. In another embodiment, when $R_4$ and $R_5$ are independently a 3 to 7 membered heterocycloalkyl, either heterocycle may be substituted or unsubstituted piperidine, pyrrolidine, morpholine or piperazine. In another embodiment, any heterocycle is optionally substituted by one or more substituents comprising halogen, cyano, nitro, COOH, COOR, NHCOR, hydroxyl, amine, alkyl, cycloalkyl, heterocycloalkyl, alkenyl, alkynyl, alkanoyl, alkylthio, alkylamino, N,N dialkylamino, aminoalkyl, haloalkyl, aryl, heteroaryl, alkoxy or haloalkoxy, wherein R is as defined for Formula VI.

In one embodiment, the compound of formula I may be represented by the structure of Formula VII:

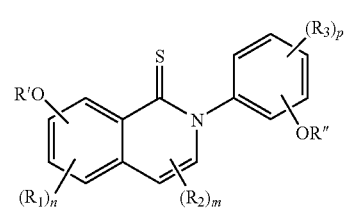

VII wherein $R_1$, $R_2$, $R_3$ are independently hydrogen, aldehyde, COOH, —C(=NH)—OH, CHNOH, CH=CHCO$_2$H, CH=CHCO$_2$R, —CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered saturated or unsaturated, substituted or unsubstituted heterocyclic ring;

R' is hydrogen, Alk or COR;

R" is hydrogen, Alk or COR;

$R_4$ and $R_5$ are independently hydrogen, phenyl, benzyl, an alkyl group of 1 to 6 carbon atoms, a 3 to 7 member cycloalkyl, heterocycloalkyl, aryl or heteroaryl group;

Z is O, NH, CH$_2$ or

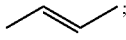

Q is SO$_3$H, CO$_2$H, CO$_2$R, NO$_2$, tetrazole, SO$_2$NH$_2$ or SO$_2$NHR;

R is alkyl, hydrogen, haloalkyl, dihaloalkyl, trihaloalkyl, CH$_2$F, CHF$_2$, CF$_3$, CF$_2$CF$_3$, aryl, phenyl, benzyl, -Ph-CF$_3$, -Ph-CH$_2$F, -Ph-CHF$_2$, -Ph-CF$_2$CF$_3$, halogen, alkenyl, CN, NO$_2$ or OH;

n is an integer between 1-3;

m is an integer between 1-2;

p is an integer between 1-4; and

Alk is a linear alkyl of 1-7 carbons, branched alkyl of 1-7 carbons or cyclic alkyl of 3-8 carbons.

In some embodiments the NRBA of Formula VII is an estrogen receptor ligand compound. In one embodiment, the estrogen receptor ligand compound is a selective estrogen receptor modulator (SERM). In one embodiment, the estrogen receptor ligand compound is a selective estrogen receptor β modulator (β-SERM). In one embodiment, the estrogen receptor ligand compound is an estrogen receptor agonist. In one embodiment, the estrogen receptor ligand compound is an estrogen receptor β (ERβ) agonist. In one embodiment, the estrogen receptor ligand compound is an estrogen receptor β (ERβ) antagonist.

In another embodiment of the compound of Formula VII, $R_2$ is a halogen. In another embodiment $R_2$ is a bromide. In another embodiment $R_2$ is a chloride. In another embodiment $R_2$ is a fluoride. In another embodiment $R_2$ is an iodide. In another embodiment $R_2$ is hydrogen. In another embodiment $R_2$ is a cyano. In another embodiment, $R_2$ is a phenyl. In another embodiment, $R_2$ is —CH=CH—CH$_3$. In another embodiment, $R_2$ is —CH=CH$_2$. In another embodiment, $R_2$ is —CH=CH—COOEt. In another embodiment $R_1$ is O—(CO)-Ph-CF$_3$. In another embodiment $R_1$ is COOH. In another embodiment $R_1$ is COOMe. In another embodiment $R_1$ is a hydroxyl group. In another embodiment $R_1$ is hydrogen. In another embodiment $R_3$ is halogen. In another embodiment $R_3$ is fluoride. In another embodiment $R_3$ is chloride. In another embodiment $R_3$ is bromide. In another embodiment $R_3$ is iodide. In another embodiment $R_3$ is hydrogen. In another embodiment R' is H. In another embodiment R' is a methyl group. In another embodiment R' is COMe. In another embodiment R" is H. In another embodiment R" is a methyl group. In another embodiment R" is a COMe. In another embodiment, when $R_1$, $R_2$, $R_3$ are independently Z-Alk-heterocycle or, in another embodiment, OCH$_2$CH$_2$-heterocycle, either heterocycle may be substituted or unsubstituted piperidine, pyrrolidine, morpholine or piperazine. In another embodiment, when $R_4$ and $R_5$ are independently a 3 to 7 membered heterocycloalkyl, either heterocycle may be substituted or unsubstituted piperidine, pyrrolidine, morpholine or piperazine. In another embodiment, any heterocycle is optionally substituted by one or more substituents comprising halogen, cyano, nitro, COOH, COOR, NHCOR, hydroxyl, amine, alkyl, cycloalkyl, heterocycloalkyl, alkenyl, alkynyl, alkanoyl, alkylthio, alkylamino, N,N dialkylamino, aminoalkyl, haloalkyl, aryl, heteroaryl, alkoxy or haloalkoxy, and R is as defined for Formula VII.

In another embodiment, the compound of formula II may be represented by the structure of Formula VIII:

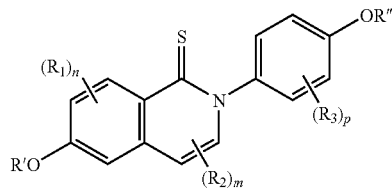

wherein
$R_1$, $R_2$, $R_3$ are independently hydrogen, aldehyde, COOH, —C(=NH)—OH, CHNOH, CH=CHCO$_2$H, CH=CHCO$_2$R, —CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered saturated or unsaturated, substituted or unsubstituted heterocyclic ring;
R' is hydrogen, Alk or COR;
R" is hydrogen, Alk or COR;
$R_4$ and $R_5$ are independently hydrogen, phenyl, benzyl, an alkyl group of 1 to 6 carbon atoms, a 3 to 7 member cycloalkyl, heterocycloalkyl, aryl or heteroaryl group;
Z is O, NH, CH$_2$ or

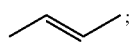

Q is SO$_3$H, CO$_2$H, CO$_2$R, NO$_2$, tetrazole, SO$_2$NH$_2$ or SO$_2$NHR;
R is alkyl, hydrogen, haloalkyl, dihaloalkyl, trihaloalkyl, CH$_2$F, CHF$_2$, CF$_3$, CF$_2$CF$_3$, aryl, phenyl, benzyl, -Ph-CF$_3$, -Ph-CH$_2$F, -Ph-CHF$_2$, -Ph-CF$_2$CF$_3$, halogen, alkenyl, CN, NO$_2$ or OH;
n is an integer between 1-3;
m is an integer between 1-2;
p is an integer between 1-4; and
Alk is a linear alkyl of 1-7 carbons, branched alkyl of 1-7 carbons or cyclic alkyl of 3-8 carbons.

In some embodiments the NRBA of Formula VIII is an estrogen receptor ligand compound. In one embodiment, the estrogen receptor ligand compound is a selective estrogen receptor modulator (SERM). In one embodiment, the estrogen receptor ligand compound is a selective estrogen receptor β modulator (β-SERM). In one embodiment, the estrogen receptor ligand compound is an estrogen receptor agonist. In one embodiment, the estrogen receptor ligand compound is an estrogen receptor (ERβ) agonist. In one embodiment, the estrogen receptor ligand compound is an estrogen receptor β (ERβ) antagonist.

In another embodiment of the compound of Formula VIII, $R_2$ is a halogen. In another embodiment $R_2$ is a bromide. In another embodiment $R_2$ is a chloride. In another embodiment $R_2$ is a fluoride. In another embodiment $R_2$ is an iodide. In another embodiment $R_2$ is hydrogen. In another embodiment $R_2$ is a cyano. In another embodiment, $R_2$ is a phenyl. In another embodiment, $R_2$ is —CH=CH—CH$_3$. In another embodiment, $R_2$ is —CH=CH$_2$. In another embodiment, $R_2$ is —CH=CH—COOEt. In another embodiment $R_1$ is O—(CO)-Ph-CF$_3$. In another embodiment $R_1$ is COOH. In another embodiment $R_1$ is COOMe. In another embodiment $R_1$ is a hydroxyl group. In another embodiment $R_1$ is hydrogen. In another embodiment $R_3$ is hydrogen. In another embodiment $R_3$ is halogen. In another embodiment $R_3$ is fluoride. In another embodiment $R_3$ is chloride. In another embodiment $R_3$ is bromide. In another embodiment $R_3$ is iodide. In another embodiment R' is H. In another embodiment R' is a methyl group. In another embodiment R' is COMe. In another embodiment R" is H. In another embodiment R" is a methyl group. In another embodiment R" is COMe. In another embodiment, when $R_1$, $R_2$, $R_3$ are independently Z-Alk-heterocycle or, in another embodiment, OCH$_2$CH$_2$-heterocycle, either heterocycle may be substituted or unsubstituted piperidine, pyrrolidine, morpholine or piperazine. In another embodiment, when $R_4$ and $R_5$ are independently a 3 to 7 membered heterocycloalkyl, either heterocycle may be substituted or unsubstituted piperidine, pyrrolidine, morpholine or piperazine. In another embodiment, any heterocycle is optionally substituted by one or more substituents comprising halogen, cyano, nitro, COOH, COOR, NHCOR, hydroxyl, amine, alkyl, cycloalkyl, heterocycloalkyl, alkenyl, alkynyl, alkanoyl, alkylthio, alkylamino, N,N dialkylamino, aminoalkyl, haloalkyl, aryl, heteroaryl, alkoxy or haloalkoxy, and R is as defined for Formula VIII.

In another embodiment, the compound of formula III may be represented by the structure of Formula IX:

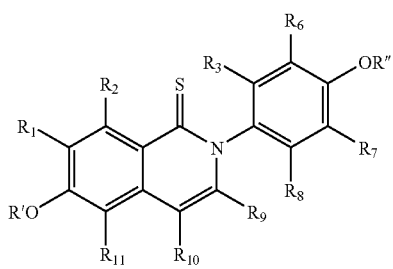

wherein $R_1$, $R_2$, $R_3$, $R_6$, $R_7$, $R_8$, $R_9$, $R_{10}$, $R_{11}$ are independently selected from hydrogen, aldehyde, COOH, —C(=NH)—OH, CHNOH, CH=CHCO$_2$H, CH=CHCO$_2$R, —CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered saturated or unsaturated, substituted or unsubstituted heterocyclic ring;

R' is hydrogen, Alk or COR;

R" is hydrogen, Alk or COR;

$R_4$ and $R_5$ are independently hydrogen, phenyl, benzyl, an alkyl group of 1 to 6 carbon atoms, a 3 to 7 member cycloalkyl, heterocycloalkyl, aryl or heteroaryl group;

Z is O, NH, CH$_2$ or

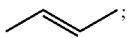;

Q is SO$_3$H, CO$_2$H, CO$_2$R, NO$_2$, tetrazole, SO$_2$NH$_2$ or SO$_2$NHR;

R is alkyl, hydrogen, haloalkyl, dihaloalkyl, trihaloalkyl, CH$_2$F, CHF$_2$, CF$_3$, CF$_2$CF$_3$, aryl, phenyl, benzyl, -Ph-CF$_3$, -Ph-CH$_2$F, -Ph-CHF$_2$, -Ph-CF$_2$CF$_3$, halogen, alkenyl, CN, NO$_2$ or OH; and Alk is a linear alkyl of 1-7 carbons, branched alkyl of 1-7 carbons or cyclic alkyl of 3-8 carbons.

In some embodiments the NRBA of Formula IX is an estrogen receptor ligand compound. In one embodiment, the estrogen receptor ligand compound is a selective estrogen receptor modulator (SERM). In one embodiment, the estrogen receptor ligand compound is a selective estrogen receptor β modulator (β-SERM). In one embodiment, the estrogen receptor ligand compound is an estrogen receptor agonist. In one embodiment, the estrogen receptor ligand compound is an estrogen receptor β (ERβ) agonist. In one embodiment, the estrogen receptor ligand compound is an estrogen receptor β (ERβ) antagonist.

In another embodiment of the compound of Formula IX, $R_{10}$ is a halogen. In another embodiment $R_{10}$ is a bromide. In another embodiment $R_{10}$ is a chloride. In another embodiment $R_2$ is a fluoride. In another embodiment $R_{10}$ is an iodide. In another embodiment $R_{10}$ is hydrogen. In another embodiment $R_{10}$ is a cyano. In another embodiment, $R_{10}$ is a phenyl. In another embodiment, $R_{10}$ is —CH=CH—CH$_3$. In another embodiment, $R_{10}$ is —CH=CH$_2$. In another embodiment, $R_{10}$ is —CH=CH—COOEt. In another embodiment $R_2$ is a hydroxyl group. In another embodiment $R_2$ is hydrogen. In another embodiment $R_2$ is O—(CO)-Ph-CF$_3$. In another embodiment $R_2$ is COOH. In another embodiment $R_2$ is COOMe. In another embodiment $R_7$ is a halogen. In another embodiment $R_7$ is fluoride. In another embodiment $R_7$ is chloride. In another embodiment $R_7$ is bromide. In another embodiment $R_7$ is iodide. In another embodiment $R_3$, $R_6$, $R_7$ and $R_8$ are hydrogens. In another embodiment R' is H. In another embodiment R' is a methyl group. In another embodiment R' is a COMe. In another embodiment R' is H. In another embodiment R" is a methyl group. In another embodiment R" is COMe. In another embodiment $R_1$, $R_3$, $R_6$, $R_7$, $R_8$, $R_9$ and $R_{11}$ are hydrogens. In another embodiment, when $R_1$, $R_2$, $R_3$, $R_6$, $R_7$, $R_8$, $R_9$, $R_{10}$, $R_{11}$ are independently Z-Alk-heterocycle or, in another embodiment, OCH$_2$CH$_2$-heterocycle, either heterocycle may be substituted or unsubstituted piperidine, pyrrolidine, morpholine or piperazine. In another embodiment, when $R_4$ and $R_5$ are independently a 3 to 7 membered heterocycloalkyl, either heterocycle may be substituted or unsubstituted piperidine, pyrrolidine, morpholine or piperazine. In another embodiment, any heterocycle is optionally substituted by one or more substituents comprising halogen, cyano, nitro, COOH, COOR, NHCOR, hydroxyl, amine, alkyl, cycloalkyl, heterocycloalkyl, alkenyl, alkynyl, alkanoyl, alkylthio, alkylamino, N,N dialkylamino, aminoalkyl, haloalkyl, aryl, heteroaryl, alkoxy or haloalkoxy, and R is as defined for Formula IX.

In one embodiment, the present invention provides a NRBA or its prodrug, analog, isomer, metabolite, derivative, pharmaceutically acceptable salt, pharmaceutical product, polymorph, crystal, impurity, N-oxide, ester, hydrate or any combination thereof, represented by the structure of Formula X:

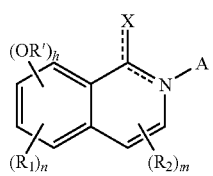

wherein

A is a 5-14 membered saturated or unsaturated, substituted or unsubstituted carbocyclic or heterocyclic ring which is optionally a fused ring system, or a combination thereof; wherein the saturated or unsaturated carbocyclic or heterocyclic ring are optionally substituted by 1 to 5 substituents independently selected from $R_3$ or OR"; and X is O or S; or A is nothing, N forms a double bond with the cyclic carbon and X is OH or OCH$_2$CH$_2$-heterocycle in which the heterocycle is a 3-7 membered saturated or unsaturated, substituted or unsubstituted heterocyclic ring;

$R_1$, $R_2$, $R_3$ are independently hydrogen, aldehyde, COOH, —C(=NH)—OH, CHNOH, CH=CHCO$_2$H, CH=CHCO$_2$R, —CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered saturated or unsaturated, substituted or unsubstituted heterocyclic ring;

R' is hydrogen, Alk or COR;

R" is hydrogen, Alk or COR;

R$_4$ and R$_5$ are independently hydrogen, phenyl, benzyl, an alkyl group of 1 to 6 carbon atoms, a 3 to 7 member cycloalkyl, heterocycloalkyl, aryl or heteroaryl group;

Z is O, NH, CH$_2$ or

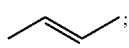

Q is SO$_3$H, CO$_2$H, CO$_2$R, NO$_2$, tetrazole, SO$_2$NH$_2$ or SO$_2$NHR;

R is alkyl, hydrogen, haloalkyl, dihaloalkyl, trihaloalkyl, CH$_2$F, CHF$_2$, CF$_3$, CF$_2$CF$_3$, aryl, phenyl, benzyl, -Ph-CF$_3$, -Ph-CH$_2$F, -Ph-CHF$_2$, -Ph-CF$_2$CF$_3$, halogen, alkenyl, CN, NO$_2$ or OH;

h is an integer between 0-3;

n is an integer between 1-4;

m is an integer between 1-2; and

Alk is a linear alkyl of 1-7 carbons, branched alkyl of 1-7 carbons or cyclic alkyl of 3-8 carbons.

In some embodiments the NRBA of Formula X is an estrogen receptor ligand compound. In one embodiment, the estrogen receptor ligand compound is a selective estrogen receptor modulator (SERM). In one embodiment, the estrogen receptor ligand compound is a selective estrogen receptor β modulator (β-SERM). In one embodiment, the estrogen receptor ligand compound is an estrogen receptor agonist. In one embodiment, the estrogen receptor ligand compound is an estrogen receptor β (ERβ) agonist. In one embodiment, the estrogen receptor ligand compound is an estrogen receptor β (ERβ) antagonist.

In one embodiment, the present invention provides a NRBA or its prodrug, analog, isomer, metabolite, derivative, pharmaceutically acceptable salt, pharmaceutical product, polymorph, crystal, impurity, N-oxide, ester, hydrate or any combination thereof, represented by the structure of Formula X:

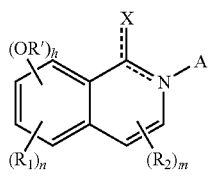

X wherein A, X, R$_1$, R$_2$, R', n, m and h are as described above, however, if X is oxo and A is phenyl, then A is not substituted with:
NHCOR and halogen without further substitution, or
NHCOR and an alkyl without further substitution.

In one embodiment, A is

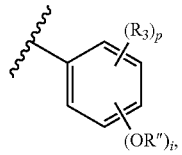

p is an integer between 1-5; i is an integer between 0-4; R" is hydrogen, Alk or COR; and R$_3$ is hydrogen, aldehyde, COOH, C(=NH)—OH, CHNOH, CH=CHCO$_2$H, —CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$. Z-Alk-heterocycle or OCH$_2$CH$_2$-heterocycle in which the heterocycle is a 3-7 membered saturated or unsaturated, substituted or unsubstituted heterocyclic ring.

In one embodiment of the compound of Formula X, A is nothing, N forms a double bond with the cyclic carbon and X is OCH$_2$CH$_2$-heterocycle in which the heterocycle is a 3-7 membered heterocycloalkyl. In one embodiment, when X is OCH$_2$CH$_2$-heterocycle, the heterocycle is substituted or unsubstituted piperidine, pyrrolidine, morpholine or piperazine. In another embodiment, when R$_1$, R$_2$, R$_3$ are independently Z-Alk-heterocycle or, in another embodiment, OCH$_2$CH$_2$-heterocycle, either heterocycle may be substituted or unsubstituted piperidine, pyrrolidine, morpholine or piperazine. In another embodiment, when R$_4$ and R$_5$ are independently a 3 to 7 membered heterocycloalkyl, either heterocycle may be substituted or unsubstituted piperidine, pyrrolidine, morpholine or piperazine. In another embodiment, any heterocycle is optionally substituted by one or more substituents comprising halogen, cyano, nitro, COOH, COOR, NHCOR, hydroxyl, amine, alkyl, haloalkyl, cycloalkyl, heterocycloalkyl, alkenyl, alkynyl, alkanoyl, alkylthio, alkylamino, N,N dialkylamino, aminoalkyl, haloalkyl, aryl, heteroaryl, alkoxy or haloalkoxy, and R is as defined for Formula X.

In another embodiment of the compound of Formula X, R$_2$ is a halogen. In another embodiment R$_2$ is a bromide. In another embodiment R$_2$ is a chloride. In another embodiment R$_2$ is a fluoride. In another embodiment R$_2$ is an iodide. In another embodiment R$_2$ is hydrogen. In another embodiment R$_2$ is a cyano. In another embodiment, R$_2$ is a phenyl. In another embodiment, R$_2$ is —CH=CH—CH$_3$. In another embodiment, R$_2$ is —CH=CH$_2$. In another embodiment, R$_2$ is —CH=CH—COOEt. In another embodiment R$_1$ is O—(CO)-Ph-CF$_3$. In another embodiment R$_1$ is COOH. In another embodiment R$_1$ is COOMe. In another embodiment R$_1$ is a hydroxyl group. In another embodiment R$_1$ is hydrogen. In another embodiment R$_3$ is halogen. In another embodiment R$_3$ is fluoride. In another embodiment R$_3$ is chloride. In another embodiment R$_3$ is bromide. In another embodiment R$_3$ is iodide. In another embodiment R$_3$ is hydrogen. In another embodiment R' is H. In another embodiment R' is a methyl group. In another embodiment R' is COMe. In another embodiment R" is H. In another embodiment R" is a methyl group. In another embodiment R" is COMe.

In one embodiment, the compound of Formula X may be represented by the structure of Formula XI:

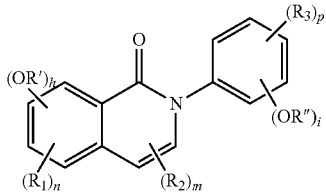

XI wherein $R_1$, $R_2$, $R_3$ are independently hydrogen, aldehyde, COOH, —C(=NH)—OH, CHNOH, CH=CHCO$_2$H, CH=CHCO$_2$R, —CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered saturated or unsaturated, substituted or unsubstituted heterocyclic ring;

R is alkyl, hydrogen, haloalkyl, dihaloalkyl, trihaloalkyl, CH$_2$F, CHF$_2$, CF$_3$, CF$_2$CF$_3$, aryl, phenyl, benzyl, -Ph-CF$_3$, -Ph-CH$_2$F, -Ph-CHF$_2$, -Ph-CF$_2$CF$_3$, halogen, alkenyl, CN, NO$_2$ or OH;

R' is hydrogen, Alk or COR;

R" is hydrogen, Alk or COR;

$R_4$ and $R_5$ are independently hydrogen, phenyl, benzyl, an alkyl group of 1 to 6 carbon atoms, a 3 to 7 member cycloalkyl, heterocycloalkyl, aryl or heteroaryl group;

Z is O, NH, CH$_2$ or

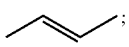;

Q is SO$_3$H, CO$_2$H, CO$_2$R, NO$_2$, tetrazole, SO$_2$NH$_2$ or SO$_2$NHR;

h is an integer between 0-3;

i is an integer between 0-4;

n is an integer between 1-4;

m is an integer between 1-2;

p is an integer between 0-5; and

Alk is a linear alkyl of 1-7 carbons, branched alkyl of 1-7 carbons, or cyclic alkyl of 3-8 carbons.

In some embodiments the NRBA of Formula XI is an estrogen receptor ligand compound. In one embodiment, the estrogen receptor ligand compound is a selective estrogen receptor modulator (SERM). In one embodiment, the estrogen receptor ligand compound is a selective estrogen receptor β modulator (β-SERM). In one embodiment, the estrogen receptor ligand compound is an estrogen receptor agonist. In one embodiment, the estrogen receptor ligand compound is an estrogen receptor β (ERβ) agonist. In one embodiment, the estrogen receptor ligand compound is an estrogen receptor β (ERβ) antagonist.

In one embodiment, the compound of formula XI is represented by the structure of Formula XIa:

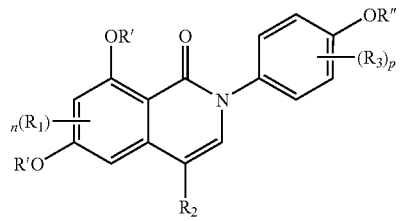

XIa wherein n is 1 or 2;

p is 0, 1, 2, 3 or 4; and $R_1$, $R_2$, $R_3$, R' and R" are as described above for Formula I, or its prodrug, analog, isomer, metabolite, derivative, pharmaceutically acceptable salt, pharmaceutical product, polymorph, crystal, impurity, N-oxide, ester, hydrate or any combination thereof.

In some embodiments the NRBA of Formula XIa is an estrogen receptor ligand compound. In one embodiment, the estrogen receptor ligand compound is a selective estrogen receptor modulator (SERM). In one embodiment, the estrogen receptor ligand compound is a selective estrogen receptor β modulator (β-SERM). In one embodiment, the estrogen receptor ligand compound is an estrogen receptor agonist. In one embodiment, the estrogen receptor ligand compound is an estrogen receptor β (ERβ) agonist. In one embodiment, the estrogen receptor ligand compound is an estrogen receptor β (ERβ) antagonist.

In another embodiment, the compound of formula XI may be represented by the structure of Formula XIb:

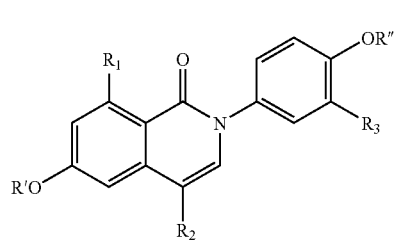

XIb wherein $R_1$, $R_2$, $R_3$, R' and R" are as described above for Formula XI;

or its prodrug, analog, isomer, metabolite, derivative, pharmaceutically acceptable salt, pharmaceutical product, polymorph, crystal, impurity, N-oxide, ester, hydrate or any combination thereof.

In some embodiments the NRBA of Formula XIb is an estrogen receptor ligand compound. In one embodiment, the estrogen receptor ligand compound is a selective estrogen receptor modulator (SERM). In one embodiment, the estrogen receptor ligand compound is a selective estrogen receptor β modulator (β-SERM). In one embodiment, the estrogen receptor ligand compound is an estrogen receptor agonist. In one embodiment, the estrogen receptor ligand compound is an estrogen receptor β (ERβ) agonist. In one embodiment, the estrogen receptor ligand compound is an estrogen receptor β (ERβ) antagonist.

In one embodiment, $R_2$ of formula XI, XIa and XIb is a halogen. In another embodiment $R_2$ is a bromide. In another embodiment $R_2$ is a chloride. In another embodiment $R_2$ is a fluoride. In another embodiment $R_2$ is an iodide. In another embodiment R₂ is hydrogen. In another embodiment R₂ is a cyano. In another embodiment, R₂ is a phenyl. In another embodiment, R₂ is —CH=CH—CH₃. In another embodiment, R₂ is —CH=CH₂. In another embodiment, R₂ is —CH=CH—COOEt. In one embodiment R₁ of formula XI, XIa and XIb is O—(CO)-Ph-CF₃. In another embodiment R₁ is COOH. In another embodiment R₁ is COOMe. In another embodiment R₁ is a hydroxyl group. In another embodiment R₁ is a hydrogen. In one embodiment R₃ of formula XI, XIa and XIb is a hydrogen. In another embodiment R₃ is a halogen. In another embodiment R₃ is fluoride. In another embodiment R₃ is chloride. In another embodiment R₃ is bromide. In another embodiment R₃ is iodide. In one embodiment R of formula XI, XIa and XIb is H. In another embodiment R' is a methyl group. In another embodiment R' is a COMe. In one embodiment R" of formula XI, XIa and XIb is H. In another embodiment R" is a methyl group. In another embodiment R" is a COMe. In one embodiment h of formula XI, XIa and XIb is 1. In another embodiment h is 2. In one embodiment, when R₁, R₂, R₃ of formula XI, XIa and XIb are independently Z-Alk-heterocycle or, in another embodiment, OCH₂CH₂-heterocycle, either heterocycle may be substituted or unsubstituted piperidine, pyrrolidine, morpholine or piperazine. In one embodiment, when R₄ and R₅ of formula XI, XIa and XIb are independently a 3 to 7 membered heterocycloalkyl, either heterocycle may be substituted or unsubstituted piperidine, pyrrolidine, morpholine or piperazine. In another embodiment, any heterocycle is optionally substituted by one or more substituents comprising halogen, cyano, nitro, COOH, COOR, NHCOR, hydroxyl, amine, alkyl, cycloalkyl, heterocycloalkyl, alkenyl, alkynyl, alkanoyl, alkylthio, alkylamino, N,N dialkylamino, aminoalkyl, haloalkyl, aryl, heteroaryl, alkoxy or haloalkoxy, and R of formula XI, XIa and XIb is as defined for Formula XI.

In one embodiment, the present invention provides a NRBA or its prodrug, analog, isomer, metabolite, derivative, pharmaceutically acceptable salt, pharmaceutical product, polymorph, crystal, impurity, N-oxide, ester, hydrate or any combination thereof, represented by the following structure:

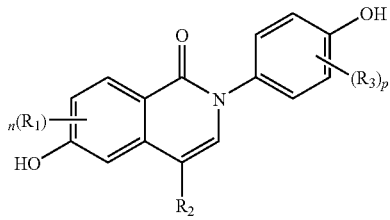

XII wherein
R₁, R₂ and R₃ are independently hydrogen, aldehyde, COOH, C(=NH)—OH, CHNOH, CH=CHCO₂H, —CH=CH₂, hydroxyalkyl, halogen, hydroxyl, alkoxy, cyano, nitro, CF₃, NH₂, 4-Ph-OMe, 4-Ph-OH, SH, COR, COOR, OCOR, alkenyl, allyl, 2-methylallyl, alkynyl, propargyl, OSO₂CF₃, OSO₂CH₃, NHR, NHCOR, N(R)₂, sulfonamide, SO₂R, alkyl, haloalkyl, aryl, phenyl, benzyl, protected hydroxyl, OCH₂CH₂NR₄R₅, Z-Alk-Q, Z-Alk-NR₄R₅, Z-Alk-heterocycle or OCH₂CH₂-heterocycle in which the heterocycle is a 3-7 membered saturated or unsaturated, substituted or unsubstituted heterocyclic ring;
R₄ and R₅ are independently hydrogen, phenyl, benzyl, an alkyl group of 1 to 6 carbon atoms, a 3 to 7 member cycloalkyl, heterocycloalkyl, aryl or heteroaryl group;
Z is O, NH, CH₂ or

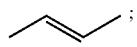;

Q is SO₃H, CO₂H, CO₂R, NO₂, tetrazole, SO₂NH₂ or SO₂NHR;
R is alkyl, hydrogen, haloalkyl, dihaloalkyl, trihaloalkyl, CH₂F, CHF₂, CF₃, CF₂CF₃, aryl, phenyl, -Ph-CF₃, -Ph-CH₂F, -Ph-CHF₂, -Ph-CF₂CF₃, halogen, alkenyl, CN, NO₂ or OH;
n is an integer between 1-3;
p is an integer between 1-4; and
Alk is a linear alkyl of 1-7 carbons, branched alkyl of 1-7 carbons, or cyclic alkyl of 3-8 carbons.

In some embodiments the NRBA of Formula XII is an estrogen receptor ligand compound. In one embodiment, the estrogen receptor ligand compound is a selective estrogen receptor modulator (SERM). In one embodiment, the estrogen receptor ligand compound is a selective estrogen receptor β modulator (β-SERM). In one embodiment, the estrogen receptor ligand compound is an estrogen receptor agonist. In one embodiment, the estrogen receptor ligand compound is an estrogen receptor β (ERβ) agonist. In one embodiment, the estrogen receptor ligand compound is an estrogen receptor β (ERβ) antagonist.

In another embodiment of the compound of Formula XII, R₂ is a halogen. In another embodiment R₂ is a bromide. In another embodiment R₂ is a chloride. In another embodiment R₂ is a fluoride. In another embodiment R₂ is an iodide. In another embodiment R₂ is hydrogen. In another embodiment R₂ is a cyano. In another embodiment, R₂ is a phenyl. In another embodiment, R₂ is —CH=CH—CH₃. In another embodiment, R₂ is —CH=CH₂. In another embodiment, R₂ is —CH=CH—COOEt. In another embodiment R₁ is O—(CO)-Ph-CF₃. In another embodiment R₁ is COOH. In another embodiment R₁ is COOMe. In another embodiment R₁ is an hydroxyl group. In another embodiment R₁ is hydrogen. In another embodiment R₃ is halogen. In another embodiment R₃ is fluoride. In another embodiment R₃ is chloride. In another embodiment R₃ is bromide. In another embodiment R₃ is iodide. In another embodiment R₃ is hydrogen. In another embodiment p is 1. In another embodiment, when R₁, R₂, R₃ are independently Z-Alk-heterocycle or, in another embodiment, OCH₂CH₂-heterocycle, either heterocycle may be substituted or unsubstituted piperidine, pyrrolidine, morpholine or piperazine. In another embodiment, when R₄ and R₅ are independently a 3 to 7 membered heterocycloalkyl, either heterocycle may be substituted or unsubstituted piperidine, pyrrolidine, morpholine or piperazine. In another embodiment, any heterocycle is optionally substituted by one or more substituents comprising halogen, cyano, nitro, COOH, COOR, NHCOR, hydroxyl, amine, alkyl, cycloalkyl, heterocycloalkyl, alkenyl, alkynyl, alkanoyl, alkylthio, alkylamino, N,N dialkylamino, aminoalkyl, haloalkyl, aryl, heteroaryl, alkoxy or haloalkoxy, and R is as defined for Formula XII.

In one embodiment the NRBA of this invention is 4-cyano-6,8-dihydroxy-2-(4-hydroxyphenyl)isoquinolin-1(2H)-one. In another embodiment the NRBA of this invention is 4-bromo-6,8-dihydroxy-2-(4-hydroxyphenyl)isoquinolin-1(2H)-one. In another embodiment the NRBA of this invention is 1-(2-(piperidin-1-yl)ethoxy)isoquinolin-6-ol. In another embodiment the NRBA of this invention is 6-hydroxy-2-(4-hydroxyphenyl)isoquinolin-1(2H)-one. In another embodiment the NRBA of this invention is 4-bromo-6-hydroxy-2-(4-hydroxyphenyl)isoquinolin-1(2H)-one. In another embodiment the NRBA of this invention is 4-bromo-2-(4-hydroxyphenyl)-6-methoxyisoquinolin-1(2H)-one. In another embodiment the NRBA of this invention is 4-bromo-2-(3-fluoro-4-hydroxyphenyl)-6-hydroxyisoquinolin-1(2H)-one. In another embodiment the NRBA of this invention is 4-bromo-2-(4-fluorophenyl)-6-hydroxyisoquinolin-1(2H)-one. In another embodiment the NRBA of this invention is 4-chloro-6-hydroxy-2-(4-hydroxyphenyl)isoquinolin-1(2H)-one. In another embodiment the NRBA of this invention is 4-chloro-2-(3-fluoro-4-hydroxyphenyl)-6-hydroxyisoquinolin-1(2H)-one. In another embodiment the NRBA of this invention is 6-hydroxy-2-(4-hydroxyphenyl)-4-iodoisoquinolin-1(2H)-one. In another embodiment the NRBA of this invention is 4-bromo-6-hydroxy-2-(3-hydroxyphenyl)isoquinolin-1(2H)-one. In another embodiment the NRBA of this invention is 8-hydroxy-2-(4-hydroxyphenyl)-6-methoxy-isoquinolin-1(2H)-one. In another embodiment the NRBA of this invention is 5-bromo-8-hydroxy-2-(4-hydroxyphenyl)-6-methoxy-isoquinolin-1(2H)-one. In another embodiment the NRBA of this invention is 6,8-dihydroxy-2-(4-hydroxyphenyl)-isoquinolin-1(2H)-one. In another embodiment the NRBA of this invention is 5-bromo-6,8-dihydroxy-2-(4-hydroxyphenyl)isoquinolin-1(2H)-one. In another embodiment the NRBA of this invention is 2-(3-fluoro-4-hydroxyphenyl)-6-hydroxy-4-iodoisoquinolin-1(2H)-one. In another embodiment the NRBA of this invention is 4-bromo-6-hydroxy-2-(4-hydroxy-3-methylphenyl)isoquinolin-1(2H)-one. In another embodiment the NRBA of this invention is 2-(4-hydroxyphenyl)-6,8-dihydroxy-isoquinoline-1(2H)-thione. In another embodiment the NRBA of this invention is 8-hydroxy-2-(4-hydroxyphenyl)-6-methoxy-1-oxo-1,2-dihydroisoquinoline-5-carbonitrile. In another embodiment the NRBA of this invention is 4-bromo-6-hydroxy-2-(4-hydroxyphenyl)isoquinoline-1(2H)-thione. In another embodiment the NRBA of this invention is 2-(3-fluoro-4-hydroxyphenyl)-6,8-dihydroxyisoquinolin-1(2H)-one. In another embodiment the NRBA of this invention is 2-(3-fluoro-4-hydroxyphenyl)-8-hydroxy-6-methoxyisoquinolin-1(2H)-one. In another embodiment the NRBA of this invention is 4-bromo-8-hydroxy-2-(4-hydroxyphenyl)-6-methoxyisoquinolin-1(2H)-one. In another embodiment the NRBA of this invention is 4-chloro-6,8-dihydroxy-2-(4-hydroxyphenyl)isoquinolin-1(2H)-one. In another embodiment the NRBA of this invention is 4-bromo-6,8-dihydroxy-2-(3-fluoro-4-hydroxyphenyl)isoquinolin-1(2H)-one. In another embodiment the NRBA of this invention is 4,5-dibromo-2-(3,5-dibromo-4-hydroxyphenyl)-6-hydroxyisoquinolin-1(2H)-one. In another embodiment the NRBA of this invention is 6,8-dihydroxy-2-(4-hydroxyphenyl)-5-(trifluoromethylsulfonyl)isoquinolin-1(2H)-one. In another embodiment the NRBA of this invention is 4-(1,2-dibromoethyl)-6-hydroxy-2-(4-hydroxyphenyl)isoquinolin-1(2H)-one. In another embodiment the NRBA of this invention is 6-methoxy-2-(4-methoxyphenyl)-1-oxo-1,2-dihydroisoquinolin-8-yltrifluoromethanesulfonate. In another embodiment the NRBA of this invention is 4,5-dibromo-6,8-dihydroxy-2-(4-hydroxyphenyl)isoquinolin-1(2H)-one. In another embodiment the NRBA of this invention is 6-hydroxy-2-(4-hydroxyphenyl)-4-vinylisoquinolin-1(2H)-one. In another embodiment the NRBA of this invention is 6-methoxy-2-(4-methoxyphenyl)-1-oxo-1,2-dihydroisoquinoline-4-carbonitrile. In another embodiment the NRBA of this invention is 6-hydroxy-2-(4-hydroxyphenyl)-1-oxo-1,2-dihydroisoquinoline-4-carbonitrile. In another embodiment the NRBA of this invention is 6-methoxy-2-(4-methoxyphenyl)-1-oxo-1,2-dihydroisoquinoline-8-carbonitrile. In another embodiment the NRBA of this invention is 4-bromo-6-methoxy-2-(4-methoxyphenyl)-1-oxo-1,2-dihydroisoquinoline-8-carbonitrile. In another embodiment the NRBA of this invention is 4-bromo-6-hydroxy-2-(4-hydroxyphenyl)-1-oxo-1,2-dihydroisoquinoline-8-carbonitrile. In another embodiment the NRBA of this invention is 6,8-dihydroxy-2-(4-hydroxyphenyl)-4-vinylisoquinolin-1(2H)-one. In another embodiment the NRBA of this invention is 6,8-dihydroxy-2-(4-hydroxyphenyl)-1-oxo-1,2-dihydroisoquinoline-4-carbonitrile or 4-cyano-6,8-dihydroxy-2-(4-hydroxyphenyl)isoquinolin-1(2H)-one. In another embodiment the NRBA of this invention is 6-hydroxy-2-(4-hydroxyphenyl)-1-oxo-1,2-dihydroisoquinoline-8-carbonitrile. In another embodiment the NRBA of this invention is 6-hydroxy-2-(4-hydroxyphenyl)-1-oxo-4-vinyl-1,2-dihydroisoquinoline-8-carbonitrile. In another embodiment the NRBA of this invention is 4-chloro-6-hydroxy-2-(4-hydroxyphenyl)-1-oxo-1,2-dihydroisoquinoline-8-carbonitrile. In another embodiment the NRBA of this invention is 4-bromo-6-methoxy-2-(4-methoxyphenyl)isoquinolin-1(2H)-one. In another embodiment the NRBA of this invention is 8-hydroxy-6-methoxy-2-(4-methoxyphenyl)isoquinolin-1(2H)-one. In another embodiment the NRBA of this invention is 4-chloro-6-methoxy-2-(4-methoxyphenyl)-1-oxo-1,2-dihydroisoquinolin-8-yl trifluoromethanesulfonate. In another embodiment the NRBA of this invention is 4-chloro-6-methoxy-2-(4-methoxyphenyl)-1-oxo-1,2-dihydroisoquinoline-8-carbonitrile. In another embodiment the NRBA of this invention is isoquinoline-1,6-diol. In another embodiment the NRBA of this invention is 4-bromo-6-hydroxy-2-(4-methoxyphenyl)isoquinolin-1(2H)-one. In another embodiment the NRBA of this invention is 4-(6-acetoxy-4-bromo-1-oxoisoquinolin-2(1H)-yl)phenyl acetate. In another embodiment the NRBA of this invention is 4-(4-bromo-6-methoxy-1-oxoisoquinolin-2(1H)-yl)phenyl acetate. In another embodiment the NRBA of this invention is 4-bromo-6-hydroxy-2-(4-hydroxyphenyl)-1-oxo-1,2-dihydroisoquinoline-8-carbimidic acid. In another embodiment the NRBA of this invention is methyl 4-bromo-6-hydroxy-2-(4-hydroxyphenyl)-1-oxo-1,2-dihydroisoquinoline-8-carboxylate. In another embodiment the NRBA of this invention is 4-bromo-6-hydroxy-2-(4-hydroxyphenyl)-1-oxo-1,2-dihydroisoquinoline-8-carboxylic acid. In another embodiment the NRBA of this invention is 6-hydroxy-2-(4-hydroxyphenyl)-4-phenylisoquinolin-1(2H)-one. In another embodiment the NRBA of this invention is 6-hydroxy-2-(4-hydroxyphenyl)-4-(4-methoxyphenyl)isoquinolin-1(2H)-one. In another embodiment the NRBA of this invention is 2-(3-fluoro-4-hydroxyphenyl)-6,8-dihydroxy-4-vinylisoquinolin-1(2H)-one. In another embodiment the NRBA of this invention is 2-(3-fluoro-4-hydroxyphenyl)-6,8-dihydroxy-1-oxo-1,2-dihydroisoquinoline-4-carbonitrile. In another embodiment the NRBA of this invention is 6-hydroxy-2-(4-hydroxyphenyl)-8-vinylisoquinolin-1(2H)-one. In another embodiment the NRBA of this invention is 4-bromo-6-hydroxy-2-(4-hydroxyphenyl)-8-vinylisoquinolin-1(2H)-one. In another embodiment the NRBA of this invention is 6,8-dihydroxy-2-(4-hydroxyphenyl)-4-(4-methoxyphenyl)isoquinolin-1(2H)-one. In another embodiment the NRBA of this invention is 6,8-dihydroxy-2-(4-hydroxyphenyl)-4-phenylisoquinolin-1(2H)-one. In another embodiment the NRBA of this invention is (E)-6,8-dihydroxy-2-(4-hydroxyphenyl)-4-(prop-1-enyl)isoquinolin-1(2H)-one. In another embodiment the NRBA of this invention is (E)-ethyl 3-(8-hydroxy-6-methoxy-2-(4- methoxyphenyl)-1-oxo-1,2-dihydroisoquinolin-4-yl)acrylate. In another embodiment the NRBA of this invention is (E)-3-(6-hydroxy-2-(4-hydroxyphenyl)-1-oxo-1,2-dihydroisoquinolin-4-yl)acrylic acid. In another embodiment the NRBA of this invention is (E)-3-(6,8-dihydroxy-2-(4-hydroxyphenyl)-1-oxo-1,2-dihydroisoquinolin-4-yl)acrylic acid. In another embodiment the NRBA of this invention is 4-chloro-6-methoxy-2-(4-methoxyphenyl)-1-oxo-1,2-dihydroisoquinolin-8-yl 4-(trifluoromethyl)benzoate or any combination thereof.

In one embodiment, the estrogen receptor ligand compound is 4-bromo-6,8-dihydroxy-2-(4-hydroxyphenyl)isoquinolin-1(2H)-one, or its prodrug, analog, isomer, metabolite, derivative, pharmaceutically acceptable salt, pharmaceutical product, polymorph, crystal, impurity, N-oxide, ester, hydrate, or any combination thereof.

In one embodiment, the estrogen receptor ligand compound is 4-chloro-6,8-dihydroxy-2-(4-hydroxyphenyl)isoquinolin-1(2H)-one, or its prodrug, analog, isomer, metabolite, derivative, pharmaceutically acceptable salt, pharmaceutical product, polymorph, crystal, impurity, N-oxide, ester, hydrate, or any combination thereof.

In one embodiment, the estrogen receptor ligand compound is 4-bromo-6,8-dihydroxy-2-(3-fluoro-4-hydroxyphenyl)isoquinolin-1(2H)-one, or its prodrug, analog, isomer, metabolite, derivative, pharmaceutically acceptable salt, pharmaceutical product, polymorph, crystal, impurity, N-oxide, ester, hydrate, or any combination thereof.

In one embodiment, the estrogen receptor ligand compound is 4-cyano-6,8-dihydroxy-2-(4-hydroxyphenyl)isoquinolin-1(2H)-one (or 6,8-dihydroxy-2-(4-hydroxyphenyl)-1-oxo-1,2-dihydroisoquinoline-4-carbonitrile), or its prodrug, analog, isomer, metabolite, derivative, pharmaceutically acceptable salt, pharmaceutical product, polymorph, crystal, impurity, N-oxide, ester, hydrate, or any combination thereof.

In some embodiments, the NRBA of this invention, compositions of this invention or uses thereof may comprise any combinations of such NRBA as described herein.

The term "alkyl" refers, in one embodiment, to a saturated aliphatic hydrocarbon, including straight-chain, branched-chain and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. In another embodiment, the cyclic alkyl group has 3-8 carbons. In another embodiment, the cyclic alkyl group has 3-12 carbons. In another embodiment, the branched alkyl is an alkyl substituted by alkyl side chains of 1 to 5 carbons. In another embodiment, the branched alkyl is an alkyl substituted by haloalkyl side chains of 1 to 5 carbons. The alkyl group may be unsubstituted or substituted by a halogen, haloalkyl, hydroxyl, cyano, alkoxy carbonyl, amido, alkylamido, dialkylamido, nitro, amino, alkylamino, dialkylamino, carboxyl, thio and/or thioalkyl.

An "alkenyl" group refers, in another embodiment, to an unsaturated hydrocarbon, including straight chain, branched chain and cyclic groups having one or more double bonds. The alkenyl group may have one double bond, two double bonds, three double bonds, etc. In another embodiment, the alkenyl group has 2-12 carbons. In another embodiment, the alkenyl group has 2-6 carbons. In another embodiment, the alkenyl group has 2-4 carbons. In another embodiment, the alkenyl group is vinyl (—CH=CH$_2$). Examples of alkenyl groups are vinyl, propenyl, butenyl, cyclohexenyl, etc. The alkenyl group may be unsubstituted or substituted by a halogen, hydroxy, cyano, alkoxy carbonyl, amido, alkylamido, dialkylamido, nitro, amino, alkylamino, dialkylamino, carboxyl, thio and/or thioalkyl.

The term "cycloalkyl" refers to a monocyclic, bicyclic or tricyclic nonaromatic saturated hydrocarbon radical having 3 to 10 carbon atoms, such as 3 to 8 carbon atoms, for example, 3 to 6 carbon atoms. Non limiting examples of cycloalkyl groups include cyclopropyl, cyclobutyl, cyclopentyl, cyclohexyl, cycloheptyl, cyclooctyl, norbornyl, 1-decalin, adamant-1-yl, and adamant-2-yl. Other suitable cycloalkyl groups include, but are not limited to, spiropentyl, bicyclo[2.1.0]pentyl, bicyclo[3.1.0]hexyl, spiro[2.4]heptyl, spiro[2.5]octyl, bicyclo[5.1.0]octyl, spiro[2.6]nonyl, bicyclo[2.2.0]hexyl, spiro[3.3]heptyl, bicyclo[4.2.0]octyl, and spiro[3.5]nonyl.

A "haloalkyl" group refers, in another embodiment, to an alkyl group as defined above, which is substituted by one or more halogen atoms, e.g. by F, Cl, Br or I.

An "aryl" group refers, in another embodiment, to an aromatic group having at least one carbocyclic aromatic group or heterocyclic aromatic group, which may be unsubstituted or substituted by one or more groups selected from halogen, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

A "hydroxyl" group refers, in another embodiment, to an OH group. In some embodiments, when $R_1$, $R_2$ or $R_3$ of the compounds of the present invention is OR, then R is not OH.

In one embodiment, the term "halo" refers to a halogen, such as F, Cl, Br or I.

In another embodiment, the phrase "phenol" refers to an alcohol (OH) derivative of benzene.

A "heterocycle" group refers, in one embodiment, to a ring structure comprising in addition to carbon atoms, sulfur, oxygen, nitrogen or any combination thereof, as part of the ring. In another embodiment the heterocycle is a 3-12 membered ring. In another embodiment the heterocycle is a 6 membered ring. In another embodiment the heterocycle is a 5-7 membered ring. In another embodiment the heterocycle is a 4-8 membered ring. In another embodiment, the heterocycle group may be unsubstituted or substituted by a halogen, haloalkyl, hydroxyl, alkoxy, carbonyl, amido, alkylamido, dialkylamido, cyano, nitro, CO$_2$H, amino, alkylamino, dialkylamino, carboxyl, thio and/or thioalkyl. In another embodiment, the heterocycle ring may be fused to another saturated or unsaturated cycloalkyl or heterocyclic 3-8 membered ring. In another embodiment, the heterocyclic ring is a saturated ring. In another embodiment, the heterocyclic ring is an unsaturated ring. Examples of a heterocycle group comprise pyridine, piperidine, morpholine, piperazine, thiophene, pyrrole or indole.

In one embodiment the 5-14 member saturated or unsaturated, substituted or unsubstituted carbocyclic or heterocyclic ring comprises a phenyl, naphthalene, anthracene, pyridine, piperidine, thiophene, morpholine, piperazine, pyrimidine, cyclohexyl, cycloheptyl, pyrrole, pyrazole, furan, oxazole, quinoline, pyrazine or indole groups.

In one embodiment unsaturated cycloalkyl or heterocycloalkyl groups refer to cycloalkyl or heterocycloalkyl comprising at list one double bond. In another embodiment unsaturated cycloalkyl or heterocycloalkyl refer to an aryl or heteroaryl group.

In some embodiments, protected hydroxyl includes the incorporation of a substituent bonded to an oxygen atom bound to a benzene ring, wherein the substituent may be readily removed. In some embodiments, phenolic protecting groups may comprise a: methyl ether, methoxymethyl (MOM) ether, benzoyloxymethyl (BOM) ether, methoxyethoxymethyl (MEM) ether, 2-(trimethylsilyl)ethoxymethyl (SEM) ether, methylthiomethyl (MTM) ether, phenylthiomethyl (PTM) ether, azidomethyl ether, cyanomethyl ether, 2,2-dichloro-1,1-difluoroethyl ether, 2-chloroethyl ether, 2-bromoethyl ether, tetrahydropyranyl (THP) ether, 1-ethoxyethyl (EE) ether, phenacyl ether, 4-bromophenacyl ether, cyclopropylmethyl ether, allyl ether, propargyl ether, isopropyl ether, cyclohexyl ether, t-butyl ether, benzyl ether, 2,6-dimethylbenzyl ether, 4-methoxybenzyl ether, o-nitrobenzyl ether, 2,6-dichlorobenzyl ether, 3,4-dichlorobenzyl ether, 4-(dimethylamino)carbonylbenzyl ether, 4-methylsulfinylbenzyl ether, 4-anthrylmethyl ether, 4-picolyl ether, heptafluoro-p-tolyl, tetrafluoro-4-pyridyl ether, trimethylsilyl (TMS) ether, t-butyldimethylsilyl (TBDMS) ether, t-butyldiphenylsilyl (TBDPS) ether, triisopropylsilyl (TIPS) ether, aryl formate, arylacetate, aryl levulinate, arylpivaloate, aryl benzoate, aryl 9-fluorencarboxylate, aryl methyl carbonate, 1-adamantyl carbonate, t-butyl carbonate, 4-methylsulfinylbenzyl carbonate, 2,4-dimethylpent-3-yl carbonate, aryl-2,2,2-trichloroethyl carbonate, aryl benzyl carbonate, aryl carbamate, dimethylphosphinyl ester (Dmp-OAr), dimethylphosphinothionyl ester (Mpt-OAr), diphenylphosphinothionyl ester (Dpt-OAr), aryl methanesulfonate, aryl toluenesulfonate or aryl 2-formylbenzenesulfonate.

In one embodiment, this invention provides a NRBA and/or its analog, derivative, isomer, metabolite, pharmaceutically acceptable salt, pharmaceutical product, hydrate, N-oxide, prodrug, ester, polymorph, impurity or crystal or combinations thereof. In one embodiment, this invention provides an analog of the NRBA. In another embodiment, this invention provides a derivative of the NRBA. In another embodiment, this invention provides an isomer of the NRBA. In another embodiment, this invention provides a metabolite of the NRBA. In another embodiment, this invention provides a pharmaceutically acceptable salt of the NRBA. In another embodiment, this invention provides a pharmaceutical product of the NRBA. In another embodiment, this invention provides a hydrate of the NRBA. In another embodiment, this invention provides an N-oxide of the NRBA. In another embodiment, this invention provides a prodrug of the NRBA. In another embodiment, this invention provides an ester of the NRBA. In another embodiment, this invention provides a polymorph of the NRBA. In another embodiment, this invention provides a crystal of the NRBA. In another embodiment, this invention provides an impurity of the NRBA. In another embodiment, this invention provides composition comprising a NRBA, as described herein, or, in another embodiment, a combination of an analog, derivative, isomer, metabolite, pharmaceutically acceptable salt, pharmaceutical product, hydrate, N-oxide, prodrug, polymorph, ester, impurity or crystal of the NRBA of the present invention.

In one embodiment, this invention provides use of an estrogen receptor ligand compound and/or its analog, derivative, isomer, metabolite, pharmaceutically acceptable salt, pharmaceutical product, hydrate, N-oxide, prodrug, ester, polymorph, impurity or crystal or combinations thereof. In one embodiment, this invention provides an analog of an estrogen receptor ligand compound. In another embodiment, this invention provides a derivative of an estrogen receptor ligand compound. In another embodiment, this invention provides an isomer of an estrogen receptor ligand compound. In another embodiment, this invention provides a metabolite of an estrogen receptor ligand compound. In another embodiment, this invention provides a pharmaceutically acceptable salt of an estrogen receptor ligand compound. In another embodiment, this invention provides a pharmaceutical product of the estrogen receptor ligand compound. In another embodiment, this invention provides a hydrate of an estrogen receptor ligand compound. In another embodiment, this invention provides an N-oxide of an estrogen receptor ligand compound. In another embodiment, this invention provides a prodrug of an estrogen receptor ligand compound. In another embodiment, this invention provides an ester of an estrogen receptor ligand compound. In another embodiment, this invention provides a polymorph of an estrogen receptor ligand compound. In another embodiment, this invention provides a crystal of an estrogen receptor ligand compound. In another embodiment, this invention provides an impurity of an estrogen receptor ligand compound.

In one embodiment, the term "isomer" includes, but is not limited to, optical isomers and analogs, structural isomers and analogs, conformational isomers and analogs, and the like.

In one embodiment, the term "isomer" is meant to encompass stereoisomers of the compound. The compounds of this invention possess an amide bond which may be in its cis or trans isomerisation. In one embodiment, the NRBAs are the pure (E)-isomers. In another embodiment, the NRBAs are the pure (Z)-isomers. In another embodiment, the NRBAs are a mixture of the (E) and the (Z) isomers. In one embodiment, the NRBAs are the pure (R)-isomers. In another embodiment, the NRBAs are the pure (S)-isomers. In another embodiment, the NRBAs are a mixture of the (R) and the (S) isomers. It is to be understood that the present invention encompasses any optically-active, or stereroisomeric form, or mixtures thereof, and use of these for any application is to be considered within the scope of this invention.

The invention includes "pharmaceutically acceptable salts" of the compounds of this invention, which may be produced, by reaction of a compound of this invention with an acid or base.

Suitable pharmaceutically-acceptable salts of amines of Formula I-XII may be prepared from an inorganic acid or from an organic acid. In one embodiment, examples of inorganic salts of amines are bisulfates, borates, bromides, chlorides, hemisulfates, hydrobromates, hydrochlorates, 2-hydroxyethylsulfonates (hydroxyethanesulfonates), iodates, iodides, isothionates, nitrate, persulfates, phosphate, sulfates, sulfamates, sulfanilates, sulfonic acids (alkylsulfonates, arylsulfonates, halogen substituted alkylsulfonates, halogen substituted arylsulfonates), sulfonates and thiocyanates.

In one embodiment, examples of organic salts of amines may be selected from aliphatic, cycloaliphatic, aromatic, araliphatic, heterocyclic, carboxylic and sulfonic classes of organic acids, examples of which are acetates, arginines, aspartates, ascorbates, adipates, anthranilate, algenates, alkane carboxylates, substituted alkane carboxylates, alginates, benzenesulfonates, benzoates, bisulfates, butyrates, bicarbonates, bitartrates, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonates gluconates, glutamates, glycolates, glucorate, glucoheptanoates, glycerophosphates, gluceptates, glycollylarsanilates, glutarates, glutamate, heptanoates, hexanoates, hydroxymaleates, hydroxycarboxlic acids, hexylresorcinates, hydroxybenzoates, hydroxynaphthoate, hydrofluorate, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, mitrates, naphthalenesulfonates, 2-naphthalenesulfonates, nicotinates, napsylates, N-methylglucamines, oxalates, octanoates, oleates, pamoates, phenylacetates, picrates, phenylbenzoates, pivalates, propionates, phthalates, phenylacetate, pectinates, phenylpropionates, palmitates, pantothenates, polygalacturates, pyruvates, quinates, salicylates, succinates, stearates, sulfanilate, subacetates, tartrates, theophyllineacetates, p-toluenesulfonates (tosylates), trifluoroacetates, terephthalates, tannates, teoclates, trihaloacetates, triethiodide, tricarboxylates, undecanoates and valerates.

In one embodiment, examples of inorganic salts of carboxylic acids or phenols may be selected from ammonium, alkali metals to include lithium, sodium, potassium, cesium; alkaline earth metals to include calcium, magnesium, aluminium; zinc, barium, cholines, quaternary ammoniums.

In another embodiment, examples of organic salts of carboxylic acids or phenols may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolies, piperazines, procain, tris(hydroxymethyl)methylamines, triethylamines, triethanolamines, trimethylamines, tromethamines and ureas.

In one embodiment, the salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of a existing salt for another ion or suitable ion-exchange resin.

In one embodiment the pharmaceutically acceptable salt is a hydrochloride salt. In one embodiment the pharmaceutically acceptable salt is an acrylate salt. In one embodiment the pharmaceutically acceptable salt is a benzoate salt. In one embodiment the pharmaceutically acceptable salt is a trifluoromethanesulfonate salt. In one embodiment the pharmaceutically acceptable salt is an acetate salt.

In one embodiment, the pharmaceutically acceptable salt of a NRBA comprising a piperidine ring is an HCl salt or an amine salt as described herein. In another embodiment, the pharmaceutically acceptable salt of a NRBA comprising a pyrrolidine ring is an HCl salt, or an amine salt as described herein. In another embodiment, the pharmaceutically acceptable salt of a NRBA comprising a morpholine ring is an HCl salt or an amine salt as described herein. In another embodiment, the pharmaceutically acceptable salt of a NRBA comprising a piperazine ring is an HCl salt, or an amine salt as described herein or others as will be appreciated by one skilled in the art.

Pharmaceutically acceptable salts can be prepared from the phenolic compounds, in other embodiments, by treatment with inorganic bases, for example, sodium hydroxide. In another embodiment, esters of the phenolic compounds can be made with aliphatic and aromatic carboxylic acids, for example, acetic acid and benzoic acid esters.

This invention provides, in some embodiments, derivatives of the NRBAs. In one embodiment, the term "derivatives" refers to ether derivatives, acid derivatives, amide derivatives, ester derivatives or others, as known in the art.

In another embodiment, this invention further includes hydrates of the NRBAs. In one embodiment, the term "hydrate" refers to hemihydrate, monohydrate, dihydrate, trihydrate or others, as known in the art.

This invention provides, in other embodiments, metabolites of the NRBAs. In one embodiment, the term "metabolite" refers to any substance produced from another substance by metabolism or a metabolic process.

In some embodiments, a NRBA this invention will comprise the compounds listed in Table 1.

In one embodiment, this invention provides use of a composition comprising an estrogen receptor ligand compound, as described herein, or, in another embodiment, any combination of an analog, derivative, isomer, metabolite, pharmaceutically acceptable salt, pharmaceutical product, hydrate, N-oxide, prodrug, polymorph, ester, impurity or crystal of an estrogen receptor ligand as described herein.

In some embodiments, the NRBAs of this invention will have a selective affinity for a particular nuclear hormone receptor, with varying affinities at other nuclear receptors. In some embodiments of this invention, NRBAs of this invention will vary in terms of their activity, for example, some NRBAs possess greater activity in terms of stimulating bone growth, while some exhibit greater antagonistic activity, etc. It is to be understood that all such NRBAs are to be considered as part of this invention.

In some embodiments, the NRBAs of this invention may exhibit nonselective affinity for or binding to a nuclear receptor, which in some embodiments, is an estrogen receptor $\alpha$ and/or estrogen receptor $\beta$ molecule. In some embodiments, the NRBAs of this invention may exhibit selective affinity for a nuclear receptor such as ER-$\beta$. In some embodiment, the NRBAs of this invention may exhibit selective affinity for receptors that do not translocate to the cell nucleus. In some embodiments, the NRBAs of this invention may exhibit agonist activity. In some embodiments, the NRBAs of this invention may exhibit antagonist activity. In some embodiments, the NRBAs of this invention may exhibit agonist activity for a particular receptor, and antagonist activity for a different receptor, or vice versa, or in some embodiments, the NRBAs of this invention may exhibit agonist activity for a particular receptor under certain experimental conditions, yet exhibit antagonist activity for the same receptor under different experimental conditions, or vice versa, or in some embodiments, the NRBAs of this invention may exhibit agonist activity for a particular receptor in a particular tissue, yet exhibit antagonist activity for the same receptor in a different tissue, or vice versa, etc. It is to be understood that a single described activity for a NRBA this invention is not to be taken as limiting the compound to such activity/condition/tissue exclusively, but rather to represent an embodiment of one such activity for the indicated NRBA.

In some embodiments, the NRBAs of this invention may exhibit anti-proliferative activity.

In some embodiments, the NRBAs of this invention may exhibit anti-inflammatory activity.

In some embodiments, the NRBAs of this invention may exhibit anti-oxidant activity.

In some embodiments, the NRBAs of this invention may exhibit vasodilatory activity.

In some embodiments, the NRBAs of this invention may exhibit pro-differentiation activity.

ER-α and ER-β binding and agonist and antagonist activities, anti-proliferative and anti-inflammatory activities for representative NRBAs are exemplified hereinbelow, where such activity is described in the context of specific experimental conditions employed, representing only certain embodiments of this invention, and in no way to be taken to limiting the invention. It is to be understood that while the indicated compounds may exhibit a particular activity under certain experimental conditions employed, as a function, in some embodiments, of the particular cells utilized, etc., such compounds may possess alternate, varied, or partial activity in different experimental settings.

Steroid nuclear hormone receptors are known to have rapid, tissue-specific effects that are mediated by cell-surface and cytosolic receptors through protein-protein interaction or phosphorylation of kinases, which are known as non-genomic effects. For instance, NRBAs are known to have distinct rapid effects in the cardiovascular and central nervous systems which may be mediated by distinct receptors. Putative receptors for these non-genomic effects include a variety of G-protein coupled receptors (GPCRs) such as GPR130, as well as cell-membrane associated or cytosolic nuclear receptors. NRBAs of this invention may also bind to receptors involved in these non-genomic effects allowing differential pharmacological exploitation of genomic, non-genomic, and tissue-selective steroid receptor activities. As such these NRBAs may have a wide variety of specific and targeted steroid responses broadening their potential to have beneficial medical properties.

In some embodiments, a NRBA of this invention is a non-genomic agonist, or in some embodiments, a non-genomic antagonist, or in some embodiments, a non-genomic partial agonist of a nuclear receptor. In some embodiments, the NRBAs of this invention are tissue selective, non-genomic nuclear receptors, such as for example, estrogen or androgen receptor agonists, or in some embodiments, tissue selective, non-genomic nuclear receptor antagonists, or in some embodiments, tissue selective, non-genomic nuclear receptor partial agonists. In some embodiments, the NRBAs of this invention are non-selective non-genomic nuclear receptor agonists, such as for example, estrogen or androgen receptor agonists, or in some embodiments, non-selective non-genomic nuclear receptor antagonists, or in some embodiments, non-selective non-genomic nuclear receptor partial agonists. In some embodiments, the NRBAs of this invention are non-selective genomic nuclear receptor agonists, such as for example, estrogen or androgen receptor agonists, or in some embodiments, antagonists, or in some embodiments, partial agonists.

In some embodiments, the NRBAs of this invention are tissue selective genomic nuclear receptor modulators, such as for example, estrogen or androgen receptor agonists, or in some embodiments, antagonists, or in some embodiments, partial agonists. In some embodiments, the NRBAs of this invention are genomic agents which selectively transactivate nuclear receptor-regulated genes. In some embodiments, selective transactivation is in a tissue selective manner. In some embodiments, the NRBAs of this invention are genomic agents which selectively transrepress nuclear receptor-regulated genes. In some embodiments, selective tranrepression is in a tissue selective manner. In some embodiments, the NRBAs are dissociated in their ability to affect non-genomic process but not genomic processes, or vice versa. In some embodiments, NRBA's are dissociated in their ability to affect transactivation but not transrepression, or vice versa.

This invention provides, in other embodiments, pharmaceutical products of the NRBAs. The term "pharmaceutical product" refers, in other embodiments, to a composition suitable for pharmaceutical use (pharmaceutical composition), for example, as described herein.

The NRBAs useful in the compositions of the present invention may exist in prodrug form. As used herein, "prodrug" is intended to include any covalently bonded carriers which release the active parent drug according to Formula (I) or other formulas or compounds of the present invention in vivo when such prodrug is administered to a subject. Since prodrugs are known to enhance numerous desirable qualities of pharmaceuticals (e.g., solubility, bioavailability, manufacturing, etc.) the compounds useful in the compositions of the present invention may be delivered in prodrug form. Thus, the present invention includes compositions containing prodrugs of the disclosed compounds and methods of delivering the same. Prodrugs of a compound of the present invention may be prepared by modifying functional groups present in the compound in such a way that the modifications are cleaved, either in routine manipulation or in vivo, to the parent compound.

Accordingly, prodrugs include, for example, compounds of the present invention wherein a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, isopropyl, butyl, isobutyl, sec-butyl, tert-butyl, cyclopropyl, phenyl, benzyl, and phenethyl esters, and the like.

As known in the art, polymorphism is an ability of a compound to crystallize as more than one distinct crystalline or "polymorphic" species. As used herein a "polymorph" is a solid crystalline phase of a compound with at least two different arrangements or polymorphic forms of that compound molecule in the solid state. Polymorphic forms of any given compound are defined by the same chemical formula or composition and are as distinct in structure as crystals of two different chemical compounds.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 1 or more than 1 standard deviations, per the practice in the art. Alternatively, "about" can mean a range of up to 20%, up to 10% or up to 5% of a given value.

In one embodiment, this invention provides a method of binding any NRBA of this invention to an estrogen receptor or an estrogen related receptors, comprising the step of contacting an estrogen receptor with said NRBA. In another embodiment, this invention provides a method of binding any NRBA of this invention to a nuclear hormone receptor or one related thereto.

In one embodiment, this invention provides general and specific synthetic routes for embodiments of isoquinolinones and isoquinolin-6-ols.

Some embodiments of a synthetic procedure for some of the NRBAs are provided below:

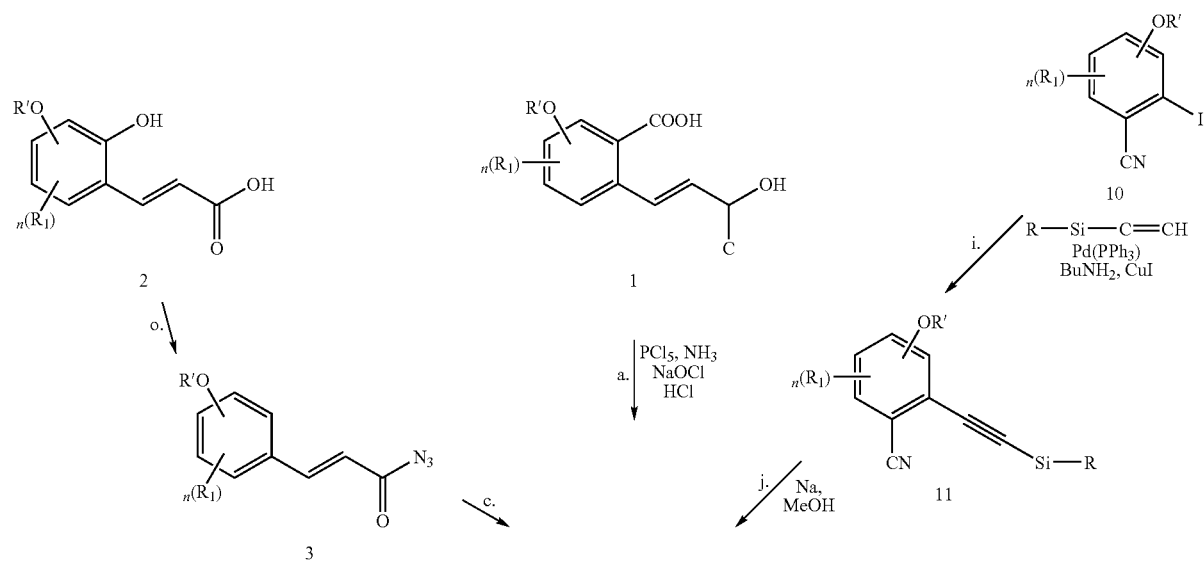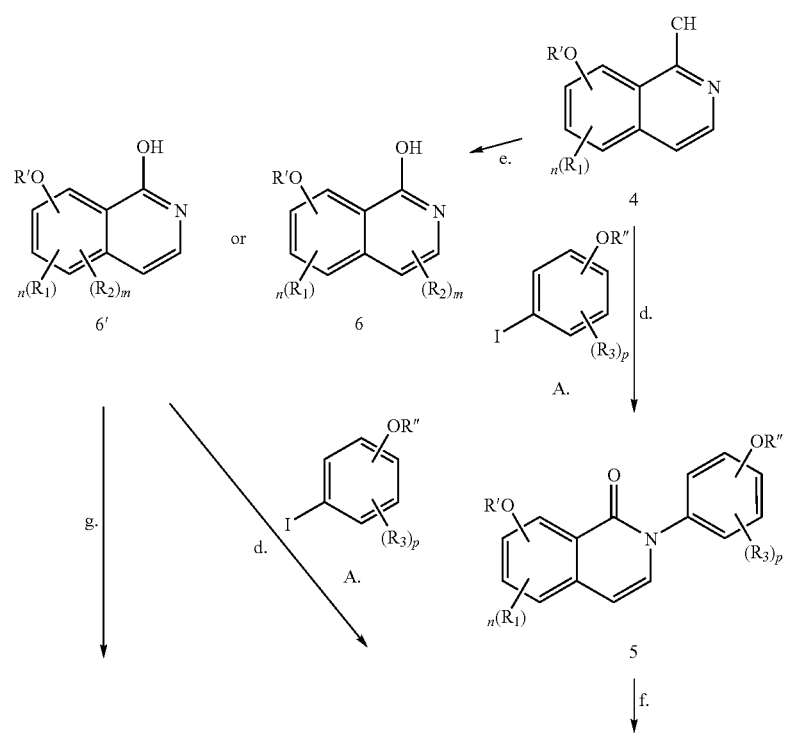

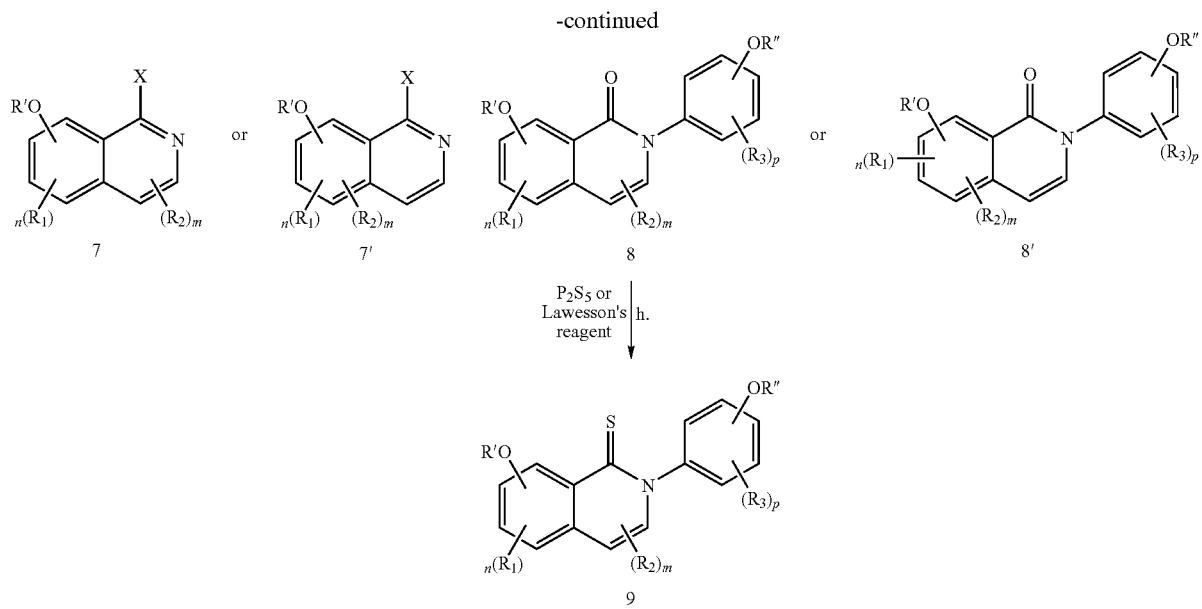

Intermediate compound 4 can be prepared by three different paths starting from 2-(2-carboxy-vinyl) benzoic acid (compound 1) via step a; or starting with 3-phenyl-acrylic acid, (compound 2) together with sodium azide (step b) to obtain an acyl derivative of compound 3, followed by Curtius rearrangement and a cyclization step (step c) in the presence of diphenyl ether and tributylamine at 230° C. to obtain compound 4; or starting with 2-iodo benzonitrile (compound 10) via the Sonogashira reaction (step i) followed by methanolysis (step j) to obtain compound 4.

Compound 4 is further coupled with an iodo substituted formula A (step d), yielding compound 5, which may be further brominated, chlorinated, or iodinated (using NBS, NCS, or NIS, respectively) followed by further substitutions to obtain the desired $R_2$ group (step f) compound 8 or compound 8', or obtain the sulfone compound 9 using $P_2S_5$ reagent (step h). Compounds 8 or 9 can be optionally demethylated with $BBr_3$ to yield the phenolic products, however if step h is executed, then the phenol must be protected.

Alternatively, compound 4 may be brominated, chlorinated, or iodinated (using NBS, NCS, or NIS, respectively) and further substituted (step e) to obtain the desired $R_2$ of compound 6 or 6'. Compound 6 or 6' may be coupled together with an iodo substituted formula A (step d), yielding compound 8 or 8', or the OH group of compound 6 or 6' is further substituted (step g) to obtain the desired X group of compound 7 or compound 7'.

In some embodiments this invention provides synthetic route for embodiments of 4-halogenated isoquinolinones. For example, one embodiment of a synthetic procedure for a compound of this invention, 4-bromo-6-hydroxy-2-(4-hydroxyphenyl)isoquinolin-1(2H)-one, is as follows:

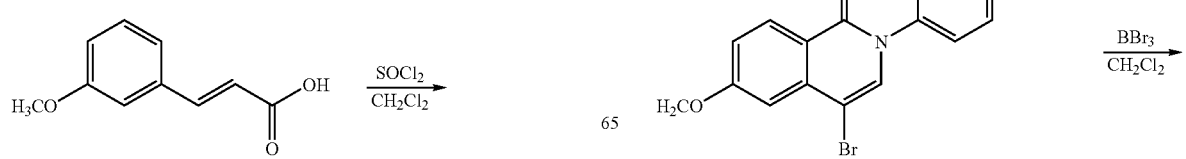

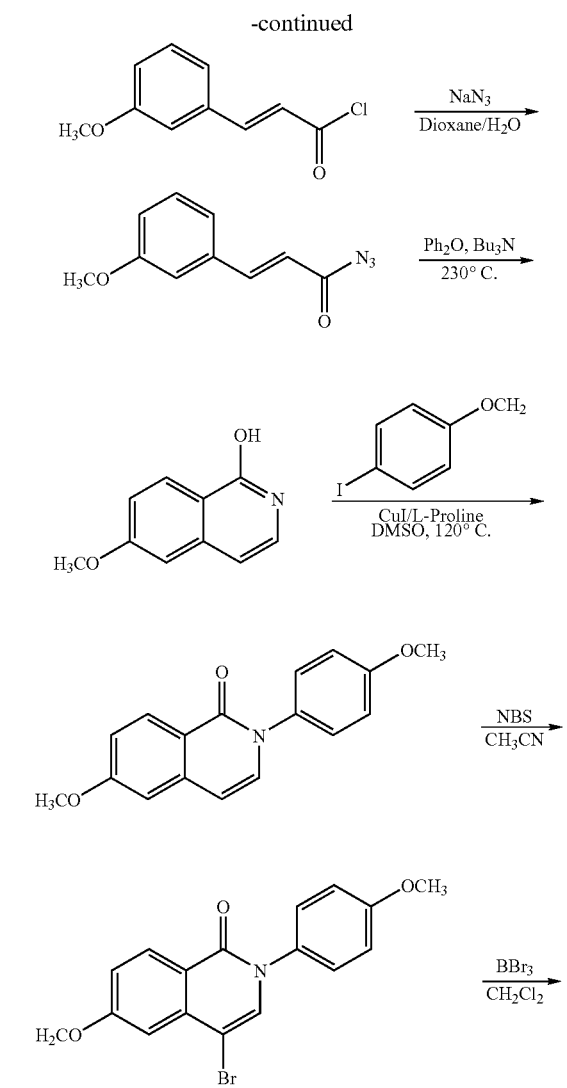

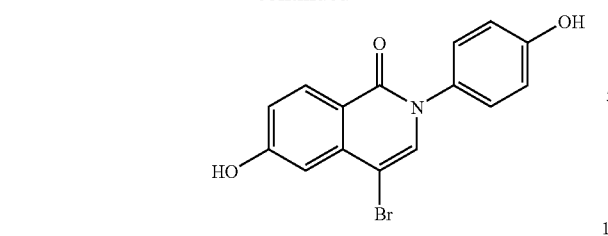

In some embodiments this invention provides synthetic route for embodiments of 6,8-dihydroxy-isoquinolinones. An example of these embodiments of this invention provides a synthetic route for 4-bromo-6, 8-dihydroxy-2-(4-hydroxyphenyl) isoquinolin-1(2H)-one (12u).

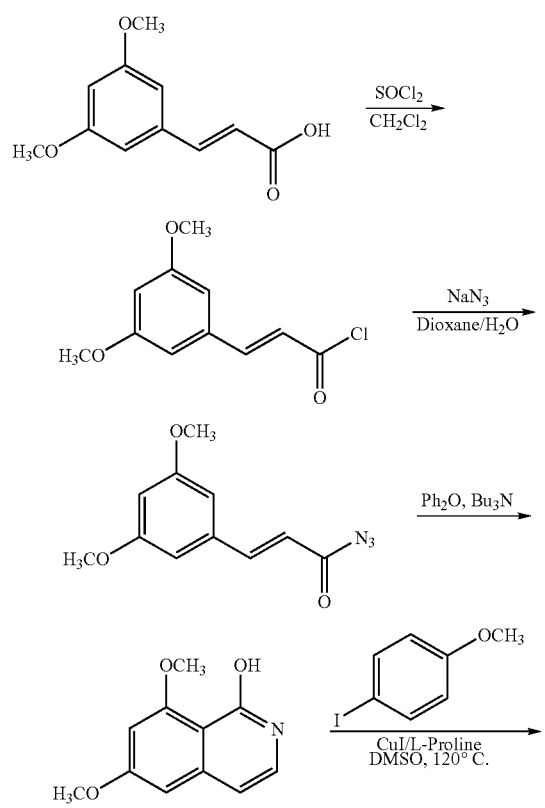

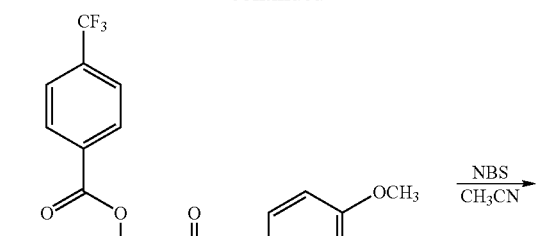

In some embodiments this invention provides synthetic route for embodiments of 4-alkenyl isoquinolinones. An example of these embodiments of this invention provides a synthetic route for 6-hydroxy-2-(4-hydroxyphenyl)-4-vinylisoquinolin-1(2H)-one (14f) compound.

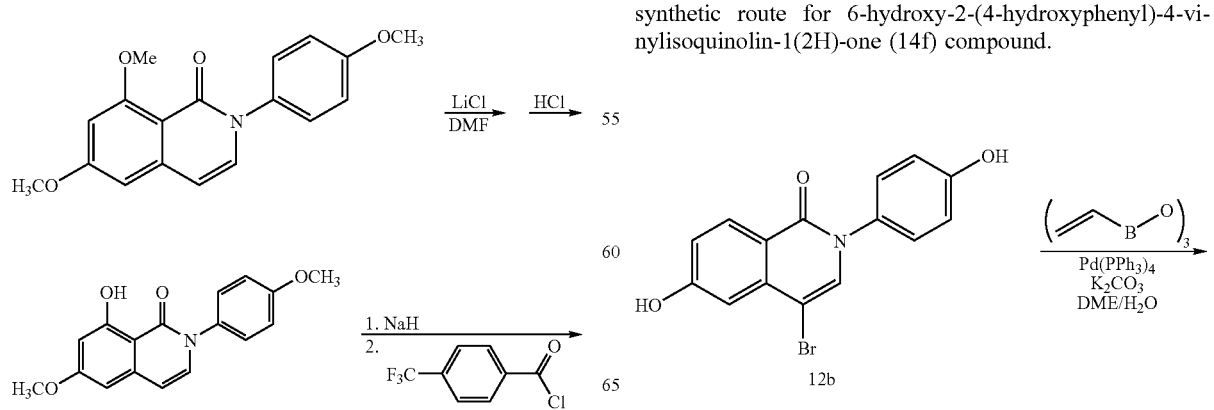

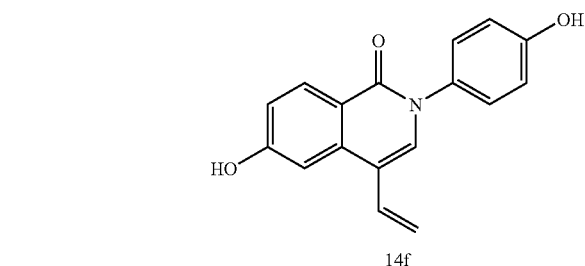

14f

In some embodiments this invention provides synthetic route for embodiments of 4-carbonitrile derivatives of 1-oxo-1,2-dihydroisoquinolines. For example, this invention provides synthetic routes for 6-hydroxy-2-(4-hydroxyphenyl)-1-oxo-1,2-dihydroisoquinoline-4-carbonitrile (14h).

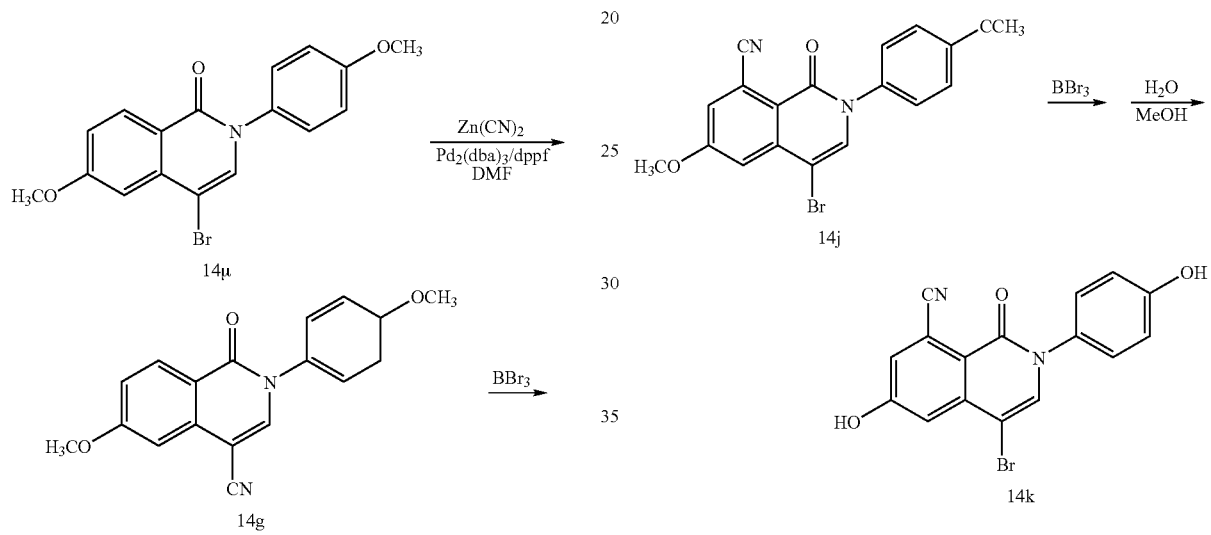

In some embodiments this invention provides synthetic route for embodiments of 8-carbonitrile derivatives of 1-oxo-1,2-dihydroisoquinolines. For example, this invention provides synthetic routes for 4-bromo-6-hydroxy-2-(4-hydroxyphenyl)-1-oxo-1,2-dihydroisoquinoline-8-carbonitrile (14k):

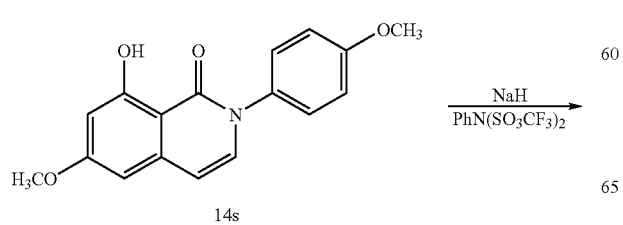

14s

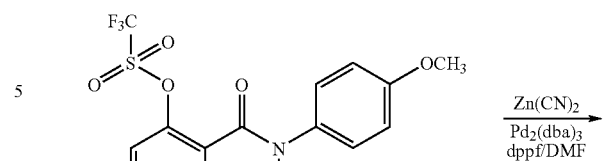

14d

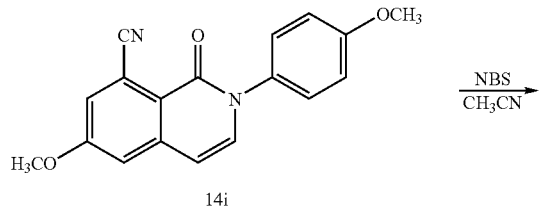

14i

In some embodiments this invention provides synthetic route for 14o compound

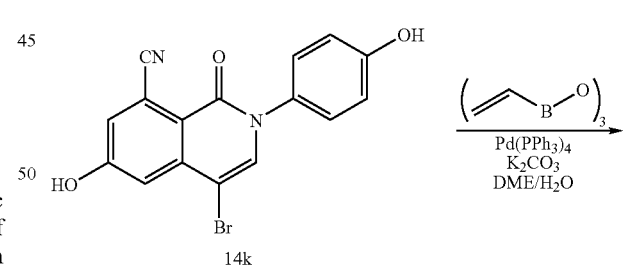

14o

In some embodiments this invention provides synthetic route for 14p compound

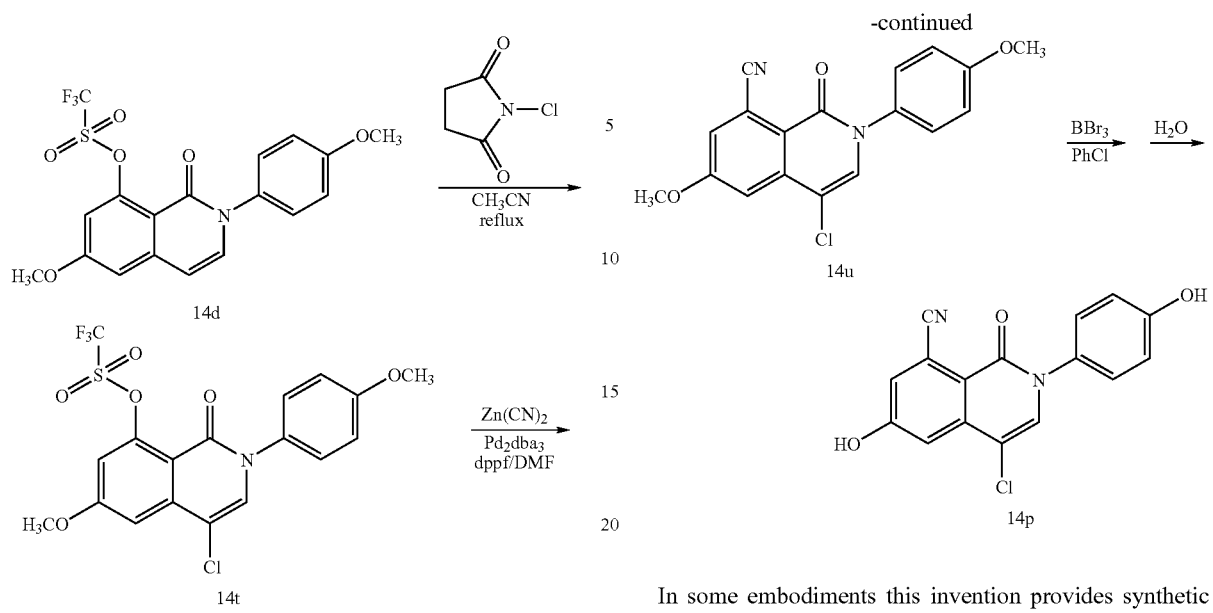
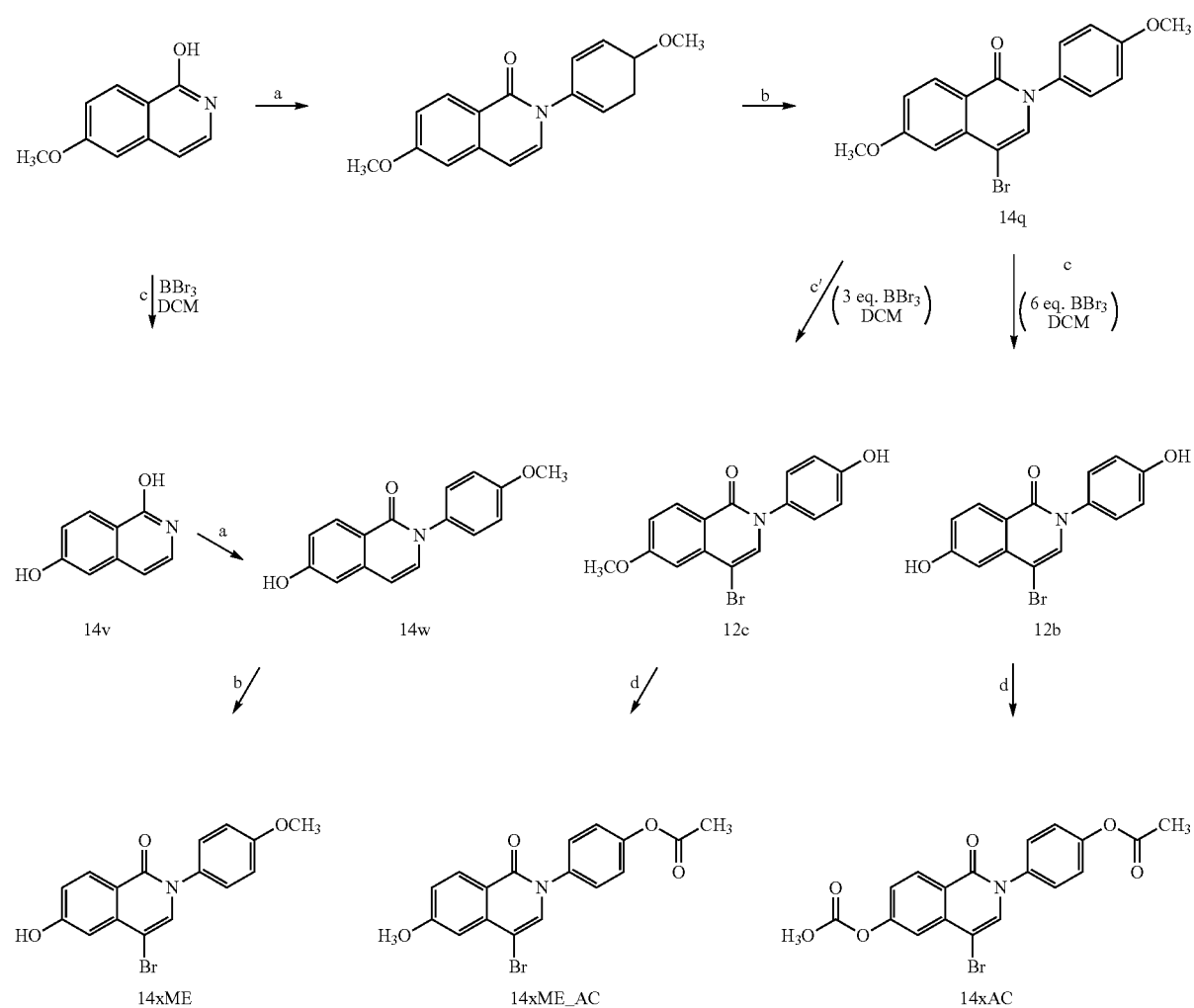
In some embodiments this invention provides synthetic routes for 14xME, 14xME_AC and 14xAC compounds.

In some embodiments this invention provides synthetic routes for 4-bromo-6-hydroxy-2-(4-hydroxyphenyl)-1-oxo-1,2-dihydroisoquinoline-8-carbimidic acid (14yAM), methyl 4-bromo-6-hydroxy-2-(4-hydroxyphenyl)-1-oxo-1,2-dihydroisoquinoline-8-carboxylate (14yME), and 4-bromo-6-hydroxy-2-(4-hydroxyphenyl)-1-oxo-1,2-dihydroisoquinoline-8-carboxylic acid (14z) compounds.
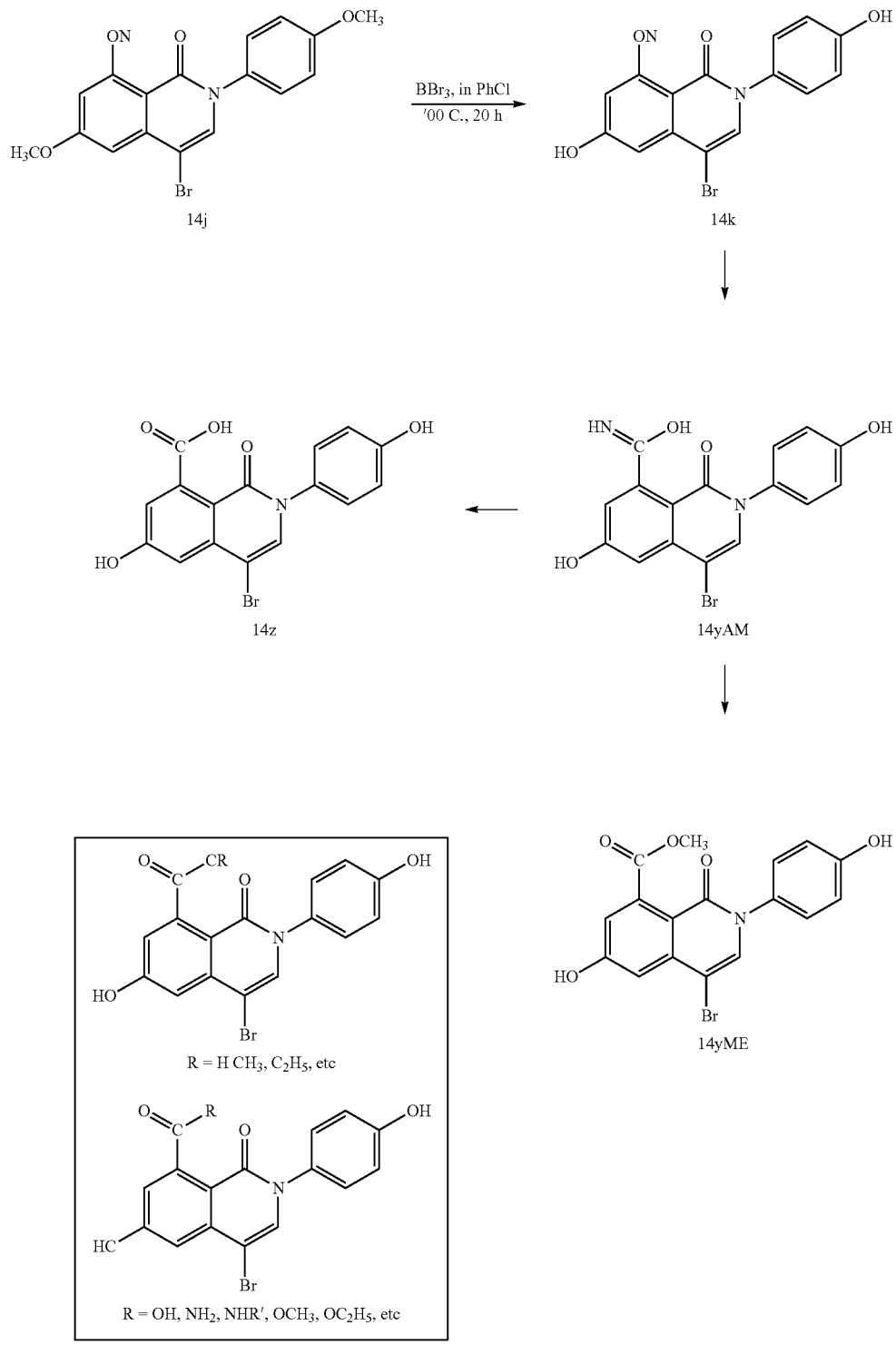

In some embodiments this invention provides synthetic routes for 6-hydroxy-2-(4-hydroxyphenyl)-4-phenylisoquinolin-1(2H)-one (15a).
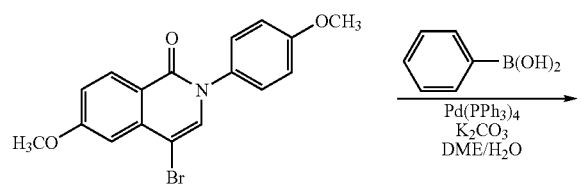
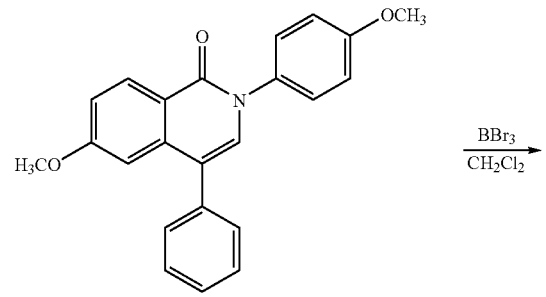
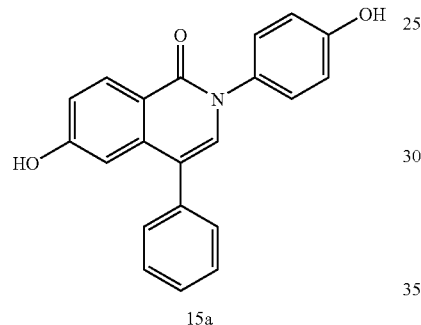
15a
In some embodiments the following compounds are synthesized via Suzuki coupling reactions as described for compound 15a.
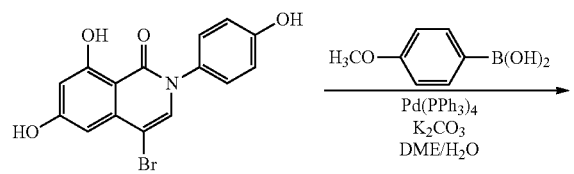
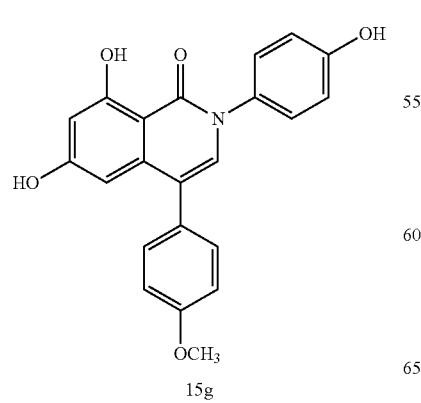
15g
-continued
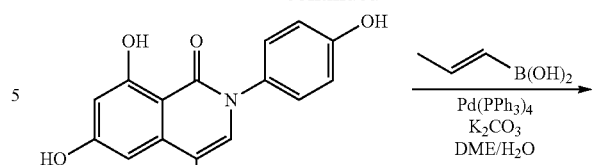
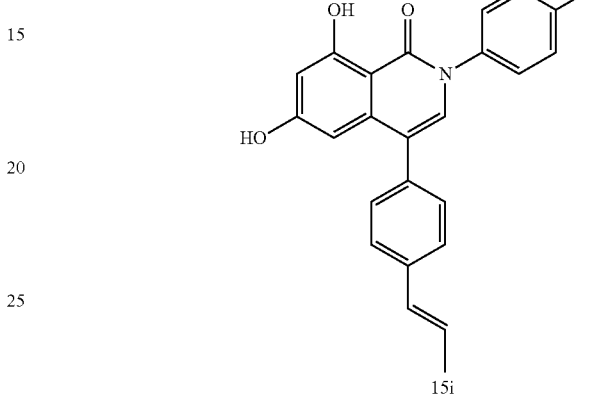
15i
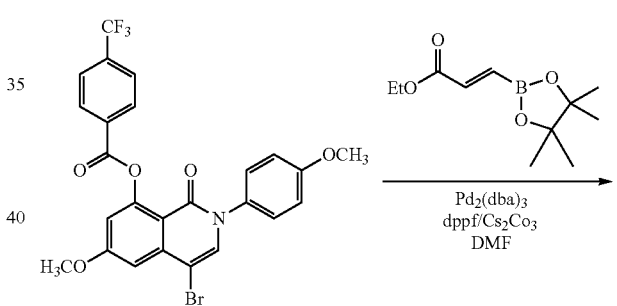
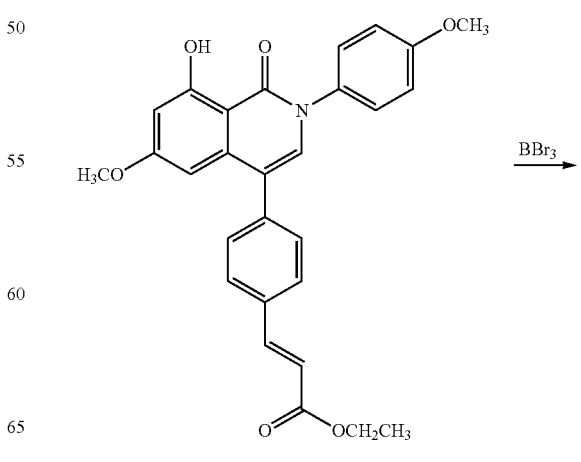

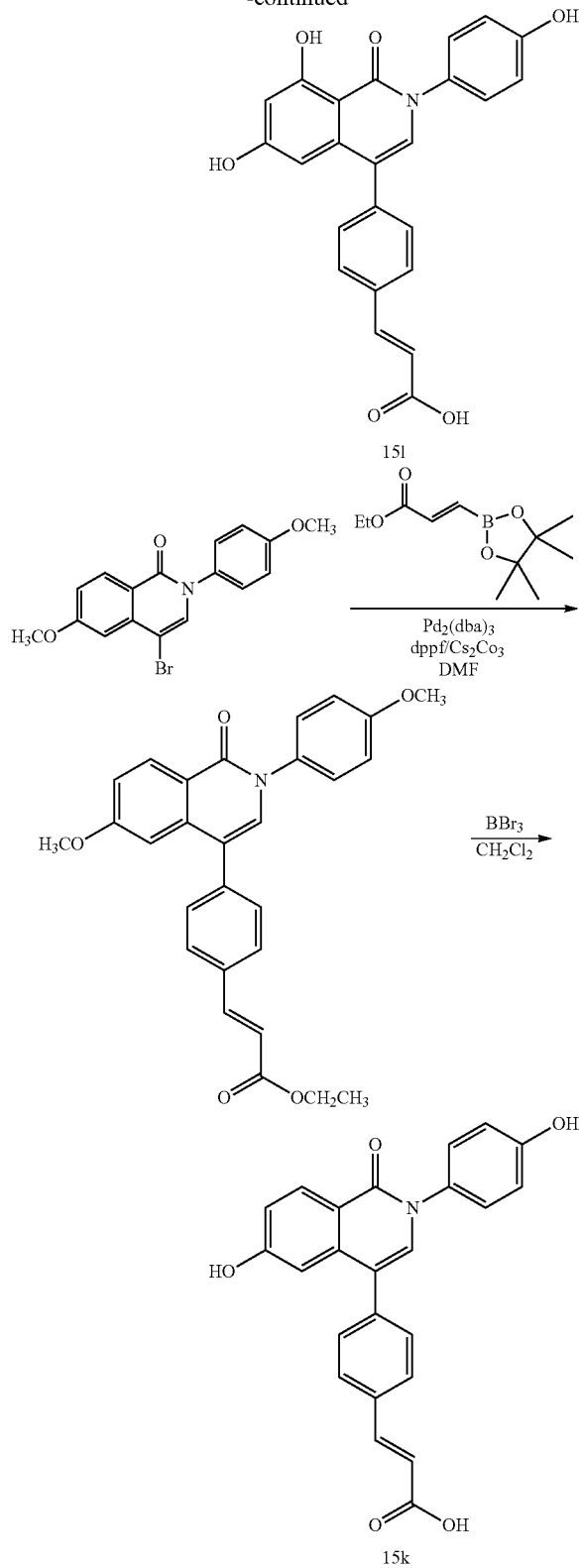

Pharmaceutical Compositions

In some embodiments, this invention provides methods of use which comprise administering a composition comprising the described compounds. As used herein, "pharmaceutical composition" means a "therapeutically effective amount" of the active ingredient, i.e. the compound of this invention, together with a pharmaceutically acceptable carrier or diluent. A "therapeutically effective amount" as used herein refers to that amount which provides a therapeutic effect for a given condition and administration regimen.

As used herein, the term "administering" refers to bringing a subject in contact with a compound of the present invention. As used herein, administration can be accomplished in vitro, i.e. in a test tube, or in vivo, i.e. in cells or tissues of living organisms, for example humans. In one embodiment, the present invention encompasses administering the compounds of the present invention to a subject.

The pharmaceutical compositions containing the compounds of this invention can be administered to a subject by any method known to a person skilled in the art, such as orally, parenterally, intravascularly, paracancerally, transmucosally, transdermally, intramuscularly, intranasally, intravenously, intradermally, subcutaneously, sublingually, intraperitoneally, intraventricularly, intracranially, intravaginally, by inhalation, rectally, intratumorally, or by any means in which the recombinant virus/composition can be delivered to tissue (e.g., needle or catheter). Alternatively, topical administration may be desired for application to mucosal cells, for skin or ocular application. Another method of administration is via aspiration or aerosol formulation.

In one embodiment, the pharmaceutical compositions are administered orally, and are thus formulated in a form suitable for oral administration, i.e. as a solid or a liquid preparation. Suitable solid oral formulations include tablets, capsules, pills, granules, pellets, powders, and the like. Suitable liquid oral formulations include solutions, suspensions, dispersions, emulsions, oils and the like. In one embodiment of the present invention, the compounds are formulated in a capsule. In accordance with this embodiment, the compositions of the present invention comprise in addition to a compound of this invention and the inert carrier or diluent, a hard gelatin capsule.

In one embodiment, the micronized capsules comprise particles containing a compound of this invention, wherein the term "micronized" used herein refers to particles having a particle size is of less than 200 microns, or in another embodiment less than 100 microns, or in another embodiment, less than 60 microns, or in another embodiment, less than 36 microns, or in another embodiment, less than 16 microns, or in another embodiment, less than 10 microns, or in another embodiment, less than 6 microns.

Further, in another embodiment, the pharmaceutical compositions are administered by intravenous, intraarterial, or intramuscular injection of a liquid preparation. Suitable liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intraarterially, and are thus formulated in a form suitable for intraarterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the compounds of this invention or their physiologically tolerated derivatives such as salts, esters, N-oxides, and the like are prepared and applied as solutions, suspensions, or emulsions in a physiologically acceptable diluent with or without a pharmaceutical carrier.

Further, in another embodiment, the pharmaceutical compositions are administered as a suppository, for example a rectal suppository or a urethral suppository. Further, in another embodiment, the pharmaceutical compositions are administered by subcutaneous implantation of a pellet. In a further embodiment, the pellet provides for controlled release of a compound as herein described over a period of time. In a further embodiment, the pharmaceutical compositions are administered intravaginally.

In another embodiment, the active compound can be delivered in a vesicle, in particular a liposome (see Langer, Science 249:1627-1633 (1990); Treat et al., in Liposomes in the Therapy of Infectious Disease and Cancer, Lopez-Berestein and Fidler (eds.), Liss, New York, pp. 363-366 (1989); Lopez-Berestein, ibid., pp. 317-327; see generally ibid).

As used herein "pharmaceutically acceptable carriers or diluents" are well known to those skilled in the art. The carrier or diluent may be a solid carrier or diluent for solid formulations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In one embodiment, the compositions of this invention may include, a compound of this invention or any combination thereof, together with one or more pharmaceutically acceptable excipients.

It is to be understood that this invention encompasses any embodiment of a compound as described herein, which in some embodiments is referred to as "a compound of this invention".

Suitable excipients and carriers may be, according to embodiments of the invention, solid or liquid and the type is generally chosen based on the type of administration being used. Liposomes may also be used to deliver the composition. Examples of suitable solid carriers include lactose, sucrose, gelatin and agar. Oral dosage forms may contain suitable binders, lubricants, diluents, disintegrating agents, coloring agents, flavoring agents, flow-inducing agents, and melting agents. Liquid dosage forms may contain, for example, suitable solvents, preservatives, emulsifying agents, suspending agents, diluents, sweeteners, thickeners, and melting agents. Parenteral and intravenous forms should also include minerals and other materials to make them compatible with the type of injection or delivery system chosen. Of course, other excipients may also be used.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, cyclodextrins, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sobitan esters, stearic acids), antioxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweetners (e.g. aspartame, citric acid), preservatives (e.g., Thimerosal, benzyl alcohol, parabens), coloring agents, lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates), and/or adjuvants.

In one embodiment, the pharmaceutical compositions provided herein are controlled release compositions, i.e. compositions in which the compound of this invention is released over a period of time after administration. Controlled or sustained release compositions include formulation in lipophilic depots (e.g. fatty acids, waxes, oils). In another embodiment, the composition is an immediate release composition, i.e. a composition in which all of the compound is released immediately after administration.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:607 (1980); Saudek et al., N. Engl. J. Med. 321:674 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 116-138 (1984). Other controlled release systems are discussed in the review by Langer (Science 249:1627-1633 (1990).

The compositions may also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The preparation of pharmaceutical compositions which contain an active component is well understood in the art, for example by mixing, granulating, or tablet-forming processes. The active therapeutic ingredient is often mixed with excipients which are pharmaceutically acceptable and compatible with the active ingredient. For oral administration, the compounds of this invention or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the compounds of this invention or their physiologically tolerated derivatives such as salts, esters, N-oxides, and the like are converted into a solution, suspension, or emulsion, if desired with the substances customary and suitable for this purpose, for example, solubilizers or other.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicine, the salts of the compound will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic: acid, oxalic acid, citric acid, tartaric acid, carbonic acid or phosphoric acid.

In one embodiment, this invention provides pharmaceutical compositions comprising a compound of this invention. In one embodiment, such compositions are useful for oral testosterone replacement therapy.

In one embodiment, this invention also provides a composition comprising two or more compounds of this invention, or polymorphs, isomers, hydrates, salts, N-oxides, etc., thereof. The present invention also relates to compositions and pharmaceutical compositions which comprise a compound of this invention alone or in combination with a progestin or estrogen, or in another embodiment, chemotherapeutic compound, osteogenic or myogenic compound, or other agents suitable for the applications as herein described. In one embodiment, the compositions of this invention will comprise a suitable carrier, diluent or salt.

In one embodiment, the methods of this invention may comprise administration of a compound of this invention at various dosages. In one embodiment, the compound of this invention is administered at a dosage of about 0.1 to about 2000 mg per day. In one embodiment, the compound of this invention is administered at a dosage of about 0.1 to about 10 mg, or in another embodiment, about 0.1 to about 25 mg, or in another embodiment, about 0.1 to about 60 mg, or in another embodiment, about 0.1 to about 200 mg, or in another embodiment, about 0.3 to about 15 mg, or in another embodiment, about 0.3 to about 30 mg, or in another embodiment, about 0.5 to about 25 mg, or in another embodiment, about 0.5 to about 60 mg, or in another embodiment, about 0.5 to about 15 mg, or in another embodiment, about 0.5 to about 60 mg, or in another embodiment, about 1 to about 5 mg, or in another embodiment, about 1 to about 20 mg, or in another embodiment, about 3 to about 15 mg, or in another embodiment, 30 to 60 mg, or in another embodiment, about 30 to 75 mg, or in another embodiment, about 100 to about 2000 mg.

In one embodiment, the methods of this invention may comprise administration of a compound of this invention at various dosages. In one embodiment, the compound of this invention is administered at a dosage of about 0.1 to about 2000 mg per day. In one embodiment, the compound of this invention is administered at a dosage of about 0.1 to about 10 mg per day, or in another embodiment, about 0.1 to about 25 mg per day, or in another embodiment, about 0.1 to about 60 mg per day, or in another embodiment, about 0.1 to about 200 mg per day, or in another embodiment, about 0.3 to about 15 mg per day, or in another embodiment, about 0.3 to about 30 mg per day, or in another embodiment, about 0.5 to about 25 mg per day, or in another embodiment, about 0.5 to about 60 mg per day, or in another embodiment, about 0.5 to about 15 mg per day, or in another embodiment, about 0.5 to about 60 mg per day, or in another embodiment, about 1 to about 5 mg per day, or in another embodiment, about 1 to about 20 mg per day, or in another embodiment, about 3 to about 15 mg per day, or in another embodiment, 30 to 60 mg per day, or in another embodiment, about 30 to 75 mg per day, or in another embodiment, about 100 to about 2000 mg per day, or in another embodiment, about 100 to about 500 mg per day.

In one embodiment, the compound of this invention is administered at a dosage of about 0.01 to about 200 mg per kg per day. In one embodiment, the compound of this invention is administered at a dosage of about 0.01 to about 10 mg per kg per day, or in another embodiment, about 0.01 to about 25 mg per kg per day, or in one embodiment, the compound of this invention is administered at a dosage of about 0.01 to about 50 mg per kg per day, or in another embodiment, about 0.01 to about 60 mg per kg per day or in another embodiment, about 0.03 to about 15 mg per kg per day, or in another embodiment, about 0.03 to about 30 mg per kg per day, or in another embodiment, about 0.05 to about 25 mg per kg per day, or in another embodiment, about 0.05 to about 60 mg per kg per day, or in another embodiment, about 30 mg per kg per day, or in another embodiment, about 20 mg per kg per day, or in another embodiment, about 15 mg per kg per day, or in another embodiment, about 10 mg per kg per day, or in another embodiment, about 5 mg per kg per day.

In one embodiment, the compound of this invention is administered at a dosage of about 1 mg. In another embodiment the compound of this invention is administered at a dosage of about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 150 mg or about 200 mg.

In one embodiment, the present invention provides methods of use comprising the administration of a pharmaceutical composition comprising a) any embodiment of a compound as described herein; and b) a pharmaceutically acceptable carrier or diluent; which is to be understood to include an analog, isomer, metabolite, derivative, pharmaceutically acceptable salt, N-oxide, hydrate or any combination thereof of a compound as herein described.

In some embodiments, the present invention provides methods of use of a pharmaceutical composition comprising a) any embodiment of the compounds as described herein, including an analog, isomer, metabolite, derivative, pharmaceutically acceptable salt, pharmaceutical product, N-oxide, hydrate thereof or any combination thereof; b) a pharmaceutically acceptable carrier or diluent; c) a flow-aid; and d) a lubricant.

In another embodiment, the present invention provides methods of use of a pharmaceutical composition comprising a) any embodiment of the compounds as described herein, including an analog, isomer, metabolite, derivative, pharmaceutically acceptable salt, pharmaceutical product, N-oxide, hydrate thereof or any combination thereof; b) lactose monohydrate; c) microcrystalline cellulose; d) magnesium stearate; and e) colloidal silicon dioxide.

In some embodiments, the methods of this invention make use of compositions comprising compounds of this invention, which offer the advantage that the compounds are nonsteroidal ligands for the estrogen receptor, and exhibit estrogenic activity in vivo. According to this aspect, such compounds are unaccompanied by serious side effects, provide convenient modes of administration, and lower production costs and are orally bioavailable, lack significant cross-reactivity with other undesired steroid receptors, and may possess long biological half-lives.

For administration to mammals, and particularly humans, it is expected that the physician will determine the actual dosage and duration of treatment, which will be most suitable for an individual and can vary with the age, weight and response of the particular individual.

In one embodiment, the compositions for administration may be sterile solutions, or in other embodiments, aqueous or non-aqueous, suspensions or emulsions. In one embodiment, the compositions may comprise propylene glycol, polyethylene glycol, injectable organic esters, for example ethyl oleate, or cyclodextrins. In another embodiment, compositions may also comprise wetting, emulsifying and/or dispersing agents. In another embodiment, the compositions may also comprise sterile water or any other sterile injectable medium.

In one embodiment, the invention provides compounds and compositions, including any embodiment described herein, for use in any of the methods of this invention, as described herein. In one embodiment, use of a compound of this invention or a composition comprising the same, will have utility in inhibiting, suppressing, enhancing or stimulating a desired response in a subject, as will be understood by one skilled in the art. In another embodiment, the compositions may further comprise additional active ingredients, whose activity is useful for the particular application for which the compound of this invention is being administered.

In some embodiments, the methods of this invention make use of compositions comprising compounds of this invention, which offer the advantage that the compounds are nonsteroidal ligands for the estrogen receptor, and exhibit estrogenic activity in vivo. According to this aspect, such compounds are unaccompanied by serious side effects, provide convenient modes of administration, and lower production costs and are orally bioavailable, lack significant cross-reactivity with other undesired steroid receptors, and may possess long biological half-lives.

For administration to mammals, and particularly humans, it is expected that the physician will determine the actual dosage and duration of treatment, which will be most suitable for an individual and can vary with the age, weight and response of the particular individual.

In one embodiment, the compositions for administration may be sterile solutions, or in other embodiments, aqueous or non-aqueous, suspensions or emulsions. In one embodiment, the compositions may comprise propylene glycol, polyethylene glycol, injectable organic esters, for example ethyl oleate, or cyclodextrins. In another embodiment, compositions may also comprise wetting, emulsifying and/or dispersing agents. In another embodiment, the compositions may also comprise sterile water or any other sterile injectable medium.

In one embodiment, the invention provides compounds and compositions, including any embodiment described herein, for use in any of the methods of this invention. In one embodiment, use of a compound of this invention or a composition comprising the same, will have utility in inhibiting, suppressing, enhancing or stimulating a desired response in a subject, as will be understood by one skilled in the art. In another embodiment, the compositions may further comprise additional active ingredients, whose activity is useful for the particular application for which the compound of this invention is being administered.

The invention contemplates, in some embodiments, administration of compositions comprising the individual agents, administered separately and by similar or alternative routes, formulated as appropriately for the route of administration. The invention contemplates, in some embodiments, administration of compositions comprising the individual agents, administered in the same formulation. The invention contemplates, in some embodiments, staggered administration, concurrent administration, of administration of the various agents over a course of time, however, their effects are synergistic in the subject.

It is to be understood that any of the above means, timings, routes, or combinations thereof, of administration of two or more agents is to be considered as being encompassed by the phrase "administered in combination", as described herein.

In one embodiment, bone turnover markers have been demonstrated as an effective, validated tool for the clinical scientist to monitor hone activity. In another embodiment, urinary hydroxyproline, serum alkaline phosphatase, tartrate-resistant acid phosphatase, and osteocalcin levels, along with the urinary calcium-creatinine ratio are used as bone turnover markers. In another embodiment osteocalcin levels is used as a bone formation marker. In another embodiment c-telopeptide is used as a bone resorption marker.

In one embodiment, this invention provides for the treatment, prevention, suppression or inhibition of, or the reduction of the risk of developing a skeletal-related event (SRE), such as bone fractures, surgery of the bone, radiation of the bone, spinal cord compression, new bone metastasis, bone loss, or a combination thereof in a subject with cancer, comprising administering to the subject a compound of this invention and/or its analog, derivative, isomer, metabolite, pharmaceutically acceptable salt, pharmaceutical product, hydrate, N-oxide, or any combination thereof. The invention relates, inter alia to treatment of an SRE with the compound of this invention in a subject with prostate cancer undergoing or having undergone androgen deprivation therapy (ADT).

In one embodiment, the skeletal-related events treated using the methods provided herein and/or utilizing the compositions provided herein, are fractures, which in one embodiment, are pathological fractures, non-traumatic fractures, vertebral fracture, non-vertebral fractures, morphometric fractures, or a combination thereof.

In another embodiment, the methods and/or compositions provided herein, are effective in treatment, prevention, suppression, inhibition or reduction of the risk of skeletal-related events such as pathologic fractures, spinal cord compression, hypercalcemia, bone-related pain, or their combination.

In another embodiment, the skeletal-related events sought to be treated using the methods provided herein and/or utilizing the compositions provided herein, comprise the necessity for bone surgery and/or bone radiation, which in some embodiments, is for the treatment of pain resulting in one embodiment from bone damage, or nerve compression. In another embodiment, the skeletal-related events sought to be treated using the methods provided herein and/or utilizing the compositions provided herein, comprise spinal cord compression, or the necessity for changes in antineoplastic therapy, including changes in hormonal therapy, in a subject. In some embodiments, skeletal-related events sought to be treated using the methods provided herein and/or utilizing the compositions provided herein, comprise treating, suppressing, preventing, reducing the incidence of, or delaying progression or severity of bone metastases, or bone loss. In one embodiment, bone loss may comprise osteoporosis, osteopenia, or a combination thereof. In one embodiment, skeletal-related events may comprise any combination of the embodiments listed herein.

In one embodiment, the methods provided herein and/or utilizing the compositions provided herein, are effective in reducing metastases to the hone, such as in terms of number of foci, the size of foci, or a combination thereof. According to this aspect of the invention and in one embodiment, provided herein is a method of preventing or inhibiting cancer metastasis to bone in a subject, comprising the step of administering to the subject a composition comprising toremifene, raloxifene, tamoxifen or an analogue, functional derivative, metabolite or a combination thereof, or a pharmaceutically acceptable salt thereof. In one embodiment, such metabolites may comprise ospemifene, fispemifene or their combination. In one embodiment, the cancer is prostate cancer.

A person skilled in the art would readily recognize that changes in the antineoplastic therapy according to the methods provided herein, utilizing the compositions provided herein may be conducted as a function of, or adjusted or varied as a function of, inter-alia, the severity of the underlying disease, the source of the underlying disease, the extent of the patients' pain and source of the patients' pain, as well as the stage of the disease. The therapeutic changes may include in certain embodiments, changes in the route of administration (e.g. intracavitarily, intraartierly, intratumorally etc.), forms of the compositions administered (e.g. tablets, elixirs, suspensions etc.), changes in dosage and the like. Each of these changes are well recognized in the art and are encompassed by the embodiments provided herein.

In one embodiment, the skeletal-related events are a result of cancer therapy. In one embodiment, the skeletal-related events are a result of hormone deprivation therapy, while in another embodiment; they are a product of ADT.

In one embodiment, the compounds of this invention are useful in prevention or reversal of ADT induced side effects such as reduced muscle mass, reduced muscle strength, frailty, hypogonadism, osteoporosis, osteopenia, decreased BMD and/or decreased bone mass.

In males, while the natural decline in sex-hormones at maturity (direct decline in androgens as well as lower levels of estrogens derived from peripheral aromatization of androgens) is associated with the frailty of bones, this effect is more pronounced in males who have undergone androgen deprivation therapy.

In one embodiment, the compound is administered in combination with an antidiabetic agent. In one embodiment, the antidiabetic agent is a sulfonylurea. In one embodiment, sulfonylureas include but are not limited to tolbutamide, acetohexamide, tolazamide, chlorpropamide, glipizide, glyburide, glimepiride, or gliclazide. In one embodiment, the antidiabetic agent is a meglitinide. In one embodiment, meglitinides include but are not limited to prandin or nateglinide. In one embodiment, the antidiabetic agent is a biguanide. In one embodiment, biguanides include but are not limited to metformin. In one embodiment, the antidiabetic agent is a thiazolidinedione. In one embodiment, thiazolidinediones include but are not limited to rosiglitazone, pioglitazone, or troglitazone. In one embodiment, the antidiabetic agent is an alpha glucosidase inhibitor. In one embodiment, alpha glucosidase inhibitors include but are not limited to miglitol or acarbose. In one embodiment, the antidiabetic agent is PPARα/γ ligand, dipeptidylpeptidase 4 (DPP-4) inhibitor, SGLT (sodium-dependent glucose transporter 1) inhibitor, or FBPase (fructose 1,6-bisphosphatase) inhibitor. In one embodiment, the antidiabetic agent is insulin. In one embodiment, the insulin is rapid-acting insulin. In one embodiment, the insulin is short-acting insulin. In one embodiment, the insulin is intermediate-acting insulin. In one embodiment, the insulin is intermediate- and short-acting insulin mixtures. In one embodiment, the insulin is long-acting insulin. In one embodiment, the antidiabetic agents are inhibitors of fatty acid binding protein (aP2) such as those disclosed in U.S. Ser. No. 09/519,079 filed Mar. 6, 2000, glucagon-like peptide-1 (GLP-1), and dipeptidyl peptidase IV (DPP4) inhibitors such as those disclosed in WO 0168603, which are incorporated by reference.

In one embodiment, the compound is administered in combination with an agent treating the cardiovascular system. In one embodiment, the agent treating the cardiovascular system is a hypercholesterolemic agent such as niacin-lovastatin, colestipol HCl, fluvastatin sodium, atorvastatin calcium, simvastatin, gemfibrozil, lovastatin, pravastatin sodium, cholestyramine, cholestyramine light, fenofibrate, colesevelam HCl, or ezetimibe.

In one embodiment, the compound of this invention is administered in combination with an agent treating a metabolic disease, disorder or condition, which in some embodiments refers to metabolic syndrome.

In some embodiments, agents treating a metabolic disease include but are not limited to a vitamin, Coenzyme Q10, glucosidase alfa, sodium bicarbonate, bisphosphonate, biotin, allopurinol, levodopa, diazepam, phenobarbital, haloperidol, folic acid, antioxidants, activators of cation channels haptoglobin, or carnitine.

In some embodiments, such agents comprise, inter alia, pancreatic lipase inhibitors, such as for example, orlistat, cetilistat, serotonin and norepinephrine reuptake inhibitors, such as sibutramine, insulin-sensitizers such as biguanides (metformin) or PPAR agonists, dual-acting PPAR agonists (muraglitazar, tesaglitazar, naveglitazar). PPAR-delta agonists (GW-501516), DPP-IV inhibitors (vildagliptin, sitagliptin), alpha glucosidase inhibitors (acarbose), anti-diabetic combinations (ActoPlusMet, AvandaMet, metformin/pioglitazone, metformin/rosiglitazone, Glucovance, etc.), glucagon-like peptide-1 analogues (exenatide, liraglutide), amylin analogues (pramlintide), statins (atorvastatin, simvastatin, rosuvastatin, pravastatin, fluvastatin, lovastatin, pitavastatin), cholesterol absorption inhibitors (ezetimibe), nicotinic acid derivatives (immediate release and controlled release niacins, niaslo, etc.), antidyslipidemic fixed combinations (simvastatin/ezetimibe, lovastatin/nicotinic acid, atorvastatin/amlodipine, atorvastatin/torcetrapib, simvastatin/nicotinic acid (ER), ACE inhibitors (ramipril, captopril, lisinopril), AT-II receptor antagonists (valsartan, telmisartan), cannabinoid receptor antagonists (rimonabant), cholesteryl ester transfer protein or CETP Inhibitors (JTT-705, CETi-1), beta3 adrenergic agonists, PPARα ligands, or combinations thereof.

In one embodiment, the compound is administered in combination with an agent treating the liver. In one embodiment, the agent treating the liver is cortisone, cortisol or corticosterone. In some embodiments, the agent treating the liver is colchicine, methotrexate, ursodeoxycholic acid, or penicillamine.

In one embodiment, the compound is administered in combination with a statin. In some embodiment, statins include but are not limited to atorvastatin, fluvastatin, lovastatin, pravastatin, simvastatin, or rosuvastatin.

In one embodiment, the compound is administered in combination with a bile acid sequestrant.

In some embodiment, bile acid sequestrants include but are not limited to cholestyramine, colestipol, or colesevelam.

In one embodiment, the compound is administered in combination with a cholesterol absorption inhibitor. In some embodiment, cholesterol absorption inhibitors include but are not limited to ezetimibe.

In one embodiment, the compound is administered in combination with a nicotinic acid agent. In some embodiments, nicotinic acid agents include but are not limited to niacin, niacor, or slo-niacin.

In one embodiment, the compound is administered in combination with a fibrate. In some embodiments, fibrates include but are not limited to gemfibrozil, or fenofibrate.

In one embodiment, the compound is administered in combination with an agent treating the endocrine system. In one embodiment, the agent treating the endocrine system is a SARM compound. In some embodiments, SARMs include but are not limited to RU-58642, RU-56279, WS9761 A and B, RU-59063, RU-58841, bexlosteride, LG-2293, L-245976, LG-121071, LG-121091, LG-121104, LGD-2226, LGD-2941, LGD-3303, YM-92088, YM-175735, LGD-1331, BMS-357597, BMS-391197, S-40503, BMS-482404, EM-4283, EM-4977, BMS-564929, BMS-391197, BMS-434588, BMS-487745, BMS-501949, SA-766, YM-92088, YM-580, LG-123303, LG-123129, PMCol, YM-175735, BMS-591305, BMS-591309, BMS-665139, BMS-665539, CE-590, 116BG33, 154BG31, arcarine, or ACP-105.

In one embodiment, the agent treating the endocrine system includes but is not limited to tamoxifen, 4-hydroxytamoxifen, idoxifene, toremifene, ospemifene, droloxifene, raloxifene, arzoxifene, bazedoxifene, PPT (1,3,5-tris (4-hydroxyphenyl)-4-propyl-1H-pyrazole), DPN, lasofoxifene, pipendoxifene, EM-800, EM-652, nafoxidine, zindoxifene, tesmilifene, miproxifene phosphate, RU 58,688, EM 139, ICI 164,384, ICI 182,780, clomiphene, MER-25, diethylstibestrol, coumestrol, genistein, GW5638, LY353581, zuclomiphene, enclomiphene, delmadinone acetate, DPPE, (N,N-diethyl-2-{4-(phenylmethyl)-phenoxy}ethanamine), TSE-424, WAY-070, WAY-292, WAY-818, cyclocommunol, prinaberel, ERB-041, WAY-397, WAY-244, ERB-196, WAY-169122, MF-101, ERb-002, ERB-037, ERB-017, BE-1060, BE-380, BE-381, WAY-358, [18F]FEDNP, LSN-500307, AA-102, Ban zhi lian, CT-101, CT-102, or VG-101.

In one embodiment, the agent treating the endocrine system is a gonadotropin-releasing hormone agonist or antagonist. In some embodiments, gonadotropin-releasing hormone agonists or antagonists include but are not limited to leuprolide, goserelin, triptorelin, alfaprostol, histrelin, detirelix, ganirelix, antide iturelix, cetrorelix, ramorelix, ganirelix, antarelix, teverelix, abarelix, ozarelix, sufugolix, prazarelix, degarelix, NBI-56418, TAK-810, or acyline.

In one embodiment, the agent treating the endocrine system is a steroidal or nonsteroidal glucocorticoid receptor ligand. In some embodiments, nonsteroidal glucocorticoid receptor ligands include but are not limited to ZK-216348, ZK-243149, ZK-243185, LGD-5552, mifepristone, RPR-106541, ORG-34517, GW-215864X, Sesquicillin, CP-472555, CP-394531, A-222977, AL-438, A-216054, A-276575, CP-394531, CP-409069, or UGR-07.

In one embodiment, the agent treating the endocrine system is a steroidal or non-steroidal progesterone receptor ligand. In one embodiment, the agent treating the endocrine system is a steroidal or nonsteroidal androgen receptor antagonist. In some embodiments, steroidal or nonsteroidal androgen receptor antagonists include but are not limited to flutamide, hydroxyflutamide, bicalutamide, nilutamide, or hydroxysteroid dehydrogenase inhibitor.

In one embodiment, the agent treating the endocrine system is a peroxisome proliferator-activated receptor ligand. In some embodiments, peroxisome proliferator-activated receptor ligands include but are not limited to bezafibrate, fenofibrate, gemfibrozil, darglitazone, pioglitazone, rosiglitazone, isaglitazone, rivoglitazone, netoglitazone, naveglitazar, farglitazar, tesaglitazar, ragaglitazar, oxeglitazar, or PN-2034.

In some embodiments, any of the compositions of this invention will comprise a compound of this invention, in any form or embodiment as described herein. In some embodiments, any of the compositions of this invention will comprise a compound of formula 12u, 14m, 12z or 12y listed in Table 1 of this invention, in any form or embodiment as described herein. In some embodiments, any of the compositions of this invention will consist of a compound of this invention, in any form or embodiment as described herein. In some embodiments, any of the compositions of this invention will consist of a compound of formula 12u, 14m, 12z or 12y listed in Table 1 of this invention, in any form or embodiment as described herein. In some embodiments, of the compositions of this invention will consist essentially of a compound of this invention, in any form or embodiment as described herein. In some embodiments, of the compositions of this invention will consist essentially of a compound of formula 12u, 14m, 12z or 12y listed in Table 1 of this invention, in any form or embodiment as described herein.

In some embodiments, the term "comprise" refers to the inclusion of the indicated active agent, such as the compound of this invention, as well as inclusion of other active agents, and pharmaceutically acceptable carriers, excipients, emollients, stabilizers, etc., as are known in the pharmaceutical industry.

In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

In one embodiment, the present invention provides combined preparations. In one embodiment, the term "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

Biological Activity of NRBA Compounds

It is to be understood that this invention is directed to compositions and combined therapies as described herein, for any disease, disorder or condition, as appropriate, as will be appreciated by one skilled in the art. Certain applications of such compositions and combined therapies have been described hereinabove, for specific diseases, disorders and conditions, representing embodiments of this invention, and methods of treating such diseases, disorders and conditions in a subject by administering a compound as herein described, or compounds 12u, 14m, 12z, or 12y listed in Table 1, alone or as part of the combined therapy or using the compositions of this invention represent additional embodiments of this invention.

In one embodiment, this invention provides: a) a method of treating a condition associated with high fat diet consumption; b) a method of preventing a condition associated with high fat diet consumption; c) a method of treating a condition associated with post-menopausal obesity; d) a method of preventing a condition associated with post-menopausal obesity; e) a method of increasing energy expenditure in a subject; f) a method of increasing lean body mass; g) a method of treating a metabolic disorder; h) a method of increasing muscle weight; comprising the step of administering to said subject a compound of this invention and/or an analog, derivative, isomer, metabolite, pharmaceutically acceptable salt, pharmaceutical product, hydrate, N-oxide, prodrug, polymorph, impurity or crystal of said compound, or any combination thereof. In another embodiment, a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In one embodiment, "high fat diet" (HFD) refers to a diet that includes more than 10% fat. In another embodiment "high fat diet" (HFD) refers to a diet that includes more than 20% fat. In another embodiment "high fat diet" (HFD) refers to a diet that includes between 10-20% fat. In another embodiment "high fat diet" (HFD) refers to a diet that includes more than 30% fat. In another embodiment "high fat diet" (HFD) refers to a diet that includes between 10-30% fat. In another embodiment "high fat diet" (HFD) refers to a diet that includes between 10-15% fat. In another embodiment "high fat diet" (HFD) refers to a diet that includes between 20-40% fat. In another embodiment "high fat diet" (HFD) refers to a diet that includes more than 30% fat. In another embodiment "high fat diet" (HFD) refers to a diet that includes between 30-60% fat. In another embodiment "high fat diet" (HFD) refers to a diet that includes between 30-40% fat. In another embodiment "high fat diet" (HFD) refers to a diet that includes between 40-50% fat. In another embodiment "high fat diet" (HFD) refers to a diet that includes between 50-60% fat. In another embodiment "high fat diet" (HFD) refers to a diet that includes between 60-70% fat. In another embodiment "high fat diet" (HFD) refers to a diet that includes protein (23.5%), carbohydrates (27.3%) and fat (34.3%), with a digestible energy of 5.1 Kcal/g.

In one embodiment, "normal diet" (N.D) refers to a diet that includes less than 10% fat. In one embodiment, "normal diet" (N.D) refers to a diet that includes less than 30% fat. In another embodiment, "normal diet" (N.D) refers to a diet that includes protein (16.7%), carbohydrates (56%) and fat (4.2%), with a digestible energy of 3.3 Kcal/g. In another embodiment, "normal diet" refers to a diet that includes 10-30% fat. In another embodiment, "normal diet" refers to a diet that includes 30-50% fat. In another embodiment, "normal diet" refers to a diet that includes 40-50% fat. In another embodiment, "normal diet" is a "high fat diet".

In one embodiment, "obesity" refers to a medical condition in which excess body fat has accumulated to the extent that it may have an adverse effect on health, leading to increased health problems. In another embodiment, "obesity" refers to a weight increase, which is at least 5% of the total body weight.

"Postmenopausal obesity" refers to body weight gain of a subject after menopause that is not induced by a diet. Postmenopausal obesity emanates due to reduced circulating estrogens and lost repression on adipose tissue proliferation and adipokine synthesis.

"Visceral obesity" refers to a form of obesity due to excessive deposition of fat in the abdominal viscera and omentum, rather than subcutaneously, associated with dyslipidemia (increased plasma triglyceride, low high-density lipoprotein cholesterol).

"Visceral obesity at andropause" refers to a body weight gain that accompanies androgen deficiency in aging men.

In one embodiment, the methods of this invention are useful for a subject, which is a human. In another embodiment, the subject is a mammal. In another embodiment the subject is an animal. In another embodiment the subject is an invertebrate. In another embodiment the subject is a vertebrate.

In one embodiment, the subject is male. In another embodiment, the subject is female. In some embodiments, while the methods as described herein may be useful for treating either males or females, females may respond more advantageously to administration of certain compounds, for certain methods, as described and exemplified herein.

In some embodiments, while the methods as described herein may be useful for treating either males or females, males may respond more advantageously to administration of certain compounds, for certain methods, as described herein.

In other embodiments, the invention provides methods comprising administering a therapeutically effective amount of an estrogen receptor ligand compound as described herein or its prodrug, analog, isomer, metabolite, derivative, pharmaceutically acceptable salt, pharmaceutical product, polymorph, crystal, impurity, N-oxide, hydrate or any combination thereof, or a composition comprising the same, to a subject in need thereof, so as to achieve a desired effect.

In one embodiment, the present invention provides methods of treating metabolic diseases comprising administering estrogen receptor ligand compounds of this invention.

In one embodiment, the present invention provides methods for treating, delaying the onset of, reducing the incidence of, or reducing the severity of condition associated with high fat diet consumption. In another embodiment, the present invention provides methods for preventing a condition associated with high fat diet consumption. In another embodiment the methods comprise administering a compound of this invention. In another embodiment, the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In one embodiment the condition associated with high fat diet consumption is body weight gain. In another embodiment the condition associated with high fat diet consumption is obesity. In another embodiment the condition associated with high fat diet consumption is fat mass formation. In another embodiment the condition associated with high fat diet consumption is bone mineral content reduction. In another embodiment the condition associated with high fat diet consumption is white adipose tissue weight gain. In another embodiment the condition associated with high fat diet consumption is increased cholesterol levels. In another embodiment the condition associated with high fat diet consumption is increased leptin levels. In another embodiment the condition associated with high fat diet consumption is insulin resistance. In another embodiment the condition associated with high fat diet consumption is type II diabetes. In another embodiment the condition associated with high fat diet consumption is increased blood glucose levels. In another embodiment the condition associated with high fat diet consumption is inflammatory diseases. In another embodiment the condition associated with high fat diet consumption is cardiovascular diseases. In another embodiment the condition associated with high fat diet consumption is fatty liver condition (accumulation of fat in the liver). In another embodiment the condition associated with high fat diet consumption is decreased uncoupling protein-1 (UCP-1) levels. In another embodiment the condition associated with high fat diet consumption is increased lipogenesis.

In one embodiment, the present invention provides methods for treating, delaying the onset of, reducing the incidence of, or reducing the severity of condition associated with post-menopausal obesity. In another embodiment, the present invention provides methods for preventing a condition associated with post-menopausal obesity. In another embodiment the methods comprise administering a compound of this invention. In another embodiment, the compound is compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In one embodiment the condition associated with post-menopausal obesity is body weight gain. In another embodiment the condition associated with post-menopausal obesity is fat mass formation. In another embodiment the condition associated with post-menopausal obesity is bone mineral content reduction. In another embodiment the condition associated with post-menopausal obesity is white adipose tissue weight gain. In another embodiment the condition associated with post-menopausal obesity is increased cholesterol levels. In another embodiment the condition associated with post-menopausal obesity is increased leptin levels. In another embodiment the condition associated with post-menopausal obesity is insulin resistance. In another embodiment the condition associated with post-menopausal obesity is type II diabetes. In another embodiment the condition associated with post-menopausal obesity is increased blood glucose levels. In another embodiment the condition associated with post-menopausal obesity is inflammatory diseases. In another embodiment the condition associated with post-menopausal obesity is cardiovascular diseases. In another embodiment the condition associated with post-menopausal obesity is fatty liver condition (accumulation of fat in the liver). In another embodiment the condition associated with post-menopausal obesity is decreased uncoupling protein-1 (UCP-1) levels. In another embodiment the condition associated with post-menopausal obesity is increased lipogenesis.

In one embodiment, the present invention provides methods for treating, delaying the onset of, reducing the incidence of, or reducing the severity of obesity. In another embodiment, the present invention provides methods for preventing obesity. In one embodiment, the obesity is post-menopausal obesity. In another embodiment, the obesity is visceral obesity. In another embodiment, the obesity is visceral obesity at andropause. In another embodiment the obesity is diet induced obesity. In another embodiment the obesity is induced by prolonged rest. In another embodiment the methods comprise administering a compound of this invention. In another embodiment the compound is compound 12u, listed in Table 1. In another embodiment the compound is compound 12y, listed in Table 1. In another embodiment, the compound is compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12z, listed in Table 1. In another embodiment the compound is compound 14m, listed in Table 1.

In another embodiment, this invention relates to a method of promoting, increasing or facilitating weight loss in a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to promote, increase or facilitate weight loss in the subject. In another embodiment, the compound is compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In another embodiment, this invention relates to a method of decreasing, suppressing, inhibiting or reducing appetite of a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to decrease, suppress, inhibit or reduce the appetite of the subject. In another embodiment the compound is compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In another embodiment, this invention relates to methods of reducing body weight gain in a subject. In another embodiment, this invention relates to methods of reducing body weight gain in a subject, without affecting total caloric intake. In another embodiment, this invention relates to methods of reducing body weight gain in a subject, without reducing lean mass or body water content. In another embodiment, this invention relates to methods of preventing body weight gain in a subject. In another embodiment, this invention relates to methods of preventing body weight gain in a subject, without affecting total caloric intake. In another embodiment, this invention relates to methods of preventing body weight gain in a subject, without reducing lean mass or body water content. In one embodiment the body weight gain is due to high fat diet consumption. In another embodiment the body weight gain is related to post-menopausal obesity. In another embodiment the body weight gain is related to visceral obesity at andropause. In another embodiment the body weight gain is related to visceral obesity. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In one embodiment this invention relates to methods of preventing body weight increase of between 10%400% of the body weight. In another embodiment, the methods of this invention prevent body weight increase of between 10-25% of the body weight. In another embodiment, the methods of this invention prevent body weight increase of between 25-50% of the body weight. In another embodiment, the methods of this invention prevent body weight increase of between 30-70% of the body weight. In another embodiment, the methods of this invention prevent body weight increase of between 50-100% of the body weight. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In another embodiment, this invention relates to a method of altering the body composition of a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to alter the body composition of the subject. In one embodiment, altering the body composition comprises altering the lean body mass, the fat free body mass of the subject, or a combination thereof. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In another embodiment, the present invention provides methods for reducing a fat mass in a subject. In another embodiment, the present invention provides methods for preventing fat mass formation in a subject. In one embodiment the fat mass formation is related to high fat diet consumption. In another embodiment, the fat mass formation is related to post-menopausal obesity. In one embodiment the fat mass formation is related to visceral obesity. In one embodiment the fat mass formation is related to visceral obesity at andropause. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In one embodiment this invention relates to methods of preventing increase in body fat mass of between 10%-100% of the body fat mass. In another embodiment this invention relates to methods of preventing increase in body fat mass of between 25%-35% of the body fat mass. In another embodiment this invention relates to methods of preventing increase in body fat mass of between 35%-45% of the body fat mass. In another embodiment this invention relates to methods of preventing increase in body fat mass of between 45%-55% of the body fat mass. In another embodiment this invention relates to methods of preventing increase in body fat mass of between 55%-65% of the body fat mass. In another embodiment this invention relates to methods of preventing increase in body fat mass of between 65%-75% of the body fat mass. In another embodiment this invention relates to methods of preventing increase in body fat mass of between 75%-100% of the body fat mass. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In one embodiment, the present invention provides methods for increasing lean mass in a subject. In another embodiment, the present invention provides methods for preventing decrease in lean mass in a subject. In one embodiment the decrease in lean mass is related to high fat diet consumption. In another embodiment the decrease in lean mass is related to post-menopausal obesity. In another embodiment the decrease in lean mass is related to visceral obesity. In another embodiment the decrease in lean mass is related to visceral obesity at andropause. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In another embodiment, this invention relates to methods of increasing muscle weight. In another embodiment, this invention relates to methods of preventing a decrease in muscle weight. In one embodiment, the decrease is related to high fat diet consumption. In another embodiment, the decrease is related to post-menopausal obesity. In another embodiment, the decrease is related to visceral obesity. In another embodiment, the decrease is related to visceral obesity at andropause. In one embodiment the muscle weight is gastrocnemius muscle weight. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In another embodiment, this invention relates to a method of altering lean body mass or fat free body mass of a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to alter the lean body mass or fat free body mass of the subject. In another embodiment the compound is a compound of formula or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In another embodiment, this invention relates to a method of converting fat to lean muscle in a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to convert fat to lean muscle in the subject. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In another embodiment, this invention provides methods for increasing bone mineral content (BMC) in a subject. In another embodiment, the present invention provides methods for preventing reduction in BMC in a subject. In one embodiment the reduction in BMC is related to high fat diet. In another embodiment the reduction in BMC is related to post-menopausal obesity. In another embodiment the reduction in BMC is related to visceral obesity. In another embodiment the reduction in BMC is related to visceral obesity at andropause. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In one embodiment, the present invention provides methods for treating, delaying the onset of, reducing the incidence of, or reducing the severity of osteoporosis. In another embodiment, the present invention provides methods for preventing osteoporosis. In one embodiment, the osteoporosis is related to a post-menopausal obesity. In another embodiment the osteoporosis is related to a high fat diet consumption. In another embodiment the osteoporosis is related to visceral obesity. In another embodiment the osteoporosis is related to visceral obesity at andropause. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In another embodiment, this invention relates to methods of reducing white adipose tissue (WAT) weight in a subject. In another embodiment, this invention relates to methods of preventing an increase in white adipose tissue weight in a subject. In one embodiment, the increase in white adipose tissue weight is related to high fat diet. In another embodiment, the increase in white adipose tissue weight is related to post-menopausal obesity. In another embodiment, the increase in white adipose tissue weight is related to visceral obesity. In another embodiment, the increase in white adipose tissue weight is related to visceral obesity at andropause. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

Cholesterol, triacylglycerol and other lipids are transported in body fluids by lipoproteins which may be classified according to their density, for example, the very low density lipoproteins (VLDL), intermediate density lipoproteins (IDL), low density lipoproteins (LDL) and high density lipoproteins (HDL).

It has been shown that high levels of LDL-Cholesterol in the blood correlate with atherosclerosis which is a progressive disease characterized in part by sedimentation of lipids in inner walls of arteries, particularly of coronary arteries. It has also been shown that a high blood level of LDL-Cholesterol correlates with coronary heart disease. Also, a negative correlation exists between blood levels of HDL cholesterol and coronary heart disease.

The level of total cholesterol in blood, which is the sum of HDL-Cholesterol, LDL-Cholesterol, VLDL-Cholesterol and chylomicron-Cholesterol, is not necessarily predictive of the risk of coronary heart disease and atherosclerosis.

The correlation between atherosclerosis and LDL cholesterol levels, however, is much higher than a similar correlation between atherosclerosis and total serum cholesterol levels.

In another embodiment, this invention relates to methods of reducing cholesterol levels in a subject. In another embodiment, this invention relates to methods of lowering LDL-cholesterol levels in a subject. In another embodiment, this invention relates to methods of lowering total cholesterol levels in a subject. In another embodiment, this invention relates to methods of preventing an increase in cholesterol levels in a subject. In one embodiment the increase in cholesterol levels is related to high fat diet. In another embodiment the increase in cholesterol levels is related to post-menopausal obesity. In another embodiment the increase in cholesterol levels is related to visceral obesity. In another embodiment the increase in cholesterol levels is related to visceral obesity at andropause. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In another embodiment, compounds of this invention are co-administered with HDL-elevating agents. In another embodiment, a compound of this invention is co-administered with an HDL-elevating agent. In another embodiment, HDL-elevating agents include niacin. In another embodiment the HDL-elevating agents include fibrates including gemfibrozil (Lopid), thiourea based gemfibrozil analogues, and fenofibrate (TriCor). In another embodiment, HDL-elevating agents include statins. In another embodiment, HDL-elevating agents include 1-hydroxyalkyl-3-phenylthiourea, and analogs thereof.

In one embodiment atherosclerosis refers to a slow, complex disease that may begin with damage to the innermost layer of the artery. In another embodiment the causes of damage to the arterial wall may include a) elevated levels of cholesterol and in the blood; b) high blood pressure; c) tobacco smoke d) diabetes. In another embodiment, the condition is treatable in a smoker, despite the fact that tobacco smoke may greatly worsen atherosclerosis and speed its growth in the coronary arteries, the aorta and arteries in the legs. Similarly, in another embodiment, the methods of this invention may be useful in treating subjects with a family history of premature cardiovascular disease who have an increased risk of atherosclerosis.

In one embodiment, the present invention provides methods for treating, delaying the onset of, reducing the incidence of, or reducing the severity of atherosclerosis. In another embodiment, the present invention provides methods for preventing atherosclerosis. In one embodiment, the atherosclerosis is related to a post-menopausal obesity. In another embodiment the atherosclerosis is related to high fat diet consumption. In another embodiment the atherosclerosis is related to visceral obesity. In another embodiment the atherosclerosis is related to visceral obesity at andropause. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In one embodiment, this invention provides a method of treating atherosclerosis and its associated diseases, such as, for example, cardiovascular disorders, cerebrovascular disorders, peripheral vascular disorders, or intestinal vascular disorders in a subject, the method comprising the step of administering to the subject compound of this invention or its pharmaceutically acceptable salt, hydrate, N-oxide, or any combination thereof, or a composition comprising the same. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1. The method may further comprise co-administration, subsequent or prior administration with an agent or agents, which are known to be useful in treating cardiovascular disorders, cerebrovascular disorders, peripheral vascular disorders, intestinal vascular disorders or combination thereof.

Hypercholesterolemia is a condition in which high levels of cholesterol are present in the blood of a subject. It is not a disease but a metabolic derangement that can be secondary to many diseases and can contribute to many forms of disease, most notably cardiovascular disease. Elevated cholesterol in the blood is caused by abnormalities in the levels of lipoproteins, the particles that carry cholesterol in the bloodstream. This may be related to diet, genetic factors (such as LDL receptor mutations in familial hypercholesterolemia) and the presence of other diseases such as diabetes and an underactive thyroid.

In one embodiment, this invention relates to methods of alleviating hypercholesterolemia. In another embodiment, this invention relates to methods of preventing hypercholesterolemia. In another embodiment the hypercholesterolemia is related to high fat diet consumption. In another embodiment the hypercholesterolemia is related to post-menopausal obesity. In another embodiment hypercholesterolemia is related to visceral obesity. In another embodiment hypercholesterolemia is related to visceral obesity at andropause. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In another embodiment, this invention relates to methods of reducing leptin levels in a subject. In another embodiment, the present invention provides methods for preventing an increase in leptin levels in a subject. In one embodiment the increase in leptin levels is related to high fat diet consumption. In another embodiment the increase in leptin levels is related to post-menopausal obesity. In another embodiment the increase in leptin levels is related to visceral obesity. In another embodiment the increase in leptin levels is related to visceral obesity at andropause. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In one embodiment, the subject for whom treatment is sought via the methods of this invention is one with insulin resistance. Insulin resistance is a condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to the metabolic syndrome and type II diabetes.

In one embodiment, the present invention provides methods for treating, delaying the onset of, reducing the incidence of, or reducing the severity of insulin resistance. In another embodiment, the present invention provides methods for preventing insulin resistance. In one embodiment, the insulin resistance is related to post-menopausal obesity. In another embodiment, the insulin resistance related to visceral obesity. In another embodiment, the insulin resistance related to visceral obesity at andropause. In another embodiment the insulin resistance is related to a high fat diet consumption. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In one embodiment, the present invention provides methods for improving insulin sensitivity in a subject. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In one embodiment, the present invention provides methods for treating, halting the progression of, or treating symptoms of, delaying the onset of, reducing the incidence of, or reducing the severity of diabetes. In another embodiment, the present invention provides methods for preventing diabetes. In one embodiment, the diabetes is Type I diabetes. In another embodiment, the diabetes is Type II diabetes. In a further embodiment, the diabetes is diabetes mellitus. In one embodiment, the diabetes is related to post-menopausal obesity. In another embodiment, the diabetes is related to visceral obesity. In another embodiment, the diabetes is related to visceral obesity at andropause. In another embodiment the diabetes is induced by a high fat diet. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In one embodiment, this invention provides a method of treating diabetic nephropathy comprising administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

Diabetic nephropathy is a complication of diabetes that evolves early, typically before clinical diagnosis of diabetes is made. The earliest clinical evidence of nephropathy is the appearance of low but abnormal levels (>30 mg/day or 20 μg/min) of albumin in the urine (microalbuminuria), followed by albuminuria (>300 mg/24 h or 200 μg/min) that develops over a period of 10-15 years. In patients with type 1 diabetes, diabetic hypertension typically becomes manifest early on, by the time that patients develop microalbuminuria. Once overt nephropathy occurs, the glomerular filtration rate (GFR) falls over a course of times, which may be several years, resulting in End Stage Renal Disease (ESRD) in diabetic individuals.

In one embodiment, this invention provides a method of treating diabetic neuropathy comprising administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

Diabetic neuropathy is a family of nerve disorders caused by diabetes. Diabetic neuropathies cause numbness and sometimes pain and weakness in the hands, arms, feet, and legs. Neurologic problems in diabetes may occur in every organ system, including the digestive tract, heart, and genitalia. Diabetic neuropathies are classified as peripheral, autonomic, proximal, and focal. Peripheral neuropathy causes pain or loss of feeling in the toes, feet, legs, hands, and arms. Autonomic neuropathy causes changes in digestion, bowel and bladder function, sexual response, and perspiration and can also affect the nerves that serve the heart and control blood pressure. Proximal neuropathy causes pain in the thighs, hips, or buttocks and leads to weakness in the legs. Focal neuropathy results in the sudden weakness of one nerve, or a group of nerves, causing muscle weakness or pain. Any nerve in the body may be affected.

In another embodiment, this invention relates to treating co-morbidities related to diabetes. These conditions include, for example, hypertension (HTN), cerebrovascular disease, atherosclerotic coronary artery disease, macular degeneration, diabetic retinopathy (eye disease) and blindness, cataracts—systemic inflammation (characterized by elevation of inflammatory markers such as erythrocyte sedimentation rate or C-reactive protein), birth defects, pregnancy related diabetes, pre-ecclampsia and hypertension in pregnancy, kidney disease (renal insufficiency, renal failure etc.), nerve disease (diabetic neuropathy), superficial and systemic fungal infections, congestive heart failure, gout/hyperuricemia, obesity, hypertriglyceridemia, hypercholesterolemia, fatty liver disease (non-alcoholic steatohepatitis, or NASH), and diabetes-related skin diseases such as Necrobiosis Lipoidica Diabeticorum (NLD), Blisters of diabetes (Bullosis Diabeticorum), Eruptive Xanthomatosis, Digital Sclerosis, Disseminated Granuloma Annulare and Acanthosis Nigricans.

In one embodiment, the subject for whom treatment is sought via the methods of this invention is one with hyperinsulinemia. Hyperinsulinemia is a sign of an underlying problem that is causing the pancreas to secrete excessive amounts of insulin. The most common cause of hyperinsulinemia is insulin resistance, a condition in which your body is resistant to the effects of insulin and the pancreas tries to compensate by making more insulin. Hyperinsulinemia is associated with type II diabetes In another embodiment, this invention relates to methods of alleviating hyperinsulinemia. In another embodiment, this invention relates to methods of preventing hyperinsulinemia. In one embodiment the hyperinsulinemia is related to high fat diet consumption. In another embodiment the hyperinsulinemia is related to post-menopausal obesity. In another embodiment hyperinsulinemia is related to visceral obesity. In another embodiment hyperinsulinemia is related to visceral obesity at andropause. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In another embodiment, this invention relates to methods of reducing glucose levels in a subject. In another embodiment, this invention relates to methods of preventing an increase in the glucose levels in a subject. In one embodiment the increase in glucose levels is related to high fat diet consumption. In another embodiment the increase in glucose levels is related to post-menopausal obesity. In another embodiment the increase in glucose levels is related to visceral obesity. In another embodiment the increase in glucose levels is related to visceral obesity at andropause. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

Inflammation is a common and potentially debilitating condition that occurs when the white blood cells and endogenous chemicals that can protect us from infection and foreign substances such as bacteria and viruses act on tissue surrounding a wound or infection. In some diseases, however, the body's defense system (immune system) triggers an inflammatory response when there are no foreign substances to fight off. In these diseases, called autoimmune diseases, the body's normally protective immune system causes damage to its own tissues. The body responds as if normal tissues are infected or somehow abnormal. Some, but not all types of arthritis are the result of misdirected inflammation. Arthritis is a general term that describes inflammation in joints and affects more than 2-4% of the world's population. There are many medications available to decrease swelling and inflammation and hopefully prevent or minimize the progression of the inflammatory disease. The medications include non-steroidal anti-inflammatory drugs (NSAIDs—such as aspirin, ibuprofen or naproxen), corticosteroids (such as prednisone), anti-malarial medications (such as hydroxychloroquine), and other medications including gold, methotrexate, sulfasalazine, penicillamine, cyclophosphamide and cyclosporine.

The role of estrogen receptor and its ligands as therapy for inflammation has been under consideration. The effects are regarded to be mediated by the isoform ER-β. Treatment of rats with estradiol or SERMs such as raloxifene and tamoxifen has been shown to reduce the incidence of lipo-polysacharride induced inflammatory responses. One of the pathways through which inflammatory responses are mediated is through the activation of NFκB pathway. Nuclear receptor ligands inhibit the NFκB activity through protein-protein interaction. Recently it was shown that SERMs inhibit the inflammatory responses by inhibiting the NFκB function without having estrogenic effects on other reproductive tissues.

In another embodiment, this invention relates to methods of treating preventing, inhibiting reducing the incidence of inflammation in a subject. In one embodiment, the inflammation is related to increased levels of macrophage inflammatory protein-1β (MIP-1β). In one embodiment the inflammation is related to high fat diet consumption. In another embodiment the inflammation is related to post-menopausal obesity. In another embodiment the inflammation is related to visceral obesity. In another embodiment the inflammation is related to visceral obesity at andropause. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In another embodiment, this invention relates to methods of treating, preventing, inhibiting reducing the incidence of increased macrophage inflammatory protein-1β (MIP-1β) levels in a subject. In another embodiment, this invention relates to methods of preventing increased macrophage inflammatory protein-1β (MIP-1β) levels in a subject. In one embodiment the increase is related to high fat diet consumption. In another embodiment the increase is related to post-menopausal obesity. In another embodiment the increase is related to visceral obesity. In another embodiment the increase is related to visceral obesity at andropause. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In one embodiment, the compound as described herein is useful in treating inflammation and related disorders such as: a) prevention, treatment, or reversal of arthritis; b) prevention, treatment, or reversal of an arthritic condition such as Behcet's disease (autoimmune vasculitis), bursitis, calcium pyrophosphate dihydrate crystal (CPPD), deposition disease (or pseudogout), carpal tunnel syndrome, connective tissue disorders, Crohn's diseases, Ehlers-Danlos syndrome (EDS), fibromyalgia, gout, infectious arthritis, inflammatory bowel disease (IBD), juvenile arthritis, systemic lupus erythematosus (SLE), Lyme's disease, Marfan syndrome, myositis, osteoarthritis, polyarteritis nodosa, polymyalgia rheumatica, psoriasis, psoriatic arthritis, Raynaud's phenomenon, reflex sympathetic dystrophy syndrome, Reiter's syndrome, rheumatoid arthritis, scleroderma, Sjögrens' syndrome, tendonitis or ulcerative colitis; c) preventing, treatment, or reversing an autoimmune disease; d) chronic kidney disease (CKD).

In another embodiment, the invention provides a method of treating, preventing, inhibiting reducing the incidence of inflammatory diseases, disorders or conditions in a subject, comprising administering a pharmaceutical composition comprising administering a compound of formula (I)-(XII) or its prodrug, analog, isomer, metabolite, derivative, pharmaceutically acceptable salt, pharmaceutical product, polymorph, crystal, impurity, N-oxide, ester, hydrate or any combination thereof, thereby treating, preventing, inhibiting reducing the incidence of inflammatory conditions in a subject. In some embodiments ER-β agonists are useful in treating, preventing, inhibiting reducing the incidence of inflammatory diseases, disorders or conditions in a subject. In another embodiment, ER-β agonist of this invention is compound 12b, listed in Table 1. In another embodiment, ER-β agonist of this invention is compound 12f, listed in Table 1. In another embodiment, ER-β agonist of this invention is compound 12h, listed in Table 1. In another embodiment, ER-β agonist of this invention is compound 12p, listed in Table 1. In another embodiment, ER-β agonist of this invention is compound 12s, listed in Table 1. In another embodiment, ER-β agonist of this invention is compound 12u, listed in Table 1. In another embodiment, ER-β agonist of this invention is compound 12z, listed in Table 1. In another embodiment, ER-β agonist of this invention is compound 12y, listed in Table 1. In another embodiment, ER-β agonist of this invention is compound 14m, listed in Table 1, or any combination thereof.

In some embodiments, ER-β agonists of this invention inhibit stroma-epithelial proliferation (FIG. 23, Example 34) which can affect the development of anatomic obstruction, which can reduce inflammation and thereby, treat inflammation. In one embodiment, ER-β agonists of this invention relax smooth muscle which can lower urine tract symptoms, affect the development of BPH, which can reduce inflammation and thereby, treat inflammation.

In some embodiments, the inflammatory diseases disorders or conditions may comprise acute inflammation, arthropathies (in general), rheumatoid arthritis, systemic lupus erythema, asthma, acute inflammation, chronic inflammation, joint damage, joint swelling, joint erosion, sepsis, or any combination thereof.

Joint inflammation is one of the most common causes of pain, lameness, and loss of physical activity, not only in humans but in animals, particularly horses. This debilitating condition is marked by edema, redness, heat and pain. If left untreated, joint inflammation also can lead to destruction of the joint synovium and the articular cartilage producing a permanent debilitating condition. The edema, redness, and pain that occur during inflammation are the result of physiological changes in the joint. For example, the permeability of the synovial membrane increases during inflammation allowing synovial fluid to leak into the tissues of the joint. Alterations in blood flow and pressure in the vascular system of the joint also occur during inflammation. In addition, the metabolic activity of the cells of the joint increases during inflammation.

In another embodiment, the invention provides a method of treating, preventing, inhibiting reducing the incidence of joint inflammation in a subject, comprising administering a pharmaceutical composition comprising a NRBA of formula (I)-(XII) or its prodrug, analog, isomer, metabolite, derivative, pharmaceutically acceptable salt, pharmaceutical product, polymorph, crystal, impurity, N-oxide, ester, hydrate or any combination thereof, thereby treating, preventing, inhibiting reducing the incidence of joint inflammation in a subject. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the NRBA is compound 12u, listed in Table 1. In another embodiment the NRBA is compound 12y, listed in Table 1. In another embodiment the NRBA is compound 12z, listed in Table 1. In another embodiment the NRBA is compound 14m, listed in Table 1.

In one embodiment, liver damage due to fat deposits refer to the build-up of fat in the liver cells forming a fatty liver which may be associated with or may lead to inflammation of the liver. This can cause scarring and hardening of the liver. When scarring becomes extensive, it is called cirrhosis.

In another embodiment, this invention relates to methods of inhibiting fat accumulation in the liver of a subject. In another embodiment, this invention relates to methods of reducing the amount of fat in the liver of a subject. In one embodiment, the present invention provides methods for treating, delaying the onset of, reducing the incidence of, or reducing the severity of fatty liver condition. In another embodiment, the present invention provides methods for preventing fatty liver condition. In one embodiment, the fatty liver condition is related to a post-menopausal obesity. In another embodiment the fatty liver condition is related to visceral obesity. In another embodiment the fatty liver condition is related to visceral obesity at andropause. In another embodiment the fatty liver condition is related to high fat diet consumption. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In one embodiment, "fatty liver condition" refers to a condition in which fat is accumulated in the liver. In another embodiment the fat accumulates in the liver as obesity. In another embodiment fatty liver is also associated with diabetes mellitus, high blood triglycerides, and the heavy use of alcohol. In another embodiment fatty Liver may occur with certain illnesses such as tuberculosis and malnutrition, intestinal bypass surgery for obesity, excess vitamin A in the body, or the use of certain drugs such as valproic acid (trade names: Depakene/Depakote) and corticosteroids (cortisone, prednisone). Sometimes fatty liver occurs as a complication of pregnancy.

In one embodiment, this invention relates to methods of altering the anti-oxidant pathways in a subject. In another embodiment, this invention relates to methods of reducing glutathione peroxidase (GPx-3) levels in a subject. In another embodiment, this invention relates to methods of preventing an increase in glutathione peroxidase (GPx-3) levels in a subject. In one embodiment the increase is related to high fat diet consumption. In another embodiment the increase is related to post-menopausal obesity. In another embodiment the increase is related to visceral obesity. In another embodiment the increase is related to visceral obesity at andropause. In another embodiment, this invention relates to methods of increasing the levels of DNA damage inducible transcript III (Ddit3) in a subject. In another embodiment, this invention relates to methods of preventing a decrease in the levels of DNA damage inducible transcript III (Ddit3) in a subject. In one embodiment the decrease is related to high fat diet consumption. In another embodiment the decrease is related to post-menopausal obesity. In another embodiment the decrease is related to visceral obesity. In another embodiment the decrease is related to visceral obesity at andropause. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In another embodiment, the invention provides a method of treating, preventing, inhibiting reducing the incidence of oxidative damage-related diseases, disorders or conditions in a subject, comprising administering a pharmaceutical composition comprising a compound of formula (I)-(XII) or its prodrug, analog, isomer, metabolite, derivative, pharmaceutically acceptable salt, pharmaceutical product, polymorph, crystal, impurity, N-oxide, ester, hydrate or any combination thereof, thereby treating, preventing, inhibiting reducing the incidence of oxidative damage-related diseases in a subject. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In some embodiments, the oxidative damage-related diseases, disorders or conditions may comprise cancers; skin disorders; neurodegenerative diseases such as Alzheimer's disease, Parkinson's disease, Huntington's disease, multiple sclerosis, and amytrophic lateral sclerosis; vascular diseases such as stroke and various age-related dementias, and atherosclerosis; or age-related macular degeneration.

Oxidative damage can comprise damage to cells and tissue, caused by oxidation of various cellular products, which through the production of peroxides and free radicals damage components of the cell and tissue, for example, damaging cell integrity, cell membranes, DNA, etc.

In one embodiment, this invention relates to methods of increasing uncoupling protein-a (UCP-1) levels in a subject. In another embodiment, this invention relates to methods of preventing a decrease in uncoupling protein-1 (UCP-1) levels in a subject. In one embodiment, the decrease is related to high fat diet consumption. In another embodiment the decrease is related to post-menopausal obesity. In another embodiment the decrease is related to visceral obesity. In another embodiment the decrease is related to visceral obesity at andropause. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In another embodiment, this invention relates to methods of increasing energy expenditure in a subject. In another embodiment, this invention relates to methods of preventing a decrease in energy expenditure in a subject. In one embodiment the decrease in energy expenditure is related to high fat diet consumption. In another embodiment the decrease in energy expenditure is related to post-menopausal obesity. In another embodiment the decrease in energy expenditure is related to visceral obesity. In another embodiment the decrease in energy expenditure is related to visceral obesity at andropause. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In another embodiment, this invention relates to methods of reducing, inhibiting or preventing lipogenesis in a subject.

In one embodiment the lipogenesis is related to decreased levels of genes promoting lipogenesis in a subject. These genes include, but are not limited to: lipoprotein lipase (LPL), fatty acid synthase (FASN), regulatory element binding protein-1 (SREBP-1), phospholipid transfer protein (PLTP) and dehydrocholesterol reductase (Dhcr24). In another embodiment, this invention relates to increasing the levels of lipoprotein lipase (LPL) in a subject. In another embodiment, this invention relates to increasing the levels of fatty acid synthase (FASN) in a subject. In another embodiment, this invention relates to increasing the levels of regulatory element binding protein-1 (SREBP-1) in a subject. In another embodiment, this invention relates to increasing the levels of phospholipid transfer protein (PLTP) in a subject. In another embodiment, this invention relates to increasing the levels of dehydrocholesterol reductase (Dhcr24) in a subject. In another embodiment, this invention relates to preventing a decrease in the levels of lipoprotein lipase (LPL) in a subject. In another embodiment, this invention relates to preventing a decrease in the levels of fatty acid synthase (FASN) in a subject. In another embodiment, this invention relates to preventing a decrease in the levels of regulatory element binding protein-1 (SREBP-1) in a subject. In another embodiment, this invention relates to preventing a decrease in the levels of phospholipid transfer protein (PLTP) in a subject. In another embodiment, this invention relates to preventing a decrease in the levels of dehydrocholesterol reductase (Dhcr24) in a subject. In one embodiment the lipogenesis is related to high fat diet consumption. In another embodiment the lipogenesis is related to post-menopausal obesity. In another embodiment the lipogenesis is related to visceral obesity. In another embodiment the lipogenesis is related to visceral obesity at andropause. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In one embodiment, this invention provides methods of use of the compounds as herein described for improving the lipid profile and/or reducing the circulating lipid levels in a subject. In some embodiments, according to this aspect of the invention, the subject suffers from one or more conditions selected from the group consisting of: atherosclerosis and its associated diseases, premature aging, Alzheimer's disease, stroke, toxic hepatitis, viral hepatitis, peripheral vascular insufficiency, renal disease, and hyperglycemia, and the invention provides for the administration of a compound or composition comprising the same, as herein described, which in some embodiments positively affects a lipid profile in the subject, which is one means by which the method is useful in treating the indicated diseases, disorders and conditions.

In another embodiment, the invention provides a method of improving a lipid profile in a subject, comprising administering a NRBA of formula (I)-(XII) or its prodrug, ester, analog, isomer, metabolite, derivative, pharmaceutically acceptable salt, pharmaceutical product, polymorph, crystal, impurity, N-oxide, hydrate or any combination thereof, or a composition comprising the same, thereby improving the lipid profile in said subject. In some embodiments ER-β agonists are useful in improving a lipid profile in a subject. In another embodiment, ER-β agonist of this invention is compound 12b, listed in Table 1. In another embodiment, ER-β agonist of this invention is compound 12f, listed in Table 1. In another embodiment, ER-β agonist of this invention is compound 12h, listed in Table 1. In another embodiment, ER-β agonist of this invention is compound 12p, listed in Table 1. In another embodiment, ER-β agonist of this invention is compound 12s, listed in Table 1. In another embodiment, ER-β agonist of this invention is compound 12u, listed in Table 1. In another embodiment, ER-β agonist of this invention is compound 12y, listed in Table 1. In another embodiment, ER-β agonist of this invention is compound 12z, listed in Table 1. In another embodiment, ER-β agonist of this invention is compound 14m, listed in Table 1, or any combination thereof.

In some embodiments, the phrase "improving a lipid profile" may refer to lowering pathogenic circulating lipid levels, lowering plaque formation in vasculature, altering circulating HDL/LDL ratios, ratios reducing the ratio of LDL levels to HDL levels, lowering circulating cholesterol levels, preventing lipid accumulation in vasculature, or any combination thereof, or other therapeutic effects related thereto, as will be appreciated by one skilled in the art.

In one embodiment, this invention provides a method of reducing circulating lipid levels in a subject, said method comprising administering a compound of this invention or its pharmaceutically acceptable salt, hydrate, N-oxide, or any combination thereof, or a composition comprising the same. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1. In one embodiment, the subject suffers from atherosclerosis and its associated diseases, premature aging, Alzheimer's disease, stroke, toxic hepatitis, viral hepatitis, peripheral vascular insufficiency, renal disease, hyperglycemia, or any combination thereof.

Hyperlipidemia is the presence of raised or abnormal levels of lipids and/or lipoproteins in the blood. Lipids (fatty molecules) are transported in a protein capsule, and the density of the lipids and type of protein determines the fate of the particle and its influence on metabolism. Lipid and lipoprotein abnormalities are extremely common in the general population, and are regarded as a highly modifiable risk factor for cardiovascular disease due to the influence of cholesterol, one of the most clinically relevant lipid substances, on atherosclerosis.

In one embodiment, the present invention provides methods for treating, delaying the onset of, reducing the incidence of, or reducing the severity of hyperlipidemia. In another embodiment, the present invention provides methods for preventing hyperlipidemia. In one embodiment, the hyperlipidemia is related to a post-menopausal obesity. In another embodiment the hyperlipidemia is related to high fat diet consumption. In another embodiment the hyperlipidemia is related to visceral obesity. In another embodiment the hyperlipidemia is related to visceral obesity at andropause. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In another embodiment, this invention relates to a method of decreasing, suppressing, inhibiting or reducing adipogenesis in a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In another embodiment, this invention relates to increasing the levels of Cell death inducing DNA fragmentation factor (CIDEA) in a subject. In another embodiment, this invention relates to preventing a decrease in the levels of Cell death inducing DNA fragmentation factor (CIDEA) in a subject. In one embodiment, the decrease is related to high fat diet consumption. In another embodiment the decrease is related to post-menopausal obesity. In another embodiment the decrease is related to visceral obesity. In another embodiment the decrease is related to visceral obesity at andropause. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In one embodiment, this invention relates to a method of inhibiting Peroxisome Proliferator Activated Receptor-γ (PPAR-γ) function. In another embodiment, this invention relates to a method of inhibiting Peroxisome Proliferator Activated Receptor-γ (PPAR-γ) function through indirectly acting agents such as ER-β agonists. In another embodiment, this invention relates to a method of inhibiting Peroxisome Proliferator Activated Receptor-γ (PPAR-γ) function without causing adverse side effects. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In one embodiment this invention provides a method of treating a subject suffering from post menopausal conditions, said method comprising the step of administering to said subject a NRBA and/or its pharmaceutically acceptable salt, hydrate, N-oxide, or any combination thereof. In another embodiment the NRBA is compound 12u, listed in Table 1. In another embodiment the NRBA is compound 12y, listed in Table 1. In another embodiment the NRBA is compound 12z, listed in Table 1. In another embodiment the NRBA is compound 14m, listed in Table 1. In another embodiment the NRBA is compound 15a, 15b, 15c, 15g, 15h, or 15i, listed in Table 1.

In another embodiment this invention provides a method of suppressing, inhibiting or reducing the risk of post menopausal conditions, said method comprising the step of administering to said subject a NRBA and/or its pharmaceutically acceptable salt, hydrate, N-oxide, or any combination thereof. In another embodiment the NRBA is compound 12u, listed in Table 1. In another embodiment the NRBA is compound 12y, listed in Table 1. In another embodiment the NRBA is compound 12z, listed in Table 1. In another embodiment the NRBA is compound 14m, listed in Table 1. In another embodiment the NRBA is compound 15a, 15b, 15c, 15g, 15h, or 15i, listed in Table 1.

In one embodiment, the present invention provides methods for treating, delaying the onset of, reducing the incidence of, or reducing the severity of a metabolic disorder, such as obesity, metabolic syndrome, insulin resistance, diabetes (e.g., Type I diabetes, Type II diabetes, diabetes mellitus), atherosclerosis, hyperlipidemia, fatty liver, osteoporosis and/or leptin related disorders. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In another embodiment, this invention relates to methods of treating an obesity-associated metabolic disorder in a subject. In another embodiment, this invention relates to a method of preventing, suppressing, inhibiting or reducing an obesity-associated metabolic disorder in a subject. In one embodiment the obesity-associated metabolic disorder is related to high fat diet consumption. In another embodiment the obesity-associated metabolic disorder is related to post-menopausal obesity. In another embodiment the obesity-associated metabolic disorder is related to visceral obesity. In another embodiment the obesity-associated metabolic disorder is related to visceral obesity at andropause. In another embodiment, this invention relates to a method of treating an obesity-associated metabolic disorder in a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to treat the obesity-associated metabolic disorder in the subject. In another embodiment, this invention relates to a method of preventing, suppressing, inhibiting or reducing an obesity-associated metabolic disorder in a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to prevent, suppress, inhibit or reduce the obesity-associated metabolic disorder in the subject. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In one embodiment, the obesity-associated metabolic disorder is hypertension. In another embodiment, the disorder is osteoarthritis. In another embodiment, the disorder is increased blood pressure. In another embodiment, the disorder is a stroke. In another embodiment, the disorder is heart disease.

Metabolic syndrome refers to a cluster of metabolic risk factors or medical disorders that together increase the risk of developing cardiovascular disease and diabetes. The main features of metabolic syndrome include insulin resistance, hypertension (high blood pressure), cholesterol abnormalities, and an increased risk for clotting. Patients are most often overweight or obese.

In one embodiment, the present invention provides methods for treating, delaying the onset of, reducing the incidence of, or reducing the severity of metabolic syndrome. In another embodiment, the present invention provides methods for preventing metabolic syndrome. In one embodiment, the metabolic syndrome is a post-menopausal metabolic syndrome. In another embodiment the metabolic syndrome is related to high fat diet consumption. In another embodiment the metabolic syndrome is related to visceral obesity. In another embodiment the metabolic syndrome is related to visceral obesity at andropause. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

"Muscle wasting" refers to the progressive loss of muscle mass and/or to the progressive weakening and degeneration of muscles, including the skeletal or voluntary muscles, which control movement, cardiac muscles, which control the heart (cardiomyopathics), and smooth muscles. Chronic muscle wasting is a chronic condition (i.e. persisting over a long period of time) characterized by progressive loss of muscle mass, weakening and degeneration of muscle.

Muscle wasting is associated with chronic, neurological, genetic or infectious pathologies, diseases, illnesses or conditions. These include Muscular Dystrophies such as Duchenne Muscular Dystrophy and Myotonic Dystrophy; Muscle Atrophies such as Post-Polio Muscle Atrophy (PPMA); Cachexias such as Cardiac Cachexia, AIDS Cachexia and Cancer Cachexia, malnutrition, Leprosy, Diabetes, Renal Disease, Chronic Obstructive Pulmonary Disease (COPD), Cancer, end stage Renal failure, Sarcopenia, Emphysema, Osteomalacia, HIV Infection, AIDS, and Cardiomyopathy In one embodiment, the present invention provides methods for treating, delaying the onset of, reducing the incidence of, or reducing the severity of muscle wasting. In another embodiment, the present invention provides methods for preventing muscle wasting. In one embodiment, the muscle wasting is a post-menopausal muscle wasting. In another embodiment the muscle wasting is due to high fat diet consumption. In another embodiment the muscle wasting is due to visceral obesity. In another embodiment the muscle wasting is due to visceral obesity at andropause. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

"Cachexia" is weakness and a loss of weight caused by a disease or as a side effect of illness. Cardiac Cachexia, i.e. a muscle protein wasting of both the cardiac and skeletal muscle, is a characteristic of congestive heart failure. Cancer Cachexia is a syndrome that occurs in patients with solid tumors and hematological malignancies and is manifested by weight loss with massive depletion of both adipose tissue and lean muscle mass. Acquired Immunodeficiency Syndrome (AIDS). Cachexia is a Human Immunodeficiency Virus (HIV) associated myopathy and/or muscle weakness/wasting that is a relatively common clinical manifestation of AIDS. Individuals with HIV-associated myopathy or muscle weakness or wasting typically experience significant weight loss, generalized or proximal muscle weakness, tenderness, and muscle atrophy.

In one embodiment, the present invention provides methods for treating, delaying the onset of, reducing the incidence of, or reducing the severity of Cachexia. In another embodiment, the present invention provides methods for preventing Cachexia. In one embodiment, the Cachexia is a post-menopausal Cachexia. In another embodiment the Cachexia is due to high fat diet consumption. In another embodiment the Cachexia is due to visceral obesity. In another embodiment the Cachexia is due to visceral obesity at andropause. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In another embodiment, this invention relates to methods of increasing myoanabolism. In another embodiment the methods comprise administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In one embodiment, this invention provides: a) a method of treating endometriosis in a subject; b) a method of treating breast cancer in a subject; c) a method of treating lung cancer in a subject; d) a method of reducing aggressive behavior in a subject; e) a method of treating anxiety in a subject; f) a method of treating hot flashes in a subject; g) a method of treating post-menopausal osteoporosis in a subject, comprising administering a compound of this invention and/or an analog, derivative, isomer, metabolite, pharmaceutically acceptable salt, pharmaceutical product, hydrate, N-oxide, prodrug, polymorph, impurity or crystal of said compound, or any combination thereof. ER-β antagonists might be useful to treat various conditions such as anxiety, hot flashes and post-menopausal osteoporosis. Most of the above mentioned indications are mediated primarily by ER-α. Mechanistically, it is a well known fact that ER-β is a dominant negative inhibitor of ER-α. Hence, in these post-menopausal conditions, the binding and activation of even the limited amount of circulating estrogens to ER-α is inhibited by the binding and activation of ER-43. Inhibiting ER-β with antagonists will provide a way to relieve its repressive effects on ER-α, leading to increase in ER-α function. Hence, ER-β antagonists could be used to treat hot flashes, post-menopausal osteoporosis and anxiety.

Endometriosis is a debilitating medical condition in females in which endometrial-like cells appear and flourish in areas outside the uterine cavity, most commonly on the ovaries. The uterine cavity is lined by endometrial cells, which are under the influence of female hormones. These endometrial-like cells in areas outside the uterus (endometriosis) are influenced by hormonal changes and respond similarly as do those cells found inside the uterus. Endometriosis is typically seen during the reproductive years; it has been estimated that it occurs in roughly 5% to 10% of women. A major symptom of endometriosis is recurring pelvic pain. Other symptoms may include nausea, vomiting, fainting, dizzy spells, vertigo, frequent or constant menstrual flow, chronic fatigue, mood swings, extreme pain in legs and thighs, back pain, mild to extreme pain during intercourse and others.

During endometriosis, ER-β is pathologically over-expressed resulting in inhibition of progestin and PR action. Combining ER-β antagonist may improve the therapeutic efficacy of progestin. Alternatively, ER-β antagonist alone may recover endogeneous progestin function.

In one embodiment this invention relates to methods of treating, preventing, inhibiting, suppressing, delaying the onset of, reducing the incidence of, or reducing the severity of endometriosis comprising administering a compound of this invention. In another embodiment the compound is a compound of formula or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is an ER-β antagonist. In another embodiment the compound is compound 15a, 15b, 15c, 15g, 15h, or 15i, listed in Table 1.

It has been shown that activation of ER-β leads to increased proliferation in breast cancer and lung cancer. Accordingly, inhibition of ER-β may be useful for treating breast cancer and lung cancer.

In one embodiment this invention relates to methods of treating, preventing, inhibiting, suppressing, delaying the onset of, reducing the incidence of, or reducing the severity of breast cancer comprising administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is an ER-β antagonist. In another embodiment the compound is compound 15a, 15b, 15c, 15g, 15h, or 15i, listed in Table 1.

In one embodiment this invention relates to methods of treating, preventing, inhibiting, suppressing, delaying the onset of, reducing the incidence of, or reducing the severity of lung cancer comprising administering a compound of this invention. In another embodiment the compound is an ER-β antagonist. In another embodiment the compound is a compound of formula or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 15a, 15b, 15c, 15g, 15h, or 15i, listed in Table 1.

In one embodiment this invention relates to methods of reducing aggressive behavior in a subject comprising administering a compound of this invention. In another embodiment the compound is an ER-β antagonist. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 15a, 15b, 15c, 15g, 15h, or 15i, listed in Table 1.

In one embodiment this invention relates to methods of treating, preventing, inhibiting, suppressing, delaying the onset of, reducing the incidence of, or reducing the severity of anxiety in a subject comprising administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is an ER-β antagonist. In another embodiment the compound is compound 15a, 15b, 15c, 15g, 15h, or 15i, listed in Table 1.

In one embodiment this invention relates to methods of treating, preventing, inhibiting, suppressing, delaying the onset of, reducing the incidence of, or reducing the severity of hot flashes in a subject comprising administering a compound of this invention. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is an ER-β antagonist. In another embodiment the compound is compound 15a, 15b, 15c, 15g, 15h, or 15i, listed in Table 1.

In one embodiment this invention relates to methods of treating, preventing, inhibiting, suppressing, delaying the onset of, reducing the incidence of, or reducing the severity of post-menopausal osteoporosis in a subject comprising administering a compound of this invention. In another embodiment the compound is an ER-β antagonist. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 15a, 15b, 15c, 15g, 15h, or 15i, listed in Table 1.

In one embodiment, this invention provides: a) a method of treating a bone-related condition in a subject; b) a method of increasing a hone mass in a subject; c) a method of improving the lipid profile in a subject; d) a method of treating atherosclerosis and its associated diseases; e) a method of improving dexterity and movement in a subject; f) a method of treating a subject having dysmenorrheal comprising the step of administering to said subject a compound of this invention and/or an analog, derivative, isomer, metabolite, pharmaceutically acceptable salt, pharmaceutical product, hydrate, N-oxide, prodrug, polymorph, impurity or crystal of said compound, or any combination thereof.

In one embodiment, the methods of this invention are useful in treating diseases or disorders caused by, or associated with a hormonal disorder, disruption or imbalance. In one embodiment, the hormonal disorder, disruption or imbalance comprises an excess of a hormone. In another embodiment, the hormonal disorder, disruption or imbalance comprises a deficiency of a hormone. In one embodiment, the hormone is a steroid hormone. In another embodiment, the hormone is an estrogen. In another embodiment, the hormone is an androgen. In another embodiment, the hormone is a glucocorticoid. In another embodiment, the hormone is a cortico-steroid. In another embodiment, the hormone is Luteinizing Hormone (LH). In another embodiment, the hormone is Follicle Stimulating Hormone (FSH). In another embodiment, the hormone is any other hormone known in the art. In another embodiment, the hormonal disorder, disruption or imbalance is associated with menopause. In another embodiment, the hormonal disorder, disruption or imbalance is associated with andropause, andropausal vasomotor symptoms, andropausal gynecomastia, muscle strength and/or function, bone strength and/or function and anger. In another embodiment, hormone deficiency is a result of specific manipulation, as a byproduct of treating a disease or disorder in the subject. For example, the hormone deficiency may be a result of androgen depletion in a subject, as a therapy for prostate cancer in the subject. Each possibility represents a separate embodiment of the present invention.

In another embodiment of the present invention, a method is provided for hormonal therapy in a patient (i.e., one suffering from an androgen-dependent condition) which includes contacting an nuclear hormone receptor of a patient with a compound and/or a non steroidal agonist of the present invention and/or its analog, derivative, isomer, metabolite, pharmaceutically acceptable salt, pharmaceutical product, polymorph, crystal, impurity, hydrate, N-oxide or any combination thereof, in an amount effective to bind the compound to the receptor and effect a change in an hormone-dependent condition. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In one embodiment of this invention, a method is provided for hormone replacement therapy in a patient, which includes administering a compound as herein described and/or its analog, derivative, isomer, metabolite, pharmaceutically acceptable salt, pharmaceutical product, polymorph, crystal, impurity, hydrate, N-oxide or any combination thereof, to a subject, in an amount sufficient to effect a change in a hormone-dependent condition in the subject. In another embodiment the compound is a compound of formula I-XII or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is a compound of formula XI or its analog, derivative, isomer, metabolite, pharmaceutically acceptable salt, pharmaceutical product, hydrate, N-oxide, prodrug, polymorph, impurity or crystal of said compound, or any combination thereof. In another embodiment the compound is compound 12u, listed in Table 1. In another embodiment the compound is compound 12y. listed in Table 1. In another embodiment the compound is compound 12z, listed in Table 1. In another embodiment the compound is compound 14m, listed in Table 1.

Hormone-dependent conditions which may be treated with the compounds and/or compositions as herein described, comprising the methods of the present invention include those conditions which are associated with aging, hypogonadism, diminished erythropoiesis, osteoporosis, and any other conditions dependent upon low estrogen levels.

Hormone-dependent conditions which may be treated with the compounds and/or compositions as herein described, and comprising a method of the invention, may comprise conditions characterized by elevated estrogen levels, including hirsutism, infertility, polycystic ovarian syndrome, endometrial carcinoma, breast cancer, male pattern baldness, prostate cancer, testicular cancer, and others, as will be known to one skilled in the art. For such conditions, the subject may be administered a compound as herein described, alone or in combination with another therapeutic agent, as will be appreciated by one skilled in the art.

In another embodiment, this invention provides a method of treating a hormone dependent disease, disorder or condition, the method comprising administering to the subject a compound as herein described, and optionally chemotherapeutics agents and therapies (methotrexate, cyclophosphamide, ifosfamide, adriamycin, doxorubicin, glucocorticoids, cyclosporine, L-thyroxine, AI, fulvestrant, GnRH agents, ADT, discontinuation of hormone replacement therapy, cranial irradiation, peripheral irradiation, etc.; prolactinemia-inducing pharmacotherapeutics (serotonergic antidepressants acting through 5HT2 receptors, selective serotonin reuptake inhibitors, monoamine oxidase inhibitors, tricyclic antidepressants, antihypertensives such as methyldopa, reserpine, clonidine, and verapamil; antidopaminergic anti-emetics such as metoclopramide, H2 receptor antagonists such as cimetidine and ranitidine, estrogens, amphetamines, AR partial antagonists (ketoconazole, spironolactone, eplerenone).

In some embodiments, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for treating reducing the severity of, reducing the incidence of, or reducing pathogenesis of cachexia and/or cachexia associated with cancer in a subject. In another embodiment, the cancer comprise adrenocortical carcinoma, anal cancer, bladder cancer, brain tumor, brain stem glioma, brain tumor, cerebellar astrocytoma, cerebral astrocytoma, ependymoma, medulloblastoma, supratentorial primitive neuroectodermal, pineal tumors, hypothalamic glioma, breast cancer, carcinoid tumor, carcinoma, cervical cancer, colon cancer, endometrial cancer, esophageal cancer, extrahepatic bile duct cancer, ewings family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, non small cell lung cancer, small cell, lymphoma, AIDS-related lymphoma, central nervous system (primary), lymphoma, cutaneous T-cell, lymphoma, Hodgkin's disease, non-Hodgkin's disease, malignant mesothelioma, melanoma, Merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cell cancer, salivary gland cancer, Sezary syndrome, skin cancer, cutaneous T-cell lymphoma, skin cancer, Kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, Wilms' tumor, or any combination thereof.

In another embodiment, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for treating reducing the severity of, reducing the incidence of, delaying the onset of lung cancer. In another embodiment the compound is a compound of formula I-XII.

In another embodiment, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for treating reducing the severity of, reducing the incidence of, delaying the onset of non small cell lung cancer.

Colon cancer is the second most frequently diagnosed malignancy in the United States, as well as the second most common cause of cancer death. Cholesterol-rich diets have had a significant epidemiological association with cancers of the colon, which in turn may be influenced by the administration of compounds which modulate nuclear hormone binding agents, in particular, compounds which modulate receptors binding components of the steroidogenic pathway, in particular, as described herein.

In one embodiment, the invention provides a method of treating, preventing the recurrence, inhibiting, reducing the incidence of, delaying onset, reducing the recurrence of, or reducing the severity of colon cancer in a subject, comprising administering a compound of formula (I)-(XII), or its prodrug, analog, isomer, metabolite, derivative, pharmaceutically acceptable salt, pharmaceutical product, polymorph, crystal, impurity, N-oxide, ester, hydrate or any combination thereof, to the subject. In another embodiment the compound is a compound of formula (I)-(XII). In some embodiments ER-β agonists are useful in treating, preventing the recurrence, inhibiting, reducing the incidence of, delaying onset, reducing the recurrence of, or reducing the severity of colon cancer in a subject. In another embodiment, ER-β agonist of this invention is compound 12b, listed in Table 1. In another embodiment, ER-β agonist of this invention is compound 12f, listed in Table 1. In another embodiment, ER-β agonist of this invention is compound 12h, listed in Table 1. In another embodiment, ER-β agonist of this invention is compound 12p, listed in Table 1. In another embodiment, ER-β agonist of this invention is compound 12s, listed in Table 1. In another embodiment, ER-β agonist of this invention is compound 12u, listed in Table 1. In another embodiment, ER-β agonist of this invention is compound 12y, listed in Table 1. In another embodiment, ER-β agonist of this invention is compound 12z, listed in Table 1, or any combination thereof.

In one embodiment, this invention provides methods of 1) improving the lipid profile of a subject; 2) reducing the circulating lipid levels in a subject; 3) increasing high density lipoprotein (HDL) cholesterol levels in a subject; 4) altering ratios of low density lipoprotein to high density lipoprotein levels in a subject; wherein said subject has prostate cancer and is undergoing or has undergone ADT, wherein said method comprises administering to said subject a compound of formula (I)-(XII) or its prodrug, ester, analog, isomer, metabolite, derivative, pharmaceutically acceptable salt, pharmaceutical product, polymorph, crystal, impurity, N-oxide, hydrate or any combination thereof. In another embodiment, the method comprises administering a composition comprising the compound of this invention. In another embodiment the compound is compound 12u, listed in Table 1. In another embodiment the compound is compound 12y, listed in Table 1. In another embodiment the compound is compound 12z, listed in Table 1. In another embodiment the compound is compound 14m, listed in Table 1.

In one embodiment, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for a) treating a bone related disorder; b) preventing a bone related disorder; c) suppressing a bone related disorder; d) inhibiting a bone related disorder; e) increasing a strength of a bone of a subject; f) increasing a bone mass in a subject; g) use for osteoclastogenesis inhibition.

In one embodiment, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for a) Accelerate bone repair; b) treating bone disorders; c) treating bone density loss; d) treating low bone mineral density (BMD); e) treating reduced bone mass; f) treating metabolic bone disease; g) promoting bone growth or regrowth; h) promoting bone restoration; i) promoting bone fracture repair; j) promoting bone remodeling; k) treating bone damage following reconstructive surgery including of the face, hip, or joints; l) enhancing of bone strength and function; m) increasing cortical bone mass; n) increasing trabecular connectivity.

In one embodiment, the invention provides a method of treating, preventing, reducing the severity of, delaying onset or reducing the recurrence of a bone-related disease or disorder in a subject, comprising administering a NRBA of this invention to the subject. In one embodiment, the subject is administered a NRBA or composition comprising the same, wherein the NRBA is a of formula (I)-(XII) or its prodrug, ester, analog, isomer, metabolite, derivative, pharmaceutically acceptable salt, pharmaceutical product, polymorph, crystal, impurity, N-oxide, hydrate or any combination thereof. In some embodiments ER-β agonists are useful in treating, preventing, reducing the severity of, delaying onset, reducing the recurrence of a bone-related disease or disorder in a subject. In another embodiment, ER-β agonist of this invention is compound 12b, listed in Table 1. In another embodiment, ER-β agonist of this invention is compound 12f, listed in Table 1. In another embodiment, ER-β agonist of this invention is compound 12h, listed in Table 1. In another embodiment, ER-β agonist of this invention is compound 12p, listed in Table 1. In another embodiment, ER-β agonist of this invention is compound 12s, listed in Table 1. In another embodiment, ER-β agonist of this invention is compound 12u, listed in Table 1. In another embodiment, ER-β agonist of this invention is compound 12y, listed in Table 1. In another embodiment, ER-β agonist of this invention is compound 12z, listed in Table 1, In another embodiment, ER-β agonist of this invention is compound 14m, listed in Table 1, or any combination thereof.

In one embodiment, the bone related disorder is a genetic disorder, or in another embodiment, is induced as a result of a treatment regimen for a given disease.

In one embodiment, the bone-related disorder is osteoporosis. In another embodiment, the bone-related disorder is osteopenia. In another embodiment, the bone-related disorder is increased bone resorption. In another embodiment, the bone-related disorder is bone fracture. In another embodiment, the bone-related disorder is bone frailty.

In another embodiment, the bone-related disorder is a loss of bone mineral density (BMD). In another embodiment, the bone-related disorder is any combination of osteoporosis, osteopenia, increased bone resorption, bone fracture, bone frailty and loss of BMD. Each disorder represents a separate embodiment of the present invention.

"Osteoporosis" refers, in one embodiment, to a thinning of the bones with reduction in bone mass due to depletion of calcium and bone protein. In another embodiment, osteoporosis is a systemic skeletal disease, characterized by low bone mass and deterioration of bone tissue, with a consequent increase in bone fragility and susceptibility to fracture. In osteoporotic patients, bone strength is abnormal, in one embodiment, with a resulting increase in the risk of fracture. In another embodiment, osteoporosis depletes both the calcium and the protein collagen normally found in the bone, in one embodiment, resulting in either abnormal bone quality or decreased bone density. In another embodiment, bones that are affected by osteoporosis can fracture with only a minor fall or injury that normally would not cause a bone fracture. The fracture can be, in one embodiment, either in the form of cracking (as in a hip fracture) or collapsing (as in a compression fracture of the spine). The spine, hips, and wrists are common areas of osteoporosis-induced bone fractures, although fractures can also occur in other skeletal areas. Unchecked osteoporosis can lead, in another embodiment, to changes in posture, physical abnormality, and decreased mobility.

In one embodiment, the osteoporosis results from androgen deprivation. In another embodiment, the osteoporosis follows androgen deprivation. In another embodiment, the osteoporosis is primary osteoporosis. In another embodiment, the osteoporosis is secondary osteoporosis. In another embodiment, the osteoporosis is postmenopausal osteoporosis. In another embodiment, the osteoporosis is juvenile osteoporosis. In another embodiment, the osteoporosis is idiopathic osteoporosis. In another embodiment, the osteoporosis is senile osteoporosis.

In another embodiment, the primary osteoporosis is Type I primary osteoporosis. In another embodiment, the primary osteoporosis is Type II primary osteoporosis. Each type of osteoporosis represents a separate embodiment of the present invention.

According to this aspect of the invention and in one embodiment, the bone-related disorder is treated with a compound as herein described, or a combination thereof. In another embodiment, other bone-stimulating compounds can be provided to the subject, prior to, concurrent with or following administration of a compound or compounds as herein described. In one embodiment, such a bone stimulating compound may comprise natural or synthetic materials.

In another embodiment, the invention provides, a method of reducing the incidence, inhibiting, suppressing, and treating osteoporosis, bone fractures and/or loss of bone mineral density (BMD) in a subject, comprising administering a NRBA/of formula (I)-(XII), or its prodrug, ester, analog, isomer, metabolite, derivative, pharmaceutically acceptable salt, pharmaceutical product, polymorph, crystal, impurity, N-oxide, hydrate or any combination thereof, or a composition comprising the same, thereby reducing the incidence, inhibiting, suppressing, and treating osteoporosis, bone fractures and/or loss of bone mineral density (BMD) in the subject. In some embodiments ER-β agonists are useful in reducing the incidence, inhibiting, suppressing, and treating osteoporosis, bone fractures and/or loss of bone mineral density (BMD) in a subject. In another embodiment, ER-β agonist of this invention is compound 12b, listed in Table 1. In another embodiment, ER-β agonist of this invention is compound 12f, listed in Table 1. In another embodiment, ER-β agonist of this invention is compound 12h, listed in Table 1. In another embodiment, ER-β agonist of this invention is compound 12p, listed in Table 1. In another embodiment, ER-β agonist of this invention is compound 12s, listed in Table 1. In another embodiment, ER-β agonist of this invention is compound 12u, listed in Table 1. In another embodiment, ER-β agonist of this invention is compound 12y, listed in Table 1. In another embodiment, ER-β agonist of this invention is compound 12z, listed in Table 1, In another embodiment, ER-β agonist of this invention is compound 14m, listed in Table for any combination thereof.

In one embodiment, the bone stimulating compound may comprise a bone morphogenetic protein (BMP), a growth factor, such as epidermal growth factor (EGF), a fibroblast growth factor (FGF), a transforming growth factor (TGF, an insulin growth factor (IGF), a platelet-derived growth factor (PDGF) hedgehog proteins such as sonic, Indian and desert hedgehog, a hormone such as follicle stimulating hormone, parathyroid hormone, parathyroid hormone related peptide, activins, inhibins, follistatin, frizzled, frzb or frazzled proteins, BMP binding proteins such as chordin and fetuin, a cytokine such as IL-3, IL-7, GM-CSF, a chemokine, such as eotaxin, a collagen, osteocalcin, osteonectin and others, as will be appreciated by one skilled in the art.

In another embodiment, the compositions for use in treating a bone disorder of this invention may comprise a compound or compounds as herein described an additional bone stimulating compound, or compounds, and osteogenic cells. In one embodiment, an osteogenic cell may be a stem cell or progenitor cell, which may be induced to differentiate into an osteoblast. In another embodiment, the cell may be an osteoblast. In another embodiment, nucleic acids which encode bone-stimulating compounds may be administered to the subject, which is to be considered as part of this invention.

In one embodiment, the methods of the present invention comprise administering the compound for treating osteoporosis. In another embodiment, the methods of this invention comprise administering a compound in combination with SERMs for treating osteoporosis. In another embodiment, the SERMs are tamoxifen, 4-hydroxytamoxifene, idoxifene, toremifene, ospemifene, droloxifene, raloxifene, arzoxifene, bazedoxifene, PPT (1,3,5-tris(4-hydroxyphenyl)-4-propyl-1H-pyrazole), DPN, lasofoxifene, pipendoxifene, EM-800, EM-652, nafoxidine, zindoxifene, tesmilifene, miproxifene phosphate, RU 58,688, EM 139, ICI 164,384, ICI 182,780, clomiphene, MER-25, diethylstibestrol, coumestrol, genistein, GW5638, LY353581, zuclomiphene, enclomiphene, delmadinone acetate, DPPE, (N,N-diethyl-2-{4-(phenylmethyl)-phenoxy}ethanamine), TSE-424, WAY-070, WAY-292, WAY-818, cyclocommunol, prinaberel, ERB-041, WAY-397, WAY-244, ERB-196, WAY-169122, MF-101, ERb-002, ERB-037, ERB-017, BE-1060, BE-380, BE-381, WAY-358, [18F]FEDNP, LSN-500307, AA-102, Ban zhi lian, CT-101, CT-102, or VG-101.

In another embodiment, the methods of the present invention comprise administering the compounds of this invention, in combination with bisphosphonates such as alendronate, tiludroate, clodroniate, pamidronate, etidronate, alendronate, zolendronate, cimadronate, neridronate, minodronic acid, ibandronate, risedronate, or homoresidronate for treating osteoporosis.

In another embodiment, the methods of the present invention comprise administering the compound, in combination with Calcitonin such as salmon, Elcatonin, SUN-8577 or TJN-135 for treating osteoporosis.

In another embodiment, the methods of treating osteoporosis of the present invention comprise administering the compound of this invention, in combination with a) vitamin D or derivative such as ZK-156979; b) vitamin D receptor ligand and analogues such as calcitriol, topitriol, ZK-150123, TEI-9647, BXL-628, Ro-26-9228, BAL-2299, Ro-65-2299 or DP-035; c) estrogen, estrogen derivative, or conjugated estrogens; d) antiestrogen, progestins, or synthetic estrogen/progestins; e) RANK ligand mAb such as denosumab formerly AMG162 (Amgen); f) αvβ3 Integrin receptor antagonist; g) osteoclast vacuolar ATPase inhibitor; h) antagonist of VEGF binding to osteoclast receptors; i) calcium receptor antagonist; j) PTh (parathyroid hormone) and analogues, PTHrP analogues (parathyroid hormone-related peptide); k) Cathepsin K inhibitors (AAE581, etc.); l) strontium ranelate; m) tibolone; n) HCT-1026, PSK3471; o) gallium maltolate; p) nutropin AQ; q) prostaglandins (for osteo); r) p38 protein kinase inhibitor; s) bone morphogenetic protein; t) inhibitor of BMP antagonism; u) HMG-CoA reductase inhibitor; v) vitamin K or derivative; w) ipriflavone; x) fluoride salts; y) dietary calcium supplement, and z) osteoprotegerin.

In some embodiments, the present invention provides a method for treating, reducing the incidence, delaying the onset or progression, or reducing and/or abrogating the symptoms associated with a nervous system disease in a subject. In one embodiment, the method comprises administering to a subject a composition comprising a compound and an anti-cancer agent, an immunomodulating agent, an agent treating the central nervous system, an anti-infective agent, an agent treating a metabolic disease, an agent treating a wasting disease, a gene therapy agent, an agent treating the endocrine system, vitamins, or a combination thereof. In some embodiments, nervous system diseases comprise autonomic nervous system diseases, central nervous system diseases, cranial nerve diseases, demyelinating diseases, nervous system malformations, neurologic manifestations, or neuromuscular diseases.

In some embodiments, autonomic nervous system diseases comprise causalgia, or reflex sympathetic dystrophy.

In some embodiments, central nervous system diseases comprise Alzheimer's disease, arachnoiditis, brain abscess, brain ischemia, central nervous system infections, cerebral palsy, cerebrovascular disorders, corticobasal ganglionic degeneration (CBGD), Creutzfeldt-Jakob syndrome, Dandy-Walker syndrome, dementia, encephalitis, encephalomyelitis, epilepsy, epilepsy induced hypogonadal and/or hypermetabolic state, essential tremor, Friedreich ataxia, Gerstmann-Straussler-Scheinker disease, Hallervorden-Spatz syndrome, Huntington disease, hydrocephalus, hypoxia, insomnia, ischemic attack, kuru, Landau-Kleffner syndrome, Lewy Body disease, Machado-Joseph disease, meige syndrome, meningitis, bacterial meningitis, viral, migraine disorders, movement disorders, multiple system atrophy, myelitis, olivopontocerebellar atrophies, Parkinson's disease, parkinsonian disorders, poliomyelitis, postpoliomyelitis syndrome, prion diseases, pseudotumor cerebri, Shy-Drager syndrome, spasms, infantile, spinal cord diseases, supranuclear palsy, syringomyelia, thalamic diseases, tic disorders, tourette syndrome, or uveomeningoencephalitic syndrome. In some embodiments, the central nervous system disease is cystic fibrosis induced hypogonadal state.

In some embodiments, cranial nerve diseases comprise bell palsy, cranial nerve diseases, facial hemiatrophy, facial neuralgia, glossopharyngeal nerve diseases, Moebius syndrome, or trigeminal neuralgia.

In some embodiments, central nervous system diseases comprise injuries or damage to the central nervous system (CNS). In some embodiments, injuries or damage to the CNS may be associated with muscle wasting disorders. Injuries or damage to the CNS can be, for example, caused by diseases, trauma or chemicals. Examples are central nerve injury or damage, peripheral nerve injury or damage and spinal cord injury or damage.

Studies involving patients with spinal cord injuries (SCI) have shown that central neurotransmitters may be altered after SCI causing hypothalamus-pituitary-adrenal axis dysfunction, whose disruption led to a significant decrease in testosterone and other hormone levels. SCI or other acute illness or trauma characteristically includes heightened catabolism in conjunction with the lowered anabolic activity resulting in a condition that is prone to loss of lean body tissue, which is often accompanied by disturbed nutrient utilization. The effects of the loss of lean body mass include the development of wounds and impaired healing mechanisms, further compounding the problem. Because of poor nutrition and protein combined with immobilization, patients with spinal cord injury are at high risk for bed sores.

In one embodiment, a wide variety of injuries of the CNS may be treated by the methods of the present invention. CNS injury may refer, in one embodiment, to a breakdown of the membrane of a nerve cell, or, in another embodiment, to the inability of the nerve to produce and propagate nerve impulses, or in another embodiment, to the death of the cell. An injury includes damage that directly or indirectly affects the normal functioning of the CNS. The injury may be a structural, physical, or mechanical impairment and may be caused by physical impact, as in the case of a crushing, compression, or stretching of nerve fibers. Alternatively, the cell membrane may be destroyed by or degraded by an illness, a chemical imbalance, or a physiological malfunction such as anoxia (e.g., stroke), aneurysm, or reperfusion. A CNS injury includes, for example and without limitation, damage to retinal ganglion cells, a traumatic brain injury, a stroke-related injury, a cerebral aneurysm-related injury, a spinal cord injury, including monoplegia, diplegia, paraplegia, hemiplegia and quadriplegia, a neuroproliferative disorder, or neuropathic pain syndrome.

Injuries or damage to the central nervous system (CNS) are also associated with muscle wasting and other wasting disorders. Injuries or damage to the CNS can be, for example, caused by diseases, trauma or chemicals. Examples are central nerve injury or damage, peripheral nerve injury or damage and spinal cord injury or damage. In one embodiment CNS damage or injury comprise Alzheimer's diseases (AD); anger (mood); anorexia, anorexia nervosa, anorexia associated with aging and/or assertiveness (mood).

In another embodiment, the invention provides a method of treating, preventing, suppressing, inhibiting, or reducing the incidence of central nervous system (CNS) disorder, disease or condition in a mammalian subject comprising administering a compound of formula (I)-(XII) or its prodrug, ester, analog, isomer, metabolite, derivative, pharmaceutically acceptable salt, pharmaceutical product, polymorph, crystal, impurity, N-oxide, hydrate or any combination thereof to the subject.

In some embodiments, the present invention provides a method for treating, reducing the incidence, delaying the onset or progression, or reducing and/or abrogating the symptoms associated with an ophthalmic disease in a subject. In one embodiment, the method comprises administering to a subject a composition comprising a NRBA compound. In one embodiment, the method comprises administering to a subject a composition comprising a NRBA compound and an anti-cancer agent, an immunomodulating agent, an agent treating the cardiovascular system, an anti-infective agent, an agent treating a wasting disease, a gene therapy agent, an agent treating the endocrine system, vitamins, or a combination thereof. In some embodiments ophthalmic disease comprise acute zonal occult outer retinopathy, abnormal color vision, Adie syndrome, albinism, ocular-amaurosis, fugax, amblyopia, aniridia, anisocoria, anterior ischemic optic neuropathy, anophthalmos, aphakia, asthenopia astigmatism, autoimmune disease blepharitis, blepharoptosis, blepharospasm, blindness, cataract, senile cataract central chorioretinopathy chalazion, chorioretinitis, chorioretinal hemorrhage, choroideremia, coloboma, color vision defects, conjunctivitis, corneal diseases, corneal dystrophies, corneal edema, corneal ulcer, corneal opacity, corneal erosion, corneal endothelial cell degeneration and dystrophy or loss of endothelial cell, corneal dystrophy or degeneration, detachment of corneal epithelium, epidemic keratoconjunctivitis, chalazion, central nerve diseases, central retinal artery or vein occlusion, arteriosclerosis of retinal artery, photopsia, diabetic retinopathy, chorioretinal atrophy, diabetic retinopathy, diplopia, distichiasis, dry eye syndromes, Duane retraction syndrome, ectropion, entropion, esotropia, exfoliation syndrome, exotropia, eye hemorrhage, eye neoplasms, eyelid diseases, floaters, general fibrosis syndrome, glaucoma, high tension glaucoma, normal tension glaucoma, gyrate atrophy, hemianopsia, Hermanski-Pudlak syndrome, hordeolum, Homer syndrome, hysteria hyperopia, hyphema, iridocyclitis iritis, Kearns-Sayer syndrome, keratitis, keratoconus, lacrimal apparatus diseases, lacrimal duct obstruction, lens diseases, lowering in dynamic visual activity, macular degeneration, macular hole microphthalmos, myopia, nystagmus, narrowing of visual field due to various kinds of diseases pathologic, ocular motility disorders, oculomotor nerve diseases, ophthalmoplegia, optic atrophies, optic nerve diseases, optic neuritis, optic neuropathy, optic nerve atrophy orbital cellulitis, papilledema, peter's anomaly, presbyopia, psychosis pterygium, pupil disorders, refractive errors, retinal detachment, retinal diseases, retinal vein occlusion, retinal and choroidal neovascular diseases, cataract due to removal of ovary, cataract due to TGFβ macular fibrosis, macular epiretinal membrane, refractive error retinal tear, retinitis proliferans, pigmentary retinal degeneration retinitis pigmentosa, retinopathy of prematurity, retinoschisis, scleritis, senile macular degeneration scotoma, strabismus, Thygeson's superficial punctate keratitis, trachoma, uveitis, white dot syndrome, vision disorders, or vitreous disorders, diseases due to cerebral pituitary gland disorder and imbalance of hormones, diseases due to gene disorder and diseases due to immune disorder, the method comprising administering a NRBA of formula (I)-(XII) or its prodrug, analog, isomer, metabolite, derivative, pharmaceutically acceptable salt, pharmaceutical product, polymorph, crystal, impurity, N-oxide, ester. hydrate or any combination thereof to the subject.

In another embodiment, the methods of treating eye diseases comprise administering a composition comprising the compounds of this invention to the subject, wherein the composition is in the form of eye drops, eye wash, ointments, conjunctival injections, or contact lens adsorbents. In another embodiment, the methods of treating eye diseases comprises administering a composition comprising the compounds of this invention in the form of a tablet, capsule, liquid, syrup, injection, hap, ointment, eye drops, and the like, and administered orally, or non-orally such as injection, locally such as dropping to eye, etc. The effective ingredient may be vaporized and inhaled, for example through the nose, mouth or trachea.

In some embodiment, the methods of treating eye diseases comprise administering a composition comprising the compounds of this invention and any other compound, which is useful in treating the indicated conditions, as known in the art.

In some embodiment, eye drops and eye wash comprise water-solubilized compounds (I)-(XII) of this invention, which are, in one embodiment, dissolved in sterilized distilled water, BSS Plus, and/or physiological saline. In another embodiment, the compounds of this invention. In another embodiment, additives are added comprising excipients, carriers, pH controllers, isotonic agents, preservatives, glutathione, glucose, various kind of salt(s), stabilizers, refrigerants, antioxidants, antiseptic agents, or any combination thereof. In another embodiment, the eye drops and eye wash comprise hydroxypropylmethyl cellulose, carboxymethyl cellulose or its sodium salt, polypyrrolidone, polyvinylpyrrolidone (this is added and heated), or any combination thereof.

In some embodiments, the present invention provides a method for treating, reducing the incidence, delaying the onset or progression, or reducing and/or abrogating the symptoms associated with an endocrine disorder in a subject. In one embodiment, the method comprises administering to a subject a composition comprising a compound and anti-cancer agent, an immunomodulating agent, an antidiabetic agent, an agent treating the cardiovascular system, an agent treating the gastrointestinal system, an agent treating a dermatological disorder, an agent treating the central nervous system, an anti-infective agent, an agent treating the liver, an agent treating the kidney, an agent treating a metabolic disease, an agent treating a wasting disease, a gene therapy agent, an agent treating the endocrine system, vitamins, or a combination thereof. In some embodiments, endocrine disorders comprise acromegaly, Addison disease, adrenal gland diseases, adrenal hyperplasia, congenital, androgen-insensitivity syndrome, congenital hypothyroidism, Cushing syndrome, diabetes insipidus, diabetes mellitus, diabetes mellitus-type 1, diabetes mellitus-type 2, diabetic, ketoacidosis, empty Sella syndrome, endocrine gland neoplasms, endocrine system diseases, gigantism, gonadal disorders, graves disease, hermaphroditism, hyperaldosteronism, hyperglycemic hyperosmolar nonketotic coma, hyperpituitarism, hyperprolactinemia, hyperthyroidism, hypogonadism, hypopituitarism, hypothyroidism, Kallmann syndrome, Nelson syndrome, parathyroid diseases, pituitary diseases, polyendocrinopathies, autoimmune, puberty, delayed, puberty, precocious, renal osteodystrophy, thyroid diseases, thyroid hormone resistance syndrome, thyroid neoplasms, thyroid nodule, thyroiditis, thyroiditis, autoimmune, thyroiditis, subacute, or Wolfram syndrome.

In one embodiment, "Hypogonadism" is a condition resulting from or characterised by abnormally decreased functional activity of the gonads, with retardation of growth and sexual development.

In some embodiments, the present invention provides a method for treating, reducing the incidence, delaying the onset or progression, or reducing and/or abrogating the symptoms associated with a liver disease in a subject. In one embodiment, the method comprises administering to a subject a composition comprising a compound of this invention and anti-cancer agent, an immunomodulating agent, an agent treating the gastrointestinal system, an anti-infective agent, an agent treating the liver, an agent treating a metabolic disease, an agent treating a wasting disease, a gene therapy agent, an agent treating the endocrine system, vitamins, or a combination thereof. In some embodiments, liver diseases comprise liver cancer, primary biliary cirrhosis, autoimmune hepatitis, chronic liver disease, cirrhosis of the liver, hepatitis, viral hepatitis (hepatitis a, hepatitis b, chronic hepatitis b, hepatitis c, chronic hepatitis c, hepatitis d, hepatitis e, hepatitis x), liver failure, jaundice, neonatal jaundice, hepatoma, liver cancer, liver abscess, alcoholic liver disease, hemochromatosis, Wilson's disease, portal hypertension, primary sclerosing cholangitis, sarcoidosis, tapeworms, alveolar hydatid disease, fascioliasis, schistosomiasis, gaucher disease, Zellweger syndrome, alcoholism, food poisoning, pneumococcal pneumonia' or vibrio vulnificus.

In some embodiments, the present invention provides a method for treating, reducing the incidence, delaying the onset or progression, or reducing and/or abrogating the symptoms associated with nerve injury, neuropathy, diabetic neuropathy, alcoholic neuropathy, subacute combined degeneration of the spinal cord, diabetes, rheumatoid arthritis.

In another embodiment, the invention provides a method of treating, preventing, suppressing, inhibiting, or reducing the incidence of hot flashes, gynecomastia, and/or hair loss in female subjects, or in another embodiment, in male human subjects. In one embodiment, invention provides a method of treating, preventing, suppressing, inhibiting, or reducing the incidence of hot flashes, gynecomastia, and/or hair loss in a male subject having prostate cancer, comprising administering a NRBA of formula (I)-(XII) or its prodrug, ester, analog, isomer, metabolite, derivative, pharmaceutically acceptable salt, pharmaceutical product, polymorph, crystal, impurity, N-oxide, hydrate or any combination thereof, or a composition comprising the same, thereby treating, preventing, suppressing, inhibiting, or reducing the incidence of hot flashes, gynecomastia, and/or hair loss in said male human subjects.

In some embodiments, the present invention provides a method for treating, reducing the incidence, delaying the onset or progression, or reducing and/or abrogating the symptoms associated with a hypogonadal state in a subject. In one embodiment, the present invention provides a method for treating, reducing the incidence, delaying the onset or progression, or reducing and/or abrogating the symptoms associated with a pharmacotherapy induced hypogonadal state in a subject. In some embodiments, hypogonadism is caused by treatments which alter the secretion of hormones from the sex glands in both women and men. In some embodiments, hypogonadism may be "primary" or "central". In primary hypogonadism, the ovaries or testes themselves do not function properly. In some embodiments, hypogonadism may be induced by surgery, radiation, genetic and developmental disorders, liver and kidney disease, infection, or certain autoimmune disorders. In some embodiments, menopause is a form of hypogonadism. Menopause may cause, in some embodiments, amenorrhea, hot flashes, vaginal dryness, or irritability due to woman's estrogen levels fall. In one embodiment, the method comprises administering to a subject a composition comprising a compound of this invention and an anti-cancer agent, an immunomodulating agent, an antidiabetic agent, an agent treating the cardiovascular system, an agent treating the gastrointestinal system, an agent treating the central nervous system, an agent treating a metabolic disease, an agent treating a wasting disease, a gene therapy agent, an agent treating the endocrine system, an agent treating a dermatological disorder, an anti-infective agent, an agent treating the liver, an agent treating the kidney, vitamins, or a combination thereof.

In one embodiment, the term "hot flashes" refers to the following: sudden feeling of heat in the upper part or all of the body, face and neck flush, red blotches appearing on the chest, back and arms, heavy sweating, cold shivering, etc.

It is to be understood that any sex hormone-dependent disease, disorder or condition may be treated via the methods of this invention, using the compositions of this invention.

In some embodiments, the present invention provides a method for treating, reducing the incidence, delaying the onset or progression, or reducing and/or abrogating the symptoms associated with osteopenic state in a subject. In one embodiment, the present invention provides a method for treating, reducing the incidence, delaying the onset or progression, or reducing and/or abrogating the symptoms associated with a pharmacotherapy induced osteopenic state in a subject. In some embodiments, osteopenia is a mild thinning of the bone mass. In some embodiments, osteopenia is a precursor to osteoporosis. In some embodiments osteopenia is defined as a bone density between one standard deviation (SD) and 2.5 SD below the bone density of a normal young adult. In one embodiment, the method comprises administering to a subject a composition comprising a compound of this invention and an anti-cancer agent, an immunomodulating agent, an antidiabetic agent, an agent treating the cardiovascular system, an agent treating the gastrointestinal system, an agent treating the central nervous system, an agent treating a metabolic disease, an agent treating a wasting disease, a gene therapy agent, an agent treating the endocrine system, an agent treating a dermatological disorder, an anti-infective agent, an agent treating the liver, an agent treating the kidney, vitamins, or a combination thereof.

In some embodiments, the present invention provides a method for treating, reducing the incidence, delaying the onset or progression, or reducing and/or abrogating the symptoms associated with a combination of diseases and/or disorders in a subject as described hereinabove. In one embodiment, the method comprises administering to a subject a composition comprising a compound of this invention and an anti-cancer agent, an immunomodulating agent, an antidiabetic agent, an agent treating the cardiovascular system, an agent treating the gastrointestinal system, an agent treating the central nervous system, an agent treating a metabolic disease, an agent treating a wasting disease, a gene therapy agent, an agent treating the endocrine system, an agent treating a dermatological disorder, an anti-infective agent, an agent treating the liver, an agent treating the kidney, vitamins, or a combination thereof.

It is to be understood that any method of this invention, as herein described, encompasses the administration of a compound as herein described, or a composition comprising the same, to the subject, in order to treat the indicated disease, disorder or condition. The methods as herein described each and/or all may further comprise administration of an additional therapeutic agent as herein described, and as will be appreciated by one skilled in the art.

In one embodiment, the method comprises administering to a subject a composition comprising a compound of this invention and an anti-cancer agent, an immunomodulating agent, an antidiabetic agent, an agent treating the cardiovascular system, an agent treating the gastrointestinal system, an agent treating the central nervous system, an agent treating a metabolic disease, an agent treating a wasting disease, a gene therapy agent, an agent treating the endocrine system, an agent treating a dermatological disorder, an anti-infective agent, an agent treating the liver, an agent treating the kidney, vitamins, nutritional additives, hormones, each and/or all as herein described, or any other therapeutic agent as herein described, or a combination thereof.

In another embodiment, this invention provides methods of treatment of cystic fibrosis and induced hypogonadal states as a result of the same, epilepsy and induced hypogonadal and/or hypermetabolic states as a result of the same, hereditary angioedema, lupus erythematosus and decreased BMD as a result of the same, alcohol and smoking induced osteoporosis, in a subject the methods comprising administering a compound as herein described to the subject.

In another embodiment, this invention provides a method of treating a nervous system disease, disorder or condition, the method comprising administering to the subject a compound as herein described, and optionally anti-psychotics, such as, for example, zotepine, haloperidol, amisulpride, risperidone, other D2 dopamine receptor antagonists; anti-epileptics, such as valproic acid, carbamazepine, oxcarbamazepine, etc. or combinations thereof.

In one embodiment cardiovascular disorders comprise of hypertension (HTN), coronary artery disease (CAD) or myocardial perfusion. In another embodiment this invention provides methods of use of the NRBA compounds as herein described for promoting aortic smooth muscle cell proliferation. In another embodiment this invention provides methods of use of the compounds as herein described for treating arteriosclerosis. In one embodiment this invention provides methods of use of the compounds as herein described in conjunction with vascular stents. In some embodiments the compounds of this embodiment could be incorporated onto the stent as a coating to retard vascular fibrosis and remodeling, vascular cell proliferation and migration, etc. that often cause stent failure or restenosis. In another embodiment this invention provides methods of use of the compounds as herein described for lowering blood pressure. In another embodiment this invention provides methods of use of the compounds as herein described for treating cardiac diseases and disorders comprising cardiomyopathy, cardiac dysfunctions such as myocardial infarction, cardiac hypertrophy and cognitive heart failure. In another embodiment this invention provides methods of use of the compounds as herein described for cardioprotection comprising cardioprotection in insulin resistance; treating diabetes type I and II, metabolic syndrome, syndrome X and/or high blood pressure.

In one embodiment, the invention provides a method of treating, preventing, reducing the risk of mortality from cardiovascular and/or cerebrovascular disease in a subject, comprising administering a compound of this invention or its prodrug, ester, analog, isomer, metabolite, derivative, pharmaceutically acceptable salt, pharmaceutical product, polymorph, crystal, impurity, N-oxide, hydrate or any combination thereof, or a pharmaceutical composition comprising the same.

In one embodiment, the invention provides a method of treating, preventing, reducing the risk of mortality from cardiovascular and/or cerebrovascular disease in a subject, comprising administering a NRBA of formula (I)-(XII) or its prodrug, ester, analog, isomer, metabolite, derivative, pharmaceutically acceptable salt, pharmaceutical product, polymorph, crystal, impurity, N-oxide, hydrate or any combination thereof, or a composition comprising the same. In some embodiments ER-β agonists are useful in treating, preventing, reducing the risk of mortality from cardiovascular and/or cerebrovascular disease in a subject. In another embodiment, ER-β agonist of this invention is compound 12b, listed in Table 1. In another embodiment, ER-β agonist of this invention is compound 12f, listed in Table 1. In another embodiment, ER-β agonist of this invention is compound 12h, listed in Table 1. In another embodiment, ER-β agonist of this invention is compound 12p, listed in Table 1. In another embodiment, ER-β agonist of this invention is compound 12s, listed in Table 1. In another embodiment, ER-β agonist of this invention is compound 12u, listed in Table 1. In another embodiment, ER-β agonist of this invention is compound 12y, listed in Table 1. In another embodiment, ER-β agonist of this invention is compound 12z, listed in Table 1. In another embodiment, ER-β agonist of this invention is compound 14m, listed in Table 1, or any combination thereof.

In one embodiment, cardiovascular disease comprises, inter alia, atherosclerosis of the coronary arteries, angina pectoris, and myocardial infarction. In one embodiment, cerebrovascular disease comprises, inter alia, atherosclerosis of the intracranial or extracranial arteries, stroke, syncope, and transient ischemic attacks.

Cardiovascular cells, as well as reproductive tissues, bone, liver, and brain, express both of the known estrogen receptors, estrogen receptor-α (ER-α) and estrogen receptor-β (ER-β). These receptors are important targets for endogenous estrogen, estrogen replacement therapy (ERT), and pharmacological estrogen agonists. Estrogen-estrogen receptor complexes serve as transcription factors that promote gene expression with a wide range of vascular effects, including regulation of vasomotor tone and response to injury, which may be protective against development of atherosclerosis and ischemic diseases. Estrogen receptors in other tissues, such as the liver, may mediate both beneficial effects (e.g., changes in apoprotein gene expression that improve lipid profiles) and adverse effects (e.g., increases in gene expression of coagulation proteins and/or decreases in fibrinolytic proteins). Two general estrogen-mediated vascular effects are recognized. Rapid, transient vasodilation occurs within a few minutes after estrogen exposure, independently of changes in gene expression. Longer-term effects of estrogen on the vasculature, such as those related to limiting the development of atherosclerotic lesions or vascular injury, occur over hours to days after estrogen treatment and have as their hallmark alterations in vascular gene expression. Progesterone and other hormonal receptors are also expressed in the vasculature.

In one embodiment, this invention provides a method of improving the dexterity and movement in a subject, for example, by treating arthritis in the subject.

The term "arthritis" refers, in another embodiment, to a non-inflammatory degenerative joint disease occurring chiefly in older people, characterized by degeneration of the articular cartilage, hypertrophy of bones and the margins, changes in the synovial membrane, etc. It is accompanied, in other embodiments, by pain and stiffness, particularly after prolonged activity.

The term "increased blood pressure" or "hypertension" refers, in other embodiments, to a repeatedly high blood pressure above 140 over 90 mmHg. Chronically-elevated blood pressure can cause blood vessel changes in the back of the eye, thickening of the heart muscle, kidney failure, and brain damage.

The term "stroke" refers, in other embodiments, to damage to nerve cells in the brain due to insufficient blood supply often caused by a bursting blood vessel or a blood clot. The term "heart disease", in other embodiments, refers to a malfunction in the heart normal function and activity, including heart failure.

In one embodiment, this invention provides a method of treating vascular disease in a human subject, comprising the step of administering to said subject a compound of this invention or its isomer, pharmaceutically acceptable salt, pharmaceutical product, hydrate, N-oxide, or any combination thereof.

In one embodiment, the NRBAs of this invention bind their cognate receptor at the cell surface, translocate to the cell's nucleus, and exert their effects. In one embodiment, such effects may comprise, inter alia, regulation of particular gene expression, and may in turn play a role in the inhibition of apoptosis, activation of protein kinase pathways, and others.

In another embodiment, the NRBAs of this invention bind cognate receptors and translocate within the mitochondria, whereupon they associate with mitochondrial DNA, and in turn play a role in the increased respiratory chain activity, inhibition of TGFβ-induced apoptosis and/or activation of manganese superoxide dismutase, and others.

Superoxide dismutases (SODs) are key enzymes in the cellular defence against free radical oxidation. By catalyzing the degradation of the superoxide free radical to water and hydrogen peroxide, SODs, play an important role in reducing the damage associated with, for example ischemic injury, chronic lung disease, Alzheimer's disease, Down syndrome, inflammatory disorders, cardiovascular disease, immune-system decline, brain dysfunction, cataracts, and other aspects of aging and degenerative disease.

In one embodiment, this invention provides a method of treating, ameliorating and/or preventing reactive species-mediated damage in a subject, comprising the step of administering a NRBA of formula (I)-(XII) or its prodrug, analog, isomer, metabolite, derivative, pharmaceutically acceptable salt, pharmaceutical product, polymorph, crystal, impurity, N-oxide, ester, hydrate or any combination thereof to the subject. In one embodiment, the reactive species comprises reactive oxygen intermediates and the NRBA promotes or enhances the activity of cellular superoxide dismutase. In one embodiment, the reactive species comprises reactive nitrogen intermediates and the NRBA promotes or enhances the activity of cellular nitric oxide synthase.

In some embodiments, such damage is associated with a variety of diseases, such as, but not limited to cardiovascular disease, such as coronary heart disease and atherosclerosis, neurodegenerative disease, such as Alzheimer's disease and/or multiple sclerosis, infection, for example, HCV infection and complications thereof, autoimmune disease, such as lupus, cancer, and others, as appreciated by one skilled in the art.

In some embodiments, such activity results in suppression of pathogenic apoptosis, for example, as occurs in various disease states, such as neurodegenerative diseases or disorders, glaucoma, autoimmune disease, and others as will be appreciated by one skilled in the art.

In some embodiments, the compounds of this invention, characterized by the structures of formulae I-XII, and including any embodiment thereof, localize within the cytosol of a cell, or within cytosolic organelles, such as mitochondrion, wherein such compounds may affect cellular signaling pathways, and thereby effect the methods as described herein. For example, and in one embodiment, the compounds may interact with cellular proteins and thereby synergize a desired effect, in some embodiments, in signaling pathways within the cell, producing the desired effect. In other embodiments, the compounds of formulae I-XII antagonize a particular response or pathway in the cell, which otherwise produces an undesired effect, for example, exacerbating disease, and thus the compounds as described herein are effective in such methods by their ability to disrupt or interfere or antagonize pathogenic mechanisms in a cell or in a subject.

In some embodiments, the agents of this invention may alter intracellar signaling pathways or responsiveness to such pathways or cascades.

In some embodiments, downstream effects of the compounds of this invention, characterized by the structures of formulae I-XII, and including any embodiment thereof, may be controlled by intracellular kinase signaling pathways activated by growth factors. In some embodiments, the compounds may affect signaling downstream of binding of a hormone to its receptor, for example, with the case of glycogen synthase kinase 3 (GSK3), an effector kinase of the phosphatidylinositol 3-kinase (PI3K) pathway, may be activated by administration of a compound of this invention and in turn affect ERalpha activity in specific cells, for example in neuroblastoma cells, and thereby effect some of the methods of this invention. In some embodiments, the compounds of this invention may result in greater expression of GSK3, which in turn stimulates or increases ER-dependent gene expression.

It is to be understood that any use of any of the compounds as herein described may be used in the treatment of any disease, disorder or condition as described herein, and represents an embodiment of this invention.

In some embodiments, any of the compositions useful in the methods disclosed herein comprise a compound of this invention, in any form or embodiment as described herein. In some embodiments, of the compositions of this invention will consist essentially of a compound of this invention, in any form or embodiment as described herein.

It is to be understood that any use of any of the compounds as herein described may be used in the treatment of any disease, disorder or condition as described herein, and represents an embodiment of this invention.

An "effective amount" means the amount of a compound or composition according to the invention that, when administered to a patient for treating a state, disorder or condition is sufficient to effect such treatment. The "effective amount" will vary depending on the active ingredient, the state, disorder, or condition to be treated and its severity, and the age, weight, physical condition and responsiveness of the subject to be treated.

The terms "treat," "treatment," and "treating" mean to relieve, alleviate, delay, reduce, reverse, improve, manage or prevent at least one symptom of a condition in a subject. The term "treating" may also mean to arrest, delay the onset (i.e., the period prior to clinical manifestation of a disease) and/or reduce the risk of developing or worsening a condition.

A subject or patient in whom administration of a therapeutic compound is an effective therapeutic regimen for a disease or disorder is in some embodiments, a human, but can be any animal. Thus, as can be readily appreciated by one of ordinary skill in the art, the compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The following examples are presented in order to more fully illustrate the preferred embodiments of the invention. They should in no way, however, be construed as limiting the broad scope of the invention.

EXAMPLES

Example 1: Chemical syntheses of 4-bromo-6,8-dihydroxy-2-(4-hydroxyphenyl)isoquinolin-1(2H)-one (12u)

Scheme and Procedures for Synthesis of 12u.

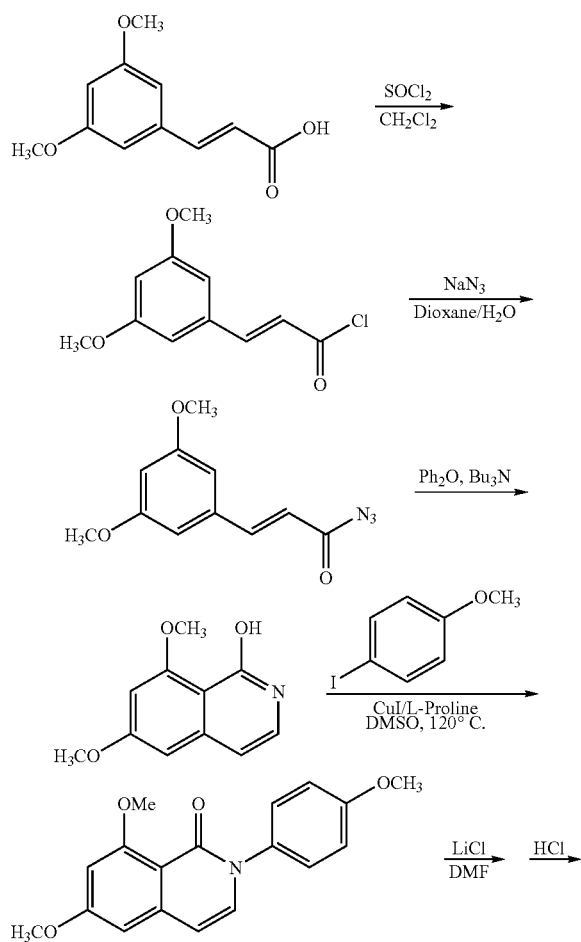

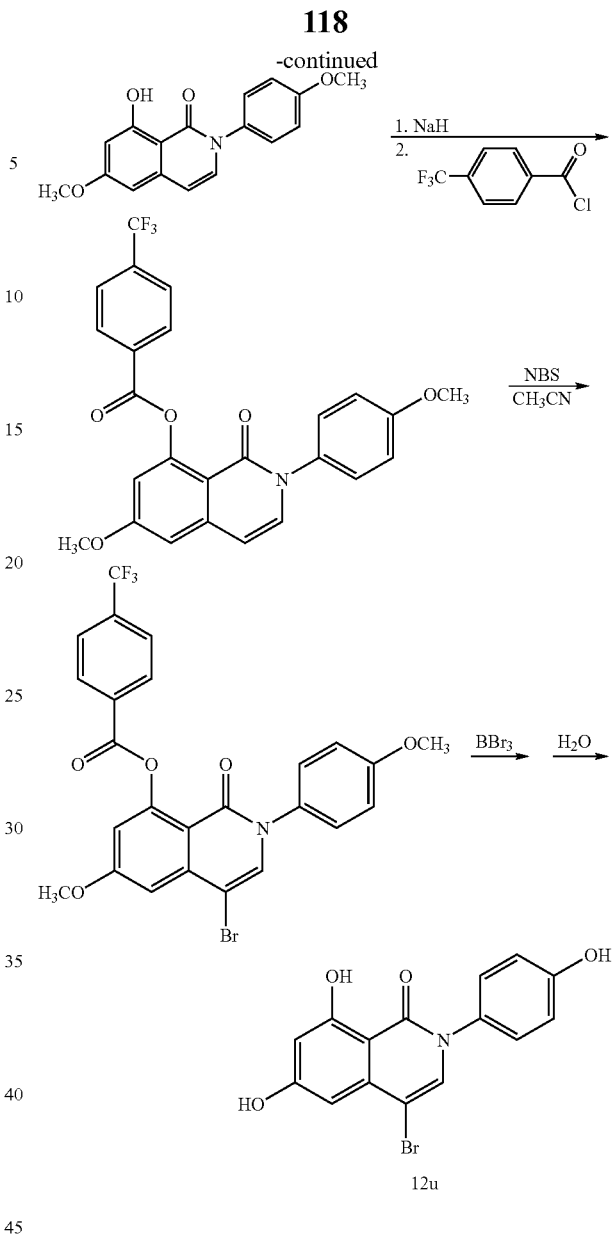

Synthesis of 6,8-dimethoxyisoquinolin-1-ol

A mixture of trans-3,5-dimethoxycinnamic acid (15.30 g, 73.48 mmol) and thionyl chloride (13.11 g, 0.11 mol) were placed in a 250 mL single-necked round-bottomed flask fitted with a magnetic stirring bar and reflux condenser. Dry methylene chloride (80.0 mL) was added to the above mixture. The resulted solution was heated to reflux for 3 hours. Then, the solvent was removed under reduced pressure. The residue was dried under vacuum overnight to give a pale-yellow solid, trans-3,5-dimethoxycinnamic acid chloride.

The pale-yellow solid acid chloride was dissolved in 20 mL of 1,4-dioxane and added drop wise over 1 hour to a 0° C. suspension of 14.33 g (0.22 mol) of sodium azide in 80 mL of 1:1 (v/v) 1,4-dioxane/water. During the addition the temperature was maintained at 0° C. in an ice-bath. After complete addition of the acid chloride, the mixture was stirred for 1 hour at 0° C., and then diluted with 75 mL of water. The mixture was extracted with methylene chloride (3×40 mL); the combined extracts were dried over anhydrous magnesium sulfate followed by filtration and concentration to ca. 100 mL. The solution was diluted with 20 mL of phenyl ether and further concentrated to remove the remaining methylene chloride (trans-3,5-dimethoxycinnamic acyl azide).

A 500 mL three-necked round-bottomed flask fitted with a nitrogen inlet, reflux condenser, an addition funnel, internal thermometer and magnetic stirring bar was charged with 29 mL of tributylamine and 80 mL of phenyl ether. The solution was heated to 230° C. and the acyl azide in 40 mL of phenyl ether was added drop wise over 3 hours from an addition funnel. During the addition, the reflux temperature gradually decreased to about 200° C. Hence, after completion of the addition, the temperature was raised to 230° C. After heating for an additional hour at 230° C., the mixture was cooled to room temperature. The mixture was poured to 500 mL of hexanes with stirring. The solid was filtered and washed with hexanes (2×100 mL). The pale-yellow solid was dried and recrystallized from ethyl acetate/methanol mixture to give a pale-yellow crystalline material, 10.58 g, 70.2% yield. MS: m/z 228.2 [M+Na]$^+$. $^1$H NMR (DMSO-$d_6$, 300 MHz): δ 10.71 (s, 1H), 7.02 (d, 1H, J=6.9 Hz), 6.63 (d, 1H, J=2.4 Hz), 6.47 (d, 1H, J=2.4 Hz), 6.31 (d, 1H, J=6.9 Hz), 3.83 (s, 3H), 3.79 (s, 3H).

Synthesis of 6,8-dimethoxy-2-(4-methoxyphenyl)isoquinolin-1(2H)-one 6,8-Dimethoxyisoquinolin-1-ol (1.59 g, 7.75 mmol), 4-iodoanisole (2.72, 11.62 mmol), copper(I) iodide (0.30 g, 1.55 mmol), L-proline (0.36 g, 3.10 mmol) and anhydrous potassium carbonate (2.14 g, 15.50 mmol) were placed in a dry 250 mL three-necked round-bottomed flask fitted with a stirring bar and reflux condenser. The system was vacuumed and refilled with dry argon. Then, anhydrous methyl sulfoxide (50 mL) was added via a syringe under argon atmosphere. The reaction solution was stirred and heated to 120° C. for 20 hours. Water (20 mL) was added to quench the reaction. The mixture was extracted with ethyl acetate (5×20 mL). The extracts were combined, washed with brine (3×10 mL) and dried over anhydrous MgSO$_4$ followed by filtration and concentration to give a yellow residue. The yellow residue was purified by flash column chromatography (silica-gel, CH$_2$Cl$_2$/Acetone=19/1 v/v) to give a pale-yellow solid product, 2.12 g, 88.0% yield. MS: m/z 312.9 [M+H]$^+$. $^1$H NMR (DMSO-$d_6$, 300 MHz): δ 7.31-7.26 (m, 3H), 7.02 (d, 2H, J=8.7 Hz), 6.71 (d, 1H, J=2.4 Hz), 6.54 (d, 1H, J=2.4 Hz), 6.45 (d, 1H, J=7.8 Hz), 3.87 (s, 3H), 3.81 (s, 3H), 3.79 (s, 3H).

Synthesis of 8-hydroxy-6-methoxy-2-(4-methoxyphenyl)isoquinolin-1(2H)-one

Compound 6,8-dimethoxy-2-(4-methoxyphenyl)isoquinolin-1(2H)-one (2.25 g, 7.23 mmol) and LiCl (6.12 g, 144.54 mmol) were placed in a dry, argon flushed 150 mL three-necked flask fitted with a stirring bar and reflux condenser. Anhydrous DMF (30 mL) was added via a syringe. The reaction mixture was heated to 140° C. under vacuum for 20 hours. Then, the reaction was quenched by addition of 30 mL of 2N HCl solution. The solution was extracted with EtOAc (3×30 mL). The extracts were combined and dried over anhydrous MgSO$_4$. The solvent was removed under reduced pressure. The residue was purified by flash column chromatography (silica-gel, CH$_2$Cl$_2$) to give a white solid product, 1.80 g. 83.7% yield. $^1$H NMR (DMSO-$d_6$, 300 MHz): δ 12.98 (s, 1H), 7.42-7.35 (m, 3H), 7.06 (d, 2H, J=9.0 Hz), 6.70-6.67 (m, 2H), 6.45 (d, 1H, J=2.1 Hz), 3.85 (s, 3H), 3.82 (s, 3H).

Synthesis of 6-methoxy-2-(4-methoxyphenyl)-1-oxo-1,2-dihydroisoquinolin-8-yl-4-(trifluoromethyl)benzoate Compound 8-hydroxy-6-methoxy-2-(4-methoxyphenyl)isoquinolin-1(2H)-one (0.60 g, 2.02 mmol) was placed in a dry 250 mL three-necked flask fitted with a stirring bar and sealed with septa. Anhydrous DMF (15 mL) was added via a syringe under argon atmosphere. The solution was cooled to 0° C. in an ice-bath. NaH (0.12 g, 3.03 mmol, 60% dispersion in mineral oil) was added. The reaction mixture was stirred at 0° C. for 30 minutes. Then, it was warmed to room temperature for 30 minutes. The mixture was cooled to 0° C. again in an ice bath. 4-(Trifluoromethyl)benzoyl chloride was added via a syringe with stirring at 0° C. The reaction mixture was stirred at 0° C. for 30 minutes and at room temperature for additional 30 minutes. The reaction was quenched by adding 20 mL of saturated NH$_4$Cl solution. The solution was diluted with 20 mL of water and stirred for one hour at room temperature. It was extracted with ethyl acetate (3×20 mL). The extracts were washed with brine (20 mL) and dried over anhydrous MgSO$_4$. The solvent was removed under reduced pressure. The residue was subjected to flash column chromatography (silica-gel, CH$_2$Cl$_2$) to give a white solid product, 0.93 g, 98.1% yield. MS: m/z 492.1 [M+Na]$^+$. $^1$H NMR (DMSO-$d_6$, 300 MHz): δ 8.25 (d, 2H, J=8.7 Hz), 7.93 (d, 2H, J=8.4 Hz), 7.40 (d, 1H, J=7.5 Hz), 7.23 (d, 2H, J=8.7 Hz), 7.21 (d, 1H, J=2.4 Hz), 7.01 (d, 1H, J=2.4 Hz), 6.98 (d, 2H, J=8.7 Hz), 6.67 (d, 1H, J=7.5 Hz), 3.93 (s, 3H), 3.76 (s, 3H).

Synthesis of 4-bromo-6-methoxy-2-(4-methoxyphenyl)-1-oxo-1,2-dihydroisoquinolin-8-yl-4-(trifluoromethyl)benzoate Compound 6-methoxy-2-(4-methoxyphenyl)-1-oxo-1,2-dihydroisoquinolin-8-yl-4-(trifluoromethyl)benzoate (0.51 g, 1.09 mmol) and N-bromosuccinimide (0.23 g, 1.30 mmol) were placed in a dry, argon flushed 150 mL single-necked flask fitted with a stirring bar and sealed with a septa. Acetonitrile (15 mL) was added via a syringe at room temperature under argon atmosphere. After the mixture was stirred at room temperature for 5 hours, the solvent was removed under reduced pressure. The residue was purified by flash column chromatography (silica-gel, CH$_2$Cl$_2$) to give a white solid product, 0.54 g, 90.0% yield. MS: m/z 572.1 [M+Na]$^+$. $^1$H NMR (DMSO-$d_6$, 300 MHz): δ 8.26 (d, 2H, J=8.1 Hz), 7.93 (d, 2H, J=8.4 Hz), 7.28 (d, 2H, J=8.7 Hz), 7.21 (d, 1H, J=2.1 Hz), 7.20 (d, 1H, J=2.4 Hz), 6.97 (d, 2H, J=9.0 Hz), 3.98 (s, 3H), 3.76 (s, 3H).

Synthesis of 4-bromo-6,8-dihydroxy-2-(4-hydroxyphenyl)isoquinolin-1(2H)-one (12u)

Compound 4-bromo-6-methoxy-2-(4-methoxyphenyl)-1-oxo-1,2-dihydroisoquinolin-8-yl-4-(trifluoromethyl)benzoate (2.46 g, 4.49 mmol) was placed in a dry 250 mL single-necked round-bottomed flask fitted with a stirring bar and sealed with a rubber stopper. Anhydrous chlorobenzene (60 mL) was added via a syringe at room temperature. BBr$_3$ (6.74 g, 26.92 mmol) was added dropwise with stirring at room temperature. The resulted solution was heated to 100° C. for 20 hours. 50 mL of water and 10 mL of methanol were added to quench the reaction at 0° C. The solution was stirred at room temperature for two hours. CH$_2$Cl$_2$ layer was separated and the aqueous layer was extracted with EtOAc (3×20 mL). The organic layers were combined and dried over anhydrous MgSO$_4$. The solvent was removed under reduced pressure. The residue was purified by column chromatography (silica-gel, CH$_2$Cl$_2$/MeOH=9/1 v/v) to give a white solid product, 1.32 g, 84.6% yield. MS: m/e 347.8 [M−H]. $^1$H NMR (DMSO-d$_6$, 300 MHz): δ 13.12 (s, 1H), 10.78 (s, 1H), 9.81 (s, 1H), 7.75 (s, 1H), 7.28 (d, 2H, J=8.7 Hz), 6.85 (d, 2H, J=8.7 Hz), 6.61 (d, 1H, J=2.1 Hz), 6.37 (d, 1H, J=2.1 Hz).

Example 2: Synthesis of 6,8-dihydroxy-2-(4-hydroxyphenyl)-1-oxo-1,2-dihydroisoquinoline-4-carbonitrile (14m)

Scheme and Procedures for Synthesis of 14m.

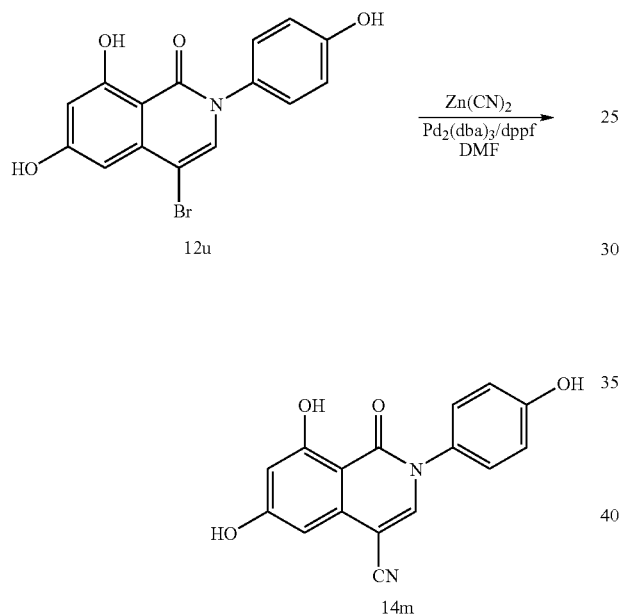

4-Bromo-6,8-dihydroxy-2-(4-hydroxyphenyl)isoquinolin-1(2H)-one (12u) (0.13 g, 0.37 mmol), Zn(CN)$_2$ (53 mg, 0.45 mmol), tris(dibenzylideneacetone)dipalladium (34 mg, 0.037 mmol), and 1,1'-bis(diphenylphosphino)ferrocene (83 mg, 0.15 mmol) were placed in a dry and argon flushed 150 mL three-necked round-bottomed flask fitted with a stirring bar, reflux condenser and an argon inlet. Then, anhydrous dimethylformamide (10 mL) was added via a syringe under argon atmosphere. The reaction solution was stirred and heated to 100° C. for 12 hours. Water (20 mL) was added to quench the reaction. The mixture was extracted with ethyl acetate (2×25 mL). The extracts were combined, washed with brine (10 mL) and dried over anhydrous MgSO$_4$ followed by filtration and concentration to give a yellow residue. The yellow residue was purified by flash column chromatography (silica-gel, CH$_2$Cl$_2$/Acetone/MeOH=80/17/3 v/v/v) to give a pale-yellow solid product, 80 mg, 72.7% yield. MS: m/z 307.0 [M+Na]$^+$. $^1$H NMR (DMSO-d$_6$, 300 MHz) δ 12.43 (s, 1H), 10.92 (s, 1H), 9.86 (s, 1H), 8.37 (s, 1H), 7.29 (d, 2H, J=8.7 Hz), 6.86 (d, 2H, J=8.7 Hz), 6.57 (d, 1H, J=2.1 Hz), 6.40 (d, 1H, J=2.1 Hz).

Example 3: Synthesis of 4-chloro-6,8-dihydroxy-2-(4-hydroxyphenyl)isoquinolin-1(2H)-one (12y)

Scheme and Procedures for Synthesis of 12y.

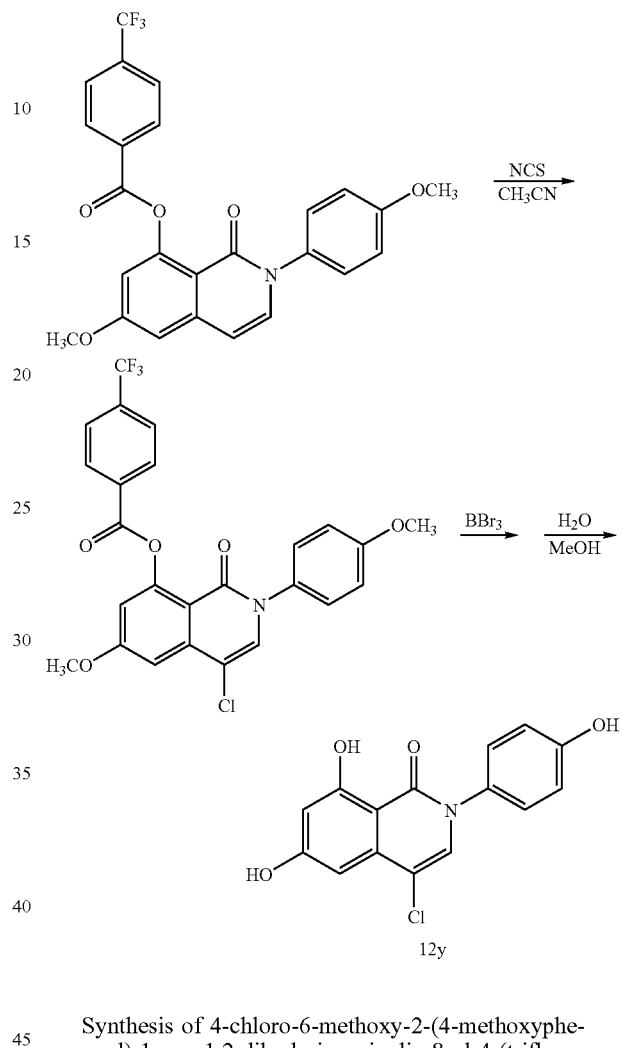

Synthesis of 4-chloro-6-methoxy-2-(4-methoxyphenyl)-1-oxo-1,2-dihydroisoquinolin-8-yl-4-(trifluoromethyl)benzoate Compound 6-methoxy-2-(4-methoxyphenyl)-1-oxo-1,2-dihydroisoquinolin-8-yl-4-(trifluoromethyl)benzoate (0.55 g, 1.17 mmol) and N-bromosuccinimide (0.19 g, 1.41 mmol) were placed in a dry, argon flushed 150 mL single-necked flask fitted with a stirring bar and sealed with a septa. Acetonitrile (15 mL) was added via a syringe at room temperature under argon atmosphere. After the mixture was stirred and heated to 60° C. for 8 hours, the solvent was removed under reduced pressure. The residue was purified by flash column chromatography (silica-gel, hexanes/EtOAc=7/3 v/v) to give a white solid product, 0.56 g, 94.9% yield. MS: m/z 526.2 [M+Na]$^+$. $^1$H NMR (DMSO-d$_6$, 300 MHz): δ 8.26 (d, 2H, J=8.1 Hz), 7.94 (d, 2H, J=8.4 Hz), 7.28 (d, 2H, J=8.7 Hz), 7.23 (d, 1H, J=2.1 Hz), 7.21 (d, 1H, J=2.4 Hz), 6.97 (d, 2H, J=9.0 Hz), 3.99 (s, 3H), 3.76 (s, 3H).

Synthesis of 4-chloro-6,8-dihydroxy-2-(4-hydroxyphenyl)isoquinolin-1(2H)-one (12v)

Compound 4-chloro-6-methoxy-2-(4-methoxyphenyl)-1-oxo-1,2-dihydroisoquinolin-8-yl-4-(trifluoromethyl)benzoate (0.24 g, 0.48 mmol) was placed in a dry 250 mL single-necked round-bottomed flask fitted with a stirring bar and sealed with a rubber stopper. Anhydrous chlorobenzene (20 mL) was added via a syringe at room temperature. BBr$_3$ (0.71 g, 2.86 mmol) was added dropwise with stirring at room temperature. The resulted solution was heated to 100° C. for 20 hours. 50 mL of water and 10 mL of methanol were added to quench the reaction at 0° C. The solution was stirred at room temperature for two hours. CH$_2$Cl$_2$ layer was separated and the aqueous layer was extracted with EtOAc (3×20 mL). The organic layers were combined and dried over anhydrous MgSO$_4$. The solvent was removed under reduced pressure. The residue was purified by column chromatography (silica-gel, CH$_2$Cl$_2$/MeOH=9/1 v/v) to give a white solid product, 0.11 g, 76.1% yield. MS m/e 301.9 (M−H)$^−$. $^1$H NMR (DMSO-d$_6$, 300 MHz) δ 13.09 (s, 1H), 10.77 (s, 1H), 9.81 (s, 1H), 7.70 (s, 1H), 7.27 (d, 2H, J=8.7 Hz), 6.85 (d, 2H, J=8.7 Hz), 6.62 (d, 1H, J=2.1 Hz), 6.38 (d, 1H, J=2.1 Hz).

Example 4: Synthesis of 4-chloro-6,8-dihydroxy-2-(4-hydroxyphenyl)isoquinolin-1(2H)-one (12z)

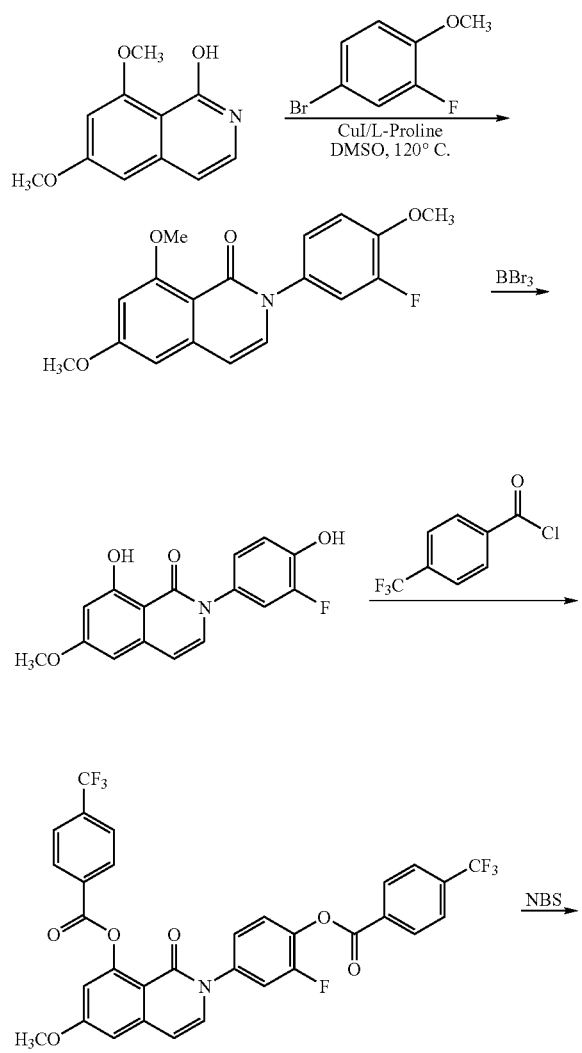

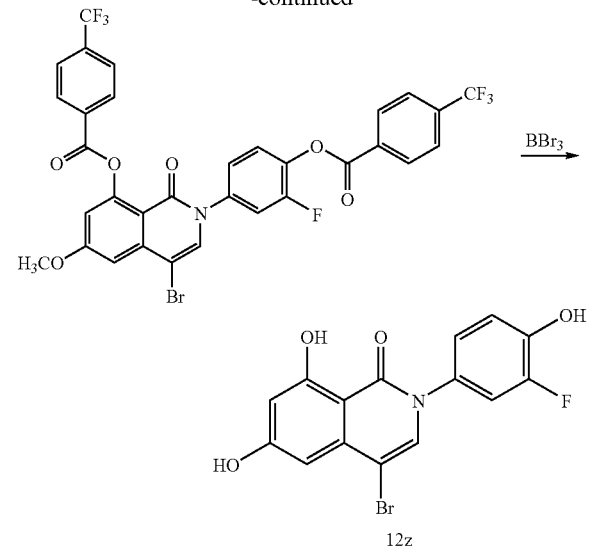

12z

Synthesis of 6,8-dimethoxy-2-(3-fluoro-4-methoxyphenyl)isoquinolin-1(2H)-one 6,8-Dimethoxyisoquinolin-1-ol (0.70 g, 3.41 mmol), 4-bromo-2-fluoroanisole (1.05 g, 5.12 mmol), copper(I) iodide (0.13 g, 0.68 mmol), L-proline (0.16 g, 1.36 mmol) and anhydrous potassium carbonate (0.94 g, 6.82 mmol) were placed in a dry 250 mL three-necked round-bottomed flask fitted with a stirring bar and reflux condenser. The system was vacuumed and refilled with dry argon. Then, anhydrous methyl sulfoxide (20 mL) was added via a syringe under argon atmosphere. The reaction solution was stirred and heated to 120° C. for 20 hours. Water (30 mL) was added to quench the reaction. The mixture was extracted with ethyl acetate (5×20 mL). The extracts were combined, washed with brine (3×10 mL) and dried over anhydrous MgSO$_4$ followed by filtration and concentration to give a yellow residue. The yellow residue was purified by flash column chromatography (silica-gel, CH$_2$Cl$_2$/Acetone=19/1 v/v) to give a pale-yellow solid product, 0.92 g, 82.1% yield. MS: m/z 330.3 [M+H]$^+$. $^1$H NMR (DMSO-d$_6$, 300 MHz): δ 7.37-7.13 (m, 4H), 6.72 (d, 1H, J=2.1 Hz), 6.55 (d, 1H, J=2.1 Hz), 6.46 (d, 1H, J=7.5 Hz), 3.89 (s, 3H), 3.87 (s, 3H), 3.80 (s, 3H).

Synthesis of 2-(3-fluoro-4-hydroxyphenyl)-8-hydroxy-6-methoxyisoquinolin-1(2H)-one Compound 2-(3-fluoro-4-hydroxyphenyl)-6,8-dimethoxyisoquinolin-1(2H)-one (0.65 g, 1.97 mmol) was placed in a dry 250 mL single-necked round-bottomed flask fitted with a stirring bar and sealed with a rubber stopper. Anhydrous methylene chloride (30 mL) was added via a syringe at room temperature. BBr$_3$ (16.0 mL of 1M CH$_2$CL$_2$ solution) was added dropwise with stirring at room temperature. The resulted mixture was stirred at room temperature for 3 days. Then, the reaction was quenched by adding 50 mL of water and 10 mL of methanol at 0° C. The solution was stirred at room temperature for two hours. CH$_2$Cl$_2$ layer was separated and the aqueous layer was extracted with EtOAc (3×20 mL). The organic layers were combined and dried over anhydrous MgSO$_4$. The solvent was removed under reduced pressure. The residue was purified by column chromatography (silica-gel, CH$_2$Cl$_2$/MeOH=9/1 v/v) to give a white solid product, 0.45 g, 76.3% yield. MS: m/z 324.2 [M+Na]$^+$. $^1$H NMR (DMSO-d$_6$, 300 MHz): δ 12.91 (s, 1H), 10.27 (s, 1H), 7.41-7.35 (m, 2H), 7.13-7.03 (m, 2H), 6.69-6.65 (m, 2H), 6.44 (d, 1H, J=2.4 Hz), 3.85 (s, 3H).

Synthesis of 2-(3-fluoro-4-(4-(trifluoromethyl)benzoyloxy)phenyl)-6-methoxy-1-oxo-1,2-dihydroisoquinolin-8-yl-4-(trifluoromethyl)benzoate Compound 2-(3-fluoro-4-hydroxyphenyl)-8-hydroxy-6-methoxyisoquinolin-1(2H)-one (0.32 g, 1.06 mmol) was placed in a dry 250 mL three-necked flask fitted with a stirring bar. Anhydrous DMF (20 mL) was added via a syringe under argon atmosphere. The solution was cooled to 0° C. in an ice-bath. NaH (0.13 g, 3.19 mmol, 60% dispersion in mineral oil) was added. The reaction mixture was stirred at 0° C. for 30 minutes. Then, it was warmed to room temperature for 30 minutes. The mixture was cooled to 0° C. again in an ice bath. 4-(Trifluoromethyl)benzoyl chloride (0.67 g, 3.19 mmol) was added via a syringe with stirring at 0° C. The reaction mixture was stirred at 0° C. for 30 minutes and at room temperature for additional 30 minutes. The reaction was quenched by adding 20 mL of saturated NH$_4$Cl solution. The solution was diluted with 20 mL of water and stirred for one hour at room temperature. It was extracted with ethyl acetate (3×20 mL). The extracts were washed with brine (20 mL) and dried over anhydrous MgSO$_4$. The solvent was removed under reduced pressure. The residue was subjected to flash column chromatography (silica-gel, CH$_2$Cl$_2$) to give a white solid product, 0.60 g, 88.2% yield. MS: m/z 668.3 [M+Na]$^+$. $^1$H NMR (DMSO-d$_6$, 300 MHz): δ 8.34 (d, 2H, J=8.1 Hz), 8.27 (d, 2H, J=8.1 Hz), 8.01 (d, 2H, J=8.4 Hz), 7.95 (d, 2H, J=8.4 Hz), 7.64-7.53 (m, 3H), 7.34 (d, 1H, J=8.7 Hz), 7.25 (d, 1H, J=2.4 Hz), 7.07 (d, 1H, J=2.4 Hz), 6.74 (d, 1H, J=7.5 Hz), 3.94 (s, 3H).

Synthesis of 4-bromo-2-(3-fluoro-4-(4-(trifluoromethyl)benzoyloxy)phenyl)-6-methoxy-1-oxo-1,2-dihydroisoquinolin-8-yl-4-(trifluoromethyl)benzoate Compound 2-(3-fluoro-4-(4-(trifluoromethyl)benzoyloxy)phenyl)-6-methoxy-1-oxo-1,2-dihydroisoquinolin-8-yl-4-(trifluoromethyl)benzoate (0.56 g, 0.87 mmol) and N-bromosuccinimide (0.20 g, 1.13 mmol) were placed in a dry, argon flushed 150 mL single-necked flask fitted with a stirring bar and sealed with a septa. Acetonitrile (20 mL) was added via a syringe at room temperature under argon atmosphere. After the mixture was stirred at room temperature for 5 hours, the solvent was removed under reduced pressure. The residue was purified by flash column chromatography (silica-gel, CH$_2$Cl$_2$) to give a white solid product, 0.35 g, 55.6% yield. MS: m/z 726.2 [M+H]$^+$. $^1$H NMR (DMSO-d$_6$, 300 MHz): δ 8.35-8.27 (m, 4H), 8.06-7.90 (m, 5H), 7.69-7.20 (m, 3H), 6.72 (d, 1H, J=2.4 Hz), 6.11 (d, 1H, J=2.4 Hz), 3.99 (s, 3H).

Synthesis of 4-bromo-2-(3-fluoro-4-hydroxyphenyl)-6,8-dihydroxyisoquinolin-1(2H)-one (12z)

Compound 4-bromo-2-(3-fluoro-4-(4-(trifluoromethyl)benzoyloxy)phenyl)-6-methoxy-1-oxo-1,2-dihydroisoquinolin-8-yl-4-(trifluoromethyl)benzoate (0.34 g, 0.47 mmol) was placed in a dry 250 mL single-necked round-bottomed flask fitted with a stirring bar and sealed with a rubber stopper. Anhydrous chlorobenzene (20 mL) was added via a syringe at room temperature. BBr$_3$ (0.71 g, 2.82 mmol) was added dropwise with stirring at room temperature. The resulted solution was heated to 100° C. for 20 hours. 50 mL of water and 10 mL of methanol were added to quench the reaction at 0° C. The solution was stirred at room temperature for two hours. CH$_2$Cl$_2$ layer was separated and the aqueous layer was extracted with EtOAc (3×20 mL). The organic layers were combined and dried over anhydrous MgSO$_4$. The solvent was removed under reduced pressure. The residue was purified by column chromatography (silica-gel, CH$_2$Cl$_2$/MeOH=9/1 v/v) to give a white solid product, 82 mg, 48.2% yield. MS: m/e 363.9 [M−H]$^−$. $^1$H NMR (DMSO-d$_6$, 300 MHz): δ 13.02 (s, 1H), 10.78 (s, 1H), 10.27 (s, 1H), 7.79 (s, 1H), 7.41 (dd, 1H, J$_1$=11.7 Hz, J$_2$=2.4 Hz), 7.16-7.01 (m, 2H), 6.61 (d, 1H, J=2.1 Hz), 6.38 (d, 1H, J=2.1 Hz).

Example 5: Synthesis of 6-methoxyisoquinolinemethoxyisoquinoline-1-ol

A mixture of 17.82 g (0.10 mol) of trans-3-methoxycinnamic acid and thionyl chloride (14.28 g, 0.12 mol) were placed in a 250 mL single-necked round-bottomed flask fitted with a stirring bar and reflux condenser. 80 mL of dry methylene chloride was added to the flask. The resulting mixture was heated to reflux for 3 hours and then the solvent was removed under reduced pressure. The residue oil was dried under vacuum overnight.

The pale-yellow solid acid chloride was dissolved in 20 mL of 1,4-dioxane and added dropwise with stirring to a 0° C. suspension of 19.50 g (0.30 mol) of sodium azide in 80 mL of 1,4-dioxane/water (1:1 mixture). During the addition the temperature was maintained at 0° C. After complete addition of the acid chloride, the mixture was stirred at 0° C. for an additional hour, and then diluted with 75 mL of water. The mixture was extracted with methylene chloride (2×40 mL). The combined extracts were dried over anhydrous magnesium sulfate, filtered and concentrated to approximately 100 mL. The solution was diluted with 20 mL of phenyl ether and further concentrated to remove the remaining methylene chloride. A 500 mL 3-necked round-bottomed flask fitted with an argon inlet, reflux condenser, additional funnel and an internal thermometer was charged with 29 mL of tributylamine and 80 mL of phenyl ether. The solution was heated to 230° C., and the acyl azide in 20 mL of phenyl ether was added dropwise with stirring over 3 hours from an addition funnel. During the addition, the reflux temperature gradually decreased to 200° C. After completion of the addition, the distillate was collected in the addition funnel (15 mL of a 1:1 mixture of tributylamine/phenyl ether) until the temperature reached 230° C. After heating for an additional hour at 230° C., the mixture was cooled to room temperature. The mixture was then combined with 500 mL hexane with stirring. The solid was filtered and washed with hexanes (2×100 mL). The pale-yellow solid was recrystallized from ethyl acetate/methanol (9/1 v/v) to give a pure pale-yellow crystalline material, 15.28 g, 87.2% yield. MS: 198.1 [M+Na]$^+$. $^1$H NMR (DMSO-d$_6$, 300 MHz): δ 11.06 (s, 1H), 8.08 (d, 1H, J=8.5 Hz), 7.14-7.14 (m, 1H), 7.10 (d, 1H, J=2.5 Hz), 7.05-7.03 (m, 1H), 7.04 (dd, 1H, J$_1$=9.0 Hz, J$_2$=2.5 Hz), 6.47 (d, 1H, J=7.0 Hz), 3.86 (s, 3H).

Example 6: Synthesis of 6-methoxy-2-(4-methoxyphenyl)isoquinolin-1(2H)-one

6-Methoxyisoquinoline-1-ol (2.00 g, 11.42 mmol), 4-iodoanisole (4.01 g, 17.13 mmol), copper (I) iodide (0.44 g, 2.28 mmol). L-proline (0.53 g, 4.57 mmol) and anhydrous potassium carbonate (3.16 g, 22.84 mmol) were placed in a dry 250 mL three-necked round-bottomed flask fitted with a stirring bar and reflux condenser. The reaction flask was vacuumed and refilled with dry argon. 50 mL of anhydrous methyl sulfoxide was added via syringe. The reaction mixture was stirred and heated to 130° C. for 20 hours. 50 mL of water was added to quench the reaction, and yellow solid precipitated out. The pale-yellow solid was filtered, washed with water (2×20 mL) and dried in air. This pale-yellow solid was purified by flash column chromatography (silica gel, ethyl acetate) to give a pale-yellow solid product, 2.90 g, 90.3% yield. MS: 282.2 [M+H]$^+$. $^1$H NMR (DMSO-d$_6$, 300 MHz): b 8.14 (d, 1H, J=8.7 Hz), 7.39-7.34 (m, 3H), 7.19 (d, 1H, J=2.4 Hz), 7.13-7.03 (m, 3H), 6.62 (dd, 1H, J=7.5 Hz), 3.89 (s, 3H), 3.81 (s, 3H).

Example 7: Synthesis of 4-bromo-6-methoxy-2-(4-methoxyphenyl)isoquinolin-1(2H)-one (14a)

6-Methoxy-2-(4-methoxyphenyl)isoquinolin-1(2H)-one (0.50 g, 1.78 mmol) was placed in a dry 250 mL single-necked round-bottomed flask fitted with a stirring bar and septa. Acetonitrile (10 mL) was added via a syringe under argon atmosphere at room temperature. N-Bromosuccinimide or NBS (0.33 g, 1.87 mmol) was added portionwise under argon atmosphere at room temperature. The reaction mixture was allowed to stir at room temperature for 2 hours. 20 mL of saturated sodium bicarbonate solution was then added. The mixture was extracted with ethyl acetate (3×10 mL). Organic layers were separated, dried over anhydrous magnesium sulfate and concentrated under vacuum. The residue was purified by flash column chromatography (silica gel, hexanes/EtOAc=2/3 v/v) to give a white solid product, 0.55 g, 85.9% yield. MS: 360.4 [M+H]$^+$. $^1$H NMR (DMSO-d$_6$, 300 MHz): δ 8.14 (d, 1H, J=8.7 Hz), 7.39-7.34 (m, 3H), 7.19 (d, 1H, J=2.4 Hz), 7.13-7.03 (m, 3H), 6.62 (dd, 1H, J=7.5 Hz), 3.89 (s, 3H), 3.81 (s, 3H).

Example 8: Synthesis of 4-Bromo-6-hydroxy-2-(4-hydroxyphenyl)isoquinolin-1(2H)-one (12b)

4-Bromo-6-methoxy-2-(4-methoxyphenyl)isoquinolin-1(2H)-one (0.22 g, 0.61 mmol) was placed in a dry 150 mL single-necked flask fitted with a stirring bar and septa. Methylene chloride (30 mL) was added via a syringe. Boron tribromide (1.83 mL of 1.0 M methylene chloride solution) was added dropwise with stirring under argon atmosphere at room temperature. The reaction mixture was allowed to stir at room temperature for 20 hours. Then, 20 mL of water was added to quench the reaction. The mixture was extracted with 50 mL of ethyl acetate. The organic layer was separated, dried over anhydrous magnesium sulfate and concentrated under vacuum. The residue was subjected to flash column chromatography (silica gel, CH$_2$Cl$_2$/MeOH=9/1 v/v) to give a white solid product, 0.10 g, 49.4% yield. MS: 334.2 [M+H]$^+$. $^1$H NMR (DMSO-d$_6$, 300 MHz): δ 10.58 (s, 1H), 9.83 (s, 1H), 8.12 (d, 1H, J=8.7 Hz), 7.71 (s, 1H), 7.22 (d, 2H, J=8.7 Hz), 7.09 (d, 1H, J=21. Hz), 7.04 (dd, 1H, J, =8.7 Hz, J$_2$=2.4 Hz), 6.84 (d, 2H, J=8.7 Hz).

Example 9: Synthesis of 6-hydroxy-2-(4-hydroxyphenyl)-4-vinylisoquinolin-1(2H)-one (14f)

4-Bromo-6-hydroxy-2-(4-hydroxyphenyl)-isoquinolin-1(2H)-one (0.60 g, 1.81 mmol), tetrakis(triphenylphosphine) palladium (42 mg, 0.036 mmol), potassium carbonate (0.25 g, 1.81 mmol) and vinylboronic anhydride pyridine complex (0.22 g, 0.91 mmol) were placed in a dry and argon flushed 150 mL three-necked round-bottomed flask fitted with a stirring bar and reflux condenser. Anhydrous 1, 2-dimethoxyethane (10 mL) and water (3 mL) were added via a syringe under argon atmosphere. The reaction solution was stirred and heated to reflux for 4 hours. The reaction was quenched by adding 20 mL of water at room temperature. The mixture was extracted with ethyl acetate/methanol (9/1 v/v) (2×20 mL). The extracts were combined, washed with brine (2×10 mL) and dried over anhydrous MgSO$_4$ followed by filtration and concentration to give a yellow residue. The yellow residue was purified by flash column chromatography (silica-gel, CH$_2$Cl$_2$/MeOH=19/1 v/v) to give a white solid product, 0.44 g, 87.0% yield. M.p. ° C. (decomposed). MS: m/z 280.0 [M+H]$^+$. $^1$H NMR (DMSO-d$_6$, 300 MHz) δ 10.43 (s, 1H), 9.71 (s, 1H), 8.13 (d, 1H, J=8.7 Hz), 7.41 (s, 1H), 7.24 (d, 2H, J=8.7 Hz), 7.10 (d, 1H, J=2.1 Hz), 7.01 (dd, 1H, J$_1$=8.7 Hz, J$_2$=2.1 Hz), 6.88 (dd, 1H, J, =17.4 Hz, J$_2$=10.8 Hz), 6.85 (d, 2H, J=8.7 Hz), 5.64 (dd, 1H, J, =17.4 Hz, J$_2$=1.2 Hz), 5.26 (dd, 1H, J$_1$=10.8 Hz, J$_2$=1.2 Hz).

Example 10: Synthesis of 6-methoxy-2-(4-methoxyphenyl)-1-oxo-1,2-dihydroisoquinoline-4-carbonitrile (14g)

4-Bromo-6-Methoxy-2-(4-methoxyphenyl)-isoquinolin-1 (2H)-one (0.80 g, 2.22 mmol), Zn(CN)$_2$ (0.40 g, 3.42 mmol), tris(dibenzylideneacetone)dipalladium (0.20 g, 0.22 mmol) and 1,1'-bis(diphenylphosphino)ferrocene (0.49 g, 0.89 mmol) were placed in a dry and argon flushed 150 mL three-necked round-bottomed flask fitted with a stirring bar and reflux condenser. Then, anhydrous dimethylformamide (30 mL) was added via a syringe under argon atmosphere. The reaction solution was stirred and heated to 100° C. for 5 hours. Water (30 mL) was added to quench the reaction. The mixture was extracted with ethyl acetate (2×20 mL). The extracts were combined, washed with brine (3×10 mL) and dried over anhydrous MgSO$_4$ followed by filtration and concentration to give a yellow residue. The yellow residue was purified by flash column chromatography (silica-gel, EtOAc/hexanes=1/1 v/v) to give a pale-yellow solid product, 0.63 g, 92.6% yield. M.p. ° C. (decomposed). MS: m/z 307.0 [M+H]$^+$. $^1$H NMR (DMSO-d$_6$, 300 MHz) δ 8.48 (s, 1H), 8.22 (d, 1H, J=9.0 Hz), 7.43 (d, 2H, J=8.7 Hz), 7.27 (dd, 1H, J, =8.7 Hz, J$_2$=2.4 Hz), 7.08 (d, 1H, J=2.4 Hz), 7.06 (d, 2H, J=8.7 Hz), 3.97 (s, 3H), 3.82 (s, 3H).

Example 11: Synthesis of 6-Hydroxy-2-(4-hydroxyphenyl)-1-oxo-1,2-dihydroisoquinoline-4-carbonitrile (14h)

6-Methoxy-2-(4-methoxyphenyl)-isoquinoline-4-carbonitrile (0.45 g, 1.47 mmol) was placed in a dry and argon flushed 150 mL single-necked round-bottomed flask fitted with a stirring bar and an argon inlet. BBr$_3$ (9.0 mL of 1.0M CH$_2$C12 solution, 9.0 mmol) was added via a syringe with stirring at room temperature. After stirred at room temperature for 24 hours, the reaction was quenched by adding 20 mL of water. The solution was stirred at room temperature for one hour, extracted with EtOAc (3×20 mL). The organic layers were separated, combined and dried over anhydrous MgSO$_4$. The solvent was removed under reduced pressure. The residue was purified by column chromatography (silica-gel, CH$_2$Cl$_2$/MeOH=9/1 v/v) to give a white solid product, 0.28g, 68.5% yield. M.p. ° C. (decomposed). MS: m/z 279.0 [M+H]$^+$. $^1$H NMR (DMSO-d$_6$, 300 MHz) δ 10.86 (s, 1H), 9.80 (s, 1H), 8.38 (s, 1H), 8.13 (d, 1H, J=8.7 Hz), 7.25 (d, 2H, J=8.7 Hz), 7.09 (dd, 1H, $J_1$=8.7 Hz, $J_2$=2.4 Hz), 7.04 (d, 1H, J=2.4 Hz), 6.85 (d, 2H, J=8.7 Hz).

Example 12: Synthesis of 6-methoxy-2-(4-methoxyphenyl)-1-oxo-1,2-dihydroisoquinolin-8-yl trifluoromethanesulfonate (14d)

8-Hydroxy-6-methoxy-2-(4-methoxyphenyl)isoquinolin-1(2H)-one (2.10 g, 7.06 mmol) was dissolved in 30 mL of anhydrous dimethylformide in a 250 mL three-necked round-bottomed flask fitted with a magnetic stirring bar, an argon inlet and sealed with rubber stoppers. The solution was cooled to 0° C. in an ice-bath. Sodium hydride (0.37 g of 60% wt. in mineral oil, 9.18 mmol) was added in 4 portions under argon atmosphere. The reaction mixture was stirred at 0° C. for 30 minutes, than at room temperature for 30 minutes. After the solution was cooled to 0° C. again, N-phenyl-bis (trifluoromethanesulfonamide) (2.65 g, 7.41 mmol) was added in portions under argon protection. The reaction mixture was stirred at 0° C. for 30 minutes and at room temperature for one hour. The reaction was quenched by adding 50 mL of saturated ammonia chloride solution, and diluted with 50 mL of water. The solution was extracted with ethyl acetate (3×50 mL). The organic layers were separated, combined, washed with brine, dried over anhydrous $MgSO_4$, filtered and concentrated under reduced pressure. The residue was purified by flash column chromatography (silica gel, hexanes/EtOAc=1/1 v/v) to give a white solid product, 2.85 g, 94.1% yield. M.p. ° C. (decomposed). MS: m/z 452.1 [M+Na]$^+$. $^1$H NMR (DMSO-$d_6$, 300 MHz) δ 7.52 (d, 1H, J=7.2 Hz), 7.38 (d, 1H, J=2.4 Hz), 7.34 (d, 2H, J=9.0 Hz), 7.07 (d, 2H, J=9.0 Hz), 7.02 (d, 1H, J=1.8 Hz), 6.72 (d, 1H, J=7.5 Hz), 3.94 (s, 3H), 3.82 (s, 3H).

Example 13: Synthesis of 6-methoxy-2-(4-methoxyphenyl)-1-oxo-1,2-dihydroisoquinoline-8-carbonitrile (14i)

6-Methoxy-2-(4-methoxyphenyl)-1-oxo-1,2-dihydroisoquinolin-8-yl trifluoromethanesulfonate (0.43 g, 1.00 mmol), $Zn(CN)_2$ (0.14 g, 1.20 mmol), tris(dibenzylideneacetone)dipalladium (92 mg, 0.1 mmol) and 1,1'-bis(diphenylphosphino)ferrocene (0.22g, 0.40 mmol) were placed in a dry and argon flushed 150 mL three-necked round-bottomed flask fitted with a stirring bar and reflux condenser. Then, anhydrous dimethylformide (20 mL) was added via a syringe under argon atmosphere. The reaction solution was stirred and heated to 100° C. for 4 hours. Water (20 mL) was added to quench the reaction. The mixture was extracted with ethyl acetate (4×30 mL). The extracts were combined, washed with brine (3×10 mL) and dried over anhydrous $MgSO_4$ followed by filtration and concentration to give a yellow residue. The yellow residue was purified by flash column chromatography (silica-gel, EtOAc/hexanes=3/2 v/v) to give a white solid product, 0.23 g, 75.2% yield. M.p. ° C. (decomposed). MS: m/z 307.2 [M+H]$^+$. $^1$H NMR (DMSO-$d_6$, 300 MHz) δ 7.63 (d, 1H, J=2.1 Hz), 7.54 (d, 1H, J=2.1 Hz), 7.51 (d, 1H, J=7.5 Hz), 7.38 (d, 2H, J=8.7 Hz), 7.06 (d, 2H, J=8.7 Hz), 6.71 (d, 1H, J=7.5 Hz), 3.95 (s, 3H), 3.82 (s, 3H).

Example 14: Synthesis of 4-bromo-6-methoxy-2-(4-methoxyphenyl)-1-oxo-1,2-dihydroisoquinoline-8-carbonitrile (14i)

Compound 6-methoxy-2-(4-methoxyphenyl)-1-oxo-1,2-dihydroisoquinoline-8-carbonitrile (0.22 g, 0.72 mmol) and N-bromosuccinimide (0.15 g, 0.86 mmol) were placed in a dry, argon flushed 150 mL single-necked flask fitted with a stirring bar and sealed with a rubber stopper. Acetonitrile (10 mL) was added via a syringe at room temperature under argon atmosphere. After the mixture was stirred at room temperature for 4 hours, the solvent was removed under reduced pressure. The residue was purified by flash column chromatography (silica-gel, hexanes/EtOAc=2/3 v/v) to give a white solid product, 0.23 g, 83.3% yield. M.p. ° C. (decomposed). MS: m/z 387.1 [M+H]$^+$. $^1$H NMR (DMSO-$d_6$, 300 MHz) δ 8.01 (s, 1H), 7.81 (d, 1H, J=2.4 Hz), 7.43 (d, 1H, J=2.4 Hz), 7.42 (d, 2H, J=8.7 Hz), 7.07 (d, 2H, J=8.7 Hz), 4.02 (s, 3H), 3.82 (s, 3H).

Example 15: Synthesis of 4-bromo-6-hydroxy-2-(4-hydroxyphenyl)-1-oxo-1,2-dihydroisoquinoline-8-carbonitrile (14k)

4-Bromo-6-methoxy-2-(4-methoxyphenyl)-1-oxo-1,2-dihydroisoquinoline-8-carbonitrile (0.15 g, 0.39 mmol) was placed in a dry and argon flushed 100 mL single-necked round-bottomed flask fitted with a stirring bar, reflux condenser and an argon inlet. Anhydrous chlorobenzene (10 mL) was added via a syringe at room temperature. $BBr_3$ (0.59, 2.33 mmol) was added via a syringe with stirring at room temperature. The resulting solution was heated to 120° C. for 4 hours. 10 mL of water was added to quench the reaction. After stirred at room temperature for one hour, the solution was extracted with EtOAc (5×20 mL). The organic layers were combined and dried over anhydrous $MgSO_4$. The solvent was removed under reduced pressure. The residue was purified by column chromatography (silica-gel, $CH_2Cl_2$/MeOH=9/1 v/v) to give a white solid product, 0.05g, 36.0% yield. M.p. ° C. (decomposed). MS: m/z 357.1 [M+H]$^+$. $^1$H NMR (DMSO-$d_6$, 300 MHz) δ 11.40 (s, 1H), 9.79 (s, 1H), 7.91 (s, 1H), 7.48 (d, 1H, J=2.1 Hz), 7.38 (d, 1H, J=2.1 Hz), 7.26 (d, 2H, J=8.7 Hz), 6.86 (d, 2H, J=8.7 Hz).

Example 16: Synthesis of 4-bromo-6-hydroxy-2-(4-hydroxyphenyl)isoquinolin-1(2H)-one (12b)

4-Bromo-6-methoxy-2-(4-methoxyphenyl)isoquinolin-1(2H)-one (14q) was prepared as described above. 14q was placed in a dry 150 mL single-necked flask fitted with a stirring bar and septa. Chlorobenzene (30 mL) was added via a syringe. Boron tribromide (6 equivalents, neat) was added dropwise with stirring under argon atmosphere at room temperature. The reaction mixture was allowed to stir at room temperature for 20 hours. Then, 20 mL of water was added to quench the reaction. The mixture was extracted with 50 mL of ethyl acetate. The organic layer was separated, dried over anhydrous magnesium sulfate and concentrated under vacuum. The residue was subjected to flash column chromatography (silica gel, $CH_2Cl_2$/MeOH=9/1 v/v) to give a white solid product, 0.10 g, 49.4% yield. MS: 334.2 [M+H]$^+$. $^1$H NMR (DMSO-$d_6$, 300 MHz): δ 10.58 (s, 1H), 9.83 (s, 1H), 8.12 (d, 1H, J=8.7 Hz), 7.71 (s, 1H), 7.22 (d, 2H, J=8.7 Hz), 7.09 (d, 1H, J=21. Hz), 7.04 (dd, 1H, $J_1$=8.7 Hz, $J_2$=2.4 Hz), 6.84 (d, 2H, J=8.7 Hz).

Example 17: Synthesis of 4-bromo-2-(4-hydroxyphenyl)-6-methoxy-isoquinolin-1(2H)-one (12c)

4-Bromo-6-methoxy-2-(4-methoxyphenyl)isoquinolin-1 (2H)-one (14q) was prepared as described above. 14q was placed in a dry 150 mL single-necked flask fitted with a stirring bar and septa. Chlorobenzene (30 mL) was added via a syringe. Boron tribromide (3 equivalents, neat) was added dropwise with stirring under argon atmosphere at room temperature. The reaction mixture was allowed to stir at room temperature for 20 hours. Then, 20 mL of water was added to quench the reaction. The mixture was extracted with 50 mL of ethyl acetate. The organic layer was separated, dried over anhydrous magnesium sulfate and concentrated under vacuum. The residue was subjected to flash column chromatography (silica gel, $CH_2Cl_2$/MeOH=9/1 v/v) to give a white solid product, 0.10 g, 49.4% yield. MS: 334.2 [M+H]$^+$. $^1$H NMR (DMSO-$d_6$, 300 MHz): δ 10.58 (s, 1H), 9.83 (s, 1H), 8.12 (d, 1H, J=8.7 Hz), 7.71 (s, 1H), 7.22 (d, 2H, J=8.7 Hz), 7.09 (d, 1H, J=21. Hz), 7.04 (dd, 1H, $J_1$=8.7 Hz, $J_2$=2.4 Hz), 6.84 (d, 2H, J=8.7 Hz).

Example 18: Synthesis of 6-methoxy-2-(4-methoxyphenyl)-4-phenylisoquinolin-1(2H)-one 4-Bromo-6-methoxy-2-(4-methoxyphenyl)-isoquinolin-1 (2H)-one (0.52 g, 1.44 mmol), tetrakis(triphenylphosphine) palladium (83 mg, 0.07 mmol), potassium carbonate (0.22 g, 1.00 mmol) and phenylboronic acid (0.21 g, 1.73 mmol) were placed in a dry and argon flushed 150 mL three-necked round-bottomed flask fitted with a stirring bar and reflux condenser. 1,2-Dimethoxyethane (10 mL) and water (3 mL) were added via a syringe under argon atmosphere. The reaction solution was stirred and heated to reflux for 20 hours. The reaction was quenched by adding 30 mL of water at room temperature. The mixture was extracted with ethyl acetate (3×20 mL). The extracts were combined, washed with brine (2×10 mL) and dried over anhydrous $MgSO_4$ and 2 g of 3-(diethylenetriamino)propylfunctionalized silical gel followed by filtration and concentration to give a yellow residue. The yellow residue was purified by flash column chromatography (silica-gel, hexanes/ethyl acetate=2/3 v/v) to give a white solid product, 0.50 g, 98.0% yield. MS: m/z 358.3 [M+H]$^+$. $^1$H NMR (DMSO-$d_6$, 300 MHz) δ 8.30 (d, 2H, J=9.0 Hz), 7.55-7.40 (m, 8H), 7.29 (s, 7.21 (dd, 1H, $J_1$=9.0 Hz, $J_2$=2.4 Hz), 7.05 (d, 2H, J=9.0 Hz), 6.94 (d, 1H, J=2.4 Hz), 3.81 (s, 3H), 3.78 (s, 3H).

Example 19: Synthesis of 6-hydroxy-2-(4-hydroxyphenyl)-4-phenylisoquinolin-1(2H)-one (15a)

6-Methoxy-2-(4-methoxyphenyl)-4-phenylisoquinolin-1 (2H)-one (0.36 g, 1.01 mmol) was placed in a dry 150 mL single-necked flask fitted with a stirring bar and septa. Methylene chloride (30 mL) was added via a syringe. Boron tribromide (5.0 mL of 1.0 M methylene chloride solution) was added dropwise with stirring under argon atmosphere at room temperature. The reaction mixture was allowed to stir at room temperature for 16 hours. Then, 20 mL of water was added to quench the reaction. The mixture was extracted with ethyl acetate (3×20 mL). The organic layers were separated, dried over anhydrous magnesium sulfate and concentrated under vacuum. The residue was subjected to flash column chromatography (silica gel, $CH_2Cl_2$/MeOH=9/1 v/v) to give a white solid product, 0.29 g, 87.9% yield. MS: 330.2 [M+H]$^+$. $^1$H NMR (DMSO-$d_6$, 300 MHz): δ 10.31 (s, 1H), 9.69 (s, 1H), 8.19 (d, 1H, J=8.7 Hz), 7.52-7.39 (m, 5H), 7.28 (d, 2H, J=8.7 Hz), 7.18 (s, 1H), 7.00 (dd, 1H, $J_1$=8.7 Hz, $J_2$=2.4 Hz), 6.87-6.82 (m, 3H).

Example 20: Synthesis of 1-(2-(piperidin-1-yl)ethoxy)isoquinolin-6-ol (13a)

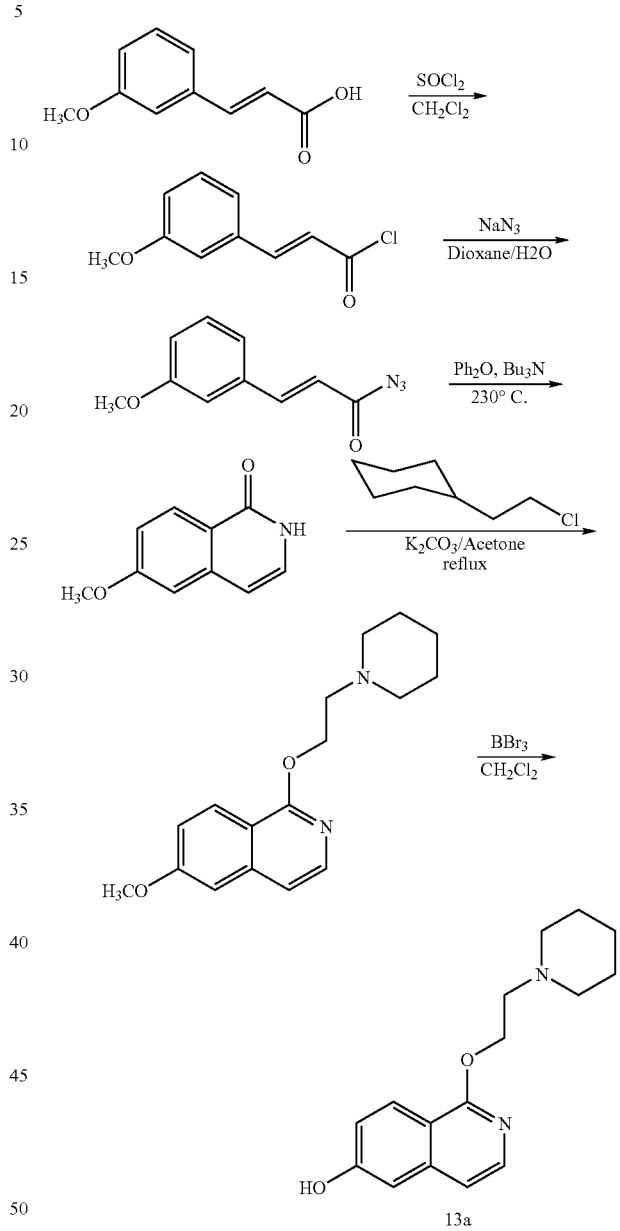

Synthesis of 6-methoxyisoquinoline-1-ol

A mixture of 17.82 g (0.10 mol) of trans-3-methoxycinnamic acid and thionyl chloride (14.28 g, 0.12 mol) were placed in a 250 mL single-necked round-bottomed flask fitted with a stirring bar and reflux condenser. 80 mL of dry methylene chloride was added to the flask. The resulted mixture was heated to reflux for 3 hours. Then, the solvent was removed under reduced pressure. The residue oil was dried under vacuum overnight. The pale-yellow solid acid chloride was dissolved in 20 mL of 1,4-dioxane and added dropwise with stirring to a 0° C. suspension of 19.50 g (0.30 mol) of sodium azide in 80 mL of 1,4-dioxane/water (1:1 mixture). During the addition the temperature was maintained at 0° C. After complete addition of the acid chloride, the mixture was stirred at 0° C. for an additional hour, then diluted with 75 mL of water. The mixture was extracted with methylene chloride (2×40 mL). The combined extracts were dried over anhydrous magnesium sulfate, filtered and concentrated to ca. 100 mL. The solution was diluted with 20 mL of phenyl ether and further concentrated to remove the remaining methylene chloride.

A 500 mL 3-necked round-bottomed flask fitted with an argon inlet, reflux condenser, additional funnel and an internal thermometer was charged with 29 mL of tributylamine and 80 mL of phenyl ether. The solution was heated to 230° C., and the acyl azide in 20 mL of phenyl ether was added dropwise with stirring over 3 hours from an addition funnel. During the addition, the reflux temperature gradually decreased to 200° C. After, completion of the addition, the distillate was collected in the addition funnel (15 mL of a 1:1 mixture of tributylamine/phenyl ether) until the temperature reached 230° C. After heating for an additional hour at 230° C., the mixture was cooled to room temperature. The mixture was then poured to 500 mL of hexanes with stirring. The solid was filtered and washed with hexanes (2×100 mL). The pale-yellow solid was recrystallized from ethyl acetate/methanol (9/1 v/v) to give a pure pale-yellow crystalline material, 15.28 g, 87.2% yield. MS: 198.1 $[M+Na]^+$. $^1$H NMR (DMSO-$d_6$, 300 MHz): δ 11.06 (s, 1H), 8.08 (d, 1H, J=8.5 Hz), 7.14-7.14 (m, 1H), 7.10 (d, 1H, J=2.5 Hz), 7.05-7.03 (m, 1H), 7.04 (dd, 1H, $J_1$=9.0 Hz, $J_2$=2.5 Hz), 6.47 (d, 1H, J=7.0 Hz), 3.86 (s, 3H).

Synthesis of
6-methoxy-1-(2-(piperidin-1-yl)ethoxy)isoquinoline

To a solution of 6-methoxyisoquinoline-1-ol (1.00 g, 5.71 mmol) in acetone, $K_2CO_3$ (4.73 g, 34.26 mmol) and N-chloroethyl-piperidine hydrochloride salt (1.37 g, 7.42 mmol) were added. The solution was heated to reflux for 6 hours. The solution was evaporated to dryness. The residue was hydrolyzed by adding water, then extracted with ethyl acetate. The organic layers were separated and dried over anhydrous $MgSO_4$. The solvent was removed under reduced pressure. The residue was purified by flash chromatography (silica-gel; methylene chloride/methanol=9/1 v/v) to give a yellow oil product, 1.50 g, 92.0% yield. MS: 287.2 $[M+H]^+$. $^1$H NMR (DMSO-$d_6$, 300 MHz) δ 8.11 (d, 1H, J=9.0 Hz), 7.39 (d, 1H, J=7.5 Hz), 7.10-7.13 (m, 2H), 6.51 (d, 1H, J=7.5 Hz), 4.02 (t, 2H, J=6.6 Hz), 3.86 (s, 3H), 2.55 (t, 2H, J=6.5 Hz), 2.41 (br, 4H), 1.52-1.44 (m, 4H), 1.37-114 (n, 2H).

Synthesis of 1-(2-(piperidin-1-yl)ethoxy)isoquinolin-6-ol (13a)

6-Methoxy-1-(2-(piperidin-1-yl)ethoxy)isoquinoline (0.60 g, 2.10 mmol) was dissolved in 30 mL of dry $CH_2Cl_2$ at room temperature. $BBr_3$ (10.50 mmol, 10.50 mL of 1.0 M $CH_2Cl_2$ solution) was added dropwise with stirring via a syringe at room temperature. The reaction solution was allowed to stir overnight at room temperature. The mixture was cooled to 0° C. in an ice bath and hydrolyzed by adding water. EtOAc was added to partition the solution. The organic layer was separated, the aqueous layer was extracted with EtOAc twice. The organic layers were combined, washed with brine and dried over anhydrous $MgSO_4$. The solvent was removed under vacuum. The residue was purified by flash column chromatography using silica-gel with $CH_3OH/CH_2Cl_2$ (1/9 v/v) to give a white solid product, 40 g, 70.2% yield. MS: 273.2 $[M+H]^+$. $^1$H NMR (DMSO-$d_6$, 300 MHz) δ 10.29 (s, 1H), 8.05 (d, 1H, J=8.7 Hz), 7.32 (d, 1H, J=7.2 Hz), 6.93 (d, 1H, J=8.4 Hz), 6.87 (s, 1H), 6.43 (d, 1H, J=7.2 Hz), 4.03 (s, br, 2H), 2.62 (s, br, 2H), 2.50 (s, br, 2H), 1.49-1.39 (m, 6H).

Example 21: In Vitro Characterization of Selected Compounds of the Invention (A) Estrogen Receptor Binding Affinities, Agonist and Antagonist Activity of Some Embodiments of NRBAs of the Invention Materials and Methods:

ER binding affinity was determined via one of the following methods:

Method 1:

Human recombinant estrogen receptor (ER) was expressed in insect Sf9 cells and a radioactive competitive binding assay was performed using tritiated estradiol. If the NRBAs tested showed a 50% inhibition of [$^3$H] estradiol binding at 1 μM (1000 nM) concentration, the compounds were assayed using four concentrations to determine $IC_{50}$ and $K_i$ estimates.

Method 2:

Estrogen receptor (ER) binding affinity of the NRBAs was also determined using an in vitro competitive radioligand-binding assay with [$^3$H]-estradiol ([$^3$H]-$E_2$, PerkinElmer), a high affinity ligand for both ERα and ERβ. The equilibrium dissociation constant ($K_d$) of [$^3$H]-$E_2$ was determined by incubating increasing concentrations of [$^3$H]-$E_2$ (0.01 to 10 nM) with bacterially expressed ERα or ERβ ligand binding domain (LBD) at 4° C. for 18 hours (h). Non-specific binding was determined by adding 1000 nM $E_2$ to the incubation mixture. It was determined that the minimum concentration of [$^3$H]-$E_2$ required to saturate ERα and ERβ binding sites in the incubation mixture was 1 nM, respectively. The binding affinity of the NRBAs was determined under identical conditions by incubating increasing concentrations ($3 \times 10^{-2}$ to 1,000 nM) of ligand with isolated ER LBD and 1 nM [$^3$H]-$E_2$. Following incubation, bound and free [$^3$H]-$E_2$ were separated by using vacuum filtration with the Harvester (PerkinElmer). Briefly, the incubation mixture was filtered through a high affinity protein binding filter, and washed several times to remove any unbound radioactivity. The filter plate was air dried and sealed on the bottom. Scintillation cocktail was added to each well and the top of the plate was sealed. Radioactivity was counted in a TopCount NXT Microplate Scintillation Counter.

Specific binding of [$^3$H]-$E_2$ (B) at each concentration of NRBA was obtained by subtracting the nonspecific binding of [$^3$H]-$E_2$, and expressed as a percentage of the specific binding of [$^3$H]-$E_2$ in the absence of the NRBA ($B_0$). The concentration of the NRBA that reduced the specific binding of [$^3$H]-$E_2$ by 50% ($IC_{50}$) was determined by computer-fitting the data by nonlinear regression analysis using SigmaPlot (SPSS Inc., Chicago, Ill.) to the following equation:

$$B = B_0 * [1 - C/(IC_{50} + C)]$$

where C is the concentration of SERM.

The equilibrium dissociation constant ($K_i$) of the NRBA was calculated by:

$$K_i = K_d * IC_{50}/(K_d + L)$$

where $K_d$ is the equilibrium dissociation constant of [$^3$H]-$E_2$ (ERα=0.65 nM, ERβ=1.83 nM), and L is the concentration of [$^3$H]-$E_2$ (1 nM).

Table 1 presents a series of NRBAs. Representative NRBAs are described hereinbelow, whose activity under specific experimental conditions is provided. It is to be understood that while the indicated compounds may exhibit a particular activity (for example, compound 12b is an agonist) under the experimental conditions employed, as a function, in some embodiments of the particular cells utilized, etc., such compounds may possess alternate or varied activity in different experimental settings.

TABLE 1

| COMPOUND # and IUPAC NAME | PHYSICAL CHARACTERIZATION |
|---|---|
| Estradiol (E2) | |
| Propyl pyrazole triol (PPT) | |
| Dipropionitrile (DPN) | |
| 12a<br>6-hydroxy-2-(4-hydroxyphenyl)-isoquinolin-1(2H)-one | white solid. 67% yield. M.p. 312.3-313.4° C. $^1$H NMR (DMSO-$d_6$, 300 MHz) δ 10.30 (s, 1H), 9.77 (s, 1H), 8.08 (d, 1H, J = 8.7 Hz), 7.26 (d, 1H, J = 7.2 Hz), 7.20 (d, 2H, J = 8.7 Hz), 6.97 (dd, 1H, $J_1$ = 8.7 Hz, $J_2$ = 2.4 Hz), 6.93 (d, 1H, J = 2.4 Hz), 6.85 (d, 2H, J = 8.7 Hz), 6.49 (d, 1H, J = 7.5 Hz). MS m/z 276 (M + Na)$^+$. |
| 12b<br>4-bromo-6-hydroxy-2-(4-hydroxyphenyl)-isoquinolin-1(2H)-one; | white solid. 49% yield. M.p. 264.0-266.0° C. $^1$H NMR (DMSO-$d_6$, 300 MHz) δ 10.58 (s, 1H), 9.83 (s, 1H), 8.12 (d, 1H, J = 8.7 Hz), 7.71 (s, 1H), 7.22 (d, 2H, J = 8.7 Hz), 7.09 (d, 1H, J = 2.1 Hz), 7.04 (dd, 1H, $J_1$ = 8.7 Hz, $J_2$ = 2.4 Hz), 6.84 (d, 2H, J = 8.7 Hz). MS m/z 334 (M + H)$^+$. |
| 12c<br>4-bromo-2-(4-hydroxyphenyl)-6-methoxy-isoquinolin-1(2H)-one | white solid. 24% yield. M.p. 266.3-266.8° C. $^1$H NMR (DMSO-$d_6$, 300 MHz) δ 9.78 (s, 1H), 8.20 (d, 1H, J = 8.7 Hz), 7.79 (s, 1H), 7.25 (d, 2H, J = 9.0 Hz), 7.22 (dd, 1H, $J_1$ = 9.0 Hz, $J_2$ = 2.4 Hz), 6.85 (d, 2H, J = 8.7 Hz). MS m/z 345 (M + H)$^+$. |
| 12d<br>4-bromo-2-(3-fluoro-4-hydroxyphenyl)-6-hydroxy-isoquinolin-1(2H)-one | white solid. 79% yield. M.p. 254.3-254.6° C. $^1$H NMR (DMSO-$d_6$, 300 MHz) δ 10.74 (s, 1H), 10.20 (s, 1H), 8.13 (d, 1H, J = 8.7 Hz), 7.77 (s, 1H), 7.36 (dd, 1H, $J_1$ = 11.7 Hz, $J_2$ = 2.4 Hz), 7.11-6.99 (m, 4H). MS m/z 351 (M + H)$^+$. |
| 12e<br>4-bromo-2-(4-fluorophenyl)-6-hydroxy-isoquinolin-1(2H)-one | white solid. 83% yield. M.p. 250.4-250.9° C. $^1$H NMR (DMSO-$d_6$, 300 MHz) δ 10.76 (s, 1H), 8.14 (d, 1H, J = 8.7 Hz), 7.71 (s, 1H), 7.56-7.51 (m, 2H), 7.37-7.31 (m, 2H), 7.11 (d, 1H, J = 2.1 Hz), 7.06 (dd, 1H, $J_1$ = 8.7 Hz, $J_2$ = 2.4 Hz). MS m/z 336 (M + H)$^+$. |
| 12f<br>4-chloro-6-hydroxy-2-(4-hydroxyphenyl)-isoquinolin-1(2H)-one | white solid. 67% yield. M.p. 288.6-289.6° C. $^1$H NMR (DMSO-$d_6$, 300 MHz) δ 10.72 (s, 1H), 9.74 (s, 1H), 8.13 (d, 1H, J = 8.7 Hz), 7.67 (s, 1H), 7.23 (d, 2H, J = 8.7 Hz), 7.11 (d, 1H, J = 2.1 Hz), 7.06 (dd, 1H, $J_1$ = 8.7 Hz, $J_2$ = 2.1 Hz), 6.84 (d, 2H, J = 8.7 Hz). MS m/z 288 (M + H)$^+$. |
| 12g<br>4-chloro-2-(3-fluoro-4-hydroxyphenyl)-6-hydroxy-isoquinolin-1(2H)-one | white solid. 50% yield. M.p. 264.0-264.5° C. $^1$H NMR (DMSO-$d_6$, 300 MHz) δ 10.75 (s, 1H), 10.20 (s, 1H), 8.14 (d, 1H, J = 8.7 Hz), 7.71 (s, 1H), 7.36 (dd, 1H, $J_1$ = 12.0 Hz, $J_2$ = 2.4 Hz), 7.12-7.00 (m, 4H). MS m/z 304 (M + H)$^+$. |
| 12h<br>6-hydroxy-2-(4-hydroxyphenyl)-4-iodoisoquinolin-1(2H)-one | white solid. 80% yield. M.p. 249.3-249.8° C. $^1$H NMR (DMSO-$d_6$, 300 MHz) δ 10.66 (s, 1H), 9.73 (s, 1H), 8.08 (d, 1H, J = 8.4 Hz), 7.74 (s, 1H), 7.21 (d, 2H, J = 8.7 Hz), 7.02-6.98 (m, 2H), 6.84 (d, 2H, J = 8.7 Hz). MS m/z 378 (M − H)$^-$. |
| 12i<br>4-bromo-6-hydroxy-2-(3-hydroxyphenyl)-isoquinolin-1(2H)-one | white solid. 84% yield. M.p. 274.2-274.8° C. $^1$H NMR (DMSO-$d_6$, 300 MHz) δ 10.74 (s, 1H), 9.80 (s, 1H), 8.14 (d, 1H, J = 8.7 Hz), 7.75 (s, 1H), 7.32-7.27 (m, 1H), 7.10 (d, 1H, J = 2.1 Hz), 7.05 (dd, 1H, $J_1$ = 8.7 Hz, $J_2$ = 2.4 Hz), 6.86-6.83 (m, 3H). MS m/z 332 (M − H)$^-$. |
| 12j<br>8-hydroxy-2-(4-hydroxyphenyl)-6-methoxy-isoquinolin-1(2H)-one | white solid. 86% yield. M.p. 223.7-224.2° C. $^1$H NMR (DMSO-$d_6$, 300 MHz) δ 13.02 (s, 1H), 9.80 (s, 1H), 7.34 (d, 1H, J = 7.8 Hz), 7.25 (d, 2H, J = 8.7 Hz), 6.87 (d, 2H, J = 8.7 Hz), 6.68 (d, 1H, J = 2.4 Hz), 6.66 (d, 1H, J = 7.5 Hz), 6.44 (d, 1H, J = 2.1 Hz), 3.85 (s, 3H). MS m/z 282 (M − H)$^-$. |
| 12k<br>5-bromo-8-hydroxy-2-(4-hydroxyphenyl)-6-methoxy-isoquinolin-1(2H)-one | white solid. 89% yield. M.p. 254.7-255.2° C. $^1$H NMR (DMSO-$d_6$, 300 MHz) δ 13.35 (s, 1H), 9.83 (s, 1H), 7.50 (d, 1H, J = 7.8 Hz), 7.27 (d, 2H, J = 8.7 Hz), 6.88 (d, 2H, J = 8.7 Hz), 6.83 (d, 1H, J = 7.8 Hz), 6.75 (s, 1H), 3.96 (s, 3H). MS m/z 360 (M − H)$^-$. |
| 12l<br>6,8-dihydroxy-2-(4-hydroxyphenyl)-isoquinolin-1(2H)-one | white solid. 42% yield. M.p. 322.9-323.5° C. $^1$H NMR (DMSO-$d_6$, 300 MHz) δ 13.98 (s, 1H), 10.40 (s, 1H), 9.78 (s, 1H), 7.27-7.21 (m, 3H), 6.86 (d, 2H, J = 8.7 Hz), 6.57 (d, 1H, J = 7.5 Hz), 6.43 (d, 1H, J = 2.4 Hz), 6.27 (d, 1H, J = 2.1 Hz). MS m/z 268 (M − H)$^-$. |
| 12m<br>5-bromo-6,8-dihydroxy-2-(4-hydroxyphenyl)isoquinolin-1(2H)-one | white solid. 52.6% yield. $^1$H NMR (DMSO-$d_6$, 300 MHz) δ 13.17 (s, 1H), 11.34 (s, 1H), 9.83 (s, 1H), 7.46 (d, 1H, J = 7.5 Hz), 7.26 (d, 2H, J = 8.4 Hz), 6.87 (d, 2H, J = 8.4 Hz), 6.79 (d, 1H, J = 7.8 Hz), 6.51 (s, 1 Hz). MS m/e 347.5 (M − H)−. |
| 12n<br>2-(3-fluoro-4-hydroxyphenyl)-6-hydroxy-4-iodoisoquinolin-1(2H)-one | pale-yellow solid. 76.7% yield. $^1$H NMR (DMSO-$d_6$, 300 MHz) δ 10.69 (s, 1H), 10.20 (s, 1H), 8.18 (d, 1H, J = 8.7 Hz), 7.78 (s, 1H), 7.34 (dd, 1H, $J_1$ = 8.7 Hz, $J_2$ = 1.8 Hz), 7.07-6.99 (m, 4H). MS m/e 395.8 (M − H)−. |
| 12o<br>4-bromo-6-hydroxy-2-(4-hydroxy-3-methylphenyl)isoquinolin-1(2H)-one | white solid. 87.5% yield. M.p. 243.5-244.0° C. (decomposed). $^1$H NMR (DMSO-$d_6$, 300 MHz) δ 10.70 (s, 1H), 9.63 (s, 1H), 8.12 (d, 1H, J = 8.4 Hz), 7.70 (s, 1H), 7.13-7.02 (m, 4H), 6.85 (d, 1H, J = 8.4 Hz), 2.15 (s, 3H). MS m/e: 345.7 [M − H]$^-$. |
| 12p<br>2-(4-hydroxyphenyl)-6,8-dihydroxy-isoquinoline-1(2H)- | yellow solid. 65.8% yield. M.p. 289.9-300.2° C. (decomposed). H NMR (DMSO-$d_6$, 300 MHz) δ 14.18 (s, 1H), 10.69 (s, 1H), 9.83 (s, 1H), 7.55 (d, 1H, J = 7.2 Hz), 7.13 (d, 2H, J = 8.7 Hz), 7.00 (d, 1H, J = 7.2 Hz), |

TABLE 1-continued

| COMPOUND # and IUPAC NAME | PHYSICAL CHARACTERIZATION |
|---|---|
| thione | 6.87 (d, 2H, J = 8.7 Hz), 6.55 (d, 1H, J = 2.4 Hz), 6.42 (d, 1H, J = 2.7 Hz). |
| 12q<br>8-hydroxy-2-(4-hydroxyphenyl)-6-methoxy-1-oxo-1,2-dihydroisoquinoline-5-carbonitrile | white solid. 54.3% yield. M.p. 328.6-330.0° C. (decomposed). $^1$H NMR (DMSO-d$_6$, 300 MHz) δ 13.89 (s, 1H), 9.86 (s, 1H), 7.65 (d, 1H, J = 7.5 Hz), 7.29 (d, 2H, J = 8.7 Hz), 6.88 (d, 2H, J = 8.7 Hz), 6.79 (d, 1H, J = 7.8 Hz), 6.76 (s, 1H), 4.00 (s, 3H). |
| 12r<br>4-bromo-6-hydroxy-2-(4-hydroxyphenyl)isoquinoline-1(2H)-thione | yellow solid. 27.1% yield. M.p. 238.7-240.1° C. (decomposed). $^1$H NMR (DMSO-d$_6$, 300 MHz) δ 11.01 (s, 1H), 9.78 (s, 1H), 8.82 (d, 1H, J = 8.7 Hz), 8.05 (s, 1H), 7.20-7.16 (m, 4H), 6.85 (d, 2H, J = 8.7 Hz). |
| 12s<br>2-(3-fluoro-4-hydroxyphenyl)-6,8-dihydroxyisoquinolin-1(2H)-one | yellow solid. 21.2% yield. M.p. 316.8-318.2° C. (decomposed). $^1$H NMR (DMSO-d$_6$, 300 MHz) δ 12.87 (s, 1H), 10.33 (s, 2H), 7.39-7.34 (m, 1H), 7.28 (d, 1H, J = 7.2 Hz), 7.11-7.02 (m, 2H), 6.58 (d, 1H, J = 7.5 Hz), 6.44 (d, 1H, J = 2.1 Hz), 6.28 (d, 1H, J = 2.1 Hz). MS: m/e 285.8 [M − H]$^−$. |
| 12t<br>2-(3-fluoro-4-hydroxyphenyl)-8-hydroxy-6-methoxyisoquinolin-1(2H)-one | white solid. 76.3% yield. M.p. 204.2-205.0° C. (decomposed). $^1$H NMR (DMSO-d$_6$, 300 MHz) δ 12.91 (s, 1H), 10.27 (s, 1H), 7.41-7.35 (m, 2H), 7.13-7.03 (m, 2H), 6.69-6.65 (m, 2H), 6.44 (d, 1H, J = 2.4 Hz), 3.85 (s, 3H). MS: m/z 324.2 [M + Na]$^+$. |
| 12u<br>4-bromo-6,8-dihydroxy-2-(4-hydroxyphenyl)isoquinolin-1(2H)-one | white solid. 67.7% yield. $^1$H NMR (DMSO-d$_6$, 300 MHz) δ 13.12 (s, 1H), 10.76 (s, 1H), 9.81 (s, 1H), 7.75 (s, 1H), 7.27 (d, 2H, J = 8.7 Hz), 6.86 (d, 2H, J = 8.7 Hz), 6.61 (d, 1H, J = 2.1 Hz), 6.37 (d, 1H, J = 2.1 Hz). MS m/e 347.8 (M − H)$^−$. |
| 12v<br>4-bromo-8-hydroxy-2-(4-hydroxyphenyl)-6-methoxyisoquinolin-1(2H)-one | white solid. 27.7% yield. M.p. 248.6-245.0° C. (decomposed). $^1$H NMR (DMSO-d$_6$, 300 MHz) δ 13.20 (s, 1H), 9.83 (s, 1H), 7.82 (s, 1H), 7.29 (d, 2H, J = 8.7 Hz), 6.86 (d, 2H, J = 8.7 Hz), 6.66 (d, 1H, J = 2.1 Hz), 6.60 (d, 1H, J = 2.4 Hz), 3.90 (s, 3H). MS: m/e 361.8 [M − H]$^−$. |
| 12y<br>4-chloro-6,8-dihydroxy-2-(4-hydroxyphenyl) isoquinolin-1(2H)-one | white solid. 49.4% yield. $^1$H NMR (DMSO-d$_6$, 300 MHz) δ 13.09 (s, 1H), 10.77 (s, 1H), 9.81 (s, 1H), 7.70 (s, 1H), 7.27 (d, 2H, J = 8.7 Hz), 6.85 (d, 2H, J = 8.7 Hz), 6.62 (d, 1H, J = 2.1 Hz), 6.38 (d, 1H, J = 2.1 Hz). MS m/e 301.8 (M − H)$^−$. |
| 12z<br>4-bromo-6,8-dihydroxy-2-(3-fluoro-4-hydroxyphenyl)isoquinolin-1(2H)-one | white solid. 48.2% yield. $^1$H NMR (DMSO-d$_6$, 300 MHz) δ 13.02 (s, 1H), 10.78 (s, 1H), 10.27 (s, 1H), 7.79 (s, 1H), 7.41 (dd, 1H, J$_1$ = 11.7 Hz, J$_2$ = 2.4 Hz), 7.16-7.01 (m, 2H), 6.61 (d, 1H, J = 2.1 Hz), 6.38 (d, 1H, J = 2.1 Hz). MS m/e 363.9 (M − H)$^−$. |
| 14a<br>4,5-dibromo-2-(3,5-dibromo-4-hydroxyphenyl)-6-hydroxyisoquinolin-1(2H)-one | white solid. 49.4% yield. $^1$H NMR (DMSO-d$_6$, 300 MHz) δ 11.49 (s, 1H), 10.30 (s, 1H), 8.22 (d, 1H, J = 8.7 Hz), 7.86 (s, 1H), 7.76 (s, 2H), 7.25 (d, 1H, J = 8.7 Hz). MS: m/z 567.0 [M − H]$^−$. |
| 14b<br>6,8-dihydroxy-2-(4-hydroxyphenyl)-5-(trifluoromethylsulfonyl)isoquinolin-1(2H)-one | white solid. 47.6% yield. Mp. 330.0-332.1° C. (decomposed). $^1$H NMR (DMSO-d$_6$, 300 MHz) δ 13.09 (s, 1H), 11.23 (s, 1H), 9.81 (s, 1H), 7.46 (d, 1H, J = 7.5 Hz), 7.25 (d, 2H, J = 8.7 Hz), 6.87 (d, 2H, J = 8.7 Hz), 6.79 (d, 1H, J = 7.5 Hz), 6.51 (s, 1H). |
| 14c<br>4-(1,2-dibromoethyl)-6-hydroxy-2-(4-hydroxyphenyl)isoquinolin-1(2H)-one | white solid. 10.5% yield. $^1$H NMR (DMSO-d$_6$, 300 MHz) δ 10.42 (s, 1H), 9.72 (s, 1H), 8.14 (d, 1H, J = 8.7 Hz), 7.34 (s, 1H), 7.24-7.21 (m, 3H), 7.00 (dd, 1H, J$_1$ = 8.7 Hz, J$_2$ = 2.4 Hz), 6.89 (d, 2H, J = 8.7 Hz), 4.66 (t, 1H, J = 5.7 Hz), 2.82 (d, 2H, J = 5.7 Hz). MS: m/z 277.8 [M − 2HBr]−. |
| 14d<br>6-methoxy-2-(4-methoxyphenyl)-1-oxo-1,2-dihydroisoquinolin-8-yl trifluoromethanesulfonate | white solid. 94.1% yield. $^1$H NMR (DMSO-d$_6$, 300 MHz) δ 7.52 (d, 1H, J = 7.2 Hz), 7.38 (d, 1H, J = 2.4 Hz), 7.34 (d, 2H, J = 9.0 Hz), 7.07 (d, 2H, J = 9.0 Hz), 7.02 (d, 1H, J = 1.8 Hz), 6.72 (d, 1H, J = 7.5 Hz), 3.94 (s, 3H), 3.82 (s, 3H). MS: m/z 452.1 [M + Na]$^+$. |
| 14e<br>4,5-dibromo-6,8-dihydroxy-2-(4-hydroxyphenyl)isoquinolin-1(2H)-one | white solid. 45.6% yield. $^1$H NMR (DMSO-d$_6$, 300 MHz) δ 14.06 (s, 1H), 11.64 (s, 1H), 9.83 (s, 1H), 7.83 (s, 1H), 7.28 (d, 2H, J = 8.7 Hz), 6.87 (d, 2H, J = 8.7 Hz), 6.86 (s, 1H). MS: m/z 428.0 [M + H]$^+$. |
| 14f<br>6-hydroxy-2-(4-hydroxyphenyl)-4-vinylisoquinolin-1(2H)-one | white solid. 87.0% yield. $^1$H NMR (DMSO-d$_6$, 300 MHz) δ 10.43 (s, 1H), 9.71 (s, 1H), 8.13 (d, 1H, J = 8.7 Hz), 7.41 (s, 1H), 7.24 (d, 2H, J = 8.7 Hz), 7.10 (d, 1H, J = 2.1 Hz), 7.01 (dd, 1H, J$_1$ = 8.7 Hz, J$_2$ = 2.1 Hz), 6.88 (dd, 1H, J$_1$ = 17.4 Hz, J$_2$ = 10.8 Hz), 6.85 (d, 2H, J = 8.7 Hz), 5.64 (dd, 1H, J$_1$ = 17.4 Hz, J$_2$ = 1.2 Hz), 5.26 (dd, 1H, J$_1$ = 10.8 Hz, J$_2$ = 1.2 Hz). MS: m/z 280.0 [M + H]$^+$. |
| 14g<br>6-methoxy-2-(4-methoxyphenyl)-1-oxo-1,2-dihydroisoquinoline-4-carbonitrile | white solid. 92.6% yield. $^1$H NMR (DMSO-d$_6$, 300 MHz) δ 8.41 (s, 1H), 8.22 (d, 1H, J = 9.0 Hz), 7.43 (d, 2H, J = 8.7 Hz), 7.27 (dd, 1H, J$_1$ = 8.7 Hz, J$_2$ = 2.4 Hz), 7.08 (d, 1H, J = 2.4 Hz), 7.06 (d, 2H, J = 8.7 Hz), 3.97 (s, 3H), 3.82 (s, 3H). MS: m/z 307.0 [M + H]$^+$. |
| 14h<br>6-hydroxy-2-(4-hydroxyphenyl)-1-oxo-1,2-dihydroisoquinoline-4-carbonitrile | white solid. 68.5% yield. $^1$H NMR (DMSO-d$_6$, 300 MHz) δ 10.86 (s, 1H), 9.80 (s, 1H), 8.38 (s, 1H), 8.13 (d, 1H, J = 8.7 Hz), 7.25 (d, 2H, J = 8.7 Hz), 7.09 (dd, 1H, J$_1$ = 8.7 Hz, J$_2$ = 2.4 Hz), 7.04 (d, 1H, J = 2.4 Hz), 6.85 (d, 2H, J = 8.7 Hz). MS: m/z 279.0 [M + H]$^+$. |

TABLE 1-continued

| COMPOUND # and IUPAC NAME | PHYSICAL CHARACTERIZATION |
|---|---|
| 14i<br>6-methoxy-2-(4-methoxyphenyl)-1-oxo-1,2-dihydroisoquinoline-8-carbonitrile | white solid. 75.2% yield. $^1$H NMR (DMSO-$d_6$, 300 MHz) δ 7.63 (d, 1H, J = 2.1 Hz), 7.54 (d, 1H, J = 2.1 Hz), 7.51 (d, 1H, J = 7.5 Hz), 7.38 (d, 2H, J = 8.7 Hz), 7.06 (d, 2H, J = 8.7 Hz), 6.71 (d, 1H, J = 7.5 Hz), 3.95 (s, 3H), 3.82 (s, 3H). MS: m/z 307.2 [M + H]$^+$. |
| 14j<br>4-bromo-6-methoxy-2-(4-methoxyphenyl)-1-oxo-1,2-dihydroisoquinoline-8-carbonitrile | white solid. 83.3% yield. $^1$H NMR (DMSO-$d_6$, 300 MHz) δ 8.01 (s, 1H), 7.81 (d, 1H, J = 2.4 Hz), 7.43 (d, 1H, J = 2.4 Hz), 7.42 (d, 2H, J = 8.7 Hz), 7.07 (d, 2H, J = 8.7 Hz), 4.02 (s, 3H), 3.82 (s, 3H). MS: m/z 387.1 [M + H]$^+$. |
| 14k<br>4-bromo-6-hydroxy-2-(4-hydroxyphenyl)-1-oxo-1,2-dihydroisoquinoline-8-carbonitrile | pale-yellow solid. 36.0% yield. $^1$H NMR (DMSO-$d_6$, 300 MHz) δ 11.40 (s, 1H), 9.79 (s, 1H), 7.91 (s, 1H), 7.48 (d, 1H, J = 2.1 Hz), 7.38 (d, 1H, J = 2.1 Hz), 7.26 (d, 2H, J = 8.7 Hz), 6.86 (d, 2H, J = 8.7 Hz). MS: m/z 357.1 [M + H]$^+$. |
| 14l<br>6,8-dihydroxy-2-(4-hydroxyphenyl)-4-vinylisoquinolin-1(2H)-one | pale-yellow solid. 75.3% yield. $^1$H NMR (DMSO-$d_6$, 300 MHz) δ 13.22 (s, 1H), 10.48 (s, 1H), 9.79 (s, 1H), 7.38 (s, 1H), 7.28 (d, 2H, J = 8.7 Hz), 6.87 (d, 2H, J = 8.7 Hz), 6.81 (dd, 1H, J$_1$ = 17.1 Hz, J$_2$ = 10.8 Hz), 6.57 (d, 1H, J = 2.1 Hz), 6.33 (d, 1H, J = 2.1 Hz), 5.66 (dd, 1H, J$_1$ = 17.1 Hz, J$_2$ = 1.2 Hz), 5.30 (dd, 1H, J$_1$ = 10.8 Hz, J$_2$ = 1.2 Hz). MS: m/e 293.9 [M − H]$^-$. |
| 14m<br>6,8-dihydroxy-2-(4-hydroxyphenyl)-1-oxo-1,2-dihydroisoquinoline-4-carbonitrile or 4-cyano-6,8-dihydroxy-2-(4-hydroxyphenyl)isoquinolin-1(2H)-one | pale-yellow solid. 72.7% yield. $^1$H NMR (DMSO-$d_6$, 300 MHz) δ 12.43 (s, 1H), 10.92 (s, 1H), 9.86 (s, 1H), 8.37 (s, 1H), 7.29 (d, 2H, J = 8.7 Hz), 6.86 (d, 2H, J = 8.7 Hz), 6.57 (d, 1H, J = 2.1 Hz), 6.40 (d, 1H, J = 2.1 Hz). MS: m/z 307.0 [M + Na]$^+$. |
| 14n<br>6-hydroxy-2-(4-hydroxyphenyl)-1-oxo-1,2-dihydroisoquinoline-8-carbonitrile | white solid. 46.1% yield. $^1$H NMR (DMSO-$d_6$, 300 MHz) δ 11.04 (s, 1H), 9.75 (s, 1H), 7.43 (d, 1H, J = 7.2 Hz), 7.37 (d, 1H, J = 2.1 Hz), 7.23 (d, 2H, J = 8.7 Hz), 7.24 (s, 1H), 6.86 (d, 2H, J = 8.7 Hz), 6.62 (d, 1H, J = 7.5 Hz). MS: m/z 279.0 [M + H]$^+$. |
| 14o<br>6-hydroxy-2-(4-hydroxyphenyl)-1-oxo-4-vinyl-1,2-dihydroisoquinoline-8-carbonitrile | yellow solid. 78.1% yield. $^1$H NMR (DMSO-$d_6$, 300 MHz) δ 11.12 (s, 1H), 9.76 (s, 1H), 7.54 (s, 1H), 7.43 (d, 1H, J = 2.4 Hz), 7.37 (d, 1H, J = 2.4 Hz), 7.27 (d, 2H, J = 8.7 Hz), 6.94-6.84 (m, 3H), 5.68 (dd, 1H, J$_1$ = 17.1 Hz, J$_2$ = 1.2 Hz), 5.31 (dd, 1H, J$_1$ = 11.1 Hz, J$_2$ = 1.2 Hz). MS: m/z 305.0 [M + H]$^+$. |
| 14p<br>4-chloro-6-hydroxy-2-(4-hydroxyphenyl)-1-oxo-1,2-dihydroisoquinoline-8-carbonitrile | yellow solid. 54.5% yield. $^1$H NMR (DMSO-$d_6$, 300 MHz) δ 11.42 (s, 1H), 9.79 (s, 1H), 7.86 (s, 1H), 7.50 (d, 1H, J = 2.1 Hz), 7.39 (d, 1H, J = 2.1 Hz), 7.26 (d, 2H, J = 8.7 Hz), 6.86 (d, 2H, J = 8.7 Hz). MS: m/z 318.8 [M − H]$^-$. |
| 14q<br>4-bromo-6-methoxy-2-(4-methoxyphenyl)isoquinolin-1(2H)-one | white solid. 85.9% yield. Mp. 153.8-154.3° C. $^1$H NMR (DMSO-$d_6$, 300 MHz) δ 8.14 (d, 1H, J = 8.7 Hz), 7.39-7.34 (m, 3H), 7.19 (d, 1H, J = 2.4 Hz), 7.13-7.03 (m, 3H), 6.62 (dd, 1H, J = 7.5 Hz), 3.89 (s, 3H), 3.81 (s, 3H). MS: 360.4 [M + H]+. |
| 14r<br>6-methoxy-2-(4-methoxyphenyl)-1-oxo-1,2-dihydroisoquinoline-4-carbonitrile | white solid. 92.6% yield. Mp. 204.8° C. (decomposed). $^1$H NMR (DMSO-$d_6$, 300 MHz) δ 8.48 (s, 1H), 8.22 (d, 1H, J = 9.0 Hz), 7.43 (d, 2H, J = 8.7 Hz), 7.27 (dd, 1H, J$_1$ = 8.7 Hz, J$_2$ = 2.4 Hz), 7.08 (d, 1H, J = 2.4 Hz), 7.06 (d, 2H, J = 8.7 Hz), 3.97 (s, 3H), 3.82 (s, 3H). MS: m/z 307.0 [M + H]+. |
| 14s<br>8-hydroxy-6-methoxy-2-(4-methoxyphenyl)isoquinolin-1(2H)-one | white solid. 83.7% yield. Mp. 154.5-155.0° C. $^1$H NMR (DMSO-$d_6$, 300 MHz) δ 12.98 (s, 1H), 7.42-7.35 (m, 3H), 7.06 (d, 2H, J = 9.0 Hz), 6.70-6.67 (m, 2H), 6.45 (d, 1H, J = 2.1 Hz), 3.85 (s, 3H), 3.82 (s, 3H). |
| 14t<br>4-chloro-6-methoxy-2-(4-methoxyphenyl)-1-oxo-1,2-dihydroisoquinolin-8-yl trifluoromethanesulfonate | white solid. 78.7% yield. $^1$H NMR (DMSO-$d_6$, 300 MHz) δ 7.97 (s, 1H), 7.39 (d, 2H, J = 9.0 Hz), 7.33 (d, 1H, J = 2.4 Hz), 7.21 (s, 1H), 7.07 (d, 2H, J = 9.0 Hz), 4.02 (s, 3H), 3.82 (s, 3H). MS: m/z 464.0 [M + H]+. |
| 14u<br>4-chloro-6-methoxy-2-(4-methoxyphenyl)-1-oxo-1,2-dihydroisoquinoline-8-carbonitrile | white solid. 69.7% yield. $^1$H NMR (DMSO-$d_6$, 300 MHz) δ 7.95 (s, 1H), 7.80 (d, 1H, J = 2.5 Hz), 7.46 (d, 1H, J = 2.5 Hz), 7.42 (d, 2H, J = 8.5 Hz), 7.07 (d, 2H, J = 8.5 Hz), 4.02 (s, 3H), 3.83 (s, 3H). MS: m/z 341.2 [M + H]+. |
| 14v<br>isoquinoline-1,6-diol | white solid (mp decomposed). Yield = 87%. $^1$H NMR (DMSO-$d_6$, 300 MHz): δ 10.90 (bs, 1H), 10.21 (s, 1H), 8.01 (d, J = 8.7 Hz, 1H), 7.05 (dd, J = 6.9, 5.7 Hz, 1H), 6.89 (m, 2 H), 6.35 (d, J = 7.2 Hz, 1H). MS (ESI) m/z 161.9 [M + H]$^+$, 184.0 [M + Na]$^+$ |
| 14w<br>6-hydroxy-2-(4-methoxyphenyl)isoquinolin-1(2H)-one | brown solid. (mp decomposed). Yield = 32%. $^1$H NMR (DMSO-$d_6$, 300 MHz): δ 10.35 (s, 1H), 8.07 (d, J = 8.7 Hz, 1H), 7.33 (m, 3H), 7.06-6.92 (m, 4H), 6.52 (d, J = 7.5 Hz, 1H), 3.81 (s, 3H). MS (ESI) m/z 268.0 [M + H]$^+$, 290.0 [M + Na]$^+$ |
| 14xME<br>4-bromo-6-hydroxy-2-(4- | white solid (mp decomposed). Yield = 42%. $^1$H NMR (CDCl$_3$, 500 MHz): δ 10.72 (s, 1H), 8.14 (d, J = 5.4 Hz, 1H), 7.53 (s, 1H), |

TABLE 1-continued

| COMPOUND # and IUPAC NAME | PHYSICAL CHARACTERIZATION |
|---|---|
| methoxyphenyl)isoquinolin-1(2H)-one | 7.38 (d, J = 5.4 Hz, 2H), 7.10 (d, J = 1.2 Hz, 1H), 7.06 (m, 1H), 7.04 (d, J = 5.4 Hz, 2H), 3.81 (s, 3H). MS (ESI) m/z 345.8 [M − H]$^-$. |
| 14xAC<br>4-(6-acetoxy-4-bromo-1-oxoisoquinolin-2(1H)-yl)phenyl acetate | white solid. M.p.; 200-201° C. Yield = 86%. $^1$H NMR (CDCl$_3$, 300 MHz): δ 8.52 (d, J = 8.7 Hz, 1H), 7.61 (d, J = 2.1 Hz, 1H), 7.52 (s, 1H), 7.45 (d, J = 8.7 Hz, 2H), 7.33 (dd, J = 8.7, 2.1 Hz, 1H), 7.25 (d, J = 8.7 Hz, 2H), 2.40 (s, 3H), 2.25 (s, 3H). Mass (ESI, positive) m/z 440.1 [M + Na]$^+$. MS (ESI) m/z 440.1 [M + Na]$^+$. |
| 14xME_AC<br>4-(4-bromo-6-methoxy-1-oxoisoquinolin-2(1H)-yl)phenyl acetate | white solid (mp; 189-190° C.). Yield = 87%. $^1$H NMR CDCl$_3$, 300 MHz): δ 8.42 (d, J = 9.0 Hz, 1H), 7.50 (s, 1H), 7.46 (d, J = 8.7 Hz, 2H), 7.25 (d, J = 8.7 Hz, 2H), 7.24 (d, J = 2.4 Hz, 1H), 7.15 (dd, J = 9.0, 2.4 Hz, 1H), 4.00 (s, 3H), 2.36 (s, 3H). MS (ESI) m/z 389.0 [M + H]$^+$, 412.1 [M + Na]$^+$. |
| 14yAM<br>4-bromo-6-hydroxy-2-(4-hydroxyphenyl)-1-oxo-1,2-dihydroisoquinoline-8-carbimidic acid | off-white solid. mp >300° C. $^1$H NMR (300 MHz, DMSO-d$_3$) δ 10.84 (s, 1H, OH), 9.74 (s, 1H, OH), 7.77 (s, 1H, ArH), 7.41 (s, 1H, OH or NH), 7.20-7.17 (m, 2H, ArH), 7.13 (s, 1H, OH or NH), 7.11 (d, J = 2.4 Hz, 1H, ArH), 6.86-6.83 (m, 2H, ArH), 6.80 (d, J = 2.4 Hz, 1H, ArH)., 2H, ArH), 6.80 (d, J = 2.4 Hz, 1H, ArH). Mass (ESI, positive) m/z 397.0 [M + Na]$^+$. |
| 14yME<br>methyl 4-bromo-6-hydroxy-2-(4-hydroxyphenyl)-1-oxo-1,2-dihydroisoquinoline-8-carboxylate | white solid. mp 296° C. (decomposition). $^1$H NMR (300 MHz, DMSO-d$_3$) δ 11.10 (s, 1H, OH), 9.76 (s, 1H, OH), 7.81 (s, 1H, ArH), 7.27-7.19 (m, 2H, ArH), 7.20 (d, J = 2.4 Hz, 1H, ArH), 6.93 (d, J = 2.4 Hz, 1H, ArH), 6.87-6.83 (m, 2H, ArH), 3.72 (s, 3H, OCH$_3$). Mass (ESI, positive) m/z 390.2 [M + H]$^+$; Mass (ESI, negative) m/z 387.8 [M − H]$^-$. |
| 14z<br>4-bromo-6-hydroxy-2-(4-hydroxyphenyl)-1-oxo-1,2-dihydroisoquinoline-8-carboxylic acid | |
| 15a<br>6-hydroxy-2-(4-hydroxyphenyl)-4-phenylisoquinolin-1(2H)-one | white solid. 87.9% yield. M.p. 296.9-297.5° C. $^1$H NMR (DMSO-d$_6$, 300 MHz) δ 10.31 (s, 1H), 9.69 (s, 1H), 8.19 (d, 1H, J = 8.7 Hz), 7.52-7.39 (m, 5H), 7.28 (d, 2H, J = 8.7 Hz), 7.18 (s, 1H), 7.00 (dd, 1H, J$_1$ = 8.7 Hz, J$_2$ = 2.4 Hz), 6.87-6.82 (m, 3H). MS: 330.2 [M + H]$^+$. |
| 15b<br>6-hydroxy-2-(4-hydroxyphenyl)-4-(4-methoxyphenyl)isoquinolin-1(2H)-one: | white solid. 72.5% yield. M.p. 295.1-296.0° C. $^1$H NMR (DMSO-d$_6$, 300 MHz) δ 10.28 (s, 1H), 9.68 (s, 1H), 8.18 (d, 1H, J = 8.7 Hz), 7.38 (d, 2H, J = 9.0 Hz), 7.27 (d, 2H, J = 8.7 Hz), 7.13 (s, 1H), 7.04 (d, 2H, J = 8.7 Hz), 6.99 (dd, 1H, J$_1$ = 8.7 Hz, J$_2$ = 2.4 Hz), 6.87-6.82 (m, 3H), 3.81 (s, 3H). MS: 360.1 [M + H]$^+$. |
| 15c<br>2-(3-fluoro-4-hydroxyphenyl)-6,8-dihydroxy-4-vinylisoquinolin-1(2H)-one | white solid. 67.6% yield. M.p. 221.9-223.0° C. $^1$H NMR (DMSO-d$_6$, 300 MHz) δ 13.12 (s, 1H), 10.51 (s, 1H), 10.24 (s, 1H), 7.44-7.40 (m, 2H), 7.17-7.03 (m, 2H), 6.80 (dd, 1H, J$_1$ = 17.1 Hz, J$_2$ = 10.8 Hz), 6.57 (d, 1H, J = 2.1 Hz), 6.34 (d, 1H, J = 2.1 Hz), 5.67 (dd, 1H, J$_1$ = 17.1 Hz, J$_2$ = 1.2 Hz), 5.30 (dd, 1H, J$_1$ = 10.8 Hz, J$_2$ = 1.2 Hz). MS: 311.9 [M − H]$^-$. |
| 15d<br>2-(3-fluoro-4-hydroxyphenyl)-6,8-dihydroxy-1-oxo-1,2-dihydroisoquinoline-4-carbonitrile | white solid. 63.4% yield. M.p. 280.8-282.0° C. $^1$H NMR (DMSO-d$_6$, 300 MHz) δ 12.35 (s, 1H), 10.94 (s, 1H), 10.33 (s, 1H), 8.39 (s, 1H), 7.44 (dd, 1H, J$_1$ = 11.7 Hz, J$_2$ = 2.4 Hz), 7.18-7.03 (m, 2H), 6.57 (d, 1H, J = 2.1 Hz), 6.41 (d, 1H, J = 2.1 Hz). MS: 310.9 [M − H]$^-$. |
| 15e<br>6-hydroxy-2-(4-hydroxyphenyl)-8-vinylisoquinolin-1(2H)-one | white solid. 36.5% yield. M.p. >240.0° C. (decomposed). $^1$H NMR (DMSO-d$_6$, 300 MHz) δ 10.33 (s, 1H), 9.66 (s, 1H), 7.79 (dd, 1H, J$_1$ = 17.4 Hz, J$_2$ = 10.8 Hz), 7.25 (d, 1H, J = 7.5 Hz), 7.15 (d, 2H, J = 8.7 Hz), 6.97 (d, 1H, J = 2.1 Hz), 6.88 (d, 1H, J = 2.1 Hz), 6.83 (d, 2H, J = 8.7 Hz), 6.46 (d, 1H, J = 7.5 Hz), 5.44 (dd, 1H, J$_1$ = 17.4 Hz, J$_2$ = 1.8 Hz), 5.19 (dd, 1H, J$_1$ = 10.8 Hz, J$_2$ = 1.8 Hz). MS: 277.9 [M − H]$^-$. |
| 15f<br>4-bromo-6-hydroxy-2-(4-hydroxyphenyl)-8-vinylisoquinolin-1(2H)-one | white solid. 54.5% yield. M.p. >188.0° C. (decomposed). $^1$H NMR (DMSO-d$_6$, 300 MHz) δ 10.71 (s, 1H), 9.71 (s, 1H), 7.89 (dd, 1H, J$_1$ = 17.4 Hz, J$_2$ = 10.5 Hz), 7.72 (s, 1H), 7.19 (d, 2H, J = 8.7 Hz), 7.12 (d, 1H, J = 2.4 Hz), 7.03 (d, 1H, J = 2.4 Hz), 6.83 (d, 2H, J = 8.7 Hz), 5.47 (dd, 1H, J$_1$ = 10.5 Hz, J$_2$ = 1.5 Hz). MS: 355.9 [M − H]$^-$. |
| 15g<br>6,8-dihydroxy-2-(4-hydroxyphenyl)-4-(4-methoxyphenyl)isoquinolin-1(2H)-one | white solid. 83.3% yield. M.p. 141.3-142.0° C. $^1$H NMR (DMSO-d$_6$, 300 MHz): δ 10.32 (s, 1H), 10.33 (s, 1H), 9.76 (s, 1H), 7.36 (d, 2H, J = 8.7 Hz), 7.30 (d, 2H, J = 8.7 Hz), 7.11 (s, 1H), 7.04 (d, 2H, J = 8.7 Hz), 6.86 (d, 2H, J = 8.7 Hz), 6.32 (d, 1H, J = 2.1 Hz), 6.30 (d, 1H, J = 2.1 Hz), 3.80 (s, 3H). MS: 373.9 [M − H]$^-$. |
| 15h<br>6,8-dihydroxy-2-(4-hydroxyphenyl)-4-phenylisoquinolin-1(2H)-one | white solid. 89.9% yield. M.p. 133.2-134.0° C. $^1$H NMR (DMSO-d$_6$, 300 MHz): δ 10.30 (s, 1H), 10.35 (s, 1H), 9.76 (s, 1H), 7.52-7.39 (m, 5H), 7.31 (d, 2H, J = 8.7 Hz), 7.16 (s, 1H), 6.86 (d, 2H, J = 8.7 Hz), 6.32 (d, 1H, J = 2.1 Hz), 6.31 (d, 1H, J = 2.1 Hz). MS: 343.9 [M − H]$^-$. |
| 15i<br>(E)-6,8-dihydroxy-2-(4-hydroxyphenyl)-4-(prop-1-enyl)isoquinolin-1(2H)-one | white solid. 78.7% yield. M.p. 206.9-207.0° C. $^1$H NMR (DMSO-d$_6$, 300 MHz) δ 13.26 (s, 1H), 10.42 (s, 1H), 9.77 (s, 1H), 7.26 (d, 2H, J = 8.5 Hz), 7.24 (s, 1H), 6.86 (d, 2H, J = 8.5 Hz), 6.55 (d, 1H, J = 2.0 Hz), 6.45 (d, 1H, J = 15.0 Hz), 6.31 (d, 1H, J = 2.0 Hz), |

TABLE 1-continued

| COMPOUND # and IUPAC NAME | PHYSICAL CHARACTERIZATION |
|---|---|
| | 6.10-6.03 (m, 1H), 1.83 (d, 3H, J = 6.5 Hz). MS: 310.0 [M + H]$^+$. |
| 15j (E)-ethyl 3-(8-hydroxy-6-methoxy-2-(4-methoxyphenyl)-1-oxo-1,2-dihydroisoquinolin-4-yl)acrylate | white solid. 76.4% yield. M.p. 160.2-160.7° C. $^1$H NMR (DMSO-$d_6$, 300 MHz) δ 13.09 (s, 1H), 7.97 (s, 1H), 7.85 (d, 1H, J = 15.9 Hz), 7.46 (d, 2H, J = 8.7 Hz), 7.07 (d, 2H, J = 8.7 Hz), 6.74 (d, 1H, J = 2.4 Hz), 6.60 (d, 1H, J = 11.4 Hz), 6.56 (d, 1H, J = 2.1 Hz), 4.18 (q, 2H, J = 7.2 Hz), 3.91 (s, 3H), 3.83 (s, 3H), 1.25 (t, 3H, J = 7.2 Hz). MS: 396.1 [M + H]$^+$. |
| 15k (E)-3-(6-hydroxy-2-(4-hydroxyphenyl)-1-oxo-1,2-dihydroisoquinolin-4-yl)acrylic acid | yellow solid. 74.9% yield. M.p. >350.0° C. $^1$H NMR (DMSO-$d_6$, 300 MHz) δ 8.11 (d, 1H, J = 9.0 Hz), 7.66 (d, 1H, J = 15.5 Hz), 7.65 (s, 1H), 7.31 (s, 1H), 7.24 (d, 2H, J = 9.0 Hz), 6.98 (d, 1H, J = 8.5 Hz), 6.85 (d, 2H, J = 8.5 Hz), 6.36 (d, 1H, J = 16.0 Hz). MS: 321.9 [M – H]$^-$. |
| 15l (E)-3-(6,8-dihydroxy-2-(4-hydroxyphenyl)-1-oxo-1,2-dihydroisoquinolin-4-yl)acrylic acid | yellow solid. 33.3% yield.. M.p. >350.0° C. $^1$H NMR (DMSO-$d_6$, 300 MHz) δ 13.09 (s, 1H), 9.86 (s, 1H), 8.59 (s, 1H), 7.73 (s, 1H), 7.60 (d, 1H, J = 15.9 Hz), 7.29 (d, 2H, J = 9.0 Hz), 6.87 (d, 2H, J = 8.7 Hz), 6.70 (d, 1H, J = 2.1 Hz), 6.40 (d, 1H, J = 15.6 Hz), 6.34 (d, 1H, J = 2.1 Hz). MS: 337.9 [M – H]$^-$. |
| 15m 4-chloro-6-methoxy-2-(4-methoxyphenyl)-1-oxo-1,2-dihydroisoquinolin-8-yl 4-(trifluoromethyl)benzoate | white solid. 94.9% yield.. M.p. 195.4-196.0° C. $^1$H NMR (DMSO-$d_6$, 300 MHz) δ 8.26 (d, 2H, J = 8.1 Hz), 7.94 (d, 2H, J = 8.4 Hz), 7.85 (d, 2H, J = 9.0 Hz), 7.23 (d, 1H, J = 2.4 Hz), 7.21 (d, 1H, J = 2.4 Hz), 6.97 (d, 2H, J = 9.0 Hz), 3.99 (s, 3H), 3.76 (s, 3H). MS: 526.2 [M + Na]$^+$. |

Representative examples of the NRBAs of this invention and their activity under the indicated conditions are as follows:

Table 2 presents competitive inhibition of the respective estrogen receptors by some embodiments of NRBAs of the invention. Recombinant ERα or ERβ ligand binding domain was incubated with [$^3$H]-estradiol and increasing concentration of some embodiments of the NRBAs of this invention, ranging in concentration from $10^{-11}$ to $10^{-4}$M. Following incubation, plates were harvested onto GF/B filters and radioactivity was measured with a TopCount NXT (PerkinElmer). Nonspecific binding was subtracted from total binding to yield specific binding. The percent inhibition of [$^3$H]-estradiol at 100 nM of compound is as follows:

TABLE 2

Percent Inhibition of [$^3$H]-Estradiol Binding to ERα and ERβ by NRBAs

| Compound | ER-α | ER-β |
|---|---|---|
| 12b | 0 | 53.6 |
| 12d | 0 | 38.7 |
| 12f | 0 | 47.5 |
| 12g | 0 | 29.4 |
| 12h | 7.7 | 40.5 |
| 12l | 2.5 | 34.4 |
| 12m | 5.2 | 0 |
| 12n | 6.2 | 8.7 |
| 12p | 25.8 | 80.7 |
| 12r | 35.7 | 75.5 |
| 12s | 4.5 | 52.8 |
| 12u | 61.3 | 96.7 |
| 12y | 51.9 | 97.5 |
| 12z | 52.8 | 95.3 |

Table 3 describes binding constants ($K_i$ values) for ER-α and ER-β with respect to some embodiments of NRBAs of this invention

TABLE 3

Binding constants ($K_i$ values) for ER-α and ER-β NRBAs.

| Compound | ER-α binding constant (nM) | ER-β binding constant (nM) |
|---|---|---|
| 12b | 998 | 49 |
| 12u | 32 | 3 |
| 12z | 40 | 3 |
| 14l | 76 | 6 |
| 14m | 94 | 7 |
| 14k | >394 | 46 |
| 15a | 1778 | 130 |
| 15b | 2097 | 252 |
| 15c | 205 | 3.96 |
| 15g | 70.0 | 0.48 |
| 15h | 124 | 3.03 |
| 15i | 102 | 1.66 |

The NRBAs of Table 3 inhibited Cyp 3A and/or Cyp 2C9 at very low concentrations, with the exception of 12b [data not shown].

(B) Effects of NRBA on ER-α and ER-β Transactivation

COS or 293 cells were plated in DME without phenol red+10% cs FBS at 90,000 cells per well in 24 well plates, and were transfected with 0.25 μg of the vector "ERE-LUC", where a firefly luciferase gene was driven by two estrogen responsive elements and 0.02 μg of the control CMV-LUC, Renilla where a luciferase gene was driven by a CMV promoter. Also 25 ng of ER-α), 50 ng of ER-β or 12.5 ng of AR were introduced by lipofectamine. All the receptors were cloned from rat tissue into the PCR3.1 vector backbone. Twenty four hours post transfection, cells were treated with compounds of this invention, estrogen, DHT, and other NRBAs or combinations thereof. Cells were harvested 48 hrs after transfection, and assayed for firefly and Renilla luciferase activity.

Representative examples of the NRBAs of this invention and their activity under the indicated conditions were as follows ER-α agonists: 12y (ER-α: $K_i$=36 nM; 12u (ER-α: $K_i$=32 nM;

% activity of 100 nM 12u compared to 1 nM estradiol=62%).

ER-β agonists: 12b (ER-β: $K_i$=49 nM; % activity of 100 nM 12b compared to 1 nM estradiol=79%), 12p (ER-β: $K_i$=17 nM; % activity of 100 nM 12p compared to 1 nM estradiol=85%).

Representative Table 4 below has the % estradiol activity at 100 nM of NRBA for representative examples of the NRBAs of this invention and their % estradiol activity at 100 nM.

TABLE 4

Estradiol activity at 100 nM of representative NRBAs (in %).

| Compound | ER-α | ER-β |
|---|---|---|
| 12b | 31.2 | 78.8 |
| 12p | 45 | 85 |
| 12q | 25 | 10 |
| 12s | 29 | 76.9 |
| 12u | 62 | 85 |
| 12v | 17 | 10 |
| 14l | 50 | 52.7 |
| 14m | 49 | 74.5 |

The compounds 12b, 12f, 12h, 12p, 12s, 12u, 12y and 12z were found to possess ER-β agonist activity. The binding affinity of the compounds is presented in FIG. 1.

Table 5 below shows the ratio between the binding constants of ER-α and ER-β for representative examples of these agonists.

TABLE 5

Ratio between the binding constants of ER-α and ER-β for representative NRBAs.

| Compound | $K_i$ Ratio (ER-α/ER-β) |
|---|---|
| Estradiol | 0.13 |
| 12b | 20 |
| 12f | 61 |
| 12h | 22 |
| 12p | 8 |
| 12s | 25 |
| 12u | 17 |
| 12y | 11 |
| 12z | 12 |
| 15a | 13.7 |
| 15b | 8.3 |
| 15c | 51.7 |
| 15g | 145.8 |
| 15h | 41.1 |
| 15i | 61.4 |

Figure 2:
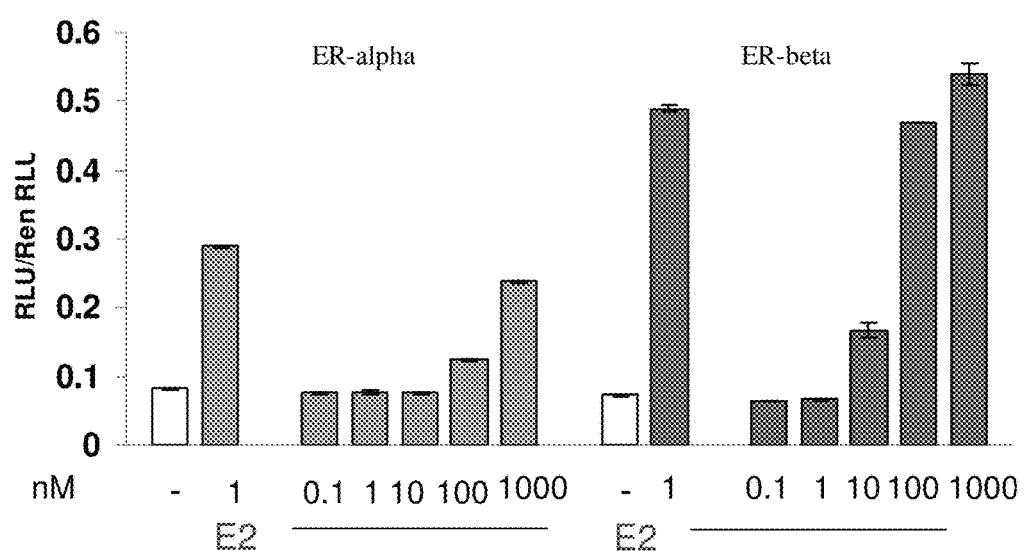
FIG. 2 depicts ER-α and ER-β activation by 121, with 0.1, 1, 10, 100, 1000 nM doses.

As an example, the in vitro activation of ER-α and ER-β of 12l compound compared to estradiol using 0.1, 1, 10, 100 and 1000 nM doses was evaluated (FIG. 2) and the data is presented in Table 6 below.

TABLE 6

In vitro activation of ER-α and ER-β by 12l compound compared to estradiol using 0.1, 1, 10, 100 and 1000 nM doses

| | ER-α RLU/RenRLU | ER-β RLU/RenRLU |
|---|---|---|
| Doses (nM) of 12l | | |
| 0.1 | 0.07 | 0.06 |
| 1 | 0.07 | 0.07 |
| 10 | 0.07 | 0.16 |
| 100 | 0.12 | 0.46 |
| 1000 | 0.24 | 0.55 |

TABLE 6-continued

In vitro activation of ER-α and ER-β by 12l compound compared to estradiol using 0.1, 1, 10, 100 and 1000 nM doses

| | ER-α RLU/RenRLU | ER-β RLU/RenRLU |
|---|---|---|
| Doses of estradiol (nM) | | |
| 1 | 0.29 | 0.48 |

Example 22A: In Vitro Characterization of 14m and 12u

Ligand Binding Assay

Recombinant ER-α or ER-β ligand binding domain (LBD) was combined with [$^3$H]E$_2$ (PerkinElmer, Waltham, Mass.) in buffer A (10 mM Tris, pH 7.4, 1.5 mM disodium EDTA, 0.25 M sucrose, 10 mM sodium molybdate, 1 mM PMSF) to determine the equilibrium dissociation constant ($K_d$) of [$^3$H]E$_2$. Protein was incubated with increasing concentrations of [$^3$H]E$_2$ with and without a high concentration of unlabeled E$_2$ at 4° C. for 18h in order to determine total and non-specific binding. Non-specific binding was then subtracted from total binding to determine specific binding. Ligand binding curves were analyzed by nonlinear regression with one site saturation to determine the $K_d$ of E$_2$ (ER-α: 0.65 nM; ER-β: 1.83 nM). In addition, the concentration of [$^3$H]E$_2$ required to saturate ER-α and ER-β LBD was determined to be 1-3 nM.

Increasing concentrations of two β-SERMs (14m and 12u) (range: $10^{-11}$ to $10^{-6}$ M) were incubated with [$^3$H]E$_2$ (1-2 nM) and ER LBD using the conditions described above. Following incubation, plates were harvested with GF/B filters on the Unifilter-96 Harvester (PerkinElmer) and washed three times with ice-cold buffer B (50 mM Tris, pH 7.2). The filter plates were dried at room temperature, then Microscint-O cocktail was added to each well and the filter plates were sealed with TopSeal-A. Radioactivity was counted in a TopCount® NXT Microplate Scintillation Counter using the settings for [$^3$H] in Microscint cocktail (PerkinElmer).

The specific binding of [$^3$H]E$_2$ at each concentration of compound was determined by subtracting the nonspecific binding of [$^3$H]E$_2$ (determined by incubating with $10^{-6}$ M unlabeled E$_2$) and expressing it as a percentage of the specific binding in the absence of compound. The concentration of compound that reduced the specific binding of [$^3$H]E$_2$ by 50% (IC$_{50}$) was determined by computer-fitting the data with SigmaPlot and non-linear regression with the four parameter logistic curve. The equilibrium binding constant ($K_i$) of each compound was then calculated by: $K_i=K_d \times IC_{50}/(K_d+L)$, where $K_d$ is the equilibrium dissociation constant of [$^3$H]E$_2$, and L is the concentration of [$^3$H]E$_2$.

Transient Transfection and Reporter Gene Assay

Human estrogen receptors (ER-α and ER-β) were cloned from prostate cDNA into a pCR3.1 plasmid vector backbone. PGC-1 was cloned into mammalian two hybrid vector pACT. ER-β H475 was mutated to alanine using site-directed mutagenesis. Sequencing was performed to determine the absence of any non specific mutations. SHP promoter (−572 to +10) (26) was cloned into pGL3 basic LUC reporter vector and human FXR was cloned into pCR3.1. HEK-293 cells were plated at 100,000 cells per well of a 24 well plate in Dulbecco's Minimal Essential Media (DMEM)+5% charcoal-stripped fetal bovine serum (csFBS). The cells were transfected using Lipofectamine (Invitrogen, Carlsbad, Calif.) with 0.25 μg ERE-LUC, 0.02 μg CMV-LUC (renilla luciferase) and 12.5 ng of rat ER-α or 25 ng rat ER-β. The cells were treated 24 hrs after transfection with various concentrations of SERMs or a combination of SERMs and estradiol to determine the antagonistic activity. Luciferase assays were performed 48 hrs after transfection.

Ishikawa Growth Assay

Ishikawa cells were plated at 15,000 cells/well in 24 well plates in DME:F12 (1:1)+5% csFBS w/o phenol red. The cells were maintained in this medium at 37° C. for 3 days. Medium was changed immediately prior to drug treatment for an additional 72 hrs. After 72 hrs, the cells were fixed with formalin and the amount of alkaline phosphatase (ALP) measured by para-nitrophenyl phosphate method.

Results

In Vitro Characterization of 14m and 12u

Figure 3:
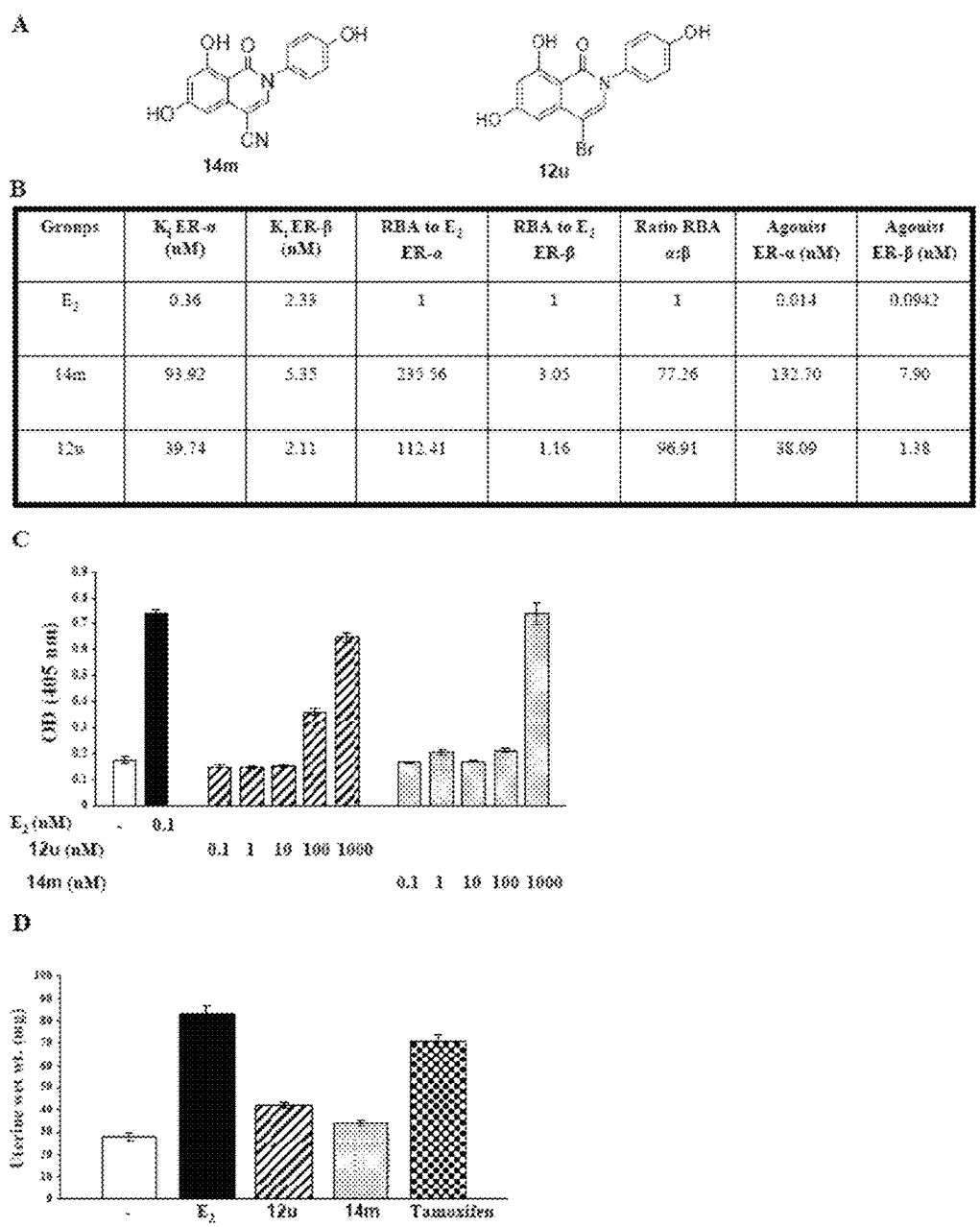
FIG. 3 depicts in vitro and in vivo characterization of ER-β selective SERMs. (A) Structure of 14m and 12u. (B) Binding and transactivation characteristics of ER-β SERMs, 14m and 12u: Ligand binding assay (columns 2-6) and transactivation assay (columns 7-8). (C) 14m and 12u weakly induce Ishikawa cell proliferation. (D) 14m and 12u does not increase uterine weights. Data is expressed as Mean±S.E. RBA—relative binding affinity; ER-α—estrogen receptor α; ER-β—estrogen receptor β; s.c.—subcutaneously.

Two ft-SERMs were selected from a library of isoform selective SERMs (FIG. 3A). 14m (4-cyano-6,8-dihydroxy-2-(4-hydroxyphenyl)isoquinolin-1(2H)-one) and 12u (4-bromo-6,8-dihydroxy-2-(4-hydroxyphenyl)isoquinolin-1(2H)-one) bound ER-β with high affinity with $K_i$ values of 5.35 and 2.11 nM respectively, which were comparable to the binding by $E_2$ (FIG. 3B). However, 14m and 12u bound to ER-α with much lower affinity than estradiol, with $K_i$ values of 94 and 40 nM, respectively (FIG. 3B). As such, 14m and 12u bound to ER-β with almost 100-fold selectivity compared to ER-α (FIG. 3B).

To determine if the selectivity in ER binding also translated into ER-β-selective activity, transient transactivation assays were performed in HEK-293 cells transfected with plasmids encoding ER-α or ER-β and ERE-LUC. The cells were treated with varying concentrations of the ligands and their $EC_{50}$ values were determined. Both, 14m and 12u functioned as agonists to both ER-α and ER-β with a selectivity of 20-30 fold towards ER-β and with $EC_{50}$ of less than 10 nM (FIG. 3B).

Since members of the NHR superfamily have moderately homologous LBDs, transactivation assays were performed to determine the cross reactivity with 13 other NHR (receptors for progesterone, mineralocorticoids, androgens, glucocorticoids, FXR, PXR, liver X receptor (LXR), retinoid X receptor (RXR), PPAR-α, PPAR-γ and ERR-α, ERR-β and ERR-γ). 14m and 12u did not cross react with any of the above mentioned receptors even at concentrations as high as 10 μM (data not shown).

Figure 12:
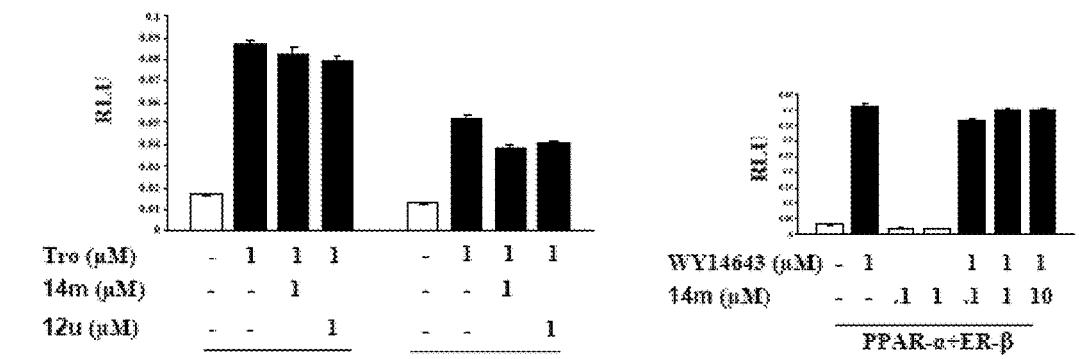
FIG. 12 depict the effect of ER-β ligand on PPAR-γ function through ligand binding domain (LBD). (A). HEK-293 cells were transfected with 0.25 μg PPRE-LUC, 5 ng CMV-renilla LUC and the indicated receptors (PPAR-γ and ER-β for the left panel and PPAR-α and ER-β for the right panel). The cells were treated 24 hrs after transfection with the indicated ligands and harvested 48 hrs after transfection and firefly luciferase activity was measured and normalized to renilla luciferase. (B). H475 in ER-β LBD is important for its function. H475 in ER-β LBD was mutated to alanine (A) using a site directed mutagenesis kit. Transactivation assay was performed as described in panel A in HEK-293 cells with a titration of ER-β ligands in wild type or ER-β H475A. (C). ER-β H475A does not inhibit PPAR-γ transactivation. HEK-293 cells were transfected with 0.25 μg PPRE-LUC, 5 ng CMV-renilla LUC and 50 ng of the indicated receptors (PPAR-γ or PPAR-γ and wild type ER-β or PPAR-γ and ER-β H475A). The cells were treated 24 hrs after transfection with the indicated ligands and harvested 48 hrs after transfection and firefly luciferase activity was measured and normalized to renilla luciferase. (D). ER-β ligand dependently inhibits PGC-1 coactivated PPAR-γ but not PPAR-α transactivation. HepG2 cells were transfected with 0.25 μg PPRE-LUC, 5 ng CMV-renilla LUC, 0.5 μg PGC-1 or vector backbone and 100 ng of the indicated receptors (PPAR-γ or PPAR-γ and wild type ER-β or PPAR-γ and ER-β H475A for top panels and PPAR-α or PPAR-α and ER-β for bottom panel). The cells were treated 24 hrs after transfection with the indicated ligands and harvested 48 hrs after transfection and firefly luciferase activity was measured and normalized to renilla luciferase. (E). SHP-1 is an ER-β specific target gene. HEK-293 cells were transfected with 0.25 μg SHP-LUC, 5 ng CMV-renilla LUC and 50 ng of the indicated receptors (FXR and ER-α for the left panel and FXR and ER-β for the right panel). The cells were treated 24 hrs after transfection with the indicated ligands and harvested 48 hrs after transfection and firefly luciferase activity was measured and normalized to renilla luciferase. PPAR—peroxisome proliferator and activated receptor; ER-estrogen receptor; H-histidine; A—alanine; RLU—relative luciferase units; Tro—troglitazone; PGC-1—PPAR-γ coactivator; SHP—small heterodimer partner; FXR—farsenoid X receptor.
Figure 12:
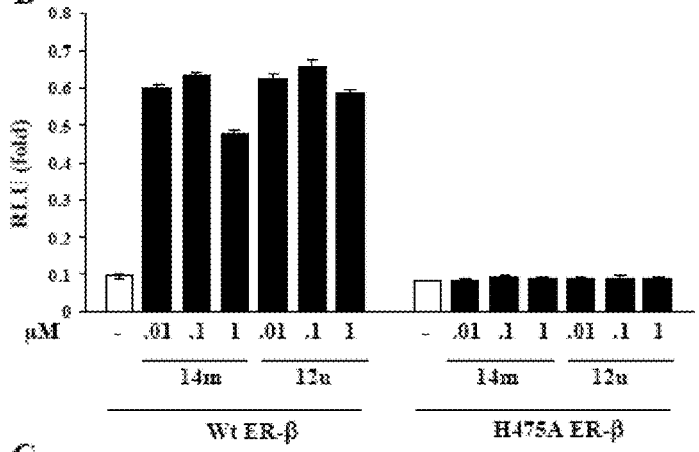
Figure 12:
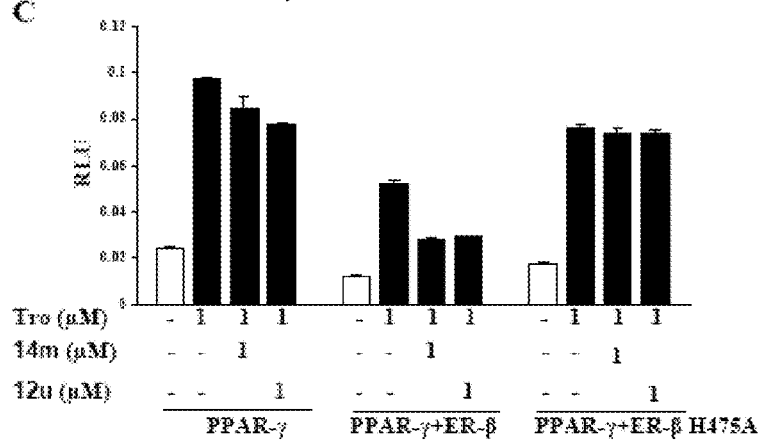

Activation of ER-α, but not ER-β, induces uterine proliferation [Morani A et al 2008 *J Intern Med* 264:128-42]. This effect is one potential concern in the development of ER-α SERMs. As such, the ability of 14m and 12u to stimulate in vitro growth of Ishikawa endometrial cells was examined using varying concentrations of the ligands and an ALP assay. As shown in FIG. 3C, 14m and 12u induced the proliferation of Ishikawa cells only at the highest concentration tested (1 μM) or the concentration at which they cross react with ER-α. On the other hand, $E_2$ promoted the proliferation of the cells at very low concentrations (i.e., 0.1 nM).

Example 22B: In Vivo Characterization of 14m and 12u

Uterotropic Assay

Sprague Dawley rats of 18-20 days age were randomized based on body weight into groups of 7 animals and treated with vehicle, 50 μg/kg/day estradiol subcutaneously (s.c), 10 mg/kg/day tamoxifen orally, or 30 mg/kg/day 14m or 12u s.c. Body weight (BW) was recorded at pretreatment (Day 0) and before necropsy (Day 4). Statistical differences among groups were evaluated by one-way ANOVA. Rats were treated for 3 consecutive days and then sacrificed 24 h after the last dose. The body of the uterus was cut just above its junction with the cervix and at the junction of the uterine horns with the ovaries. The uterus was weighed with and without intrauterine fluid. Statistical comparisons were made between the weights of empty uteri.

The effects of 14m and 12u on the proliferation of uterus in vivo were also examined. 14m and 12u were administered subcutaneously at a dose of 30 mg/kg/day, while E2 was administered subcutaneously at a dose of 50 μg/kg/day and tamoxifen at a dose of 10 mg/kg/day orally for 3 days. Tamoxifen was used as a tissue-selective positive control SERM. $E_2$ and tamoxifen stimulated the proliferation of uterus significantly, as demonstrated by the increase in uterine weight, whereas both 14m and 12u did not induce uterine growth (FIG. 3D). In addition to confirming the absence of uterotropic activity in vivo, these studies also were used for dose determination (30 mg/kg/day s.c) for the obesity studies.

Example 23: Obesity Studies

To determine the metabolic effects of 14m (4-cyano-6,8-dihydroxy-2-(4-hydroxyphenyl)isoquinolin-1(2H)-one) and 12u (4-bromo-6,8-dihydroxy-2-(4-hydroxyphenyl)isoquinolin-1(2H)-one) in a high fat diet (HFD) induced obesity model the following study was conducted:

Study A: C57BL6 male mice of 4 weeks of age were divided into different groups and were fed with a normal or high fat diet (Harlan, Ind.). The normal diet included protein (16.7%), carbohydrates (56%) and fat (4.2%), with a digestible energy of 3.3 Kcal/g. The high fat diet included protein (23.5%), carbohydrates (27.3%) and fat (34.3%), with a digestible energy of 5.1 Kcal/g.

For the prevention studies (studies 1 and 2), the animals were treated with vehicle, 14m or 12u 30 mg/kg/day s.c beginning on day 1 of the study and continuing for 12 weeks. For the treatment study (study 3), the animals were maintained on the irrespective diets for 6 weeks and then treated daily as indicated for an additional 18 weeks. Biweekly body weights and food consumption were measured. The animals were sacrificed at the end of each study and blood and tissues were collected for RNA isolation, histology and protein estimation. DEXA scanning was performed at the end of the first obesity study with 14m and MRI scanning (EchoMRI, 4-in-1 composition analyzer, Echo medical systems, Houston, Tex.) was performed at weeks 0, 6 and 12 for the second obesity study performed with 14m and 12u.

For the treatment obesity study (where the animals were fed with high fat diet for six weeks prior to beginning drug treatment for 18 weeks), MRI scans were performed at weeks 0, 6, 12, 18 and 24.

Cholesterol and leptin concentrations were measured in serum using ELISA-based methods.

MIP-1b is a part of the luminex beads inflammation panel of cytokines obtained from Millipore (Billerica, Mass.). The list of cytokines is given in Table 7 below.

TABLE 7

| | |
|---|---|
| Interferon-γ | MIP-1a |
| MIP-1a | IL-6 |
| Keratinocyte chemoattractant (KC) | IL-5 |
| Interferon inducible protein-10 | IL-3 |

TABLE 7-continued

| | |
|---|---|
| IL-7 | IL-4 |
| IL-9 | IL-12p70 |
| IL-10 | Eotaxin |
| VEGF | IL-12p40 |
| Monocyte induced by γ-interferon | IL-15 |
| Monocyte chemoattractant protein-1 | IL-2 |
| M-CSF | IL-13 |
| G-CSF | IL-1β |
| Leukemia inhibitory factor cytokine | IL-17 |
| GM-CSF | RANTES |
| Lipopolysaccharide induced CXC chemokine | IL-1α |
| TNF-α | MIP-2 |

Histology was performed on cryosections and stained with oil 0 red. Serum testosterone and FSH were measured using luminex beads method (Millipore).

Oral glucose tolerance tests (OGTT) were performed on 16-h fasted mice. Mice were given 150 mg glucose by oral gavage through a gastric tube. Blood samples were taken at 0, 15, 30, 60, 90, and 120 min after glucose administration and glucose levels were recorded.

For the ovariectomy-induced obesity model, 6 week old female C57BL6 mice were sham operated or ovariectomized and the study was carried out for 9 weeks as indicated above.

RNA extracted from WAT, BAT, liver and muscle were reverse transcribed using cDNA synthesis kit (Applied biosystems, Foster city, CA). Realtime PCR was performed for a selected list of genes involved in obesity and metabolic diseases (Table 8 below) using realtime PCR TaqMan gene expression array cards (Applied Biosystems).

TABLE 8

| Genes involved in obesity and metabolic diseases for which PCR was performed. | |
|---|---|
| ER-α | Glycerol-3-phosphate acyltransferase |
| ER-β | SREBP-1c |
| PGC-1α | GAPDH |
| PGC-1β | 18S |
| UCP-1 | Leptin receptor |
| C/EBP-δ | Phospholipids transfer protein |
| mCPT-1 | C/EBP-α |
| PPAR-δ | STAT-1 |
| SHP | GADD153 |
| PRDM16 | Glutathione peroxidase 3 |
| Dio2 | CIDEA |
| FASN | Lipoprotein lipase |
| CPT-1 | Farnesoid X-receptor |
| LXR-α | Amyloid precursor protein |
| Apolipoprotein E | PPAR-γ |
| Glucose-6-phosphate dehydrogenase | PPAR-α |

Example 23.1: 14m Represses High Fat Diet Induced Body Weight Gain (Study A—Example 23)

Figure 4:
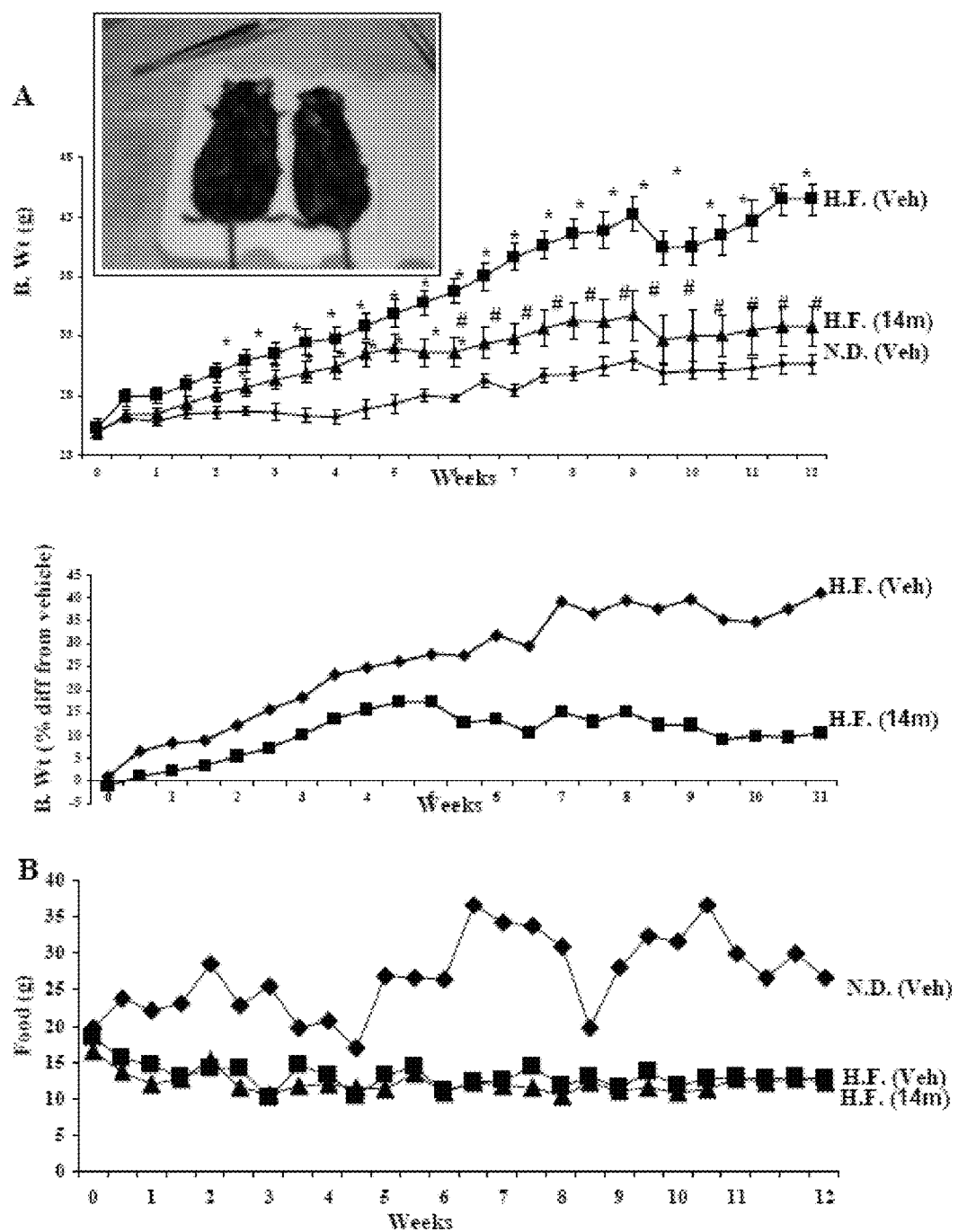
FIG. 4 depicts the effect of 14m on diet induced obesity. (A) Biweekly body weight. (B) Feed consumption. Panel A lower graph shows the percent difference in body weight of high fat diet fed receiving vehicle and 14m, respectively. Panel A inset shows a representative mouse from H.F. and normal diets. Values are expressed as Mean±S.E. H.F.—high fat; N.D.—normal diet; B.Wt-body weight; *—significance at p<0.05 from normal diet fed vehicle treated animals; #—significance at p<0.05 from high fat diet fed vehicle treated animals.

Maintenance on a high fat diet increased the body weight of the mice significantly compared to the control mice starting from week 3 (FIG. 4A). High fat diet mice treated with 14m showed only a moderate increase in body weight and were statistically indistinguishable from control mice demonstrating the ability of 14m to repress the body weight gain induced by a high fat diet. FIG. 4A (inset) shows representative pictures of mice in the high fat groups that were treated with vehicle (left) or 14m (right). Mice in the high fat diet groups that received vehicle alone gained 40% more weight than animals receiving a normal diet (FIG. 4A lower panel). However, mice in the high fat diet group treated with 14m gained only 5% more weight than the normal diet-fed controls demonstrating a greater than 85% reduction in body weight by 14m compared to animals receiving the high fat diet and vehicle.

Though the feed consumption of both groups of high fat diet fed animals were lower than that observed for the control mice, 14m treatment did not affect total caloric intake, indicating that alteration in feed consumption or satiety was not the mechanism for the observed body weight reduction (FIG. 4B).

Treatment with 14m in Study 2 replicated the effects observed in the prior study shown in FIG. 4A with significant reduction in body weight (FIG. 5A) without altering the feed consumption (data not shown). 12u also reduced the body weight of high fat diet-fed mice, with results comparable to those observed with 14m. Both ligands prevented the body weight increase caused by the high fat diet by more than 50%. The body weights of mice treated with 14m and 12u were statistically indistinguishable from the normal diet controls.

Example 23.2: 14m Alters Metabolic Disease Markers (Study A—Example 23)

Dual energy X-ray absorptiometry (DEXA) was used to examine the body composition changes that accompanied the body weight difference observed in mice that received the high fat diet and 14m. Animals that received the high fat diet and vehicle had significantly higher body fat than animals in normal diet (control) group or those receiving 14m (FIG. 6A left panel). This result indicates that 14m did not repress body weight by reducing lean mass or body water content, but brought about this body weight loss by suppressing fat mass formation.

Figure 5:
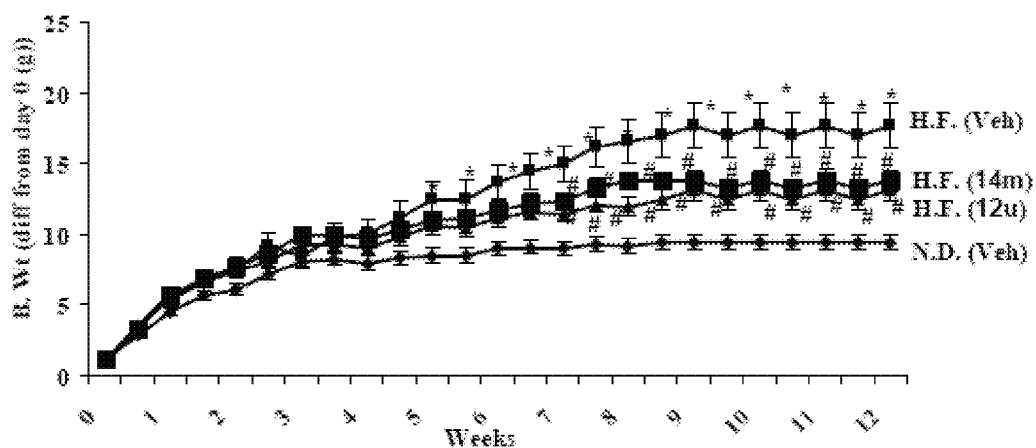
FIG. 5 depicts the effects of 14m and 12u on high fat diet induced obesity. (A) Biweekly body weight represented as body weight difference from day 0. (B) 14m and 12u reduce fat mass (top panel) and increase muscle mass (bottom panel). The data are expressed as percent fat and lean mass of body weight. N.D.—normal diet; H.F.—high fat diet; *—significance at p<0.05 from normal diet fed vehicle treated animals; #—significance at p<0.05 from high fat diet fed vehicle treated animals.
Figure 5:
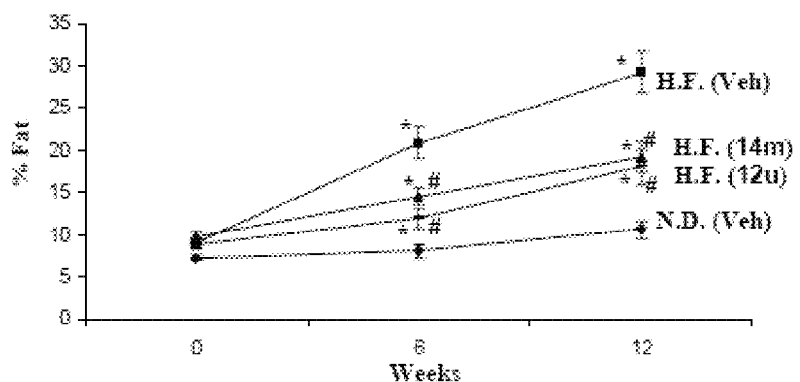
Figure 5:
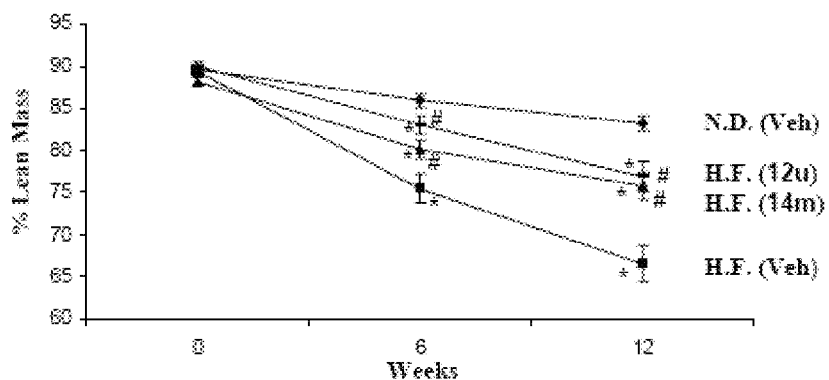

MRI demonstrated a significant reduction in fat mass in both 14m and 12u treated groups compared to animals receiving the high fat diet and vehicle (FIG. 5B upper panel). Both ligands prevented the increase in body fat by more than 50%, comparable to the reduction in body weight observed by gravimetry.

Maintenance on a high fat diet and vehicle reduced the lean mass significantly compared to normal diet controls (FIG. 5B lower panel).

Both 14m and 12u increased the lean mass in animals fed with the high fat diet, indicating that ER-β selective ligands not only repress body weight in high fat diet fed mice but do so by promoting favorable changes in body composition (i.e., by decreasing fat mass and increasing lean mass). These changes were obvious as early as 6 weeks into treatment and the differences were magnified by 12 weeks of treatment.

Example 23.3: 14m Prevents Loss in Bone Mineral Content (BMC) (Study A—Example 23)

As obesity inversely correlates with bone mineral density and content, the effects of diet and 14m on bone mineral content (BMC) was examined using DEXA. Maintenance on a high fat diet reduced BMC significantly compared to controls. Treatment of high fat diet-fed mice with 14m prevented the loss in BMC and was actually statistically significantly increased relative to N. D. (FIG. 6A right panel), suggesting that secondary beneficial effects on bone accompany reduced obesity.

Example 23.4: 14m Prevents Increase in Blood Glucose Levels. (Study A—Example 23)

One of the many pathological conditions associated with obesity is insulin resistance resulting in type II diabetes mellitus (T2DM). Glucose tolerance test were performed to determine if high fat diet-fed animals exhibited signs of insulin resistance and T2DM. Administration of glucose increased the blood sugar level as early as 15 min in all the groups. Animals fed the high fat diet and treated with vehicle demonstrated a significant increase in blood glucose levels compared to normal diet controls (FIG. 6D). However, the blood glucose levels of high fat diet-fed mice with 14m were not statistically different from the normal diet controls.

Example 23.5: 14m Prevents Increase in Serum Cholesterol and Leptin Levels. (Study A—Example 23)

Serum cholesterol (FIG. 6C) and leptin levels (FIG. 6E) were significantly increased in animals fed the high fat diet and treated with vehicle as compared to normal diet controls and this increase was significantly reversed by 14m.

Example 23.6: 14m Prevents Increase in White Adipose Tissue (WAT) Weight and Decrease in Gastrocnemius Muscle Weight Six week old C57BL/6 mice were randomized, based on body weight, into three study groups as shown in the Study Parameters Table below. In the First Study, the Group I mice (n=5) received regular rodent chow and vehicle, the Group II mice (n=5) received the high fat diet and vehicle, and the Group III mice (n=5) received the high fat diet and 30 mg/kg/day 14m. In the Second Study, the Group III mice (n=12) received the high fat diet and 30 mg/kg/day 12u.

TABLE

Study Parameters

| Group | Diet | Treatment (s.c.) |
|---|---|---|
| The First Study | | |
| 1 | Normal | Vehicle |
| 2 | High Fat | Vehicle |
| 3 | High Fat | 30 mg/kg/day 14m |
| The Second Study | | |
| 3 | High Fat | 30 mg/kg/day 12u |

The normal diet included protein (16.7%), carbohydrates (56%) and fat (4.2%), with a digestible energy of 3.3 Kcal/g. The high fat diet included protein (23.5%), carbohydrates (27.3%) and fat (34.3%), with a digestible energy of 5.1 Kcal/g.

The mice were treated for 12 weeks. Twice weekly, the body weight and feed consumption were measured.

A glucose tolerance test was also performed at the completion of the study by administering 150 mg glucose orally to the mice and measuring blood glucose levels at 0, 15, 30 and 60 minutes post glucose administration.

At sacrifice, the mice organ weights were measured and collected for histology, gene expression and protein expressions. Blood was collected for serum marker determination (cholesterol, glucose, leptin).

Dual energy X-ray absorptiometry (DEXA) was performed to measure the body composition in Study 1.

An MRI scan was performed at the beginning of the study, after 6 weeks and at the completion of the study.

Figure 6:
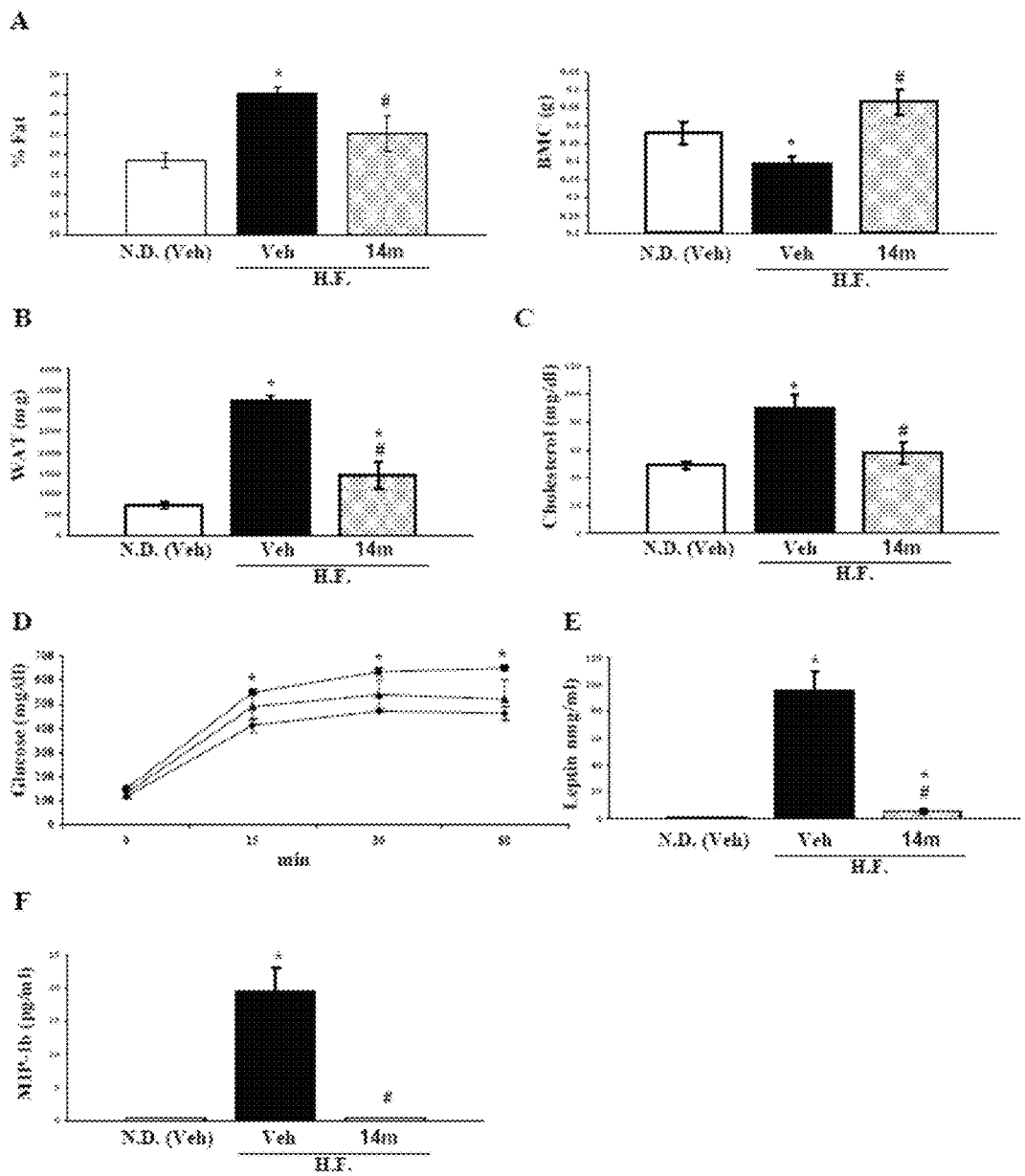
FIG. 6 depicts the effect of 14m on the reduction of fat mass and metabolic diseases markers. (A) demonstrates the effect of 14m on body fat (left panel) and bone mineral content (BMC, right panel). Body fat content is expressed as percent fat of body weight. (B), (C), (E) and (F) demonstrate the effect of 14m on metabolic diseases markers: white adipose tissue (WAT; panel B); cholesterol (panel C); leptin (panel E); and the inflammatory marker MIP-1β (panel F). (D) demonstrates the effect of 14m on serum glucose levels after glucose tolerance test.
Figure 7:
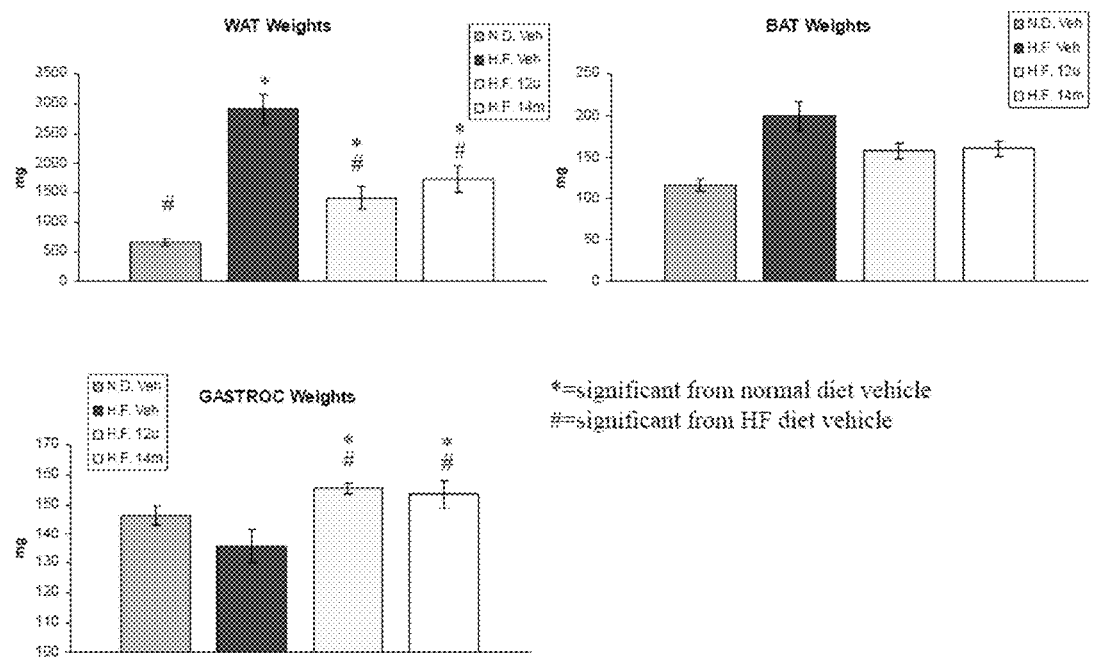
FIG. 7 depicts the white adipose tissue (WAT) weight, brown adipose tissue (BAT) weight and gastrocnemius muscle (GASTROC) weight at study completion for the mice following completion of the study. Maintenance on a high fat diet significantly increased the weight of WAT and decreased the weight of gastrocnemius muscle compared to a normal diet. 14m and 12u prevented the increase in the WAT weight and increased gastrocnemius muscle weight in the high fat diet fed group compared to vehicle treated. (* significant from normal diet+vehicle, # significant from high fat diet+vehicle).

WAT, brown adipose tissue (BAT), liver and muscle weights were measured at mice sacrifice. No significant difference in BAT, liver and muscle weights were observed between the groups (data not shown). However, WAT weight was significantly increased by 2-2.5 fold in animals maintained on the high fat diet treated with vehicle compared to normal diet controls. This increase in WAT weight was significantly reduced in 14m treated mice (FIG. 6B). Tissue weights indicated that both 14m and 12u comparably decreased WAT weight and increased gastrocnemius muscle (FIG. 7) weight without altering the weights of other tissues (data not shown), reproducing the results demonstrated in FIG. 6.

Example 23.7: 14m Prevents Fatty Liver Condition. (Study A—Example 23)

Figure 8:
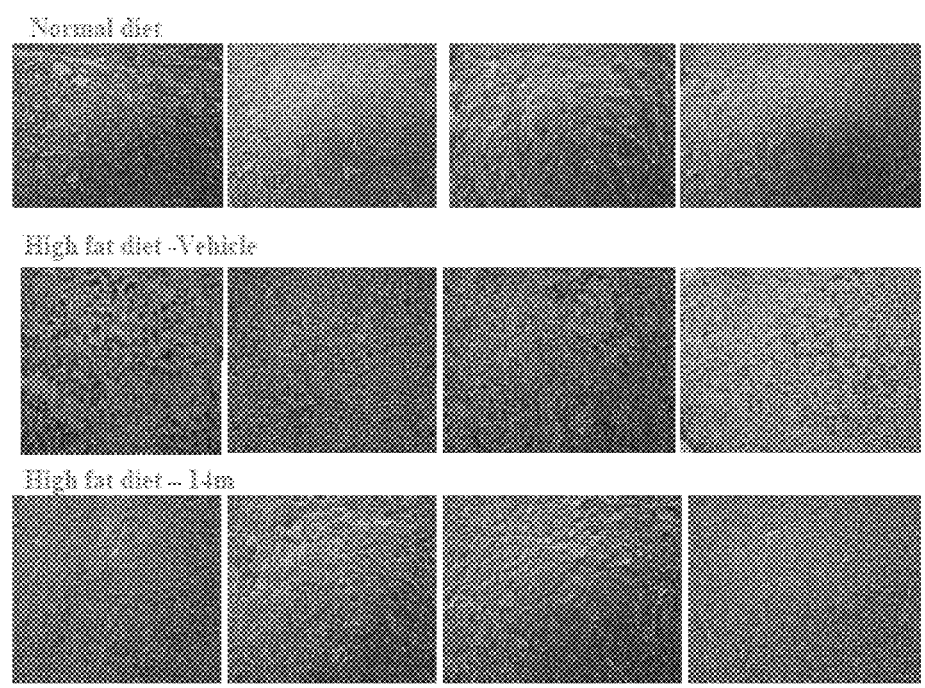
FIG. 8 depicts representative liver sections obtained from normal diet fed mice, mice fed with a high fat diet and vehicle treated, and mice fed with a high fat diet and treated with 14m. The administration of 14m attenuated the accumulation of lipid droplets in the liver. (Example 23.7). N.D.—normal diet; H.F.—high fat diet.

One of the perilous secondary effects of obesity and hypercholesterolemia is the accumulation of fat in the liver, a condition called fatty liver. Liver cryosections were obtained from studied mice and stained with oil O-red to determine the accumulation of fat in liver. Photographs shown in FIG. 8 demonstrate that maintenance on a high fat diet increased the accumulation of fat in liver sections as evident from the increased oil red staining. However, liver sections obtained from high fat diet-fed mice treated with 14m did not stain for oil red suggesting that 14m completely prevented the accumulation of fat in the liver.

Example 23.8: Cross Reactivity Studies with ER-α: 14m does not Affect FSH and Testosterone Levels. (Study A—Example 23)

Figure 9:
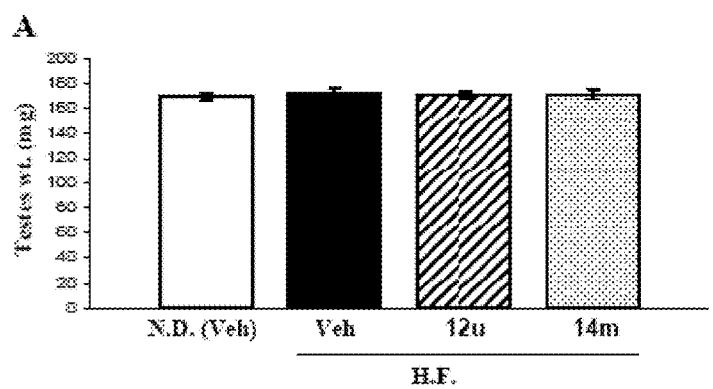
FIG. 9 depicts the mouse testes weight (panel A), serum testosterone (T) levels (panel B) and serum follicle stimulating hormone (FSH) levels (panel C) following completion of the study (Example 23.8). The levels were determined immediately after sacrifice. 14m and 12u did not affect the serum testosterone levels. 14m did not affect serum testosterone and follicle stimulating hormone (FSH) levels. Serum levels of total testosterone and FSH were determined immediately prior to sacrifice after week 12 of treatment. 14m did not suppress these endocrine hormones, suggesting that its effects were not mediated through ERα.
Figure 9:
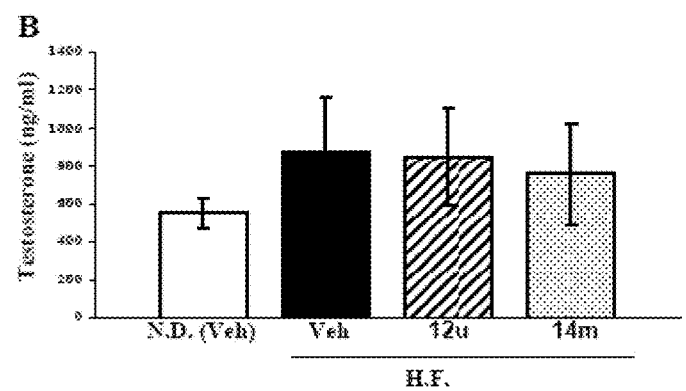
Figure 9:
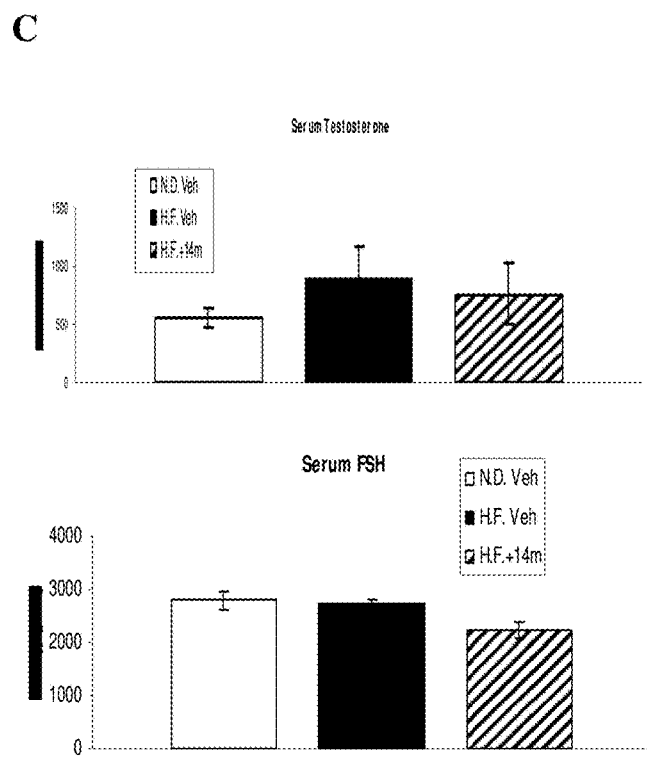

To ensure that the effects on body composition and weight were not mediated by cross reactivity with ER-α, parameters in the hypothalamus:pituitary:gonadal (HPG) axis were measured in studied mice. As ER-α is associated with a variety of side effects such as thromboembolism, cardiovascular problems, breast cancer and others, any functional cross reactivity of the ER-β ligands in vivo with this receptor isoform might be considered undesirable and preclude its use for a chronic medical condition like obesity. Testes weights (FIG. 9A) and serum testosterone (FIG. 9B) levels were not altered by 14m or 12u in animals fed with the high fat diet and treated with vehicle, 14m or 12u for 12 weeks. Follicle stimulating hormone (FSH), another hormone in the HPG axis, was also not altered by diet or drug treatment (FIG. 9C). These results suggest that the anti-obesity effects of the 3-SERMs were not mediated through cross reactivity with ER-α or effects on sex hormone levels.

Example 23.9: 14m Prevents Increase in Macrophage Inflammatory Protein-1β (MIP-1β). (Study, A—Example 23)

Inflammation is a central component of obesity and recent studies emphasize that obesity is an inflammatory disease. In order to determine the role of inflammation in high fat diet-induced obesity, a panel of 32 inflammatory cytokines was measured in serum using luminex beads from Millipore (See Table 7 above). Of the 32 cytokines measured, only macrophage inflammatory protein-1β (MIP-1β) was significantly increased by the high fat diet in the studied mice.

However, this increase was completely reversed and the levels were brought down to undetectable levels by 14m (FIG. 6F).

Example 23.10: 14m Alters the Expression of Genes Involved in Adipogenesis and Anti-Oxidant Pathways (Study A—Example 23)

Figure 10:
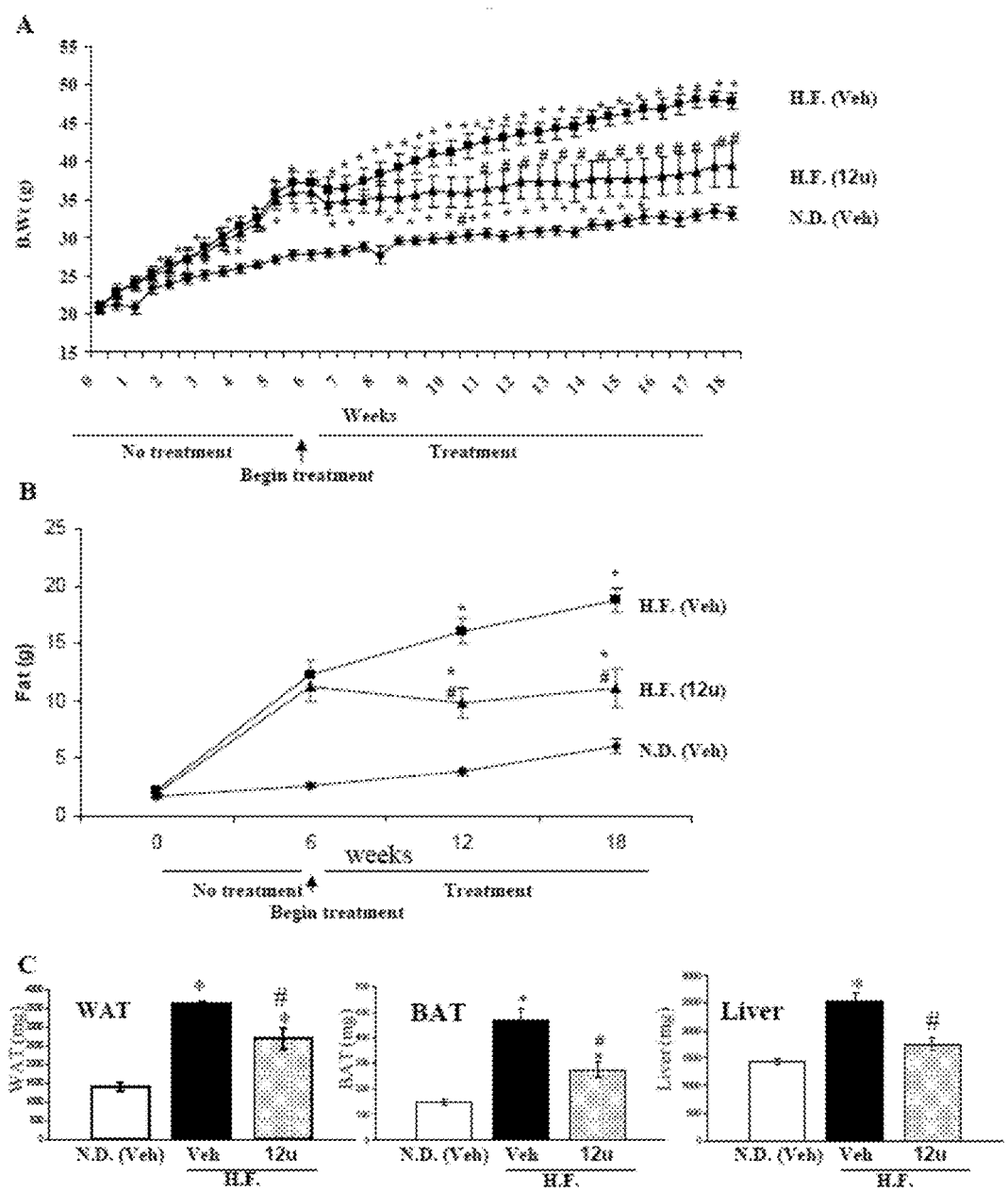
FIG. 10 depicts the effect of 12u on treating high-fat diet induced obesity. (A) Biweekly body weight. (B) Fat mass. N.D.—normal diet. (C) WAT, BAT, liver weights. H.F.—high fat diet; *—significance at p<0.05 from normal diet fed vehicle treated animals; #—significance at p<0.05 from high fat diet fed vehicle treated animals.

A subset of 32 genes that are implicated in lipogenesis, lypolysis, anti-oxidant and other related pathways were selected and the effect of 14m on these genes was evaluated using TaqMan PCR based arrays. RNA from liver, muscle, WAT and BAT were applied to these arrays. Genes for which their expression was more than 2-fold different and significant at p<0.01 in 14m treated mice compared to high fat diet animals treated with vehicle are summarized in Table 9.

obese. Mice were divided into three groups with one group fed with normal diet (control) and the other two groups fed with the high fat diet for 6 weeks. After 6 weeks, the animals were treated daily with vehicle or 30 mg/kg/day 12u s.c. for another 12 weeks. All the animals were maintained in their respective diets during the entire course of the study. Maintenance on the high fat diet significantly increased the body weight by 3 weeks compared to normal diet controls. Initiation of 12u treatment at week 6 prevented further gains in body weight throughout the remainder the study. By week 16, the body weight of high fat diet-fed animals treated with 12u was not significantly different from normal diet control mice (FIG. 10 A). MRI demonstrated that the body fat increase observed in animals on the high fat diet was reduced by treatment with 12u (FIG. 10B).

TABLE 9

| Gene Name | Increase/Decrease | Function |
|---|---|---|
| Brown Adipose Tissue | | |
| Ddit3 (DNA damage inducible transcript III) | Decrease | Promotes obesity, oxidative stress, β-cell damage |
| GPx-3 (glutathione peroxidase) | Increase | Prevents obesity, oxidative stress, insulin resistance, inflammation and major antioxidant in plasma |
| LPL (lipoprotein lipase) | Decrease | High levels increase insulin resistance and type IIDM. High fat diet increase LPL in tissues |
| PLTP (phospholipid transfer protein) | Decrease | Involved in atherogenesis, hypercholesterolemia and atherosclerosis |
| ER-β (Estrogen receptor β) | Increased | |
| Dhcr24 (dehydrocholesterol reductase) | Decreased | Encodes cholesterol synthesizing enzyme Seladin-1 |
| UCP-1 (uncoupled protein-1) | Increased | Promotes energy expenditure, reduces cholesterol |
| White Adipose Tissue | | |
| SREBP1 (Sterol regulatory element binding protein 1) | Decrease | Increases fatty acid synthesis and cholesterol |
| FASN (fatty acid synthase) | Decrease | Fatty acid synthesis. Mostly in association with SREBP |
| Ddit3 (DNA damage inducible transcript III) | Decrease | Promotes obesity, oxidative stress, β-cell damage |
| LPL (lipoprotein lipase) | Decrease | High levels increase insulin resistance and type IIDM. High fat diet increase LPL in tissues |
| Liver | | |
| GPx-3 (glutathione peroxidase) | Increase | Prevents obesity, oxidative stress, insulin resistance, inflammation and major antioxidant in plasma |
| CIDEA (Cell death inducing DNA fragmentation factor) | Decrease | Very important factor in adipose cell function and obesity |

Example 23.11: 14m Increases Uncoupling Protein-1 (UCP-1) Gene Expression

Uncoupling protein-1 (UCP-1), a thermogenic mitochondrial protein and a marker for BAT, was decreased in animals that received the high fat diet and vehicle compared to normal diet controls. However, 14m reversed and in fact demonstrated an increase in UCP-1 gene expression (Table 9), suggestive of increased energy expenditure.

Example 23.12: 12u Inhibits Body Weight and Fat Mass in Obese Animals (Study 3: Treatment Phase)

As the first two studies were designed to prevent obesity (i.e. animals were fed with a high fat diet and treated simultaneously), a subsequent study was conducted to evaluate the ability of 12u to affect body composition in mice that were already fed with the high fat diet and were Example 23.13: β-SERMs Alter Body Composition in an Animal Model of Postmenopausal Obesity. (Study A—Example 23)

Figure 11:
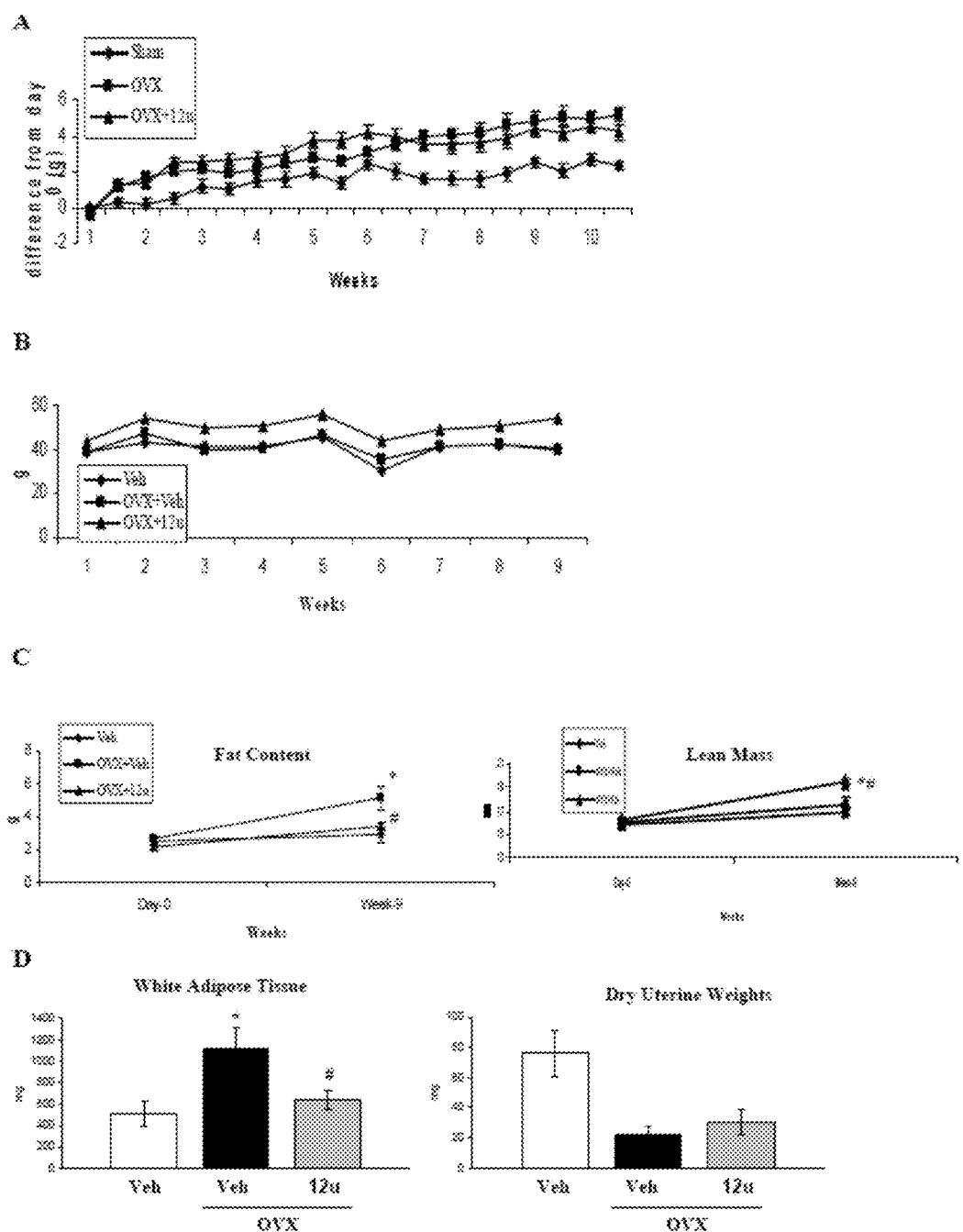
FIG. 11 depicts the effect of 12u on altering body composition of ovariectomized mice. (A) Biweekly body weight (B) feed consumption (C) fat mass (left panel) and lean mass (right panel). (D) white adipose tissue (WAT) and uterus weights. OVX—Ovariectomy; *—significance at p<0.05 from normal diet fed vehicle treated animals; #—significance at p<0.05 from high fat diet fed vehicle treated animals.

Postmenopausal obesity increases the susceptibility of women to cardiovascular risks [Turgeon J L et al 2006 *Endocr Rev* 27:575-605]. Since it was shown that β-SERMs affected body composition in an animal model of high fat diet-induced obesity, they might also be effective in an animal model of postmenopausal obesity. Ovariectomy (OVX) increased the body weight significantly over the sham operated animals (FIG. 11A). Surprisingly, 12u did not inhibit body weight gain in this model. Unlike the observation in high fat diet model, 12u increased the feed consumption of OVX mice (FIG. 11B). As shown in the high fat diet model, MRI scan demonstrated that OVX increased the fat mass significantly and that 12u completely prevented the increase in fat mass (FIG. 11C left panel). 12u also significantly increased lean mass (FIG. 11C right panel) indicating that 12u caused consistent changes in body composition in the high fat diet- and OVX-induced animal model; of obesity. Measurement of WAT and uterus weights indicated that 12u completely inhibited the WAT accrued due to OVX without affecting uterine weight, indicating absence of ER-α cross reactivity (FIG. 11D).

Example 23.14: ER-β Ligand Dependently Inhibits PPAR-γ Function (Study A—Example 23)

Foryst-Ludwig et al [Foryst-Ludwig A et al 2008 *PLoS Genet* 4:e1000108] previously demonstrated that ER-β ligand independently inhibits PPAR-γ through N-terminal interactions. PPAR-γ was also demonstrated to be a proadipogenic transcription factor [Tontonoz P et al 2008 Annu Rev Biochem 77:289-312]. In addition, one of the genes completely repressed by 14m in BAT and WAT (i.e., LPL) is a PPAR-γ target gene (Table-10) [Kersten S 2008 *PPAR Res* 2008:132960]. Transactivation studies were thus performed in HEK-293 cells transfected with ER-β, PPAR-γ or PPAR-α and PPRE-LUC to determine the direct or indirect effects of 14m and 12u on PPAR activity. Both β-SERMs partially inhibited troglitazone-induced PPAR-γ activity when co-transfected with ER-β (FIG. 12A left panel) but did not affect WY14643 induced PPAR-α transactivation (FIG. 12A right panel). Ligand independent or constitutive inhibition of PPAR-γ by ER-β was also observed, confirming the earlier report [Foryst-Ludwig A et al 2008 *PLoS Genet* 4:e1000108].

To determine whether the ligand binding domain (LBD) of ER-β was required to inhibit PPAR-γ transactivation, histidine 475 in the ER-β LBD was mutated to alanine. This residue is critical for ligand binding to ER-β. This was confirmed by mutating H475 to alanine and comparing its transactivation to wildtype ER-ft Transfection of HEK-293 cells with ERE-LUC, ER-β or H475A ER-confirmed that mutation of H475 to alanine abrogated the ability of estradiol to activate ER-β (FIG. 12B).

Since H475A impaired estradiol-dependent ER-β transactivation, the ability of this mutant receptor to inhibit PPAR-γ transactivation was determined and compared to wildtype. As shown in FIG. 12C, wildtype ER-β inhibited ligand-dependently and independently the troglitazone-induced PPAR-γ transactivation, whereas H475A ER-β did not inhibit PPAR-γ transactivation indicating the importance of ligand binding and ER-β-LBD to inhibit PPAR-γ transactivation.

PPAR-γ coactivator-1 (PGC-1) functions selectively as a PPAR-γ coactivator in many tissues such as WAT, BAT and pancreatic islets. To determine whether ER-β ligands inhibit the ability of PGC-1 to coactivate PPAR-γ, PPAR-γ transactivation studies were performed in the presence or absence of PGC-1. In the absence of ER-β, troglitazone activated PPAR-γ, while PGC-1 robustly increased both the basal and ligand dependent activity (FIG. 12D upper panel). However, wildtype ER-β, but not H475A ER-β, ligand-dependently abolished the troglitazone-dependent PPAR-γ transactivation, indicating that ER-β not only inhibits uncoactivated PPAR-γ but also inhibits PGC-1 coactivated PPAR-γ transactivation. Conversely, coactivation of PPAR-α by PGC-1 was not inhibited by ER-β (FIG. 12D lower panel) confirming the selectivity of inhibition and lack of cross reactivity.

Small heterodimeric partner (SHP) is an orphan member of the NHR family that is also known to play a role in metabolic diseases [Nishigori H et al 2001 *Proc Natl Acad Sci USA* 98:575-80]. The SHP promoter contains an estrogen response element (ERE) and its activity was increased by estradiol through ER-α [Lai K et al 2003 *J Biol Chem* 278:36418-29]. HEK-293 cells transfected with SHP promoter-luciferase, FXR and ER-β plasmids were used to determine whether 14m and 12u activate SHP through ER-β. FIG. 12E (right panel) demonstrates that neither of the ligands activated SHP whereas FXR ligand GW4064 increased its activity significantly. The left panel of FIG. 12E shows that an ER-α selective ligand PPT increased SHP activity reproducing the earlier published results that SHP is an ER-α target gene.

The results obtained in this study suggest that estrogen receptor ligands, e.g., the ERβ agonists Compounds 14m and 12u, show surprising effectiveness in the treatment of metabolic diseases such as obesity and related diseases.

Figure 13A:
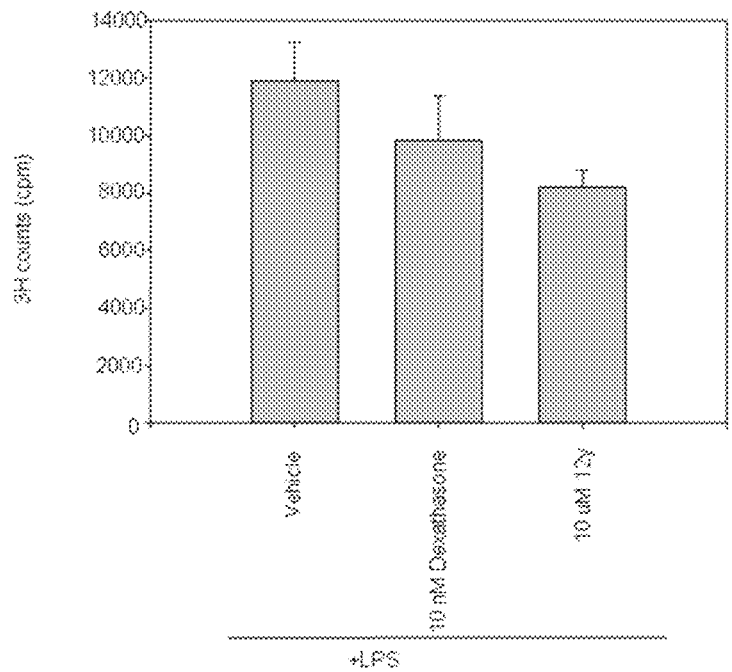
FIG. 13 depicts the effect of 12y (FIG. 13A) and 12u (FIG. 13B) on macrophage adhesion to endothelial cells.
Figure 13B:
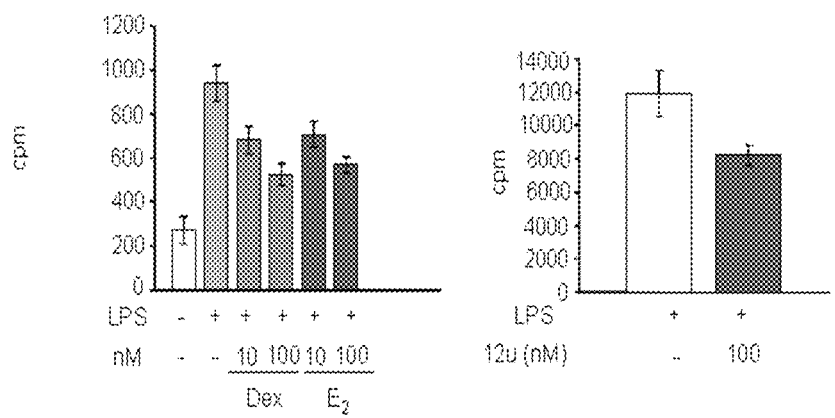

Example 24: Anti-Inflammatory Effect of NRBAs on Macrophage-Endothelial Cell Adhesion To determine the anti-inflammatory effects of ER-β NRBAs in vitro, a macrophage adhesion assay was performed. Macrophages adhere to endothelial cells due to elevated levels of pro-inflammatory cytokines. This principle was used in this assay to determine the effect of one of the ER-β NRBAs on bacterial lipopolysaccharide (LPS) induced THP-1 macrophage cell adhesion to bEND-3 endothelial cells. As shown in the FIG. 13, 12y (panel A) and 12u (panel B) significantly inhibited the adhesion of $^3$H labeled THP-1 cells to bEND-3 cells indicative of reduced inflammatory cytokine levels and a subsequent anti-inflammatory effect.

Example 25: Effect of the Compounds on TRAP Positive Multinucleated Osteoclasts

Bone marrow cells isolated from rat femur are cultured in Alpha MEM without phenol red+10% sterile FBS without phenol red in the presence or absence of 30 ng/mL RANKL and 10 ng/ml GMCSF, and the compounds. The cells treated for 12 days are stained for tartarate resistant acid phosphatase activity (TRAP) positive multinucleated osteoclasts and are counted. Suppression of osteoclast activity is evaluated.

Example 26: In Vivo Estrogenic Activity of Some Embodiments of the Compounds

Female rats are administered increasing doses of toremifene, estrogen and the respective NRBAs, and uterine weights are determined. Rats administered the vehicle alone serve as controls.

Example 27: Metabolic Stability of Some Embodiments of the Compounds in Human Liver Microsomes Human liver microsomes are utilized as a representative system in order to assess the potential of the compounds to form pharmacologically inactive or undesired potentially toxic metabolites due to phase I metabolism.

Each substrate or reference control is dissolved at a concentration of 10 mM in DMSO, from which a 5 μM spiking solution prepared by dilution in water. Substrates (1 μM) are incubated in the presence of human liver microsomes (Xenotech LLC, Kansas City Mo.) at 0.5 mg/mL fortified with an NADPH regenerating system at 37° C. and pH 7.4. The NADPH regenerating system consists of glucose-6-phosphate dehydrogenase (1 units/mL) in 0.05M $K_2HPO_4$. Duplicate incubations are performed in 96-well polypropylene cluster tubes in a final volume of 250 μL per reaction. At 0, 2, 4, 6, 10, 30, and 60 minutes a stop solution (300 μL acetonitrile) is added to aliquots of the reaction mixture. Precipitated protein is removed by centrifugation (3000 rpm for 15 minutes) and the supernatants are transferred to clean 96-well plates for analysis.

LC-MS/MS Analysis:

The samples are injected onto a Phenomenex Luna hexylphenyl 50×2 mm i.d. 5 uM, column fitted with a guard column. An isocratic mobile phase consisting of 50% acetonitrile and 0.1% formic acid in water is used at a flow rate of 0.3 mL/min. The protonated molecular ion $(M+H)^+$ of the analyte is monitored by MDS/Sciex API 4000QTrap triple quadrupole mass spectrometer using electrospray positive mode ionization with a temperature of 500° C. and a spray voltage of 4000V.

Data Evaluation:

Metabolic stability is defined as the amount of substrate metabolized by the incubation with hepatic microsomes and expressed as a percentage of the initial amount of substrate (% remaining) based on peak area. The initial peak area of each substrate is determined at time zero and metabolic stability is assessed based on the change in analyte peak area from time 0 min to a single fixed timepoint for each sample.

Example 28: Compound Lowering of LDL Cholesterol Levels

The compounds may be evaluated in clinical trial settings. Following administration of the compounds, their effect in altering lipid profiles in subjects with prostate cancer, undergoing or having undergone ADT may be similarly evaluated.

Example 29: In Vivo Anti-Inflammation Activity

Figure 14:
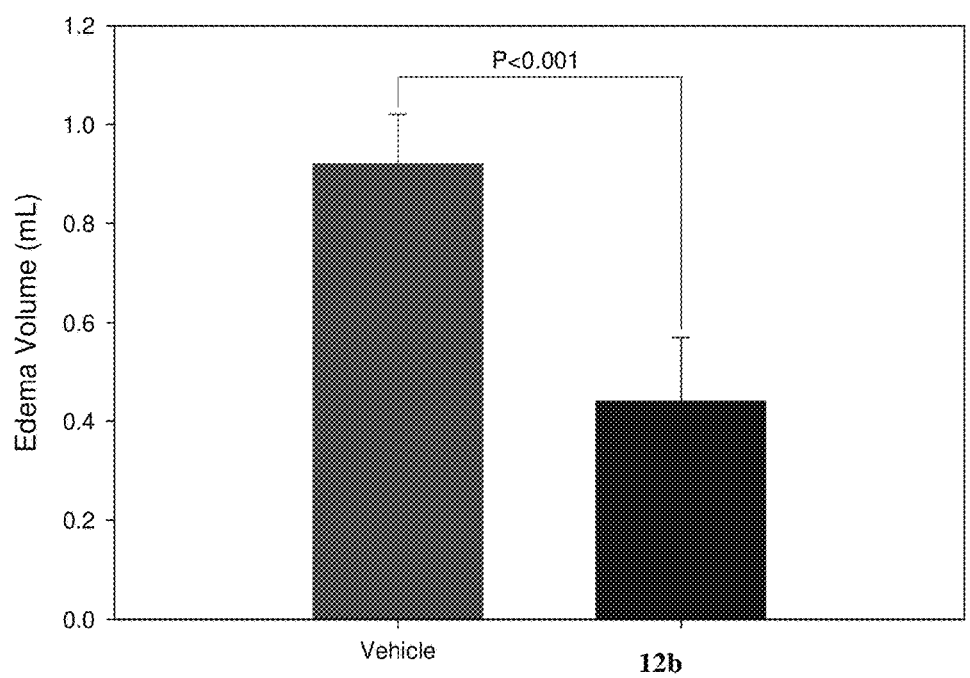
FIG. 14 depicts the effect of 12b on the edema volume which was induced by Carrageenan (i.e. Carrageenan-induce raw paw edema as an acute inflammation model).

To determine the anti-inflammatory effects of ER-β NRBAs in vivo, animal paws were injected with carrageenan, which elicits an acute local inflammatory response. Per-oral treatment of 12b. 1 hr prior to Carrageenan challenge resulted in a 53% reduction in paw edema, measured 4 hours post-Carrageenan injection, as shown in FIG. 14, indicating the compound's anti-inflammatory affect.

Example 30: The Effect of NRBAs on the Rat Aorta

Experimental Protocol.

Equipment used in these studies included a 4-tissue bath system with reservoirs and circulators (RadnotiGlass Technology, Monrovia, Calif.), DSUPonemah tissue force analyzer 7700 (Valley View, Ohio), and iWorx/CB Sciences-force transducers FT-302. The 250 g rats were anesthetized with isoflurane to produce deep anesthesia. The chest of the rat was opened, and about 3 cm length of aorta was removed and placed in a Petri dish containing room temperature Krebs salt solution (KSS, in mM: 120 NaCl, 5 KCl, 1.2 $MgSO_4$ 0.7H2O, 2.5 $CaCl_2.2H_2O$, 1 $KH_2PO_4$, 25 $NaHCO_3$, and 11 glucose). Fat and connective tissue were removed from the aorta taking care not to stretch the vessel. The aorta was then divided into 3-mm-wide rings. Triangular wire holders were inserted through the lumen of the vessel and connected to the force transducer and tissue holder rod in the vessel bath.

Data and Statistical Analyses.

Analog-to-digital conversions of force waveforms were accomplished with a DSI/Ponemah tissue force analyzer 7700. The converted data were automatically analyzed with Ponemah Physiology-Smooth Muscle software. All data are summarized as means±standard error. Differences between means were assessed by a conventional ANOVA. This was followed by Student's test. $P<0.05$ was considered to be statistically significant.

Preload and Equilibration.

The tension on the rings was adjusted to 1.0 g passive force using the tension adjustment dial for each transducer and allowed to equilibrate for 60 min in the bath with a 95% $O_2$-5% $CO_2$ gas mixture. The rings were washed with fresh buffer every 20 min. Passive force was readjusted to 1.0 g as needed during this period. When rings were stable at 1.0 g of passive force, the baseline was calculated.

Preconditioning of Aortic Rings.

Phenylephrine (PE) at a final concentration of $10^{-7}$ M was added to the bath to contract the ring, and force was allowed to stabilize for 10 min. Then acetylcholine (ACH) at a final concentration of $10^{-5}$ M was added to the precontracted rings to test for endothelial integrity (10 min). After the initial test for vessel viability and endothelial integrity, the rings were washed three times for 10 min with buffer, allowing it to equilibrate to active force stabilized at 1 g.

Relaxation Protocol.

Figure 15:
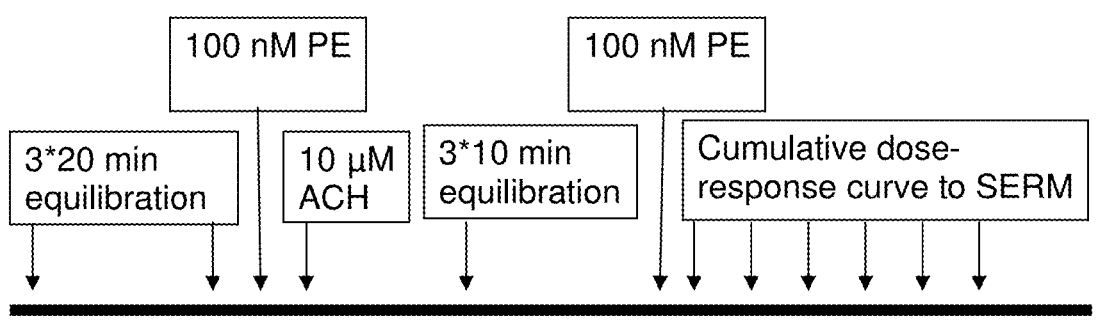
FIG. 15 depicts treatment protocol for measuring rapid (non-genomic) aortic ring relaxation by NRBA's of this invention.
Figure 16:
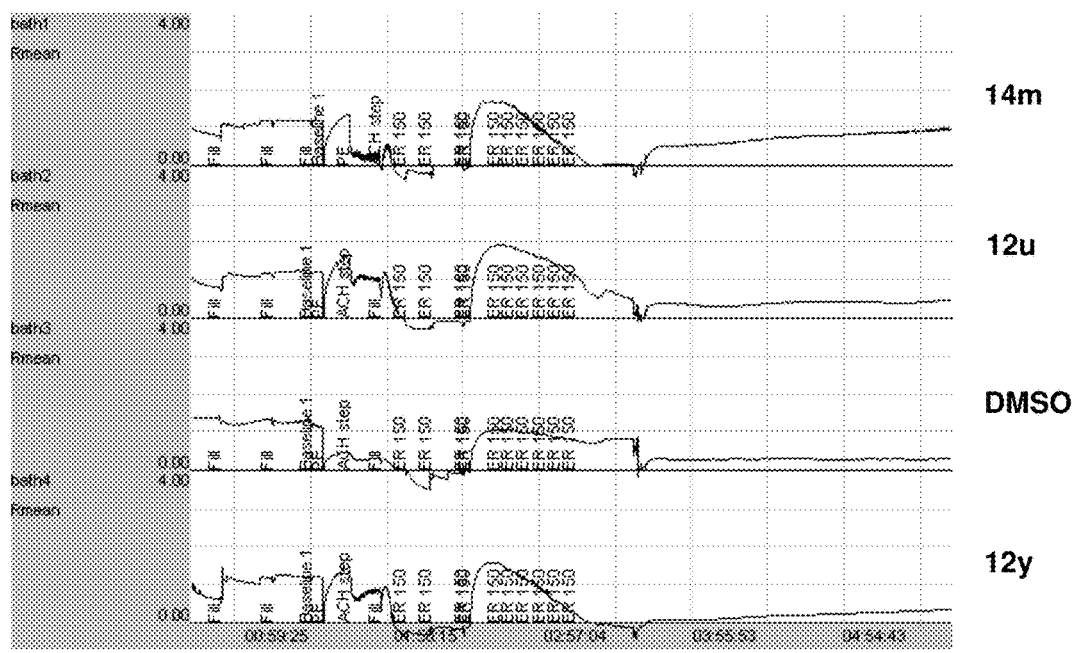
FIG. 16 depicts concentration-response curves generated as in FIG. 15 for 14m, 12u and 12y.

FIG. 15 shows a typical concentration-response protocol for NRBAs. Cumulative concentration-response curves to NRBAs were created by increasing the NRBAs concentration in the tissue bath by successive addition of appropriate dilutions of stock solutions to achieve final bath concentrations of 300 nM to 0.15 mM NRBAs. FIG. 16 shows a typical concentration-response curve generated for NRBAs.

Figure 17:
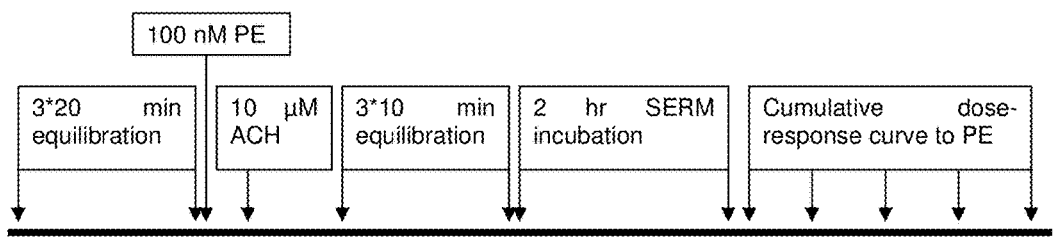
FIG. 17 depicts response treatment protocol for measuring dose response effects attenuation of Phenylephrineaortic ring constriction by phenylephrine (PE).
Figure 18:
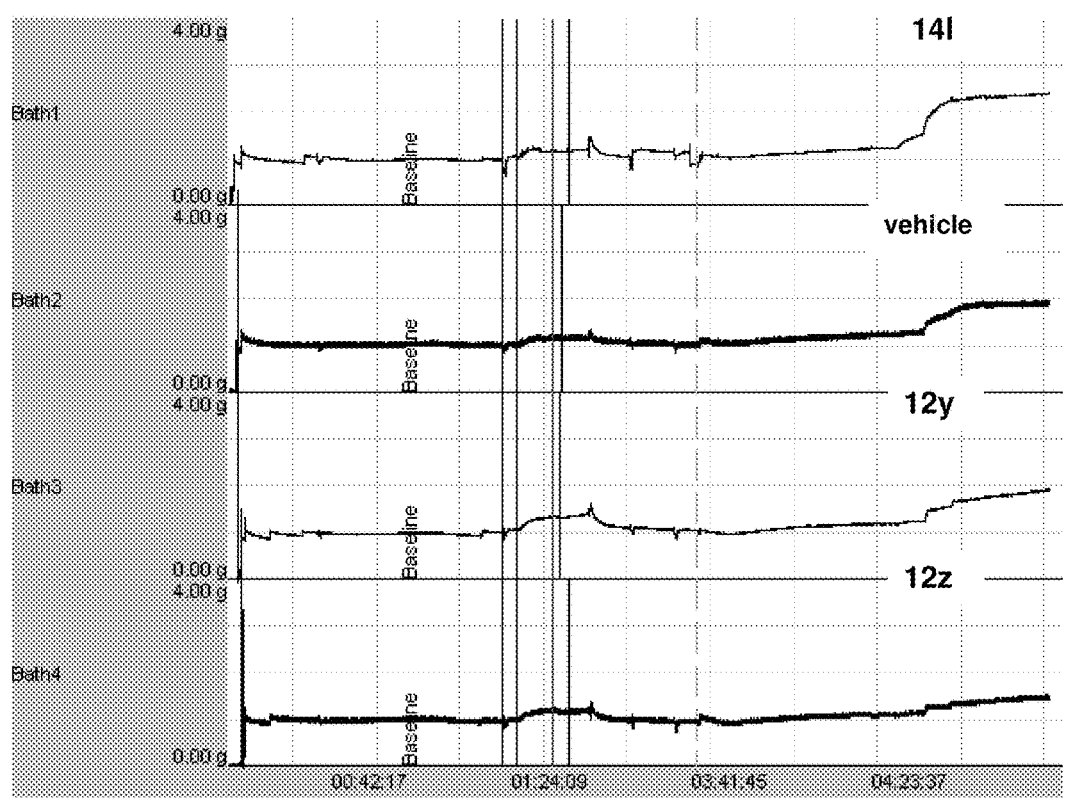
FIG. 18 depicts a concentration-response curve generated as in FIG. 17 for 12y, 12z, and 14l.

Contraction protocol. FIG. 17 shows a typical concentration-response protocol for PE. After the preconditioning step, the rings were incubated in the baths with the NRBAs for 2 hrs. Then cumulative concentration-response curves to PE were created by increasing the PE concentration in the tissue bath by successive addition of appropriate dilutions of stock solutions to achieve final bath concentrations of 1 nM to 300 μM PE. FIG. 18 shows a typical concentration-response curve generated for PE.

Figure 19:
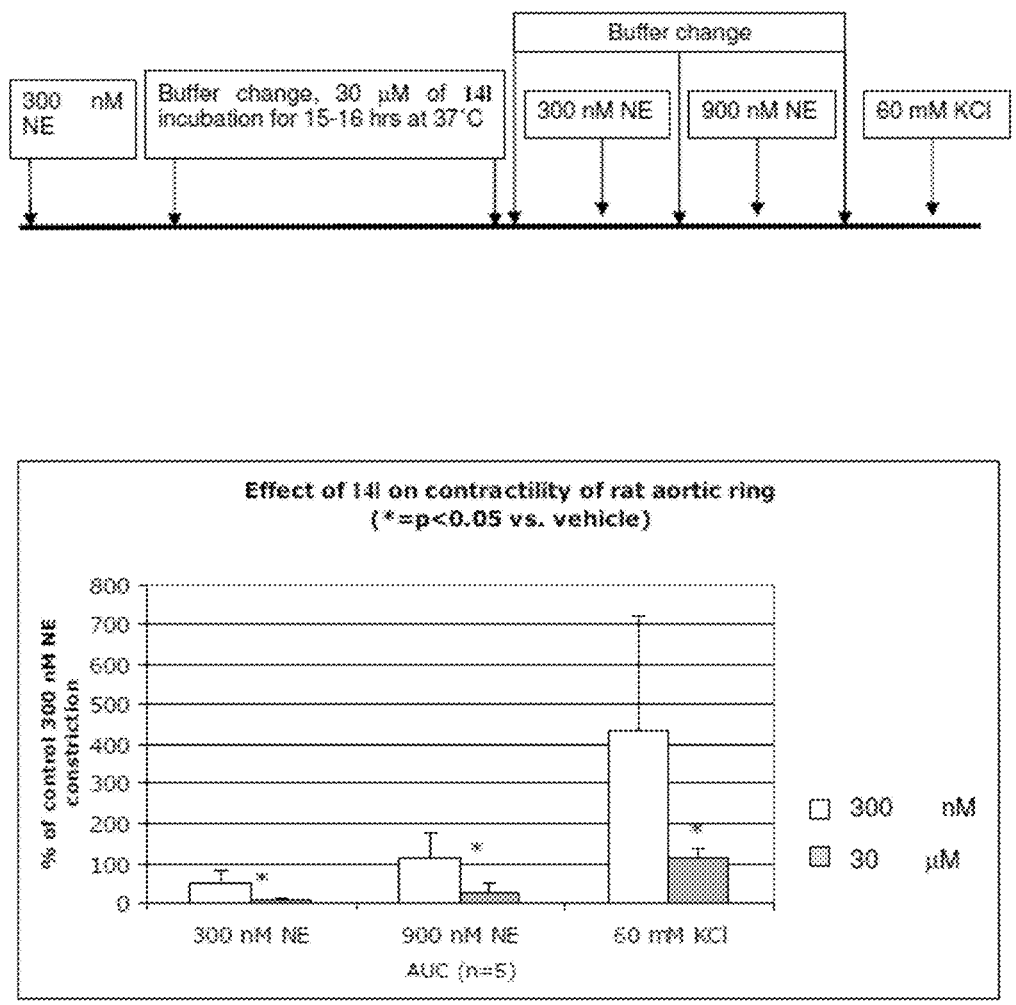
FIG. 19 depicts a protocol to measure the effect of long-term incubation of aortic rings with NRBAs of this invention, and an example graph for 14l.

The effect of long-term incubation of aortic rings with NRBAs on aortic ring contractility was studied after 15-16 hr incubation of the aortic rings with NRBAs in oxygenated KSS under 0 g tension. Then two subsequent concentrations of norepinephrine (NE) were added each for 10 min and the tension was recorded. At the end of the experiment 60 mM KCl was used to further constrict the aortic rings. The results expressed as the percentage of the maximal constriction prior to the NRBAs incubation are summarized on FIG. 19.

Table 10 summarizes $EC_{50}$ values and maximal % decrease of the $10^{-6}$ PE constriction of the aortic ring for individual NRBAs tested

TABLE 10

| | Mean $EC_{50}$ (μM) | SD | Mean of Maximal % Decrease | SD |
|---|---|---|---|---|
| 14l (n = 1) | 19.8 | | 45.01 | |
| 14m (r = 3) | 7.64 | 3.34 | 94.49 | 3.09 |
| 12u (n = 2) | 30 | 14.28 | 50.97 | 12.23 |
| 12y (n = 2) | 13.24 | 11.12 | 80.63 | 13.94 |
| 12z (n = 1) | 15.1 | | 83.58 | |
| DMSO (n = 3) | 8.05 | 5.64 | 40.01 | 20.74 |

Conclusions.

The experiments show effects of the some embodiments of the NRBAs of this invention, on rat aorta relaxation. The effects occur at low micromolar concentrations and have rapid time-course effects suggesting non-genomic action as well as long time-course action possibly involving genomic effects. These effects were similar in aortas from male or female rats indicating there is no gender difference in vascular response under studied conditions.

These effects might confer protective outcome in cardiovascular system and be clinically useful as a substitute for estrogens in preventing cardiovascular diseases in post-menopausal women as well as men.

Example 31: The Effect of ER-Beta Agonists on Proliferation of Rat Aortic Smooth Muscle Cells Rationale: Cardiovascular diseases such as hypertension, coronary heart disease and atherosclerosis have a higher incidence in post-menopausal women than in premenopausal women. This loss of cardiovascular protection is often attributed to the deficiency in circulating estrogen levels in post-menopausal women. Hormone replacement therapy (HRT) can markedly reduce the risk of cardiovascular disease in post-menopausal women. However, the use of HRT for cardioprotection is limited due to the increased incidence of endometrial cancer in women and gynecomastia in men. This has led to a search for compound that can provide the beneficial effects of estrogen on the heart but do not have the undesirable side effects on uterus or breast.

Estrogen action in target tissues is mediated by its interaction with its cognate receptors ER-α and ER-β. Both ER-α as well as ER-β specific ligands have been shown to modulate cardioprotection in rats. Using isotype selective knockout models, proliferative effects of estrogen on uterus and breast were shown to be mediated predominantly through ER-α and not through ER-β. These data indicate that an ideal compound for cardioprotection would be an ER-β specific ligand that would provide cardioprotection alone and have a better safety profile for breast and uterine tissues.

The pathogenesis of vasculoproliferative disorders like congestive heart disease, arteriosclerosis and restenosis involves structural changes in the vessel wall characterized by migration of smooth muscle cells (SMC) from the media into the intima and proliferation and deposition of extracellular matrix proteins (ECM) such as collagen. The role of ER-β ligands in preventing an early stage in this process was determined; namely, the proliferation of Rat Aortic Smooth Muscle Cells (RASMC) in culture.

Materials and Methods
Cells and Reagents:

HyQ-DMEM/F12 1:1 modified medium and fetal bovine serum was obtained from HyClone Laboratories Inc. DMEM/F12 50:50 was obtained from Cellgro Technologies. 1713 Estradiol, Biochanin A, and tamoxifen were obtained from Sigma Chemical Co. WST-1 reagent was obtained from Roche. Rat Aortic Smooth Muscle cells (RASMC) were obtained from Lonza, Switzerland.

Cell Proliferation Assay:

All cells used in the assay were between passage 3 to 5. RASMCs were plated at a density of $1 \times 10^4$ cells/well in a 24 well plate, allowed to attach and grown to subconfluence in HyQ-DMEM/F12+10% FBS overnight. Cells were then growth arrested by replacing the medium with DMEM (phenol-red free) containing 0.4% BSA for 48 hrs. After 48 hrs, growth was initiated by replacing the medium with DMEM (phenol-red free)+2.5% FCS containing vehicle or appropriate drug concentration for 4 days. Fresh drug-containing medium was added to the cells every 2 days. On the $5^{th}$ day 50 μl of WST-1 reagent (Roche) was then added to the cells and incubated for 1 hr at 37° C. Absorbance was then determined in the samples at 450 nm wavelength in a Victor plate reader (Perkin-Elmer Inc, USA). The WST-1 assay is based on the estimation of the cleavage of tetrazolium salts to formazan by cellular enzymes. An expansion in the number of viable cells results in an increase in activity of the mitochondrial dehydrogenases in the sample. This increased activity results in increased formazan dye formation which gives an absorbance between 420-480 nm. Absorbance measured is directly correlated to the number of metabolically active cells in culture. Absorbance of the cells in control wells on day 0 (G0) of drug treatment was obtained and the cell proliferation following drug treatment was expressed as a percentage of the day 0 growth.

Results

Figure 20:
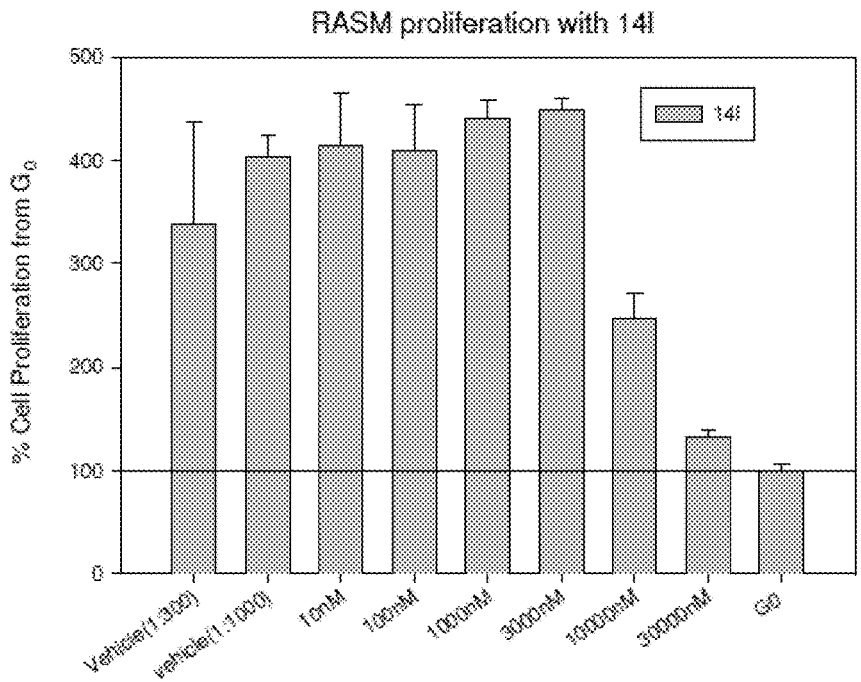
FIG. 20 depicts (A) Inhibition of RASMC proliferation by ER-β Ligand 14l. Cell proliferation was estimated using the WST-1 calorimetric assay. Absorbance at 450 nm was measured and expressed as a percentage of the absorbance in control wells containing cells only on day 0 (G0). (B) Fluorescent detection of intracellular ROS. Subconfluent monolayer of ARPE-19 cells were pretreated with the respective drugs with or without ICI, before exposure to oxidative stress with tBH. Values for cells treated with dye only were subtracted from the raw fluorescence data. Fluorescence is reported relative to cells containing dye in the presence of oxidant alone. Each drug treatment was done in triplicate and is plotted+/−s.e.m.
Figure 20:
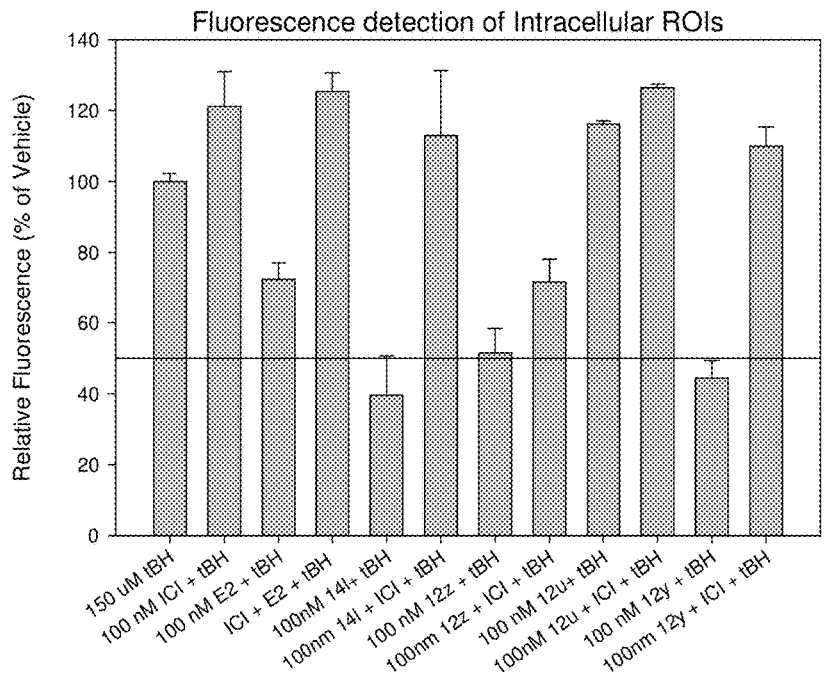

A range of compounds was tested in this assay, including an ER-α antagonist (tamoxifen), ER-β agonist (Biochanin A, 14l, 12u 14m, 12z) and mixed agonist (estradiol). Cell proliferation was calculated as a percentage of cell number on Day 0 of drug treatment. The ER-β ligands Biochanin A, 14l, 12u, and 14m inhibited the proliferation of RASMC in a dose-dependent manner at concentration between 10-30 μM. An increase in absorbance (increase in cell number) from Day 0 was seen in all drug treatments except for the two highest concentrations of tamoxifen (10 μM and 30 μM) indicating that all the ER-β ligands were well tolerated by cells even at the highest concentration. The reduced cell numbers in the tamoxifen (10 μM and 30 μM) compared to day 0 treated wells indicates toxicity of the drug. The $EC_{50}$ values for the reduction in cell proliferation were calculated for all the drugs and is shown in Table 11. A representative titration of 14l is shown in FIG. 20A.

TABLE 11

$EC_{50}$ values for inhibition of RASMC proliferation by ER-β ligands. $EC_{50}$ values were calculated using WinNonLin 5.0.1 using the inhibitory effect sigmoid $E_{max}$ model.

| Compound | $EC_{50}$ (μM) |
| --- | --- |
| Estradiol | 36.41 |
| Biochanin A | 9.79 |
| 12z | 25.05 |
| 12u | 9.56 |
| 14l | 9.63 |
| 14m | 7.89 |
| Tamoxifen | 4.03 |

Conclusions:

ER-β specific ligands in general inhibited the proliferation of RASMC better than a mixed agonist like estradiol. The ER-α antagonist tamoxifen at lower concentration did not have any effect on cell proliferation while at the higher concentration it was shown to be toxic to cells leading to significant reduction in cell numbers. Interestingly the ER-β ligands did not seem to have any toxic effects on cells even at the highest concentration tested, indicating that the observed effect on cell numbers is more a function on cell cycle arrest/progression than apoptosis and cell death. These data indicate that ER-β ligands can significantly inhibit an early step in vascular remodeling and could be of benefit for treatment of vasculooccusive disorders like arteriosclerosis and restenosis.

Example 32A: Effect of ER-Beta SERMs on Preventing Oxidative Stress in ARPE Cells Rationale:

Cardiovascular diseases such as hypertension, coronary heart disease, atherosclerosis have a higher incidence in post-menopausal women than in premenopausal women. This loss of cardiovascular protection is attributed to the deficiency in circulating estrogen levels in the post-menopausal women. Hormone replacement therapy (HRT) can markedly reduce the risk of cardiovascular disease in post-menopausal women. However, the use of HRT for cardio-protection is limited due to the increased incidence of endometrial cancer in women and gynecomastia in men. This has led to a search for compounds that can provide the beneficial effects of estrogen on the heart but do not have the undesirable side effects on uterus or breast.

Estrogen action in target tissues is mediated by its interaction with its cognate receptors ER-α and ER-β. Both ER-α as well as ER-β specific ligands have been shown to modulate cardioprotection in rats. The proliferative effects of estrogen on uterus and breast is mediated predominantly through the ER-α while the ER-β does not have any stimulatory effect on these tissues. These studies make a case for using ER-β specific ligands for cardiovascular protection without the systemic effects that could be expected from ER-α ligands. Oxidative stress is one of the main etiological factors of cardiovascular diseases like hypertension, CHD and atherosclerosis. Estrogens through various molecular mechanisms (genomic and nongenomic) have been shown to activate intracellular signaling cascades that are involved in the transcriptional activation of eNOS and other antioxidant defense genes.

In this study the ability of ER-β compounds to prevent the oxidative damage caused by tert-butyl hydroperoxide (t-BH) on retinal pigmented epithelial cells (RPE) was measured. The retinal pigment epithelium (RPE) due to their location between the photoreceptors and choroid are continuously exposed to high oxygen fluxes. A high level of oxidative stress occurs in the RPE as a result of the formation of abnormal levels of reactive oxygen species (ROS). These features apart from ready availability of the transformed cell line from ATCC makes RPE an ideal system to study the effects of oxidative stress.

Materials and Methods

Cells and Reagents:

Human ARPE-19 cells were obtained from ATCC (Manassas, Va.). All cells used in the experiments were between passage 9 to 12. HyQ-DMEM/F12 1:1 modified medium and fetal bovine serum was obtained from HyClone Laboratories Inc. DMEM/F12 50:50 was obtained from Cellgro technologies. 17β Estradiol, Biochanin A were obtained from Sigma Chemical Co. WST-1 reagent was obtained from Roche. HBSS media was from Gibco. Dichlorodihydrofluorescein diacetate was obtained from (H2DCFDA; Molecular Probes, Eugene Oreg.). ICI was from Tocris.

Fluorescent Detection of Intracellular ROS:

ARPE-19 cells were plated at 100,000 cells/well in a 24 well plate in complete medium (HyQ-DMEM/F12 1:1 modified medium). Cells were allowed to adhere overnight. The next day, media was removed and cells were washed 1× with HBSS. 10 µM H2DCFDA diluted in HBSS was then added to the cells and cells were incubated at 37° C. for 30 mins. After the incubation period the excess dye was removed and cells washed 1× with HBSS. The cells were then preincubated with the respective concentrations of drugs for 1 hour. Following the incubation period oxidative stress was induced with 150 µM tBH for 1 hr at 37° C. Removed and washed cells once with HBSS. The ability of intracellular ROS to oxidize the dye to its fluorescent product was measured and quantified using a Victor plate reader (Perkin Elmer Corporation, Norwalk, Conn.; excitation at 485 nm; emission at 535 nm). Each drug concentration was done in triplicates. The relative fluorescence was calculated as a percentage of tBH only control.

Results

The ability of ER-β SERMs to prevent oxidative damage induced by 150 µM tBH was measured in ARPE-19 cells using a fluorescence based assay. Estradiol was used as a control for the experiment. The experiment was done in the presence and absence of estrogen receptor antagonist ICI. As seen in FIG. 20B, 150 µM tBH was sufficient to cause the accumulation of reactive oxidative species (ROS) in the ARPE cells following 1 hour of incubation at 37° C. Estradiol at a concentration of 100 nM was able to prevent ROS formation with a reduction in ROS formation of approximately 30%. This inhibitory effect of estradiol was reversed with treatment with 100 nM ICI. The ER-β ligands 14l and 12y were also able to prevent the ROS formation with inhibition of more than 50%. 12z was able to prevent ROS formation as well as estradiol while 12u did not seem to have any effect on prevention of oxidative stress in the ARPE cells. As seen with estradiol the inhibitory effect of the ER-β was reversed with ICI indicating a receptor dependent mechanism of action. Cells treated with oxidant in absence of dye did not result in background fluorescence (data not shown).

Conclusions

ER-β compounds 14l, 12z and 12y protected ARPE-19 cells from oxidative damage. This protective effect was reversed with a non-selective ER antagonist ICI indicating that the protective effect is mediated through an estrogen receptor mediated mechanism.

Example 32B: Effect of ER-Beta SERMs on Preventing Oxidative Stress

The expression of genes that promote lipogenesis such as lipoprotein lipase (LPL), fatty acid synthase (FASN), sterol regulatory element binding protein-1 (SREBP-1), phospholipid transfer protein (PLTP) and dehydrocholesterol reductase (Dhcr24) were increased in BAT and WAT isolated from high fat diet-fed mice treated with vehicle. This increase was reversed by the administration of 14m. In addition, genes such as glutathione peroxidase (GPx-3) and DNA damage inducible transcript III (Ddit3) that are involved in the anti-oxidant and oxidative stress pathways were significantly altered by 14m (Table 9). Cumulatively, these results suggest that 14m mediates its anti-obesity effects by inhibiting lipogenesis, increasing energy expenditure and altering the anti-oxidant pathways.

Figure 21:
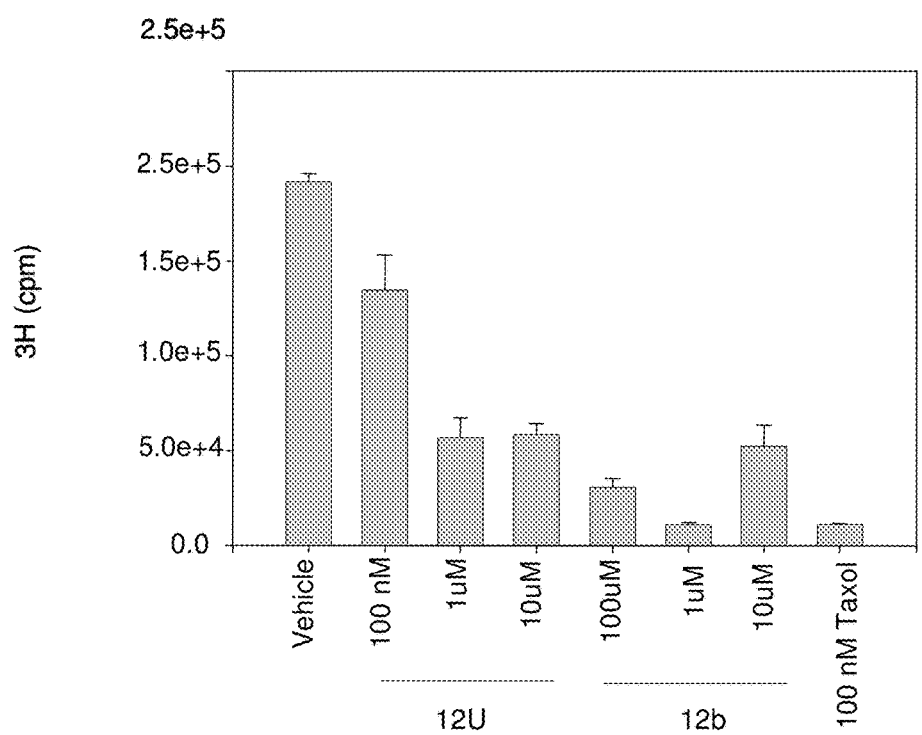
FIG. 21 depicts the effect of 12b and 12u on LNCaP (prostate cancer) cell proliferation.
Figure 22:
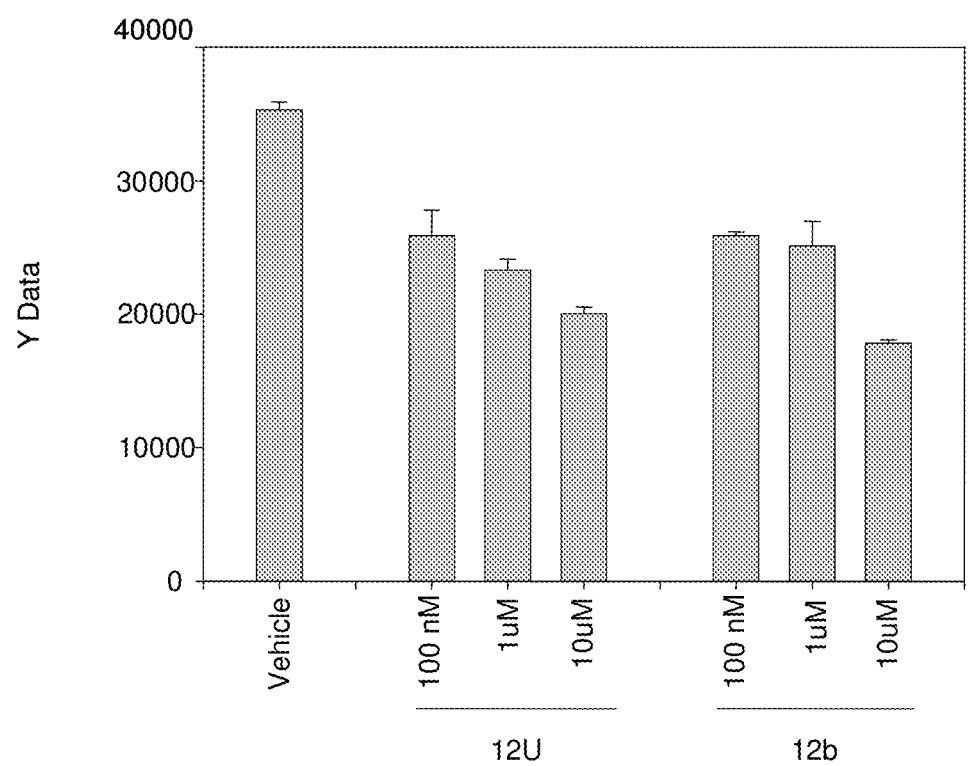
FIG. 22 depicts the effect of 12b and 12u on C-26 (colon cancer) cell proliferation.

Example 33: Anti-Proliferative Effect of NRBAs on Prostate and Colon Cancer Cell Lines The effects of treatment of an ER-β selective NRBA of this invention on cancer cell proliferation was examined using LNCaP prostate cancer cells and C-26 colon cancer cells. LNCaP or C-26 cells were plated in growth medium in 24 well and 6 well plates, respectively. LNCaP cells were treated for 6 days and C-26 cells were treated for 3 days at the indicated concentration. $^3$H thymidine incorporation was measured at the end of treatment as an indicator of cell proliferation. FIGS. 21 and 22 shows that 12b and 12u significantly inhibited the growth of LNCaP prostate cancer and C-26 colon cancer cells, respectively, indicative of their potent anti-proliferative effects.

Figure 23:
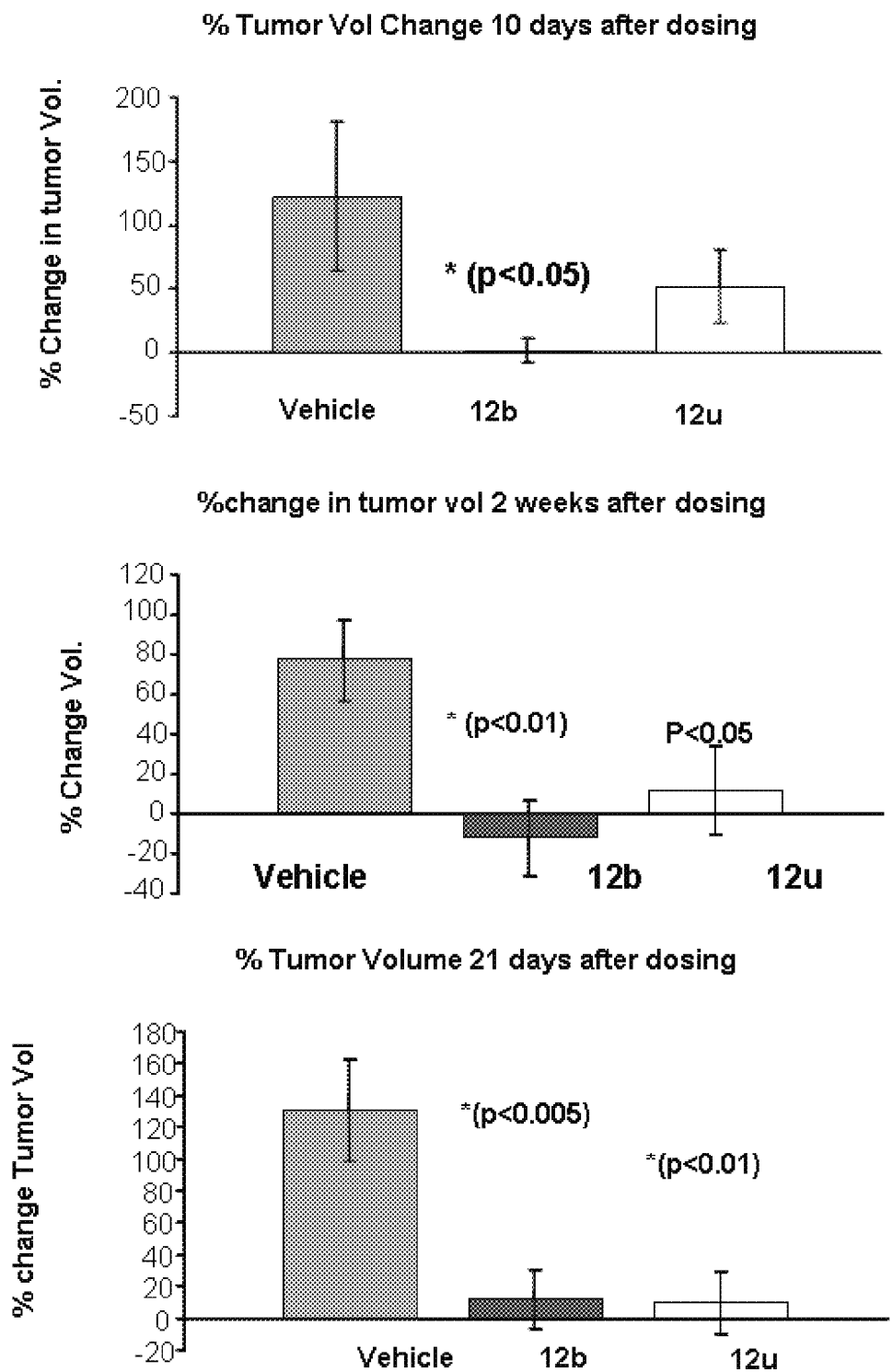
FIG. 23 depicts the effect of 12b and 12u on LNCaP-stromal cell xenograft tumor growth, after 10, 14 and 21 days.

Example 34: In Vivo Anti-Proliferative Effect of NRBAs on Prostate Cancer Xenograft Tumor Growth Prostate tumor xenografts were established with LNCaP cells and human prostate stromal cells in nude mice to establish the in vivo anti-proliferative effects of these ER-β NRBAs. A 4:1 ratio (based on cell number) of LNCaP: stroma cells was injected subcutaneously in nude mice and allowed to grow until they attained 100 mm$^3$ in volume, as measured by calipers. The animals were treated with 12b and 12u at 30 mg/kg/day for 21 days. Tumor volumes were measured twice a week and percent tumor volume calculated, after 10, 14 and 21 days. FIG. 23 shows that both 12b and 12u inhibited the growth of tumor significantly by day 21, indicating that these NRBAs are anti-proliferative both in vitro and in vivo.

Example 35: The Compounds Inhibit Androgen Independent Prostate Cancer Cell Growth The prostate cancer cell line PC-3 is plated in RPMI+10% csFBS at 6000 cells per well of a 96 well plate. Medium is changed to RPMI+1% csFBS without phenol red and cells are treated for 72 hrs with increasing concentrations of NRBAs. Growth inhibition is evaluated.

Example 36: Synthesis of 6-hydroxy-2-(4-hydroxyphenyl)-4-(4-methoxyphenyl)isoquinolin-1(2H)-one (15b)

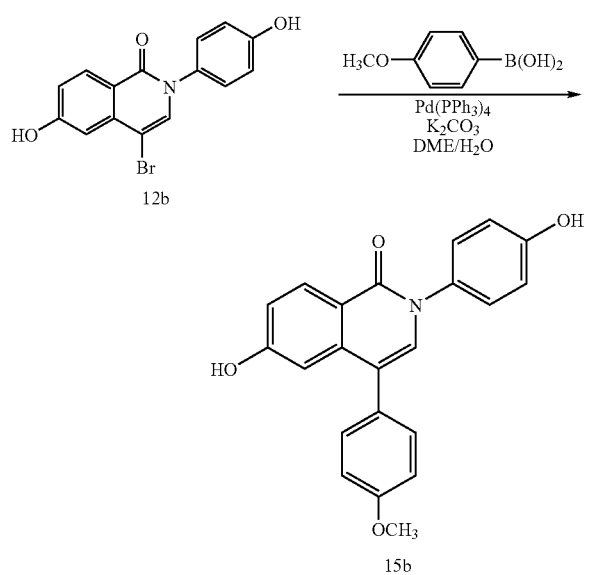

4-Bromo-6-hydroxy-2-(4-hydroxyphenyl)-isoquinolin-1 (2H)-one (12b) (0.32 g, 0.96 mmol), tetrakis(triphenylphosphine)palladium (56 mg, 0.05 mmol), potassium carbonate (0.13 g, 0.96 mmol) and 4-methoxyphenylboronic acid (0.18 g, 1.15 mmol) were placed in a dry and argon flushed 150 mL three-necked round-bottomed flask fitted with a stirring bar and reflux condenser. 1,2-Dimethoxyethane (10 mL) and water (3 mL) were added via a syringe under argon atmosphere. The reaction solution was stirred and heated to reflux for 6 hours. The reaction was quenched by adding 30 mL of water at room temperature. The mixture was extracted with ethyl acetate (3×20 mL). The extracts were combined, washed with brine (2×10 mL) and dried over anhydrous MgSO$_4$ and 2 g of 3-(diethylenetriamino)propyl functionalized silical gel followed by filtration and concentration to give a yellow residue. The yellow residue was purified by flash column chromatography (silica-gel, CH$_2$Cl$_2$/MeOH=9/1 v/v) to give a white solid product, 0.25 g, 72.5% yield. MS: m/z 360.1 [M+H]$^+$. $^1$H NMR (DMSO-d$_6$, 300 MHz) δ 10.28 (s, 1H), 9.68 (s, 1H), 8.18 (d, 1H, J=8.7 Hz), 7.38 (d, 2H, J=9.0 Hz), 7.27 (d, 2H, J=8.7 Hz), 7.13 (s, 1H), 7.04 (d, 2H, J=8.7 Hz), 6.99 (dd, 1H, J$_1$=8.7 Hz, J$_2$=2.4 Hz), 6.86-6.83 (m, 3H), 3.81 (s, 3H).

Example 38: Synthesis of 6,8-Dihydroxy-2-(4-hydroxyphenyl)-4-(4-methoxyphenyl)isoquinolin-1 (2H)-one (15b)

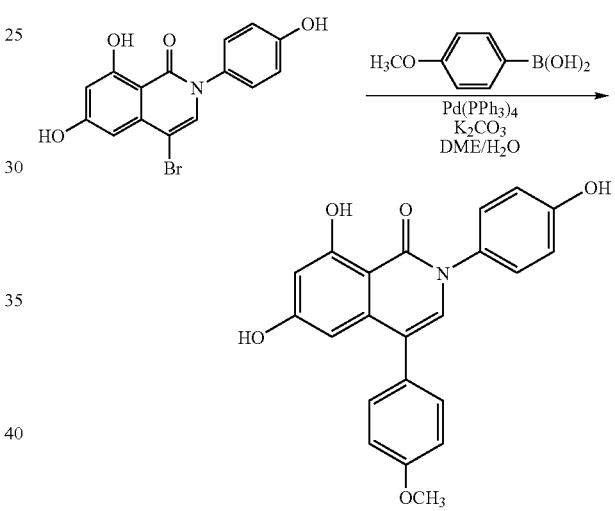

4-Bromo-6,8-dihydroxy-2-(4-hydroxyphenyl)isoquinolin-1(2H)-one (12u) (0.50 g, 1.44 mmol), tetrakis(triphenylphosphine)palladium (83 mg, 0.07 mmol), potassium carbonate (0.40 g, 2.88 mmol) and 4-methoxyphenylboronic acid (0.26 g, 1.72 mmol) were placed in a dry and argon flushed 150 mL three-necked round-bottomed flask fitted with a stirring bar and reflux condenser. 1,2-Dimethoxyethane (15 mL) and water (5 mL) were added via a syringe under argon atmosphere. The reaction solution was stirred and heated to reflux for 16 hours. The reaction was quenched by adding 50 mL of water at room temperature. The mixture was extracted with ethyl acetate (3×20 mL). The extracts were combined, washed with brine (2×10 mL) and dried over anhydrous MgSO$_4$ and 2 g of 3-(diethylenetriamino) propyl functionalized silical gel followed by filtration and concentration to give a yellow residue. The yellow residue was purified by flash column chromatography (silica-gel, CH$_2$Cl$_2$/MeOH=9/1 v/v) to give a white solid product, 0.45 g, 83.3% yield. MS: m/e 373.9 [M+H]$^+$. $^1$H NMR (DMSO-d$_6$, 300 MHz) δ 13.32 (s, 1H), 10.33 (s, 1H), 9.76 (s, 1H), 7.36 (d, 2H, J=9.0 Hz), 7.30 (d, 2H, J=8.7 Hz), 7.11 (s, 1H), 7.04 (d, 2H, J=8.7 Hz), 6.86 (d, 2H, J=8.7 Hz), 6.32 (d, 1H, J=2.1 Hz), 6.30 (d, 1H, J=2.1 Hz), 3.80 (s, 3H).

Example 39: Synthesis of 2-(3-Fluoro-4-hydroxyphenyl)-6,8-dihydroxy-4-vinylisoquinolin-1(2H)-one (15c)

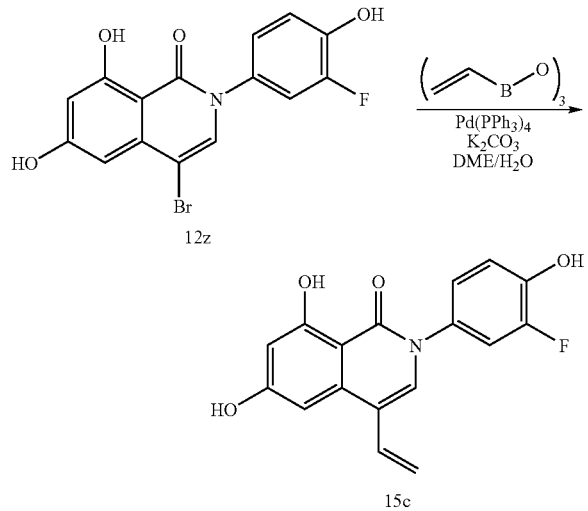

4-Bromo-2-(3-fluoro-4-hydroxyphenyl)-6,8-dihydroxyisoquinolin-1(2H)-one (12z) (0.40 g, 1.09 mmol), tetrakis(triphenylphosphine)palladium (25 mg, 0.02 mmol), potassium carbonate (0.60 g, 4.36 mmol) and vinylboronic anhydride pyridine complex (0.13 g, 0.55 mmol) were placed in a dry and argon flushed 150 mL three-necked round-bottomed flask fitted with a stirring bar and reflux condenser. Anhydrous 1,2-dimethoxyethane (10 mL) and water (3 mL) were added via a syringe under argon atmosphere. The reaction solution was stirred and heated to reflux for 20 hours. The reaction was quenched by adding 20 mL of water at room temperature. The mixture was extracted with ethyl acetate/methanol (9/1 v/v) (3×20 mL). The extracts were combined, washed with brine (2×10 mL) and dried over anhydrous MgSO$_4$ followed by filtration and concentration to give a yellow residue. The yellow residue was purified by flash column chromatography (silica-gel, CH$_2$Cl$_2$/MeOH=9/1 v/v) to give a white solid product, 0.23 g, 67.6% yield. MS: m/e 311.9 [M–H]$^-$. $^1$H NMR (DMSO-d$_6$, 300 MHz) δ 13.12 (s, 1H), 10.51 (s, 1H), 10.24 (s, 1H), 7.44-7.40 (m, 2H), 7.17-7.03 (m, 2H), 6.80 (dd, 1H, J$_1$=17.1 Hz, J$_2$=10.8 Hz), 6.57 (d, 1H, J=2.1 Hz), 6.34 (d, 1H, J=2.1 Hz), 5.67 (dd, 1H, J$_1$=17.1 Hz, J$_2$=1.2 Hz).

Example 40: Synthesis of 6,8-Dihydroxy-2-(4-hydroxyphenyl)-4-phenylisoquinolin-1(2H)-one (15h)

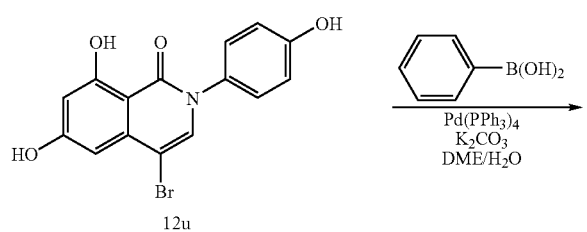

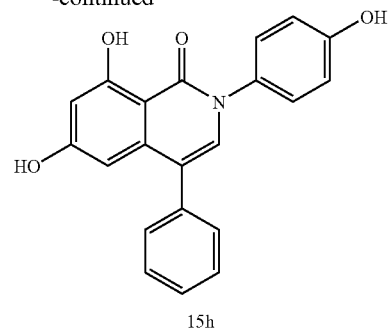

4-Bromo-6,8-dihydroxy-2-(4-hydroxyphenyl)isoquinolin-1(2H)-one (12u) (0.45 g, 1.29 mmol), tetrakis(triphenylphosphine)palladium (75 mg, 0.065 mmol), potassium carbonate (0.38 g, 2.58 mmol) and phenylboronic acid (0.19 g, 1.55 mmol) were placed in a dry and argon flushed 150 mL three-necked round-bottomed flask fitted with a stirring bar and reflux condenser. 1,2-Dimethoxyethane (15 mL) and water (5 mL) were added via a syringe under argon atmosphere. The reaction solution was stirred and heated to reflux for 16 hours. The reaction was quenched by adding 50 mL of water at room temperature. The mixture was extracted with ethyl acetate (3×20 mL). The extracts were combined, washed with brine (2×10 mL) and dried over anhydrous MgSO$_4$ and 2 g of 3-(diethylenetriamino)propyl functionalized silical gel followed by filtration and concentration to give a yellow residue. The yellow residue was purified by flash column chromatography (silica-gel, CH$_2$Cl$_2$/MeOH=9/1 v/v) to give a white solid product, 0.40 g, 89.9% yield. MS: m/e 343.9 [M–H]$^-$. $^1$H NMR (DMSO-d$_6$, 300 MHz) δ 13.30 (s, 1H), 10.35 (s, 1H), 9.76 (s, 1H), 7.52-7.39 (m, 5H), 7.31 (d, 2H, J=8.7 Hz), 7.16 (s, 1H), 6.86 (d, 2H, J=8.7 Hz), 6.33 (d, 1H, J=2.1 Hz), 6.31 (d, 1H, J=2.1 Hz).

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:
1. A method of treating or reducing the likelihood of developing a condition associated with a high fat diet in a subject consuming a high fat diet, comprising administering to said subject in need thereof a therapeutically effective amount of an estrogen receptor ligand compound represented by the structure of Formula XI:

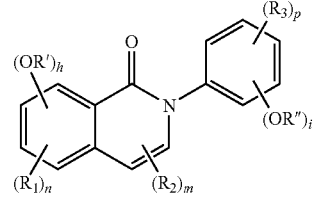

wherein
R$_1$ and R$_3$ are each, independently, hydrogen, —CH=CH$_2$, halogen, cyano, nitro, CF$_3$, 4-methoxyphenyl, 4-hydroxyphenyl, alkenyl, alkyl, haloalkyl, aryl, or benzyl;

$R_2$ is $CH=CH_2$, halogen, cyano, nitro, $CF_3$, 4-methoxyphenyl, 4-hydroxyphenyl, alkenyl, NHR, alkyl, haloalkyl, aryl, or benzyl; and wherein said $R_2$ is at position 4 of formula XI;

R is alkyl, cycloalkyl, hydrogen, haloalkyl, aryl, halogen, alkenyl, CN, $NO_2$ or OH;

R' is hydrogen or Alk;

R" is hydrogen or Alk;

h is 0, 1, or 2;

i is 0 or 1;

n is 1 or 2;

m is 1;

p is 0, 1, or 2; and

Alk is a linear alkyl of 1-7 carbons, branched alkyl of 1-7 carbons, or cycloalkyl of 3-8 carbons;

with the proviso that at least one of h and i is not 0, wherein said high fat diet is not a normal diet, and wherein said condition is obesity, body weight gain, fat mass formation, white adipose tissue weight gain, fatty liver condition (accumulation of fat in the liver), or any combination.

2. The method according to claim 1, wherein said estrogen receptor ligand compound is an estrogen receptor β agonist.

3. The method according to claim 1, wherein said compound is:
- 4-bromo-6,8-dihydroxy-2-(4-hydroxyphenyl)isoquinolin-1(2H)-one,
- 4-cyano-6,8-dihydroxy-2-(4-hydroxyphenyl)isoquinolin-1(2H)-one, or
- 4-bromo-6-hydroxy-2-(4-hydroxyphenyl)-isoquinolin-1(2H)-one.

4. The method according to claim 1, wherein said compound is administered in a dosage of 0.01-50 mg/kg/day.

5. The method according to claim 1, wherein said condition is a fatty liver condition (accumulation of fat in the liver).

6. The method according to claim 5, wherein said fatty liver condition is non-alcoholic steatohepatitis (NASH).

* * * * *